US010864217B2

(12) United States Patent
Pache et al.

(10) Patent No.: US 10,864,217 B2
(45) Date of Patent: Dec. 15, 2020

(54) USE OF INHIBITOR OF APOPTOSIS PROTEIN (IAP) ANTAGONISTS IN HIV THERAPY

(71) Applicants: Sanford Burnham Prebys Medical Discovery Institute, La Jolla, CA (US); Salk Institute for Biological Studies, La Jolla, CA (US)

(72) Inventors: Lars Pache, La Jolla, CA (US); Sumit K. Chanda, La Jolla, CA (US); Mitchell Dennis Vamos, La Jolla, CA (US); Nicholas David Peter Cosford, La Jolla, CA (US); Peter Teriete, La Jolla, CA (US); John Marlett, La Jolla, CA (US); Arturo Diaz, La Jolla, CA (US); John A. T. Young, La Jolla, CA (US)

(73) Assignees: SANFORD BURNHAM PREBYS MEDICAL DISCOVERY INSTITUTE, La Jolla, CA (US); SALK INSTITUTE FOR BIOLOGICAL STUDIES, La Jolla, CA (US)

(*) Notice: Subject to any disclaimer, the term of this patent is extended or adjusted under 35 U.S.C. 154(b) by 0 days.

(21) Appl. No.: 16/421,966

(22) Filed: May 24, 2019

(65) Prior Publication Data

US 2020/0121693 A1 Apr. 23, 2020

Related U.S. Application Data

(63) Continuation of application No. 15/313,286, filed as application No. PCT/US2015/034281 on Jun. 4, 2015, now Pat. No. 10,300,074.

(60) Provisional application No. 62/007,702, filed on Jun. 4, 2014.

(51) Int. Cl.
| | | |
|---|---|---|
| A61K 31/553 | (2006.01) |
| A61P 31/18 | (2006.01) |
| C07D 487/04 | (2006.01) |
| A61K 31/554 | (2006.01) |
| A61K 45/06 | (2006.01) |
| A61K 31/167 | (2006.01) |
| A61K 31/18 | (2006.01) |
| A61K 31/20 | (2006.01) |
| A61K 31/27 | (2006.01) |
| A61K 31/4045 | (2006.01) |
| A61K 31/4406 | (2006.01) |
| A61K 31/5365 | (2006.01) |
| A61K 31/55 | (2006.01) |
| A61K 31/551 | (2006.01) |

(52) U.S. Cl.
CPC .......... *A61K 31/553* (2013.01); *A61K 31/167* (2013.01); *A61K 31/18* (2013.01); *A61K 31/20* (2013.01); *A61K 31/27* (2013.01); *A61K 31/4045* (2013.01); *A61K 31/4406* (2013.01); *A61K 31/5365* (2013.01); *A61K 31/55* (2013.01); *A61K 31/551* (2013.01); *A61K 31/554* (2013.01); *A61K 45/06* (2013.01)

(58) Field of Classification Search
CPC ...... A61K 31/553; A61P 31/18; C07D 487/04
See application file for complete search history.

(56) References Cited

U.S. PATENT DOCUMENTS

| | | | |
|---|---|---|---|
| 4,107,288 A | 8/1978 | Oppenheim et al. |
| 5,455,242 A | 10/1995 | Warshawsky et al. |
| 5,457,196 A | 10/1995 | Warshawsky et al. |
| 5,508,272 A | 4/1996 | Robl |
| 5,635,502 A | 6/1997 | Flynn |
| 7,244,851 B2 | 7/2007 | Cohen et al. |
| 7,309,792 B2 | 12/2007 | Harran et al. |
| 7,345,081 B2 | 3/2008 | Cohen et al. |
| 7,419,975 B2 | 9/2008 | Palermo et al. |
| 7,456,209 B2 | 11/2008 | Condon et al. |
| 7,517,906 B2 | 4/2009 | Condon et al. |
| 7,547,724 B2 | 6/2009 | Laurent et al. |
| 7,674,787 B2 | 3/2010 | Wang et al. |
| 9,546,174 B2 | 1/2017 | Cosford et al. |
| 10,047,119 B2 | 8/2018 | Cosford et al. |
| 10,300,074 B2 | 5/2019 | Pache et al. |
| 10,544,188 B2 | 1/2020 | Cosford et al. |
| 2008/0132485 A1 | 6/2008 | Wang et al. |
| 2008/0269140 A1 | 10/2008 | Wang et al. |
| 2009/0010941 A1 | 1/2009 | Stevenson et al. |
| 2010/0190688 A1 | 7/2010 | Chao et al. |
| 2010/0273812 A1 | 10/2010 | Wang et al. |
| 2011/0046189 A1 | 2/2011 | Wang et al. |
| 2017/0081362 A1 | 3/2017 | Cosford et al. |

FOREIGN PATENT DOCUMENTS

| | | |
|---|---|---|
| EP | 0629627 A2 | 12/1994 |
| JP | 2007522116 A | 8/2007 |
| JP | 2008505976 A | 2/2008 |

(Continued)

OTHER PUBLICATIONS

Badley et al. Altering cell death pathways as an approach to cure HIV infection. Cell Death Dis 4:e718 (2013).
Baldwin et al. Synthesis of potential β-turn bicyclic dipeptide mimetics.J Chem Soc Chem Commun 9:935-936 (1993).
Bosque et al. Induction of HIV-1 latency and reactivation in primary memory CD4+ T cells. Blood 113:58-65 (2009).
Cai et al. A potent and orally active antagonist (SM-406/AT-406) of multiple inhibitor of apoptosis proteins (IAPs) in clinical development for cancer treatment. J Med Chem 54(8):2714-2726 (2011).
Chiou et al. Highly efficient synthesis of azabicyclo[x.y.0]alkane amino acids and congeners by means of Rh-catalyzed cyclohydrocarbonylation. J Org Chem 72(6):1871-1882 (2007).

(Continued)

*Primary Examiner* — Brenda L Coleman
(74) *Attorney, Agent, or Firm* — Wilson Sonsini Goodrich & Rosati

(57) ABSTRACT

Provided herein is the use of compounds that modulate the activity of inhibitor of apoptosis proteins (IAPs), alone or in combination with other therapeutic agents, in the treatment of human immunodeficiency virus (HIV).

9 Claims, 8 Drawing Sheets

(56) References Cited

FOREIGN PATENT DOCUMENTS

| JP | 2008545780 | A | 12/2008 |
|----|------------|---|---------|
| JP | 2011516581 | A | 5/2011 |
| WO | WO-2004007529 | A2 | 1/2004 |
| WO | WO-2006017295 | A2 | 2/2006 |
| WO | WO-2006069063 | A1 | 6/2006 |
| WO | WO-2007041775 | A1 | 4/2007 |
| WO | WO-2007101347 | A1 | 9/2007 |
| WO | WO-2007130626 | A2 | 11/2007 |
| WO | WO-2008073305 | A1 | 6/2008 |
| WO | WO-2008128121 | A1 | 10/2008 |
| WO | WO-2008128171 | A2 | 10/2008 |
| WO | WO-2008134679 | A1 | 11/2008 |
| WO | WO-2009060292 | A2 | 5/2009 |
| WO | WO-2009126947 | A2 | 10/2009 |
| WO | WO-2011094150 | A1 | 8/2011 |
| WO | WO-2012125622 | A1 | 9/2012 |
| WO | WO-2014085489 | A1 | 6/2014 |
| WO | WO-2015187998 | A2 | 12/2015 |

OTHER PUBLICATIONS

Claridge et al. Synthesis and analysis of Leu-enkephalin analogues containing reverse turn peptidomimetics. Bioorg Med Chem Lett 6(4):485-490 (1996).

Cohen et al. Antagonists of inhibitor of apoptosis proteins based on thiazole amide isosteres. Bioorg Med Chem Lett. 20(7):2229-2233 (2010).

Cohen et al. Orally bioavailable antagonists of inhibitor of apoptosis proteins based on an azabicyclooctane scaffold. J Med Chem 52(6):1723-1730 (2009).

Cornille et al. Electrochemical Cyclization of Dipeptides toward Novel Bicyclic, Reverse-Turn Peptidomimetics. 1. Synthesis and Conformational Analysis of 7,5-Bicyclic Systems. J Am Chem Soc 117(3):909-917 (1995).

Database Registry 2009 RN 1177797-11-3. Retrieved from STN International on Sep. 20, 2017 (1 pg.).

Finlay et al. Small-molecule IAP antagonists sensitize cancer cells to TRAIL-induced apoptosis: roles of XIAP and cIAPs. Mol Cancer Ther 13(1):5-15 (2014).

Flygare et al. Small-molecule pan-IAP antagonists: a patent review. Expert Opinion on Therapeutic Patents 20(2):251-267 (2010).

Gilley et al. New entry to convertible isocyanides for the Ugi reaction and its application to the stereocontrolled formal total synthesis of the proteasome inhibitor omuralide. Org. Lett. 9:3631-3634 (2007).

Gonzalez-Lopez et al. Design, synthesis and evaluation of monovalent Smac mimetics that bind to the BIR2 domain of the antiapoptotic protein XIAP. Bioorg Med Chem Lett 21(14):4332-4336 (2011).

Griesbaum et al. Difunctional and heterocyclic products from the ozonolysis of conjugated C5-C8-cyclodienes. J Org Chem 55:6024-6027 (1990).

Huang et al. Fragment-based design of small molecule X-linked inhibitor of apoptosis protein inhibitors. J Med Chem 51(22):7111-7118 (2008).

Hyvl et al. Copper-Catalyzed Activation of Disulfides as a Key Step in the Synthesis of Benzothiazole Moieties. Eur. J. Org. Chem. 15:2849-2851 (2010).

Konig et al. Global analysis of host-pathogen interactions that regulate early-stage HIV-1 replication. Cell 135:49-60 (2008).

Li et al. A small molecule Smac mimic potentiates TRAIL- and TNFalpha-mediated cell death. Science 305(5689):1471-1474 (2004).

Ling et al. Theoretical studies on the interactions of XIAP-BIR3 domain with bicyclic and tricyclic core monovalent Smac mimetics. J Mol Graph Model 29(3):354-362 (2010).

Monfardini et al. Screening multicomponent reactions for X-linked inhibitor of apoptosis-baculoviral inhibitor of apoptosis protein repeats domain binder. J Med Chem 54(3):890-900 (2011).

Ndubaku et al. Antagonism of c-IAP and XIAP proteins is required for efficient induction of cell death by small-molecule IAP antagonists. ACS Chem Biol 4(7):577-566 (2009).

Nikolovska-Coleska et al. Development and optimization of a binding assay for the XIAP BIR3 domain using fluorescence polarization. Anal Biochem 332(2):261-273 (2004).

O'Doherty et al. A sensitive, quantitative assay for human immunodeficiency virus type 1 integration. J Virol 76:10942-10950 (2002).

Oost et al. Discovery of potent antagonists of the antiapoptotic protein XIAP for the treatment of cancer. J Med Chem 47(18):4417-4426 (2004).

Orzaez et al. Characterization of dequalinium as a XIAP antagonist that targets the BIR2 domain. Apoptosis 16(5):460-467 (2011).

Park et al. Non-peptidic small molecule inhibitors of XIAP. Bioorg Med Chem Lett. 15(3):771-775 (2005).

PCT/US2015/034281 International Search Report and Written Opinion dated Dec. 11, 2015.

Peng et al. Design and synthesis of a 1,5-diazabicyclo[6,3,0] dodecane amino acid derivative as a novel dipeptide reverse-turn mimetic. Tetrahedron Letters 47(27):4769-4770 (2006).

Peng et al. Potent, orally bioavailable diazabicyclic small-molecule mimetics of second mitochondria-derived activator of caspases. J Med Chem 51(24):8158-8162 (2008).

Robl et al. Dual metalloprotease inhibitors: mercaptoacetyl-based fused heterocyclic dipeptide mimetics as inhibitors of angiotensin-converting enzyme and neutral endopeptidase. J Med Chem 40(11):1570-1577 (1997).

Seneci et al. Rational design, synthesis and characterization of potent, non-peptidic Smac mimics/XIAP inhibitors as proapoptotic agents for cancer therapy. Bioorg Med Chem 17(16):5834-5856 (2009).

Slomczynska et al. Electrochemical Cyclization of Dipeptides to Form Novel Bicyclic, Reverse-Turn Peptidomimetics. 2. Synthesis and Conformational Analysis of 6,5-Bicyclic Systems. J Org Chem 61:1198-1204 (1996).

Sun et al. Building functionalized peptidomimetics: use of electroauxiliaries for introducing N-acyliminium ions into peptides. J Am Chem Soc 128(42):13761-13771 (2006).

Sun et al. Cyclopeptide Smac mimetics as antagonists of IAP proteins. Bioorg Med Chem Lett 20(10):3043-3046 (2010).

Sun et al. Design, Synthesis and Characterization of a Potent, Non-Peptide, Cell-Permeable, Bivalent Smac Mimetic that Concurrently Targets both the BIR2 and BIR3 Domains in XIAP. J Am Chem Soc 129(49):15279-15294 (2007).

Sun et al. Design, synthesis, and evaluation of potent, nonpeptidic mimetics of second mitochondria-derived activator of caspases. J Med Chem 52(3):593-596 (2009).

Sun et al. Potent Bivalent Smac Mimetics: Effect of the Linker on binding to Inhibitor of Apoptosis Proteins (IAPs) and Anticancer Activity. J Med Chem 54(9):3306-3318 (2011).

Sun et al. Structure-based design, synthesis, evaluation, and crystallographic studies of conformationally constrained Smac mimetics as inhibitors of the X-linked inhibitor of apoptosis protein (XIAP). J Med Chem 51(22):7169-7180 (2008).

Ueda et al. Efficient entry into 2-substituted tetrahydroquinoline systems through alkylative ring expansion: stereoselective formal synthesis of (+/−)-martinellic acid. J Org Chem 75:914-921 (2010).

U.S. Appl. No. 14/648,435 Office Action dated Feb. 4, 2016.
U.S. Appl. No. 14/648,435 Office Action dated May 23, 2016.
U.S. Appl. No. 15/313,286 Office Action dated Aug. 9, 2018.
U.S. Appl. No. 15/313,286 Office Action dated Mar. 13, 2018.
U.S. Appl. No. 15/363,935 Office Action dated Aug. 16, 2017.
U.S. Appl. No. 16/031,837 Office Action dated Mar. 14, 2019.

Vamos et al. Expedient synthesis of highly potent antagonists of inhibitor of apoptosis proteins (IAPs) with unique selectivity for ML-IAP. ACS Chem Biol 8(4):725-732 (2013).

Wang. Design of small-molecule Smac mimetics as IAP antagonists. Curr Top Microbiol Immunol. 348:89-113 (2011).

Yang et al. Importance of Ligand Reorganization Free Energy in Protein—Ligand Binding-Affinity Prediction. J Am Chem Soc 131(38):13709-13721 (2009).

(56) References Cited

OTHER PUBLICATIONS

Zhang et al. A convenient and versatile synthesis of 6,5- and 7,5-fused bicyclic lactams as peptidomimetics. Tetrahedron Letters 42(30):4943-4945 (2001).
Zhang et al. Design, synthesis, and evaluation of tricyclic, conformationally constrained small-molecule mimetics of second mitochondria-derived activator of caspases. J Med Chem 51(23)7352-7355 (2008).
Zobel et al. Design, synthesis, and biological activity of a potent Smac mimetic that sensitizes cancer cells to apoptosis by antagonizing IAPs. ACS Chem Biol. 1(8):525-533 (2006).

… … …

USE OF INHIBITOR OF APOPTOSIS PROTEIN (IAP) ANTAGONISTS IN HIV THERAPY

RELATED APPLICATIONS

This application is a continuation of U.S. patent application Ser. No. 15/313,286, filed Nov. 22, 2016, which is a U.S. National Stage entry of International Application No. PCT/US2015/034281, filed Jun. 4, 2015, which claims the benefit of U.S. Provisional Patent Application No. 62/007,702 filed on Jun. 4, 2014, all of which are incorporated herein by reference in their entirety.

STATEMENT AS TO FEDERALLY SPONSORED RESEARCH

This invention was made with government support under Contract number P01 AI090935 awarded by the National Institutes of Health (NIH). The government has certain rights in the invention.

SUMMARY OF THE INVENTION

Described herein is the use of IAP antagonists in the treatment of human immunodeficiency virus (HIV) in a mammal, alone or in combination with other therapeutic agents used in HIV therapy.

In one aspect, provided herein is a method of treating human immunodeficiency virus (HIV) in an individual in need thereof comprising administering a therapeutically effective amount of at least one inhibitor of apoptosis proteins (IAP) antagonist.

In another aspect, provided herein is a method of reducing dormant, replication competent human immunodeficiency virus (HIV) in an individual in need thereof comprising administering a therapeutically effective amount of at least one inhibitor of apoptosis proteins (IAP) antagonist.

In a further aspect, provided herein is a method of making dormant, replication competent human immunodeficiency virus (HIV) susceptible to immune system clearance in an individual in need thereof comprising administering a therapeutically effective amount of at least one inhibitor of apoptosis proteins (IAP) antagonist.

In a further aspect, provided herein is a method of making dormant, replication competent human immunodeficiency virus (HIV) susceptible to the effects of antiretroviral therapy in an individual in need thereof comprising administering a therapeutically effective amount of at least one inhibitor of apoptosis proteins (IAP) antagonist.

In a further aspect, provided herein is a method of eliminating replication competent human immunodeficiency virus (HIV) in an individual in need thereof comprising administering a therapeutically effective amount of at least one inhibitor of apoptosis proteins (IAP) antagonist.

In a further aspect, provided herein is a method of inducing long term control of human immunodeficiency virus (HIV) replication and growth in the absence of antiretroviral therapy in an individual in need thereof comprising administering a therapeutically effective amount of at least one inhibitor of apoptosis proteins (IAP) antagonist.

In a further aspect, provided herein is a method of activating human immunodeficiency virus (HIV) transcription in latently infected cells in an individual in need thereof comprising administering a therapeutically effective amount of at least one inhibitor of apoptosis proteins (IAP) antagonist.

In a further aspect, provided herein is a method of reducing human immunodeficiency virus (HIV) reservoirs of latently infected cells in an individual in need thereof comprising administering a therapeutically effective amount of at least one inhibitor of apoptosis proteins (IAP) antagonist.

In some embodiments, the individual in need is on concomitant antiretroviral therapy. In other embodiments, the IAP antagonist activates HIV transcription in latently infected cells. In some embodiments, the latently infected cells are CD4$^+$ T cells.

In some embodiments, the IAP antagonist is a small molecule. In other embodiments, the IAP antagonist is a small molecule comprising a bicyclic, non-aromatic lactam. In some embodiments, the IAP antagonist is a small molecule comprising a fused bicyclic, non-aromatic lactam containing a six-five, seven-five, eight-five, seven-six, or eight-six ring system. In some embodiments, the IAP antagonist is a small molecule comprising a six-five fused bicyclic ring system.

In some embodiments, the IAP antagonist is a small molecule that has the following structure of Formula A-I, or pharmaceutically acceptable salt, N-oxide, racemate or stereoisomer thereof:

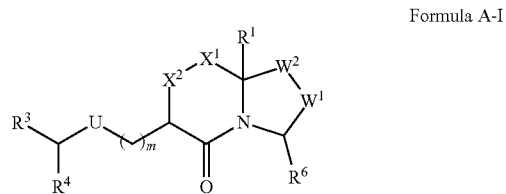

Formula A-I wherein,

W$^1$ is O, S, N—R$^A$, or C(R$^{8a}$)(R$^{8b}$);

W$^2$ is O, S, N—R$^A$, or C(R$^{8c}$)(R$^{8d}$); provided that W$^1$ and W$^2$ are not both O, or both S;

R$^1$ is H, C$_1$-C$_6$alkyl, C$_3$-C$_6$cycloalkyl, —C$_1$-C$_6$alkyl-(substituted or unsubstituted C$_3$-C$_6$cycloalkyl), substituted or unsubstituted aryl, substituted or unsubstituted heteroaryl, —C$_1$-C$_6$alkyl-(substituted or unsubstituted aryl), or —C$_1$-C$_6$alkyl-(substituted or unsubstituted heteroaryl);

when X$^1$ is O, N—R$^A$, S, S(O), or S(O)$_2$, then X$^2$ is C(R$^{2a}$R$^{2b}$);

or:

X$^1$ is CR$^{2c}$R$^{2d}$ and X$^2$ is CR$^{2a}$R$^{2b}$, and R$^{2c}$ and R$^{2a}$ together form a bond;

or:

X$^1$ and X$^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring;

or:

X$^1$ is CH$_2$ and X$^2$ is C=O, C=C(R$^C$)$_2$, or C=NR$^C$; where each R$^C$ is independently selected from H, —CN, —OH, alkoxy, substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-

$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

$R^A$ is H, $C_1$-$C_6$alkyl, —C(=O)$C_1$-$C_6$alkyl, substituted or unsubstituted aryl, or substituted or unsubstituted heteroaryl;

$R^{2a}$, $R^{2b}$, $R^{2c}$, $R^{2d}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —N$R^D R^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ is $C_1$-$C_3$alkyl, or $C_1$-$C_3$fluoroalkyl;

$R^4$ is —NH$R^5$, —N($R^5$)$_2$, —N$^+$($R^5$)$_3$ or —O$R^5$;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ together with the atoms to which they are attached form a substituted or unsubstituted 5-7 membered ring;

or:

$R^3$ is bonded to a nitrogen atom of U to form a substituted or unsubstituted 5-7 membered ring;

$R^6$ is —NHC(=O)$R^7$, —C(=O)NH$R^7$, —NHS(=O)$_2$$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^5$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p is 0, 1 or 2;

$R^{8a}$, $R^{8b}$, $R^{8c}$, and $R^{8d}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —NH$_2$, —NH($C_1$-$C_4$alkyl), —N($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In some embodiments, the IAP antagonist is a small molecule that has the following structure of Formula A-III-1, or the pharmaceutically acceptable salt, N-oxide, racemate or stereoisomer thereof:

Formula A-III-1

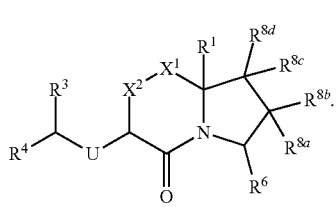

In some embodiments, the IAP antagonist is a small molecule that has the following structure of Formula A-V-2, or pharmaceutically acceptable salt, N-oxide, racemate or stereoisomer thereof:

Formula A-V-2

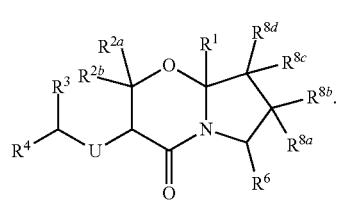

In some embodiments, the IAP antagonist is a small molecule that has the following structure of Formula A-XI, or pharmaceutically acceptable salt, N-oxide, racemate or stereoisomer thereof:

Formula A-XI

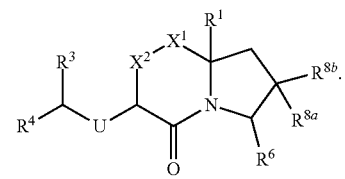

In some embodiments, the IAP antagonist is a small molecule that has the following structure of Formula A-XII, or pharmaceutically acceptable salt, N-oxide, racemate or stereoisomer thereof:

Formula A-XII

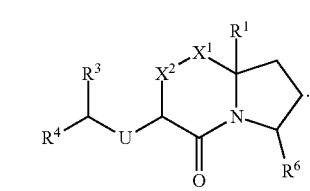

In some embodiments, the IAP antagonist is a small molecule that has the following structure of Formula A-XIX, or pharmaceutically acceptable salt, N-oxide, racemate or stereoisomer thereof:

Formula A-XIX

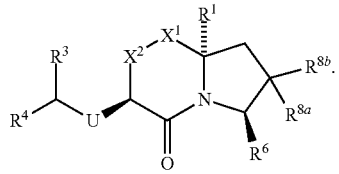

In some embodiments, the IAP antagonist is a small molecule that has the following structure of Formula A-XXI, pharmaceutically acceptable salt, N-oxide, racemate or stereoisomer thereof:

Formula A-XXI wherein,
$W^2$ is O, S, or $C(R^{8c})(R^{8d})$;
$R^1$ is H, or $C_1$-$C_6$alkyl;
$X^1$ is O, N—$R^A$, S, S(O), or $S(O)_2$;
$R^A$ is H, $C_1$-$C_6$alkyl, —C(=O)$C_1$-$C_6$alkyl, substituted or unsubstituted aryl, or substituted or unsubstituted heteroaryl;
$R^{2a}$, and $R^{2b}$ are independently selected from H, substituted or unsubstituted $C_1$-$C_6$alkyl, and —C(=O)$R^B$;
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;
$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
$R^3$ is $C_1$-$C_3$alkyl, or $C_1$-$C_3$fluoroalkyl;
each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH (substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$ and $R^{8b}$ are independently selected from H, $C_1$-$C_6$alkyl, and $C_1$-$C_6$fluoroalkyl;

$R^{8c}$ and $R^{8d}$ are independently selected from H, $C_1$-$C_6$alkyl, and $C_1$-$C_6$fluoroalkyl;

where each substituted alkyl, heteroalkyl, cycloalkyl, heterocycloalkyl, aryl or heteroaryl is substituted with 1-3 $R^9$; and each $R^9$ is independently selected from halogen, —OH, —SH, (C═O), CN, $C_1$-$C_4$alkyl, $C_1$-$C_4$ fluoroalkyl, $C_1$-$C_4$ alkoxy, $C_1$-$C_4$ fluoroalkoxy, —NH$_2$, —NH($C_1$-$C_4$alkyl), —N($C_1$-$C_4$alkyl)$_2$, —C(═O)OH, —C(═O)NH$_2$, —C(═O)$C_1$-$C_3$alkyl, —S(═O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In some embodiments, the IAP antagonist is a small molecule that has one of the following structures:

or pharmaceutically acceptable salt, N-oxide, racemate or stereoisomer thereof.

In some embodiments, the IAP antagonist is a small molecule comprising a seven-five fused bicyclic ring system.

In some embodiments, the IAP antagonist is a small molecule that has the following structure of Formula B-I, or pharmaceutically acceptable salt, N-oxide, racemate or stereoisomer thereof:

Formula B-I wherein, $R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl);

when $X^1$ is selected from N—$R^4$, then $X^2$ is C═O, or $CR^{2c}R^{2d}$, and $X^3$ is $CR^{2a}R^{2b}$;

or when $X^1$ is selected from S, S(O) and S(O)$_2$, then $X^2$ is $CR^{2c}R^{2d}$, and $X^3$ is $CR^{2a}R^{2b}$;

or when $X^1$ is O, then $X^2$ is selected from $CR^{2c}R^{2d}$ and N—$R^4$, and $X^3$ is $CR^{2a}R^{2b}$;

or:

when $X^1$ is CH$_2$, then $X^2$ is selected from O, N—$R^4$, S, S(O), and S(O)$_2$, and $X^3$ is $CR^{2a}R^{2b}$;

or:

$X^1$ is $CR^{2e}R^{2f}$ and $X^2$ is $CR^{2c}R^{2d}$, and $R^{2e}$ and $R^{2c}$ together form a bond, and $X^3$ is $CR^{2a}R^{2b}$;

or:
- $X^1$ and $X^3$ are both $CH_2$ and $X^2$ is $C=O$, $C=C(R^C)_2$, or $C=NR^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:
- $X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:
- $X^2$ and $X^3$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ is $CR^{2e}R^{2f}$;

$R^A$ is H, $C_1$-$C_6$alkyl, —$C(=O)C_1$-$C_6$alkyl, substituted or unsubstituted aryl, or substituted or unsubstituted heteroaryl;

$W^1$ is O, S, N—$R^A$, or $C(R^{8a})(R^{8b})$;
$W^2$ is O, S, N—$R^A$, or $C(R^{8c})(R^{8d})$; provided that $W^1$ and $W^2$ are not both O, or both S;

$R^{2a}$, $R^{2b}$, $R^{2c}$, $R^{2d}$, $R^{2e}$, and $R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —$C(=O)R^B$;

$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^D R^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;
—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ is $C_1$-$C_3$alkyl, or $C_1$-$C_3$fluoroalkyl;
$R^4$ is —$NHR^5$, —$N(R^5)_2$, —$N^+(R^5)_3$ or —$OR^5$;
each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:
- $R^3$ and $R^5$ together with the atoms to which they are attached form a substituted or unsubstituted 5-7 membered ring;

or:
- $R^3$ is bonded to a nitrogen atom of U to form a substituted or unsubstituted 5-7 membered ring;

$R^6$ is —NHC(=O)$R^7$, —C(=O)NH$R^7$, —NHS(=O)$_2$$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^5$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p is 0, 1 or 2;
$R^{8a}$, $R^{8b}$, $R^{8c}$, and $R^{8d}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:
- $R^{8a}$ and $R^{8d}$ are as defined above, and $R^{8b}$ and $R^{8c}$ together form a bond;

or:
- $R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:
- $R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N; or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —NH$_2$, —NH($C_1$-$C_4$alkyl), —N($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In some embodiments, the IAP antagonist is a small molecule that has the following structure of Formula B-III-1, or pharmaceutically acceptable salt, N-oxide, racemate or stereoisomer thereof:

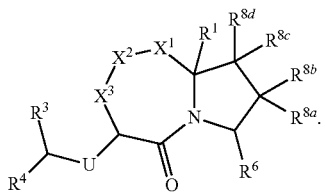

Formula B-III-1

In some embodiments, the IAP antagonist is a small molecule that has the following structure of Formula B-V-2, Formula B-VI-2, or Formula B-VII-2, or a pharmaceutically acceptable salt, N-oxide, racemate or stereoisomer thereof:

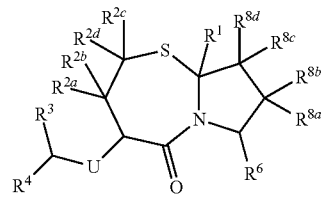

Formula B-V-2

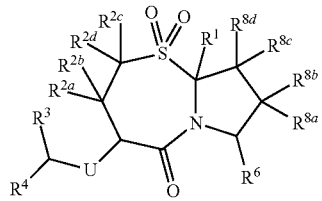

Formula B-VI-2

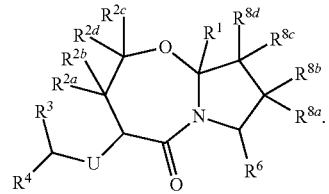

Formula B-VII-2

In some embodiments, the IAP antagonist is a small molecule that has the following structure of Formula B-XI-1, or pharmaceutically acceptable salt, N-oxide, racemate or stereoisomer thereof:

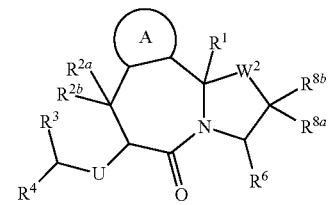

Formula B-XI-1 wherein,
ring A is a fused substituted or unsubstituted saturated or partially saturated 3-10 membered cycloalkyl ring, substituted or unsubstituted saturated or partially saturated 3-10 membered heterocycloalkyl ring, substituted or unsubstituted 5-10 membered aryl ring, or substituted or unsubstituted 5-10 membered heteroaryl ring.

In some embodiments, the IAP antagonist is a small molecule that has the following structure of Formula B-XII, or pharmaceutically acceptable salt, N-oxide, racemate or stereoisomer thereof:

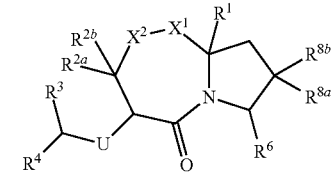

Formula B-XII wherein $R^{8a}$ and $R^{8b}$ are independently selected from H and $C_1$-$C_3$alkyl.

In some embodiments, the IAP antagonist is a small molecule that has the following structure of Formula B-XV, or pharmaceutically acceptable salt, N-oxide, racemate or stereoisomer thereof:

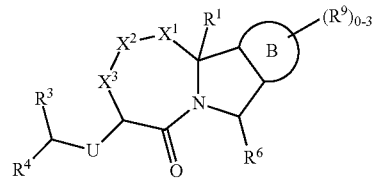

Formula B-XV wherein ring B is an aryl or heteroaryl ring.

In some embodiments, the IAP antagonist is a small molecule that has the following structure of Formula B-XVI-1, Formula B-XVI-2, Formula B-XVI-3, or Formula B-XVI-4, or pharmaceutically acceptable salt, N-oxide, racemate or stereoisomer thereof:

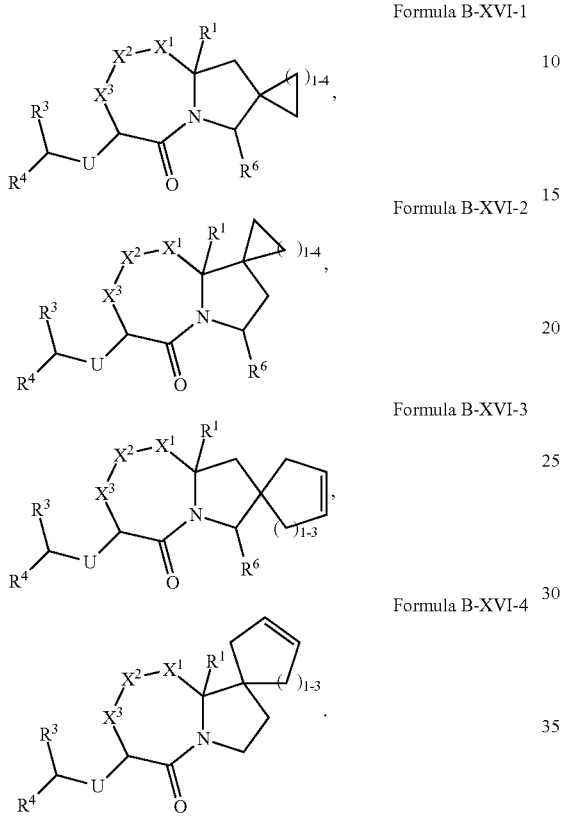

In some embodiments, the compound of Formula B-I has the structure of Formula B-XXII, or pharmaceutically acceptable salt, N-oxide, racemate or stereoisomer thereof:

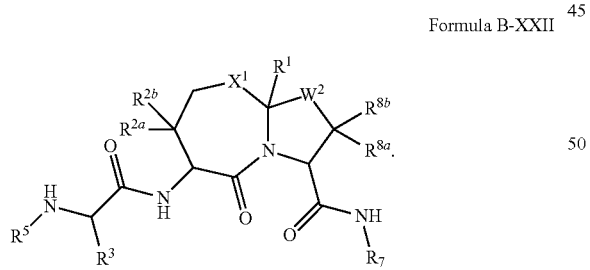

wherein, $W^2$ is O, S, or $C(R^{8c})(R^{8d})$;

$R^1$ is H, or $C_1$-$C_6$alkyl;

$X^1$ is O, N—$R^A$, S, S(O), or $S(O)_2$;

$R^A$ is H, $C_1$-$C_6$alkyl, —C(=O)$C_1$-$C_6$alkyl, substituted or unsubstituted aryl, or substituted or unsubstituted heteroaryl;

$R^{2a}$ and $R^{2b}$ are independently selected from H, substituted or unsubstituted $C_1$-$C_6$alkyl, and —C(=O)$R^B$;

$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

$R^3$ is $C_1$-$C_3$alkyl, or $C_1$-$C_3$fluoroalkyl;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$ and $R^{8b}$ are independently selected from H, $C_1$-$C_6$alkyl, and $C_1$-$C_6$fluoroalkyl;

$R^{8c}$ and $R^{8d}$ are independently selected from H, $C_1$-$C_6$alkyl, and $C_1$-$C_6$fluoroalkyl;

where each substituted alkyl, heteroalkyl, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —N($C_1$-$C_4$alkyl)$_2$, —C(=O)OH, —C(=O)$NH_2$, —C(=O)$C_1$-$C_3$alkyl, —S(=O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In some embodiments, the IAP antagonist is a small molecule that has one of the following structures:

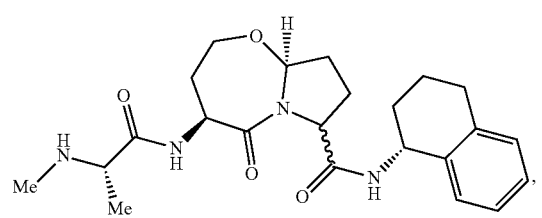
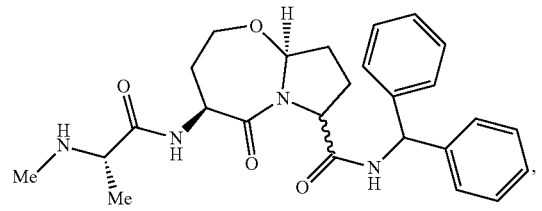
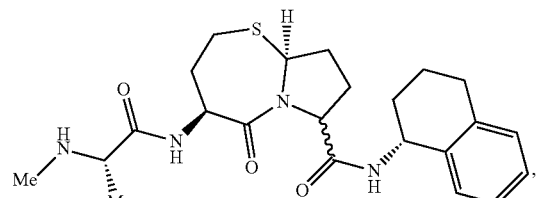
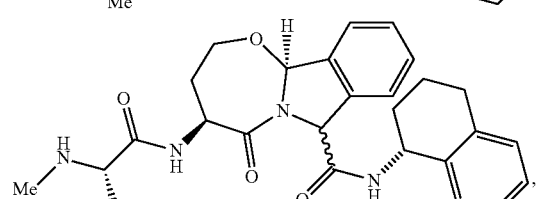
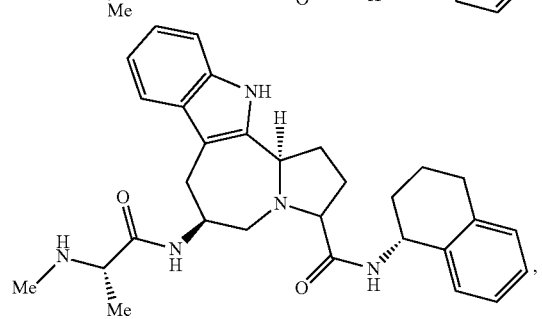
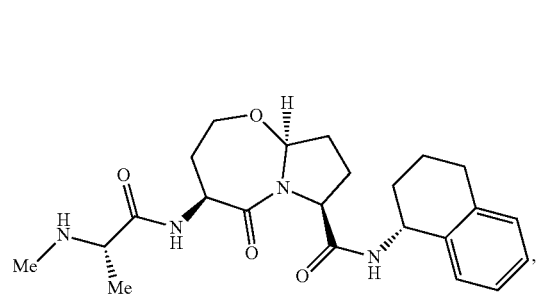
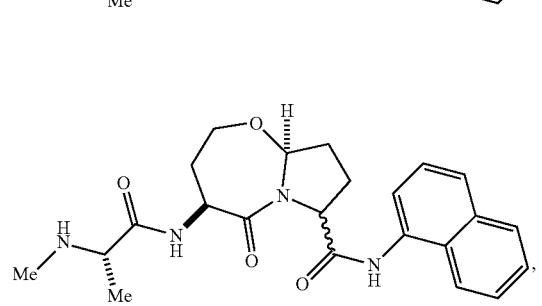
-continued
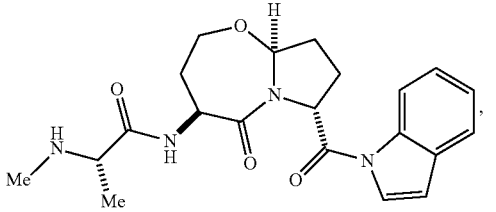
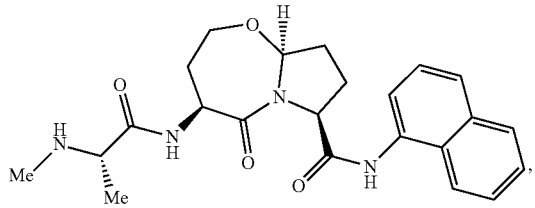
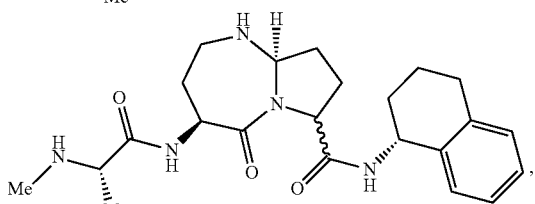
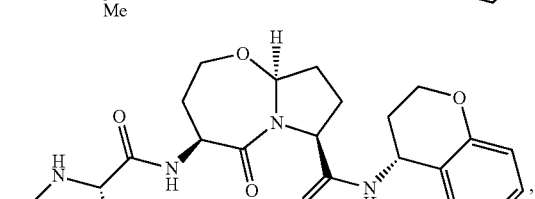
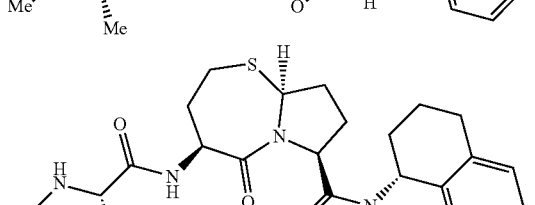
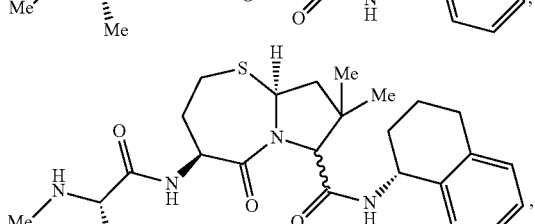
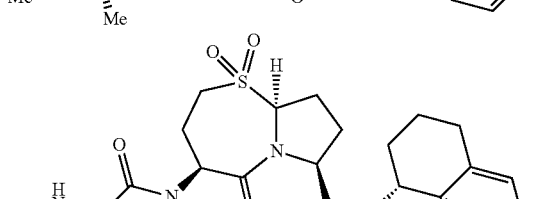
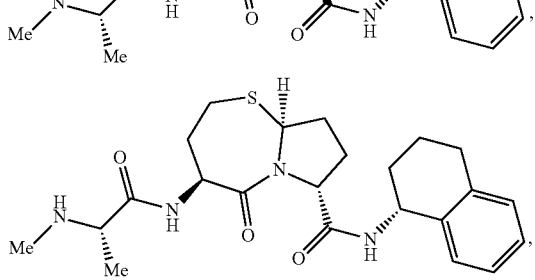

-continued

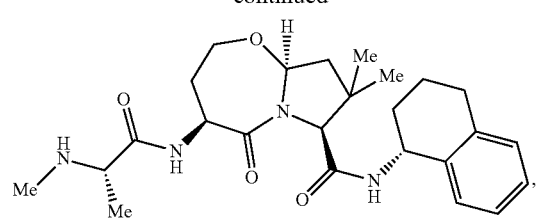

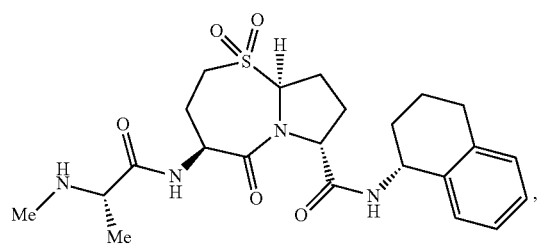

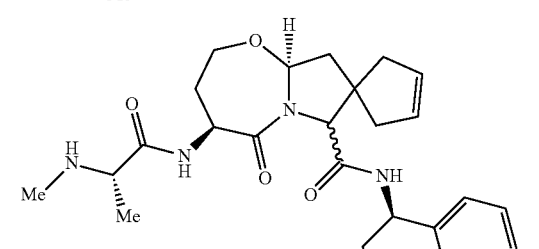

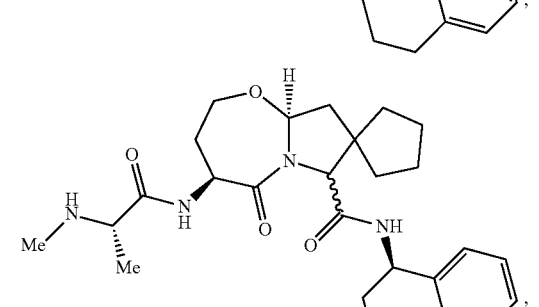

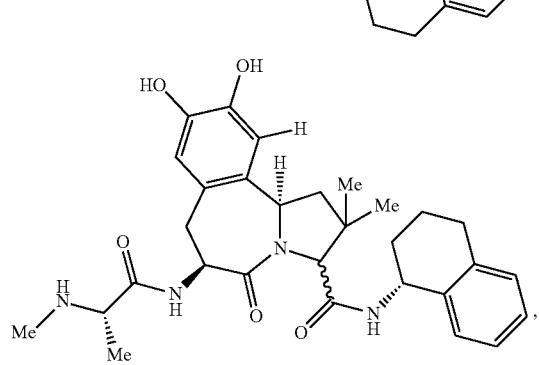

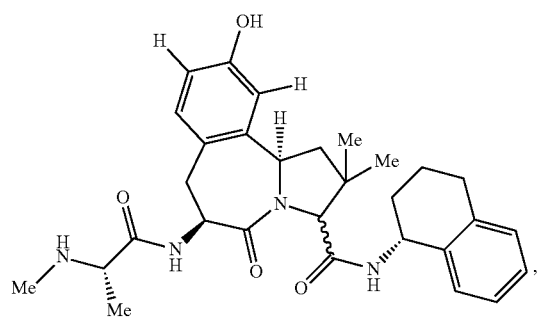

-continued

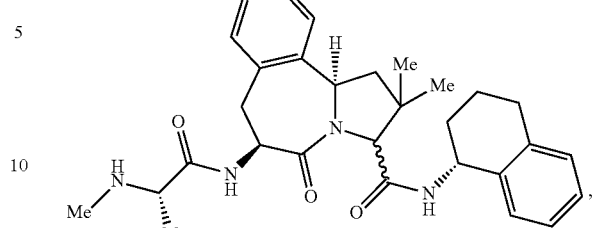

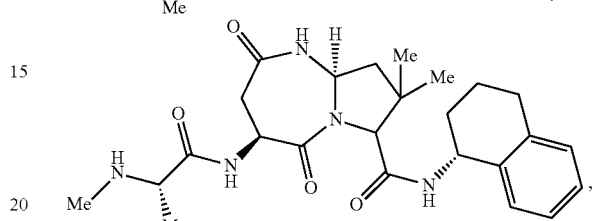

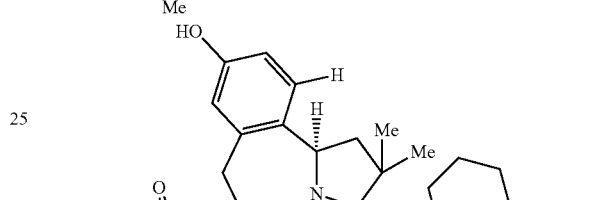

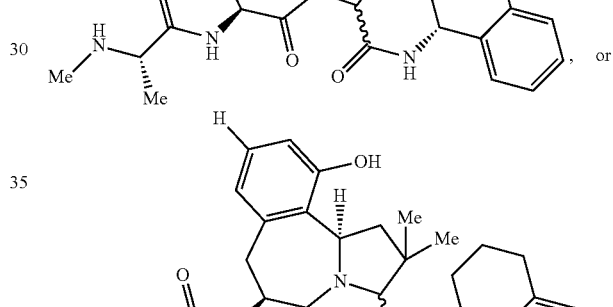

or pharmaceutically acceptable salt, N-oxide, racemate or stereoisomer thereof.

In some embodiments, the IAP antagonist is a small molecule comprising a eight-five fused bicyclic ring system.

In some embodiments, the IAP antagonist is a small molecule that has the following structure of Formula C-I, or a pharmaceutically acceptable salt, N-oxide, racemate or stereoisomer thereof:

Formula C-I

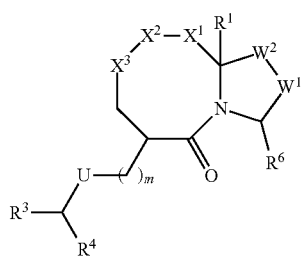

wherein, $R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl);

when $X^1$ is selected from N—$R^A$, S, S(O) and S(O)$_2$, then $X^2$ is $CR^{2c}R^{2d}$, and $X^3$ is $CR^{2a}R^{2b}$;

or:

when $X^1$ is O, then $X^2$ is selected from $CR^{2c}R^{2d}$ and N—$R^A$, and $X^3$ is $CR^{2a}R^{2b}$;

or:

when $X^1$ is $CH_2$, then $X^2$ is selected from O, N—$R^A$, S, S(O), and S(O)$_2$, and $X^3$ is $CR^{2a}R^{2b}$;

or:

$X^1$ is $CR^2R^{2f}$ and $X^2$ is $CR^2CR^{2d}$, and $R^{2e}$ and $R^{2c}$ together form a bond, and $X^3$ is $CR^{2a}R^{2b}$;

or:

$X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:

$X^2$ and $X^3$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ is $CR^{2e}R^{2f}$;

$R^A$ is H, $C_1$-$C_6$alkyl, —C(=O)$C_1$-$C_6$alkyl, substituted or unsubstituted aryl, or substituted or unsubstituted heteroaryl;

$W^1$ is O, S, N—$R^A$, or $C(R^{8a})(R^{8b})$;

$W^2$ is O, S, N—$R^A$, or $C(R^{8c})(R^{8d})$; provided that $W^1$ and $W^2$ are not both O, or both S;

$R^{2a}$, $R^{2b}$, $R^{2c}$, $R^{2d}$ $R^{2e}$, and $R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$ NH—;

$R^3$ is $C_1$-$C_3$alkyl, or $C_1$-$C_3$fluoroalkyl;

$R^4$ is —$NHR^5$, —$N(R^5)_2$, —$N(R^5)_3$ or —$OR^5$;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ together with the atoms to which they are attached form a substituted or unsubstituted 5-7 membered ring;

or:

$R^3$ is bonded to a nitrogen atom of U to form a substituted or unsubstituted 5-7 membered ring;

$R^6$ is —NHC(=O)$R^7$, —C(=O)NHR$^7$, —NHS(=O)$_2$ $R^7$, —S(=O)$_2$NHR$^7$, —NHC(=O)NHR$^7$, —NHS(=O)$_2$NHR$^7$, —($C_1$-$C_3$alkyl)-NHC(=O)$R^7$, —($C_1$-$C_3$alkyl)-C(=O)NHR$^5$, —($C_1$-$C_3$alkyl)-NHS(=O)$_2$ $R^7$, —($C_1$-$C_3$alkyl)-S(=O)$_2$NHR$^7$; —($C_1$-$C_3$alkyl)-NHC(=O)NHR$^7$, —($C_1$-$C_3$alkyl)-NHS(=O)$_2$NHR$^7$, substituted or unsubstituted $C_2$-$C_{10}$heterocycloalkyl, or substituted or unsubstituted heteroaryl;

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$, $R^{8b}$, $R^{8c}$, and $R^{8d}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —N($C_1$-$C_4$alkyl)$_2$, —C(=O)OH, —C(=O)$NH_2$, —C(=O)$C_1$-$C_3$alkyl, —S(=O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In some embodiments, the IAP antagonist is a small molecule that has the following structure of Formula C-III-1, or pharmaceutically acceptable salt, N-oxide, racemate or stereoisomer thereof:

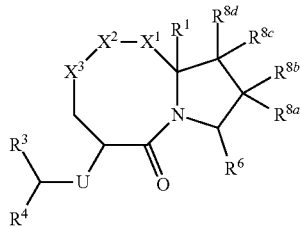

Formula C-III-1

In some embodiments, the IAP antagonist is a small molecule that has the following structure of Formula C-V-2, Formula C-VI-2, Formula C-VII-2, or Formula C-VIII-2, or a pharmaceutically acceptable salt, N-oxide, racemate or stereoisomer thereof:

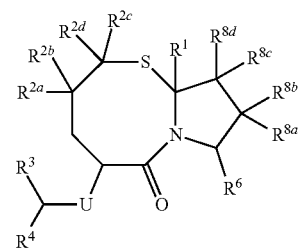

Formula C-V-2

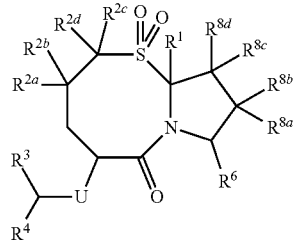

Formula C-VI-2

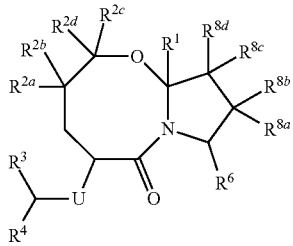

Formula C-VII-2

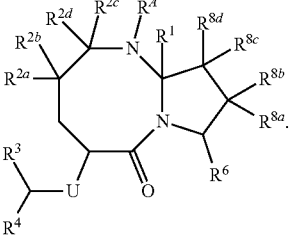

Formula C-VIII-2

In some embodiments, the IAP antagonist is a small molecule that has the following structure of Formula C-XII, or a pharmaceutically acceptable salt, N-oxide, racemate or stereoisomer thereof:

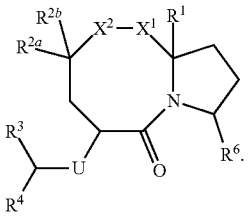

Formula C-XII

In some embodiments, the compound of Formula C-I has the structure of C-XXI, or a pharmaceutically acceptable salt, N-oxide, racemate or stereoisomer thereof:

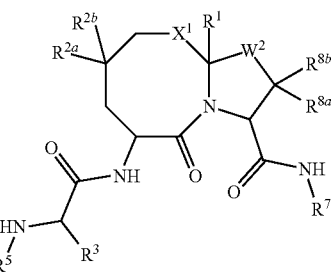

Formula C-XXI wherein,

W² is O, S, or C(R^{8c})(R^{8d});

R¹ is H, or C₁-C₆alkyl;

X¹ is O, N—R^A, S, S(O), or S(O)₂;

R^A is H, C₁-C₆alkyl, —C(=O)C₁-C₆alkyl, substituted or unsubstituted aryl, or substituted or unsubstituted heteroaryl;

R^{2a} and R^{2b} are independently selected from H, substituted or unsubstituted C₁-C₆alkyl, and —C(=O)R^B;

R^B is substituted or unsubstituted C₁-C₆alkyl, —C₁-C₆alkyl-(substituted or unsubstituted C₃-C₆cycloalkyl), —C₁-C₆alkyl-(substituted or unsubstituted C₂-C₅heterocycloalkyl), —C₁-C₆alkyl-(substituted or unsubstituted aryl), —C₁-C₆alkyl-(substituted or unsubstituted heteroaryl), or —NR^DR^E;

R^D and R^E are independently selected from H, substituted or unsubstituted C₁-C₆alkyl, substituted or unsubstituted C₃-C₆cycloalkyl, substituted or unsubstituted C₂-C₅heterocycloalkyl, substituted or unsubstituted aryl, substituted or unsubstituted heteroaryl, —C₁-C₆alkyl-(substituted or unsubstituted C₃-C₆cycloalkyl), —C₁-C₆alkyl-(substituted or unsubstituted C₂-C₅heterocycloalkyl), —C₁-C₆alkyl-(substituted or unsubstituted aryl), or —C₁-C₆alkyl-(substituted or unsubstituted heteroaryl);

R³ is C₁-C₃alkyl, or C₁-C₃fluoroalkyl;

each R⁵ is independently selected from H, C₁-C₃alkyl, C₁-C₃haloalkyl, C₁-C₃heteroalkyl and —C₁-C₃alkyl-(C₃-C₅cycloalkyl);

each R⁷ is independently selected from C₁-C₆alkyl, C₁-C₆haloalkyl, C₁-C₆heteroalkyl, a substituted or unsubstituted C₃-C₁₀cycloalkyl, a substituted or unsubstituted C₂-C₁₀heterocycloalkyl, a substituted or unsubstituted aryl, a substituted or unsubstituted heteroaryl, —C₁-C₆alkyl-(substituted or unsubstituted C₃-C₁₀cycloalkyl), —C₁-C₆alkyl-(substituted or unsubstituted C₂-C₁₀heterocycloalkyl), —C₁-C₆alkyl-(substituted or unsubstituted aryl), —C₁-C₆alkyl-(substituted or unsubstituted heteroaryl), —(CH₂)_p—CH(substituted or unsubstituted aryl)₂, —(CH₂)_p—CH(substituted or unsubstituted heteroaryl)₂, —(CH₂)_p—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

R^{8a} and R^{8b} are independently selected from H, C₁-C₆alkyl, and C₁-C₆fluoroalkyl;

R^{8c} and R^{8d} are independently selected from H, C₁-C₆alkyl, and C₁-C₆fluoroalkyl;

where each substituted alkyl, heteroalkyl, cycloalkyl, heterocycloalkyl, aryl or heteroaryl is substituted with 1-3 R⁹; and each R⁹ is independently selected from halogen, —OH, —SH, (C=O), CN, C₁-C₄alkyl, C₁-C₄ fluoroalkyl, C₁-C₄ alkoxy, C₁-C₄ fluoroalkoxy, —NH₂, —NH(C₁-C₄alkyl), —N(C₁-C₄alkyl)₂, —C(=O)OH, —C(=O)NH₂, —C(=O)C₁-C₃alkyl, —S(=O)₂CH₃, —NH(C₁-C₄alkyl)-OH, —NH(C₁-C₄alkyl)-O—(C₁-C₄alkyl), —O(C₁-C₄alkyl)-NH₂, —O(C₁-C₄alkyl)-NH—(C₁-C₄alkyl), and —O(C₁-C₄alkyl)-N—(C₁-C₄alkyl)₂, or two R⁹ together with the atoms to which they are attached form a methylene dioxy or ethylene dioxy ring substituted or unsubstituted with halogen, —OH, or C₁-C₃alkyl.

In some embodiments, the IAP antagonist is a small molecule that has one of the following structures:

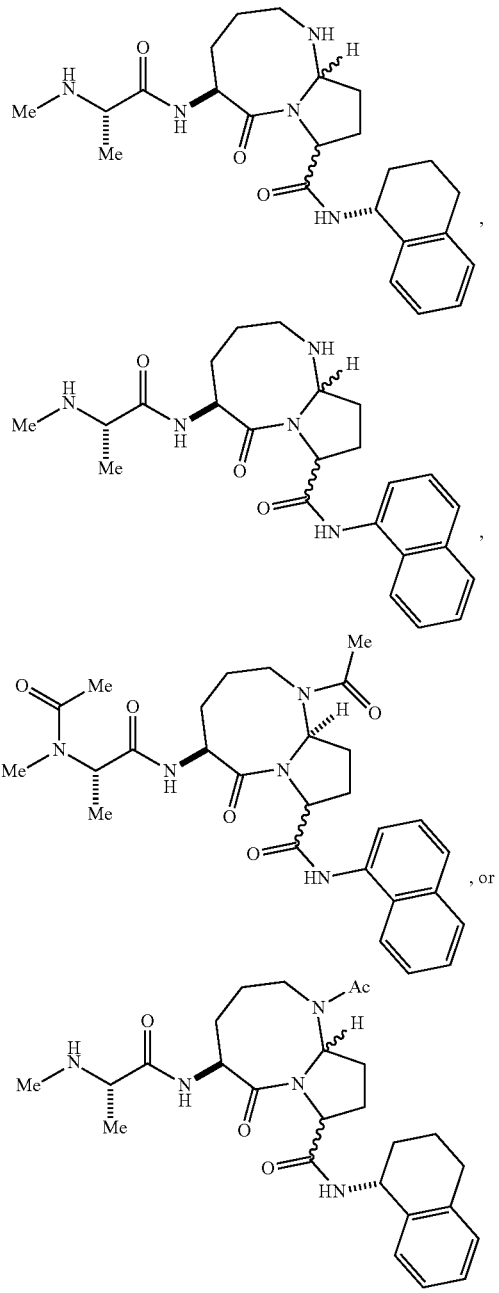

or pharmaceutically acceptable salt, N-oxide, racemate or stereoisomer thereof.

In some embodiments, wherein the IAP antagonist is a small molecule that has the following comprises a seven-six fused bicyclic ring system.

In some embodiments, the IAP antagonist is a small molecule that has the following structure of Formula D-I, or a pharmaceutically acceptable salt, N-oxide, racemate or stereoisomer thereof:

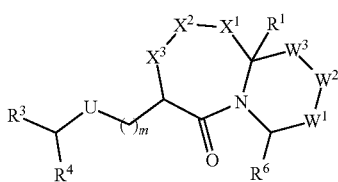

Formula D-I wherein,
R¹ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl);
when $X^1$ is selected from N—$R^A$, S, S(O) and S(O)$_2$, then $X^2$ is $CR^{2c}R^{2d}$, and $X^3$ is $CR^{2a}R^{2b}$;
or
when $X^1$ is O, then $X^2$ is selected from $CR^{2c}R^{2d}$ and N—$R^A$, and $X^3$ is $CR^{2a}R^{2b}$;
or:
when $X^1$ is $CH_2$, then $X^2$ is selected from O, N—$R^A$, S, S(O), and S(O)$_2$, and $X^3$ is $CR^{2a}R^{2b}$;
or:
$X^1$ is $CR^{2e}R^{2f}$ and $X^2$ is $CR^{2c}R^{2d}$, and $R^{2e}$ and $R^{2c}$ together form a bond, and $X^3$ is $CR^{2a}R^{2b}$;
or:
$X^1$ and $X^3$ are both $CH_2$ and $X^2$ is C=O, C=C($R^C$)$_2$, or C=N$R^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
or:
$X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;
or:
$X^2$ and $X^3$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ is $CR^{2e}R^{2f}$;
$W^1$ is O, S, N—$R^A$, or C($R^{8a}$)($R^{8b}$);
$W^2$ is O, S, N—$R^A$, or C($R^{8c}$)($R^{8d}$);
$W^3$ is O, S, N—$R^A$, or C($R^{8e}$)($R^{8f}$); provided that the ring comprising $W^1$, $W^2$ and $W^3$ does not comprise two adjacent oxygen atoms or sulfur atoms;
$R^A$ is H, $C_1$-$C_6$alkyl, —C(=O)$C_1$-$C_6$alkyl, substituted or unsubstituted aryl, or substituted or unsubstituted heteroaryl;

R¹ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl);
$R^{2a}$, $R^{2b}$, $R^{2c}$, $R^{2d}$ $R^{2e}$, and $R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;
$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —N$R^D R^E$;
$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
m is 0, 1 or 2;
—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;
$R^3$ is $C_1$-$C_3$alkyl, or $C_1$-$C_3$fluoroalkyl;
$R^4$ is —NH$R^5$, —N($R^5$)$_2$, —N⁺($R^5$)$_3$ or —O$R^5$;
each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
or:
$R^3$ and $R^5$ together with the atoms to which they are attached form a substituted or unsubstituted 5-7 membered ring;
or:
$R^3$ is bonded to a nitrogen atom of U to form a substituted or unsubstituted 5-7 membered ring;
$R^6$ is —NHC(=O)$R^7$, —C(=O)NH$R^7$, —NHS(=O)$_2$$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^5$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;
each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$, $R^{8b}$, $R^{8c}$, $R^{8d}$, $R^{8e}$ and $R^{8f}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl; or:

$R^{8a}$, $R^{8d}$, $R^{8e}$ and $R^{8f}$ are as defined above, and $R^{8b}$ and $R^{8c}$ together form a bond;

or:

$R^{8a}$, $R^{8b}$, $R^{8d}$, and $R^{8f}$ are as defined above, and $R^{8c}$ and $R^{8e}$ together form a bond;

or:

$R^{8a}$, $R^{8d}$, $R^{8e}$ and $R^{8f}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8a}$, $R^{8b}$, $R^{8d}$, and $R^{8f}$ are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$, $R^{8d}$, $R^{8e}$ and $R^{8f}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8e}$ and $R^{8f}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8c}$, and $R^{8d}$ are as defined above, and $R^{8e}$ and $R^{8f}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —N($C_1$-$C_4$alkyl)$_2$, —C(=O)OH, —C(=O)$NH_2$, —C(=O)$C_1$-$C_3$alkyl, —S(=O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In some embodiments, the IAP antagonist is a small molecule that has the following structure of Formula D-III, or pharmaceutically acceptable salt, N-oxide, racemate or stereoisomer thereof:

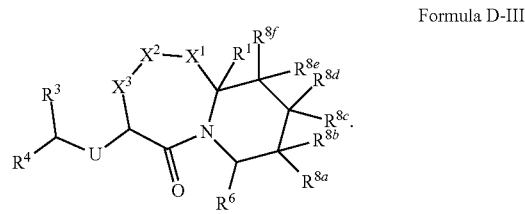

Formula D-III

In some embodiments, the IAP antagonist is a small molecule that has the following structure of Formula D-V-2, Formula D-VI-2, or Formula D-VII-2, or a pharmaceutically acceptable salt, N-oxide, racemate or stereoisomer thereof:

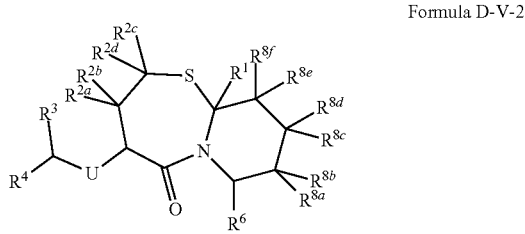

Formula D-V-2

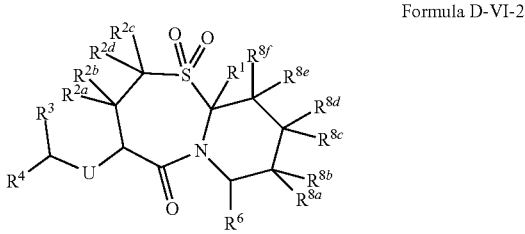

Formula D-VI-2

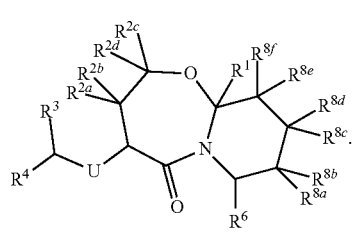

Formula D-VII-2

In some embodiments, the IAP antagonist is a small molecule that has the following structure of Formula D-XIII, or a pharmaceutically acceptable salt, N-oxide, racemate or stereoisomer thereof:

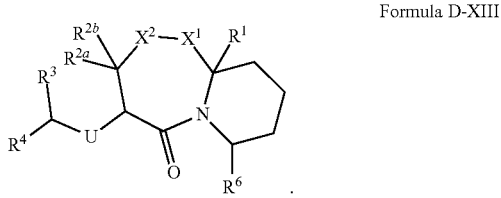

Formula D-XIII

In some embodiments, the compound of Formula D-I, or pharmaceutically acceptable salt, N-oxide, racemate or stereoisomer thereof, has the structure of Formula D-XXII, or pharmaceutically acceptable salt, N-oxide, racemate or stereoisomer thereof:

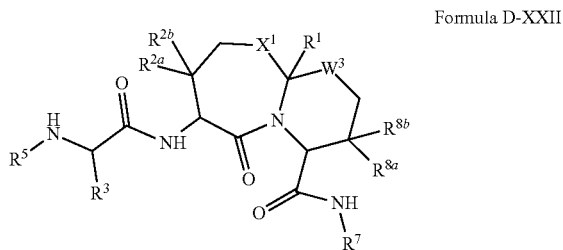

Formula D-XXII wherein,
$W^3$ is O, S, or $C(R^{8e})(R^{8f})$;
$R^1$ is H, or $C_1$-$C_6$alkyl;
$X^1$ is O, N—$R^A$, S, S(O), or $S(O)_2$;
$R^A$ is H, $C_1$-$C_6$alkyl, —C(=O)$C_1$-$C_6$alkyl, substituted or unsubstituted aryl, or substituted or unsubstituted heteroaryl;
$R^{2a}$ and $R^{2b}$ are independently selected from H, substituted or unsubstituted $C_1$-$C_6$alkyl, and —C(=O)$R^B$;
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^D R^E$;
$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
$R^3$ is $C_1$-$C_3$alkyl, or $C_1$-$C_3$fluoroalkyl;
each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH (substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);
p is 0, 1 or 2;
$R^{8a}$ and $R^{8b}$ are independently selected from H, $C_1$-$C_6$alkyl and $C_1$-$C_6$fluoroalkyl;
$R^{8e}$ and $R^{8f}$ are independently selected from H, $C_1$-$C_6$alkyl and $C_1$-$C_6$fluoroalkyl;
where each substituted alkyl, heteroalkyl, cycloalkyl, heterocycloalkyl, aryl or heteroaryl is substituted with 1-3 $R^9$; and
each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —N($C_1$-$C_4$alkyl)$_2$, —C(=O)OH, —C(=O)$NH_2$, —C(=O)$C_1$-$C_3$alkyl, —$S(=O)_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In some embodiments, the IAP antagonist is a small molecule that has the following structure:

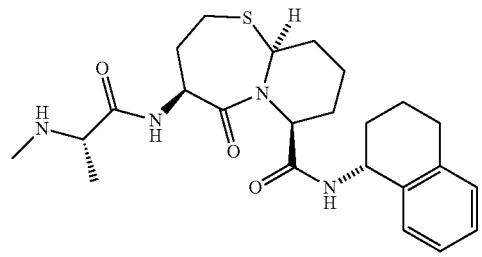

or pharmaceutically acceptable salt, N-oxide, racemate or stereoisomer thereof.

In some embodiments, the IAP antagonist is a small molecule that comprises a eight-six fused bicyclic ring system.

In some embodiments, the method further comprises administering at least one additional therapeutic agent. In other embodiments, the additional therapeutic agent activates HIV transcription in latently infected cells. In some embodiments, the additional therapeutic agent activates HIV transcription in latently infected cells by inhibiting histone deacetylase. In other embodiments, the additional therapeutic agent is a HDAC inhibitor. In some embodiments, the HDAC inhibitor is a hydroxamic acid, a short chart aliphatic acid, a benzamide, a cyclic tetrapeptide, or a cyclic depsidpeptide. In some embodiments, the HDAC inhibitor is vorinostat, valproic acid, belinostat, panobinostat, givinostat, entinostat or romidepsin. In some embodiments, the HDAC inhibitor is vorinostat, valproic acid, belinostat, panobinostat, givinostat, or entinostat. In other embodiments, the HDAC inhibitor is vorinostat. In some embodiments, the HDAC inhibitor is romidepsin.

In some embodiments, the additional therapeutic agent inhibits active HIV replication. In other embodiments, the additional therapeutic agent inhibits any stage of the HIV life cycle. In some embodiments, the additional therapeutic agent inhibits HIV reverse transcriptase, HIV protease, HIV receptor proteins, or HIV integrase. In other embodiments, the additional therapeutic agent inhibits the binding and fusion of HIV into cells, HIV reverse transcription, HIV integration, or assembly of HIV virus. In some embodiments, the additional therapeutic agent is an antiretroviral drug. In other embodiments, the additional therapeutic agent is a nucleoside/nucleotide reverse transcriptase inhibitor (NRTI), non-nucleoside reverse transcriptase inhibitor (NNRTI), protease inhibitor (PI), entry/fusion inhibitor, integrase inhibitor, or any combination thereof. In some embodiments, the nucleoside/nucleotide reverse transcriptase inhibitor is zidovudine, abacavir, lamivudine, emtricitabine, tenofovir, zalcitabine, didanosine, stavudine, entecavir, or adefovir, or any combination thereof. In other embodiments, the non-nucleoside reverse transcriptase inhibitor is nevirapine, efavirenz, etravirine, rilpivirine, or delavirdine, or any combination thereof. In some embodiments, the protease inhibitor is lopinavir, indinavir, nelfinavir, amprenavir, ritonavir, darunavir, atazanavir, fosamprenavir, saquinavir, or tipranavir, or any combination thereof. In other embodiments, the entry/fusion inhibitor is maraviroc or enfuvirtide. In some embodiments, integrase inhibitor is raltegravir, elvitegravir, or dolutegravir. In some embodiments, the additional therapeutic agent is a combination of (lamivudine and zidovudine), (abacavir and lamivudine and zidovudine), (lopinavir andritonavir), (abacavir and lamivudine), (tenofovir and emtricitabine), (emtricitabineand tenofovirand efavirenz), (emtricitabine andrilpivirine and tenofovir), or (elvitegravir and cobicistat and emtricitabine and tenofovir).

In one aspect, provided herein is a pharmaceutical composition comprising an inhibitor of apoptosis protein (IAP) antagonist, at least one additional therapeutic agent used to treat human immunodeficiency virus (HIV), and at least one excipient or carrier.

In some embodiments, the IAP antagonist is a small molecule. In other embodiments, the IAP antagonist is a small molecule comprising a bicyclic, non-aromatic lactam. In some embodiments, the IAP antagonist is a small molecule comprising a fused bicyclic, non-aromatic lactam containing a six-five, seven-five, eight-five, seven-six, or eight-six ring system. In other embodiments, the IAP antagonist is a compound of Formula A, Formula B, Formula C, Formula D, Formula, E, Formula F, Formula G, or a pharmaceutically acceptable salt, N-oxide, racemate or stereoisomer thereof.

In some embodiments, the additional therapeutic agent activates HIV transcription in latently infected cells. In other embodiments, the additional therapeutic agent activates HIV transcription in latently infected cells by inhibiting histone deacetylase. In some embodiments, the additional therapeutic agent is a HDAC inhibitor. In other embodiments, the HDAC inhibitor is vorinostat, valproic acid, belinostat, panobinostat, givinostat, or entinostat. In some embodiments, the HDAC inhibitor is vorinostat, valproic acid, belinostat, panobinostat, givinostat, entinostat, or romidepsin. In some embodiments, the HDAC inhibitor is romidepsin.

In some embodiments, the additional therapeutic agent inhibits active HIV replication. In other embodiments, the additional therapeutic agent inhibits any stage of the HIV life cycle. In some embodiments, the additional therapeutic agent is an antiretroviral drug. In other embodiments, the additional therapeutic agent is a nucleoside/nucleotide reverse transcriptase inhibitor (NRTI), non-nucleoside reverse transcriptase inhibitor (NNRTI), protease inhibitor (PI), entry/fusion inhibitor, integrase inhibitor, or combination thereof. In some embodiments, wherein the nucleoside/nucleotide reverse transcriptase inhibitor is zidovudine, abacavir, lamivudine, emtricitabine, tenofovir, zalcitabine, didanosine, stavudine, entecavir, or adefovir. In other embodiments, the non-nucleoside reverse transcriptase inhibitor is nevirapine, efavirenz, etravirine, rilpivirine, or delavirdine. In some embodiments, the protease inhibitor is lopinavir, indinavir, nelfinavir, amprenavir, ritonavir, darunavir, atazanavir, fosamprenavir, saquinavir, or tipranavir. In other embodiments, the entry/fusion inhibitor is maraviroc or enfuvirtide. In some embodiments, the integrase inhibitor is raltegravir, elvitegravir, or dolutegravir. In other embodiments, the additional therapeutic agent is a combination of: (lamivudine and zidovudine), (abacavir, lamivudine and zidovudine), (lopinavir and ritonavir), (abacavirand lamivudine), (tenofovir and emtricitabine), (emtricitabine, tenofovir and efavirenz), (emtricitabine, rilpivirine and tenofovir), or (elvitegravir, cobicistat, emtricitabine and tenofovir).

DETAILED DESCRIPTION OF THE INVENTION

Figure 1A:
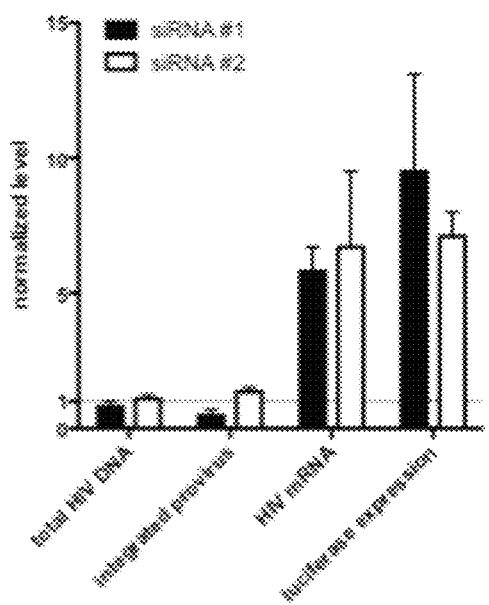
FIG. 1A shows the levels of total HIV DNA, integrated provirus, HIV mRNA and luciferase reporter expression of HEK 293T cells transfected with siRNAs targeting BIRC2 and infected with a VSVg-pseudotyped HIV-1 pNL4.3 lucieraerse reporter virus.

Recent advances in combinatorial antiretroviral therapy (ART) have allowed individuals infected with human immunodeficiency virus (HIV) to live long and otherwise normal lives. However, antiretroviral therapy only targets actively replicating HIV and not the dormant, replication competent HIV that resides in certain types of cells. These dormant HIV viruses can reactivate and trigger new rounds of viral replication upon discontinuation of antiretroviral therapy. Thus, HIV-infected individuals must remain on ART indefinitely. Furthermore, as ART requires costly ongoing medical care, universal access to such important drugs is limited, which poses a significant problem as 35.3 million people worldwide are currently living with HIV with 95% of new infections occurring in individuals living in low and middle-income countries. There exists a need for developing more effective HIV treatment strategies.

In addition to targeting actively replicating HIV, a strategy for improving HIV treatment is to also target the dormant, replication competent HIV virus residing in latently infected cells, which are cells that are infected with HIV but are not actively producing HIV. These latently infected cells are not undergoing active virus replication and the viral genome has been integrated into the host DNA in such a manner that the virus DNA is indistinguishable from the host's DNA. Latently infected cells are not recognized by the immune system and are not susceptible to ART. Thus, the dormant virus and latently infected cells can remain hidden and persist indefinitely. One approach for targeting latently infected cells is to develop new therapeutic agents or drugs that can reverse latency in infected cells by inducing active HIV replication. Once the dormant HIV virus is "awakened", the reactivated virus becomes susceptible to immune system clearance and the effects of antiretroviral therapy. Concurrent treatment with antiretroviral drugs will prevent the spread of the reactivated virus and suppress new rounds of HIV infection. The combination of therapeutic agents that can reverse the latency of HIV-infected cells and ART drugs to eradicate the awakened HIV virus is termed the "shock and kill" or "kick and kill" approach.

Inhibitor of apoptosis proteins (IAP) antagonists modulate the activity of certain proteins involved in apoptotic pathways and signal transduction pathways. Recently, IAP inhibition has been implicated in the activation of HIV transcription. Described herein are the uses of inhibitor of apoptosis proteins (IAP) antagonists for the treatment of HIV. Described herein are the uses of IAP antagonists for the treatment of HIV as part of the "shock and kill" approach. Described herein are the uses of IAP antagonists to activate HIV transcription of latently infected cells. The IAP antagonists may be used alone or in combination with other therapeutic agents, such as those that are used to treat HIV. In some embodiments, other therapeutic agents that could be used in combination with IAP antagonists include therapeutic agents that activate HIV transcription in latently infected cells, therapeutic agents that inhibit active HIV replication, or any combination thereof. In some embodiments, the additional therapeutic agents that inhibit active HIV replication include antiretroviral therapy drugs. In some embodiments, the pharmaceutical compositions are described comprising IAP antagonists, alone or in combination with one or more additional therapeutics agents that are useful for the treatment of HIV in a mammal. In some embodiments, the mammal is a human.

HIV Latency and HIV Reservoirs

In general, viral latency refers to a state of non-productive infection of individual cells, wherein the pathogenic virus lies dormant in infected cells. Viral latency is reversible and the dormant pathogenic virus can reactivate and begin producing large amounts of viral progeny without the infected cells being infected by a new outside host. For some viruses, latency is important for viral persistence and escape from immune recognition.

For the human immunodeficiency virus (HIV), HIV latency arises when a small number of actively infected CD4+ T cells, which are the major target cells for HIV, revert to a resting memory state, wherein active viral gene expression has been arrested. These resting CD4+ T cells are referred to as latently infected cells. Active HIV transcription is suppressed in these resting CD4$^+$ T cell, and the viral DNA has been integrated into the host genome such that the integrated viral DNA is indistinguishable from the host's genomic material. Latently infected cells are not susceptible to immune system clearance or the effects of drugs typically used in the treatment of HIV infection, such as antiretroviral drugs used in antiretroviral therapy. While the exact molecular mechanisms for achieving, maintaining and reversing HIV latency remain unclear, HIV latency is associated with transcriptional silencing. Thus, HIV latency in infected cells is reversed by activating HIV transcription, which leads to the release of new copies of the HIV virus and new rounds of HIV infection.

Because latently infected cells can reactivate and lead to new rounds of HIV infection, there has been interest in developing methods that are directed at targeting cells latently infected with HIV and eliminating the collection of these latently infected HIV cells, known as HIV reservoirs. HIV reservoirs are considered a major barrier in curing HIV infection. These latently infected cells persist indefinitely even in patients where antiretroviral therapy has reduced the viral load, or amount of HIV in the blood, to near undetectable levels. CD4$^+$ T cells are the primary target of HIV, and methods have been focused on targeting the latently infected CD4$^+$ T cells, which are often resting memory CD4$^+$ T cells. One approach is the "shock and kill" or "kick and kill" method, wherein a drug or therapeutic agent is used to specifically activate HIV transcription in latently infected cells to force the dormant, replication competent HIV out of hiding and thereby reducing the HIV reservoirs (the "shock or kick"). Once reactivated, the actively replicating virus will be vulnerable to immune system clearance or therapeutic agents used in the treatment of HIV, such as the drugs used in antiretroviral therapy ("the kill"). The "shock and kill" or "kick and kill" approach proposes that all replication competent forms of the virus will be cleared, which is an important step towards the complete eradication of HIV infection. Furthermore, the "shock and kill" approach also proposes a functional cure, wherein a state of stringent control over HIV replication and growth can be achieved without continual antiretroviral therapy.

Described herein are the uses of IAP antagonists as activators of viral latency. Described herein are the uses of IAP antagonists as activators of viral latency by activating transcription in latently infected cells. Described herein are the uses of IAP antagonists to reverse viral latency. Described herein are the uses of IAP antagonists to reverse viral latency by activating transcription in latently infected cells.

Described herein are the uses of inhibitor of apoptosis proteins (IAP) antagonists for the treatment of HIV. Described herein are the uses of IAP antagonists for reducing HIV reservoirs of latently infected cells. Described herein are the uses of inhibitor of apoptosis proteins (IAP) antagonists for reducing dormant, replication competent HIV. Described herein are the uses of inhibitor of apoptosis proteins (IAP) antagonists for making dormant, replication competent HIV susceptible to immune system clearance or to the effect of antiretroviral therapy. The inhibitor of apoptosis proteins (IAP) antagonists may be used alone or in combination with additional therapeutic agents, such as those that are used to treat HIV. These additional therapeutic agents include therapeutic agents that activate HIV transcription of latently infected cells, therapeutic agents that inhibit active HIV replication, or any combination thereof. Furthermore, described herein are uses of inhibitor of apoptosis proteins (IAP) antagonists for eliminating dormant, replication competent HIV. Furthermore, described herein are uses of inhibitor of apoptosis proteins (IAP) antagonists for inducing long term control of HIV replication and growth in the absence of antiretroviral therapy. In some embodiments, the IAP antagonists are used on individuals on concomitant antiretroviral therapy. In other embodiments, the IAP antagonists are used in combination with antiretroviral therapy. In some embodiments, the latently infected cells are CD4+ T cells.

Inhibitor of Apoptosis Proteins (IAP) Antagonists

Inhibitor of Apoptosis Proteins (IAP) antagonists are compounds that can modulate the activity of certain proteins involved in apoptotic pathways, or signaling pathways associated with inflammation and/or autoimmune diseases and/or cell division and/or angiogenesis. The members of the IAP family are functionally and structurally related proteins, which inhibit apoptosis. IAPs share a Baculovirus IAP Repeat (BIR) domain, each having one to three copies. Eight members of the IAP family have currently been identified, in both baculovirus and humans. Human members of the IAP family include but are not limited to: XIAP, cIAP1 (also, BIRC2), cIAP2 (also, BIRC3), NAIP, survivin, ML-IAP, apollon, and ILP2. In certain instances, XIAP inhibits apoptosis by binding to and inhibiting the activity of caspase-9, caspase-3 or caspase-7.

One protein implicated in binding with IAPs is SMAC. SMAC is a mitochondrial protein that negatively regulates apoptosis or programmed cell death. When a cell is primed for apoptosis by the final execution step of caspase activation, SMAC binds to IAP, which prevents IAP from binding to, and deactivating caspases. SMAC promotes apoptosis by activating caspases. SMAC mimetics inhibit IAP proteins.

Cellular IAP proteins (cIAP1 and 2) have been implicated in the regulation of both the classical and alternative NF-κB signal transduction pathway. NF-κB proteins are dimeric transcription factors that control genes regulating a broad range of biological processes, including innate and adaptive immunity, survival and proliferation. Stimulation of a tumor necrosis factor (TNF) superfamily receptor initiates a signaling cascade that results in NF-κB activation. Upon activation, these NF-κB heterodimers translocate from the cytoplasm into the nucleus and induce transcription by binding to response elements and recruiting coactivators.

In the classical, or canonical, NF-κB pathway, NF-κB is maintained in a non-active state and is sequestered in the cytoplasm via non-covalent interactions with IκB proteins. Stimulation of a TNF superfamily receptor induces the recruitment of cIAP1 and cIAP2 and ultimately results in the activation of the IKK complex. The IKK complex mediates the phosphorylation of IκB proteins, which leads to the degradation of the IκB associated with NF-κB, allowing for NF-κB to translocate into the nucleus and induce transcription. Thus, IAPs are positive regulators of the classical NF-κB pathway.

In the alternative, or non-canonical, NF-κB pathway, NF-κB is maintained in an inactive state in the cytoplasm. Stimulation of a TNF superfamily receptor leads to the accumulation of the NF-κB-inducing kinase (NIK), which in turn results in the activation of IKKα. IKKα mediates the phosphorylation of the inactive NF-κB subunit, and ultimately leads to the formation of transcriptionally active NF-κB, which then translocates into the nucleus. cIAP1 and cIAP2 promote the degradation of NIK; thus, IAPs are negative regulators of the alternative NF-κB pathway IAPs have been implicated specifically in the regulation of HIV transcription. NF-κB activation has been demonstrated to induce transcription at the HIV long terminal repeat (LTR), which is the control center for gene expression. Loss of function studies have demonstrated that the loss of BIRC2/cIAP1 expression leads to enhanced HIV expression through a NF-κB dependent mechanism. BIRC2/cIAP1 is a known positive regulator of the classical NF-κB pathway and a known negative regulator of the alternative NF-κB pathway. These knockdown studies suggest that the alternative NF-κB pathway may be beneficial to HIV infection. A further report has also implicated that activation of the alternative NF-κB pathway also activates the classical NF-κB pathway. Thus, IAP antagonists promote HIV transcription via the NF-κB pathway. In some embodiments, the IAP antagonists promote HIV transcription via the alternative NF-κB pathway. In other embodiments, the IAP antagonists promote HIV transcription via the classical NF-κB pathway. IAP antagonists are useful in the treatment of HIV, wherein IAP antagonists reverse HIV latency by activating transcription in latently infected HIV cells. The reactivated HIV virus is then susceptible to eradication by therapeutic agents that inhibit active HIV replication, such as antiretroviral drugs.

In some embodiments, compounds described herein that inhibit the action of IAP are useful in activating HIV transcription. Furthermore, the compounds described herein that inhibit the action of IAP are useful in activating transcription of latently infected HIV cells. Furthermore, the compounds described herein that inhibit the action of IAP are useful in reversing HIV latency. Furthermore, the compounds described herein that inhibit the action of IAP are useful in reversing HIV latency by activating HIV transcription in latently infected cells.

In some embodiments, the IAP antagonist contemplated for use in any of the methods and uses described herein is a small molecule IAP antagonist. In some embodiments, the IAP antagonist inhibits the activity of an IAP protein, wherein the IAP protein is XIAP, cIAP1, cIAP2, ML-IAP, survivin, NAIP, apollon, or ILP2. In some embodiments, the IAP antagonist binds the IAP BIR3 domain. In some embodiments, the IAP antagonist binds the IAP BIR2 domain. In some embodiments, the IAP antagonist binds the IAP BIR2 domain and the IAP BIR3 domain. In some embodiments, the IAP antagonist binds the XIAP BIR3 domain. In some embodiments, the IAP antagonist binds the XIAP BIR2 domain. In some embodiments, the IAP antagonist binds the XIAP BIR2 domain and XIAP BIR3 domain. In some embodiments, the IAP antagonist binds the cIAP1 BIR3 domain. In some embodiments, the IAP antagonist binds the cIAP1 BIR2 domain. In some embodiments, the IAP antagonist binds the cIAP1 BIR2 domain and cIAP1 BIR3 domain. In some embodiments, the IAP antagonist binds the cIAP2 BIR3 domain. In some embodiments, the IAP antagonist binds the cIAP2 BIR2 domain. In some embodiments, the IAP antagonist binds the cIAP2 BIR2 domain and cIAP2 BIR3 domain. In some embodiments, the IAP antagonist is a pan-IAP antagonist. In some embodiments, the IAP antagonist is selective for one or more IAP proteins. In some embodiments, the IAP antagonist is selective for the BIR2 domain. In some embodiments, the IAP antagonist is selective for the BIR3 domain.

In other embodiments, the IAP antagonist contemplated for use in any of the methods and uses described herein include a SMAC mimetic. In some embodiments, the IAP antagonist is a compound having a structure that mimics the SMAC amino-terminal AVPI peptide. In some embodiments, the IAP antagonist is a peptidic SMAC mimetic. In some embodiments, the IAP antagonist is a monovalent peptidic SMAC mimetic. In some embodiments, the IAP antagonist is a bivalent peptidic SMAC mimetic. In some embodiments, the IAP antagonist is a small molecule SMAC mimetic. In some embodiments, the IAP antagonist is a polyphenylurea. In some embodiments, the IAP antagonist is delaquinium. In some embodiments, the IAP antagonist is a nonpeptidic SMAC mimetic.

In other embodiments, the IAP antagonist is a bicyclic, non-aromatic lactam. In other embodiments, the IAP antagonist is a fused bicyclic, non-aromatic lactam containing a six-five, seven-five, eight-five, seven-six, or eight-six ring system. In some embodiments, the IAP antagonist activates HIV transcription in latently infected cells by promoting the NF-κB signaling pathway.

Formula A—Six-Five Ring Systems

In one aspect, the IAP antagonist for use in any of the methods, uses, compositions described herein is a Formula A compound. As used herein, Formula A includes compounds of Formula A-I, Formula A-II, Formula A-III-1, Formula A-III-2, Formula A-III-3, Formula A-IV, Formula A-V-1, Formula A-V-2, Formula A-V-3, Formula A-VI-1, Formula A-VI-2, Formula A-VI-3, Formula A-VII-1, Formula A-VII-2, Formula A-VII-3, Formula A-VIII, Formula A-IX-1, Formula A-IX-2, Formula A-X, Formula A-XI, Formula A-XII, Formula A-XIII, Formula A-XIV, Formula A-XV-1, Formula A-XV-2, Formula A-XV-3, Formula A-XV-4, Formula A-XVI-1, Formula A-XVI-2, Formula A-XVII, Formula A-XVIII, Formula A-XIX, Formula A-XX, and Formula A-XXI.

In one aspect, described herein is a compound of Formula A-I, or a pharmaceutically acceptable salt, N-oxide, racemate or stereoisomer thereof, as described in the summary of the invention.

In one aspect, provided herein are compounds having the structure of Formula A-I, pharmaceutically acceptable salt, N-oxide, racemate or stereoisomer thereof:

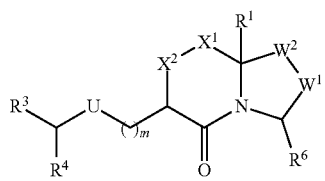

Formula A-I wherein, $W^1$ is O, S, N—$R^A$, or $C(R^{8a})(R^{8b})$;

$W^2$ is O, S, N—$R^A$, or $C(R^{8c})(R^{8d})$; provided that $W^1$ and $W^2$ are not both O, or both S;

$R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl);

when $X^1$ is O, N—$R^A$, S, S(O), or $S(O)_2$, then $X^2$ is $C(R^{2a}R^{2b})$;

or:

$X^1$ is $CR^{2c}R^{2d}$ and $X^2$ is $CR^{2a}R^{2b}$, and $R^{2c}$ and $R^{2a}$ together form a bond;

or:

$X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring;

or:

$X^1$ is $CH_2$ and $X^2$ is C=O, C=$C(R^C)_2$, or C=$NR^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

$R^A$ is H, $C_1$-$C_6$alkyl, —C(=O)$C_1$-$C_6$alkyl, substituted or unsubstituted aryl, or substituted or unsubstituted heteroaryl;

$R^{2a}$, $R^{2b}$, $R^{2c}$, $R^{2d}$, are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$ NH—;

$R^3$ is $C_1$-$C_3$alkyl, or $C_1$-$C_3$fluoroalkyl;

$R^4$ is —$NHR^5$, —$N(R^5)_2$, —$N^+(R^5)_3$ or —$OR^5$;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ together with the atoms to which they are attached form a substituted or unsubstituted 5-7 membered ring;

or:

$R^3$ is bonded to a nitrogen atom of U to form a substituted or unsubstituted 5-7 membered ring;

$R^6$ is —NHC(=O)$R^7$, —C(=O)NH$R^7$, —NHS(=O)$_2$$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^5$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$, $R^{8b}$, $R^{8c}$, and $R^{8d}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —N($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula A-I described above or below, or pharmaceutically acceptable salt, N-oxide, racemate or stereoisomer thereof, one group of compounds has the structure of Formula A-II:

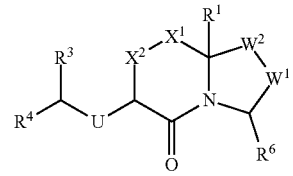

Formula A-II

Among the compounds of Formula A-I described above or below, or pharmaceutically acceptable salt, N-oxide, racemate or stereoisomer thereof, one group of compounds that has the structure of Formula A-III-1, Formula A-III-2 or Formula A-III-3:

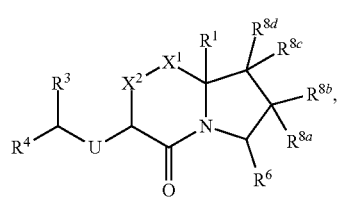

Formula A-III-1

Formula A-III-2

[chemical structure]

Formula A-III-3

[chemical structure]

Among the compounds of Formula A-I described above or below, or pharmaceutically acceptable salt, N-oxide, racemate or stereoisomer thereof, one group of compounds that has the structure of Formula A-III-1:

[chemical structure]

Among the compounds of Formula A-I described above or below, or pharmaceutically acceptable salt, N-oxide, racemate or stereoisomer thereof, one group of compounds has the structure of Formula A-IV:

Formula A-IV

[chemical structure]

Among the compounds of Formula A described above or below, or pharmaceutically acceptable salt, N-oxide, racemate or stereoisomer thereof, is one group of compounds wherein,
—U— is —NHC(=O)—, —C(=O)NH—, —NHS(=O)$_2$—, or —S(=O)$_2$NH—.

Among the compounds of Formula A described above or below, or pharmaceutically acceptable salt, N-oxide, racemate or stereoisomer thereof, is one group of compounds wherein,
—U— is —NHC(=O)—, or —C(=O)NH—.

Among the compounds of Formula A described above or below, or pharmaceutically acceptable salt, N-oxide, racemate or stereoisomer thereof, is one group of compounds wherein,
$R^3$ is $C_1$-$C_3$alkyl.

Among the compounds of Formula A described above or below, or pharmaceutically acceptable salt, N-oxide, racemate or stereoisomer thereof, is one group of compounds wherein, $R^4$ is-$NHR^5$, —$N(R^5)_2$, or —$N^+(R^5)_3$; and each $R^5$ is independently selected from H, $C_1$-$C_3$alkyl, and —$C_1$-$C_3$alkyl-($C_3$-$C_5$cycloalkyl).

Among the compounds of Formula A described above or below, or pharmaceutically acceptable salt, N-oxide, racemate or stereoisomer thereof, is one group of compounds wherein,
—U— is —NHC(=O)—, or —C(=O)NH—;
$R^3$ is $C_1$-$C_3$alkyl;
$R^4$ is-$NHR^5$, —$N(R^5)_2$, or —$N^+(R^5)_3$; and
each $R^5$ is independently selected from H, $C_1$-$C_3$alkyl, and —$C_1$-$C_3$alkyl-($C_3$-$C_5$cycloalkyl).

Among the compounds of Formula A described above or below, or pharmaceutically acceptable salt, N-oxide, racemate or stereoisomer thereof, is one group of compounds wherein,

[chemical structure] is [chemical structure].

Among the compounds of Formula A described above or below, or pharmaceutically acceptable salt, N-oxide, racemate or stereoisomer thereof, is one group of compounds wherein,

[chemical structure] is [chemical structure].

Among the compounds of Formula A described above or below, or pharmaceutically acceptable salt, N-oxide, racemate or stereoisomer thereof, is one group of compounds wherein $R^3$ and $R^5$ together with the atoms to which they are attached form a substituted or unsubstituted 5-7 membered ring. Within this group of compounds are compounds wherein

[chemical structure] is [chemical structure];

and
q is 1, 2 or 3.

Among the compounds of Formula A described above or below, or pharmaceutically acceptable salt, N-oxide, racemate or stereoisomer thereof, is one group of compounds wherein $R^3$ is bonded to a nitrogen atom of U to form a substituted or unsubstituted 5-7 membered ring. Within this group of compounds are compounds wherein

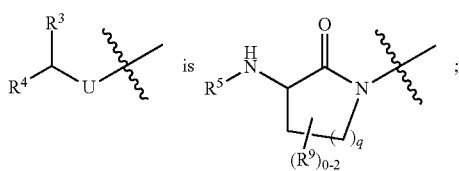

and q is 1, 2 or 3.

Among the compounds of Formula A-I described above or below, or pharmaceutically acceptable salt, N-oxide, racemate or stereoisomer thereof, is one group of compounds having the structure of Formula A-V-1, Formula A-V-2, or Formula A-V-3:

Formula A-V-1

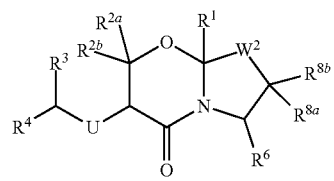

Formula A-V-2

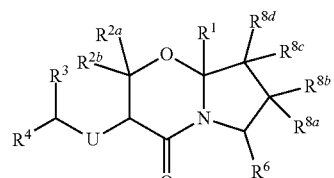

Formula A-V-3

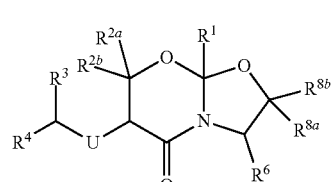

Among the compounds of Formula A-I described above or below, or pharmaceutically acceptable salt, N-oxide, racemate or stereoisomer thereof, is one group of compounds having the structure of Formula A-V-2:

Formula A-V-2

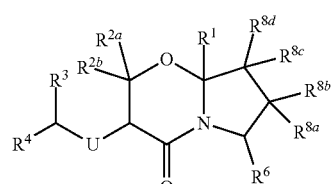

Among the compounds of Formula A-I described above or below, or pharmaceutically acceptable salt, N-oxide, racemate or stereoisomer thereof, is one group of compounds having the structure of Formula A-VI-1, Formula A-VI-2, or Formula A-VI-3:

Formula A-VI-1

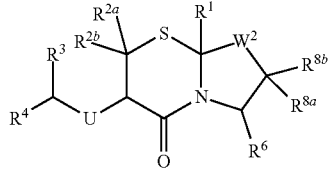

Formula A-VI-2

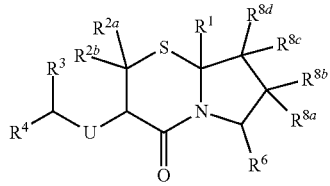

Formula A-VI-3

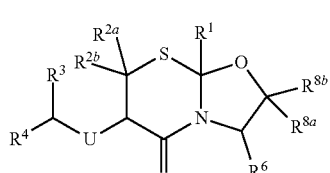

Among the compounds of Formula A-I described above or below, or pharmaceutically acceptable salt, N-oxide, racemate or stereoisomer thereof, is one group of compounds having the structure of Formula A-VII-1, Formula A-VII-2, or Formula A-VII-3:

Formula A-VII-1

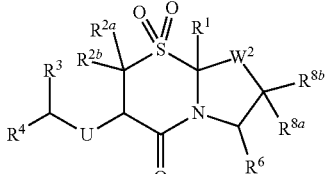

Formula A-VII-2

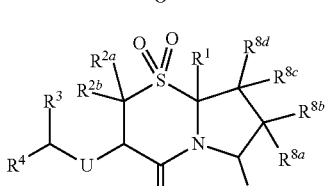

Formula A-VII-3

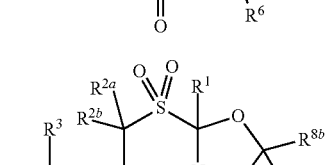

Among the compounds of Formula A-I described above or below, or pharmaceutically acceptable salt, N-oxide, racemate or stereoisomer thereof, is one group of compounds wherein $X^1$ is N—$R^4$.

Among the compounds of Formula A-I described above or below, or pharmaceutically acceptable salt, N-oxide, racemate or stereoisomer thereof, is one group of compounds having the structure of Formula A-VIII:

Formula A-VIII

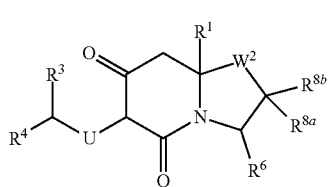

Among the compounds of Formula A-I described above or below, or pharmaceutically acceptable salt, N-oxide, racemate or stereoisomer thereof, is one group of compounds having the structure of Formula A-IX-1 or Formula A-IX-2:

Formula A-IX-1

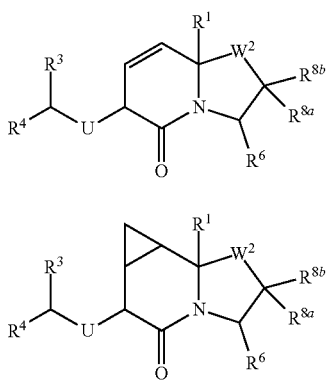

Formula A-IX-2

Among the compounds of Formula A-I described above or below, or pharmaceutically acceptable salt, N-oxide, racemate or stereoisomer thereof, is one group of compounds having the structure of Formula A-X:

Formula A-X

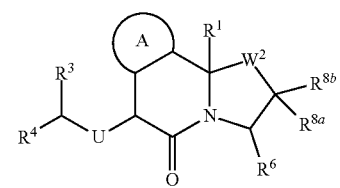

wherein, ring A is a fused substituted or unsubstituted saturated or partially saturated 3-10 membered cycloalkyl ring, substituted or unsubstituted saturated or partially saturated 3-10 membered heterocycloalkyl ring, substituted or unsubstituted 5-10 membered aryl ring, or substituted or unsubstituted 5-10 membered heteroaryl ring.

In some embodiments of Formula A-X, ring A is selected from indolyl, and phenyl.

Among the compounds of Formula A-I described above or below, or pharmaceutically acceptable salt, N-oxide, racemate or stereoisomer thereof, is one group of compounds having the structure of Formula A-XI:

Formula A-XI

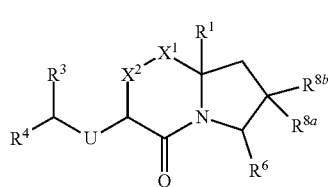

In some embodiments of Formula A-XI, $R^{8a}$ and $R^{8b}$ are independently selected from H and $C_1$-$C_3$alkyl.

Among the compounds of Formula A-I described above or below, or pharmaceutically acceptable salt, N-oxide, racemate or stereoisomer thereof, is one group of compounds having the structure of Formula A-XII:

Formula A-XII

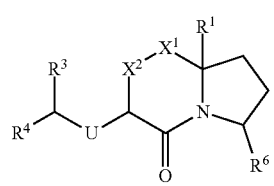

Among the compounds of Formula A-I described above or below, or pharmaceutically acceptable salt, N-oxide, racemate or stereoisomer thereof, is one group of compounds having the structure of Formula A-XIII:

Formula A-XIII

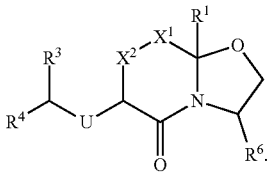

Within the group of compounds of Formula A are compounds wherein $X^1$ is O, S or $S(O)_2$, and $X^2$ is $CH_2$.

Among the compounds of Formula A-I described above or below, or pharmaceutically acceptable salt, N-oxide, racemate or stereoisomer thereof, is one group of compounds wherein $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N.

Within such a group of compounds are compounds of Formula A-I, or pharmaceutically acceptable salt, N-oxide, racemate or stereoisomer thereof, having the structure of Formula A-XIV:

Formula A-XIV

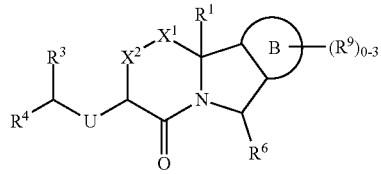

wherein ring B is an aryl or heteroaryl ring.

In some embodiments, ring B is an aryl. In some embodiments, ring B is phenyl. In some embodiments, ring B is a heteroaryl ring. In some embodiments, ring B is a monocyclic heteroaryl ring or a bicyclic heteroaryl ring. In some embodiments, ring B is a monocyclic heteroaryl ring. In some embodiments, ring B is a bicyclic heteroaryl ring. In some embodiments, ring B is selected from phenyl, pyridinyl and thiophenyl. In some embodiments, ring B is selected from pyridinyl and thiophenyl.

Among the compounds of Formula A-I described above or below, or pharmaceutically acceptable salt, N-oxide, racemate or stereoisomer thereof, is one group of compounds wherein $R^{8a}$ and $R^{8b}$ together with the atoms to which they are attached form a substituted or unsubstituted saturated or partially saturated 3-7 membered spirocycle or heterospirocycle comprising 1-3 heteroatoms selected from S, O and N; or $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N. Within such a group of compounds are compounds having the structure of Formula A-XV-1, Formula A-XV-2, Formula A-XV-3 or Formula A-XV-4:

Formula A-XV-1

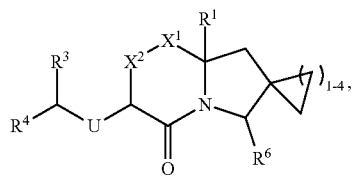

Formula A-XV-2

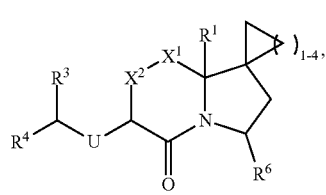

Formula A-XV-3

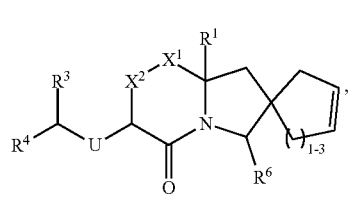

Formula A-XV-4

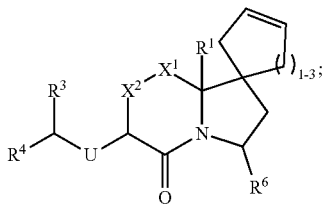

or Formula A-XVI-1 or Formula A-XVI-2:

Formula A-XVI-1

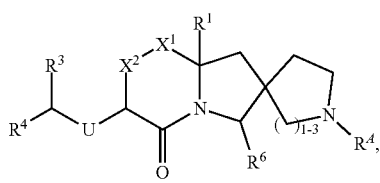

Formula A-XVI-2

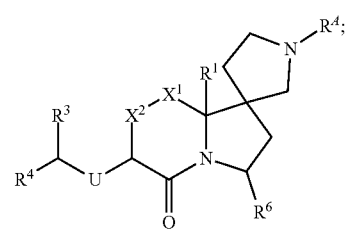

wherein $R^A$ is H, $C_1$-$C_3$alkyl or —C(=O)$C_1$-$C_3$alkyl.

Among the compounds of Formula A-I described above or below, or pharmaceutically acceptable salt, N-oxide, racemate or stereoisomer thereof, is one group of compounds wherein $R^{8b}$ and $R^{8c}$ together form a bond. Within such a group of compounds are compounds having the structure of Formula A-XVII:

Formula A-XVII

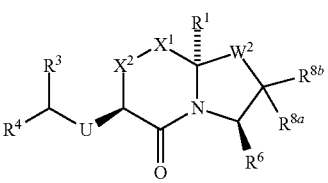

Among the compounds of Formula A-I described above or below, or pharmaceutically acceptable salt, N-oxide, racemate or stereoisomer thereof, is one group of compounds having the structure of Formula A-XVIII:

Formula A-XVIII

Among the compounds of Formula A-I described above or below, or pharmaceutically acceptable salt, N-oxide, racemate or stereoisomer thereof, is one group of compounds having the structure of Formula A-XIX:

Formula A-XIX

Among the compounds of Formula A-I described above or below, or pharmaceutically acceptable salt, N-oxide, racemate or stereoisomer thereof, is one group of compounds having the structure of Formula A-XX:

Formula A-XX

Among the compounds of Formula A are compounds having the structure of Formula A-XXI, pharmaceutically acceptable salt, N-oxide, racemate or stereoisomer thereof:

Formula A-XXI wherein,
$W^2$ is O, S, or $C(R^{8c})(R^{8d})$;
$R^1$ is H, or $C_1$-$C_6$alkyl;
$X^1$ is O, N—$R^A$, S, S(O), or $S(O)_2$;
$R^A$ is H, $C_1$-$C_6$alkyl, —C(=O)$C_1$-$C_6$alkyl, substituted or unsubstituted aryl, or substituted or unsubstituted heteroaryl;
$R^{2a}$, and $R^{2b}$ are independently selected from H, substituted or unsubstituted $C_1$-$C_6$alkyl, and —C(=O)$R^B$;
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;
$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
$R^3$ is $C_1$-$C_3$alkyl, or $C_1$-$C_3$fluoroalkyl;
each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl), a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);
p is 0, 1 or 2;
$R^{8a}$ and $R^{8b}$ are independently selected from H, $C_1$-$C_6$alkyl, and $C_1$-$C_6$fluoroalkyl;
$R^{8c}$ and $R^{8d}$ are independently selected from H, $C_1$-$C_6$alkyl, and $C_1$-$C_6$fluoroalkyl;
where each substituted alkyl, heteroalkyl, cycloalkyl, heterocycloalkyl, aryl or heteroaryl is substituted with 1-3 $R^9$; and
each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —N($C_1$-$C_4$alkyl)$_2$, —C(=O)OH, —C(=O)$NH_2$, —C(=O)$C_1$-$C_3$alkyl, —S(=O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among any of the compounds of Formula A described above and below, are compounds wherein,
$R^{2a}$, $R^{2b}$, $R^{2c}$, $R^{2d}$ are independently selected from H, $C_1$-$C_3$alkyl or —C(=O)$R^B$; and
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl).

Among any of the compounds of Formula A described above and below, are compounds wherein,
$R^{2a}$, $R^{2b}$, $R^{2c}$, $R^{2d}$ are independently selected from H, and $C_1$-$C_3$alkyl.

Among any of the compounds of Formula A described above and below, are compounds wherein $R^1$ is H or methyl.

Among any of the compounds of Formula A described above and below, are compounds wherein $R^1$ is H.

Among any of the compounds of Formula A described above and below, are compounds wherein, $R^6$ is —NHC(=O)$R^7$, —C(=O)NH$R^7$, —NHS(=O)$_2$$R^7$, —S(=O)$_2$NH$R^7$; —NHC(=O)NH$R^7$, —NHS(=O)$_2$NH$R^7$, —(C$_1$-C$_3$alkyl)-NHC(=O)$R^7$, —(C$_1$-C$_3$alkyl)-C(=O)NH$R^5$, —(C$_1$-C$_3$alkyl)-NHS(=O)$_2$$R^7$, —(C$_1$-C$_3$alkyl)-S(=O)$_2$NH$R^7$; —(C$_1$-C$_3$alkyl)-NHC(=O)NH$R^7$, or —(C$_1$-C$_3$alkyl)-NHS(=O)$_2$NH$R^7$.

Among any of the compounds of Formula A described above and below, are compounds wherein,
$R^6$ is substituted or unsubstituted C$_2$-C$_{10}$heterocycloalkyl, or substituted or unsubstituted heteroaryl.

Among any of the compounds of Formula A described above and below, are compounds wherein,
$R^6$ is a substituted or unsubstituted C$_2$-C$_{10}$heterocycloalkyl.

Among any of the compounds of Formula A described above and below, are compounds wherein,
$R^6$ is a substituted or unsubstituted heteroaryl.

Among any of the compounds of Formula A described above and below, are compounds wherein,
$R^6$ is —C(=O)NH$R^7$, —S(=O)$_2$NH$R^7$, —(C$_1$-C$_3$alkyl)-C(=O)NH$R^5$, or —(C$_1$-C$_3$alkyl)-S(=O)$_2$NH$R^7$.

Among any of the compounds of Formula A described above and below, are compounds wherein,
$R^6$ is —C(=O)NH$R^7$, or —S(=O)$_2$NH$R^7$.

Among any of the compounds of Formula A described above and below, are compounds wherein $R^6$ is —C(=O)NH$R^7$.

Among any of the compounds of Formula A described above and below, are compounds wherein,
each $R^7$ is independently selected from a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_6$alkyl-(substituted or unsubstituted C$_3$-C$_{10}$cycloalkyl), —C$_1$-C$_6$alkyl-(substituted or unsubstituted C$_2$-C$_{10}$heterocycloalkyl, —C$_1$-C$_6$alkyl-(substituted or unsubstituted aryl), —C$_1$-C$_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl).

Among any of the compounds of Formula A described above and below, are compounds wherein,
$R^7$ is independently selected from a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted heteroaryl, and —(CH$_2$)$_p$—CH(substituted or unsubstituted aryl)$_2$.

Among any of the compounds of Formula A described above and below, are compounds wherein,
$R^7$ is selected from

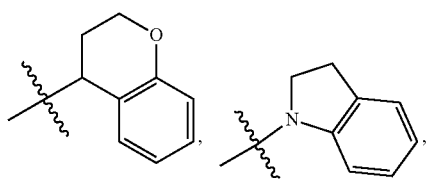

-continued

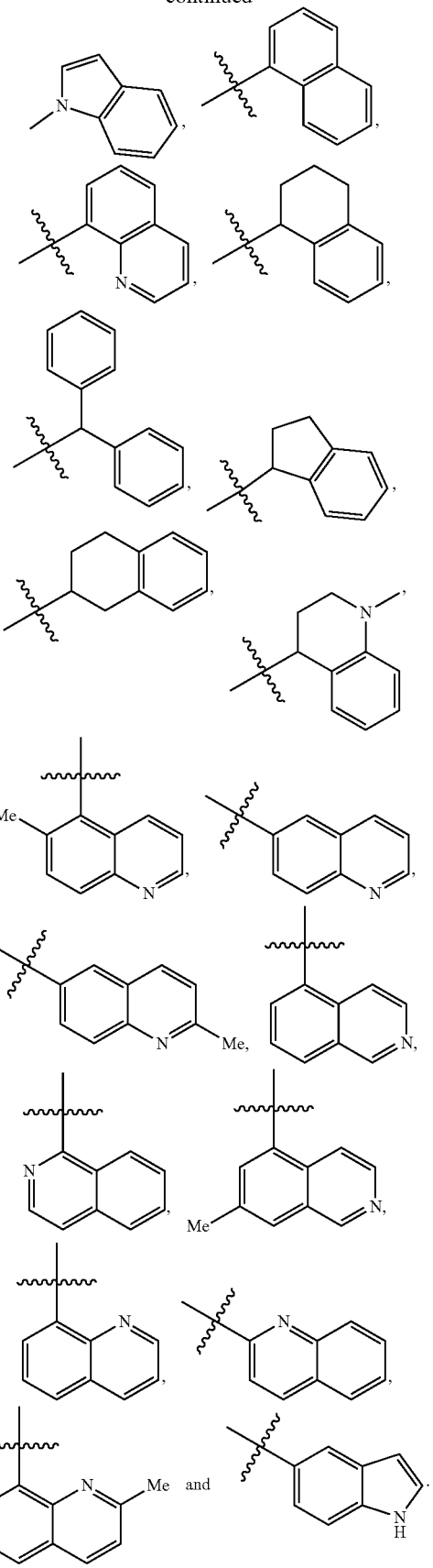

Among any of the compounds of Formula A described above and below, are compounds wherein, $W^2$ is $C(R^{8c})(R^{8d})$;
$R^1$ is H;
$X^1$ is O;
$R^{2a}$, $R^{2b}$ are independently selected from H, and $C_1$-$C_3$alkyl;

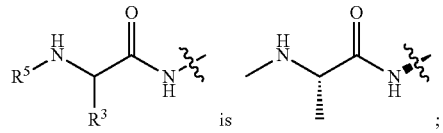

$R^{8a}$, $R^{8b}$, $R^{8c}$, $R^{8d}$ are independently selected from H and $C_1$-$C_3$alkyl.

Any combination of the groups described above or below for the various variables is contemplated herein. Throughout the specification, groups and substituents thereof are chosen by one skilled in the field to provide stable moieties and compounds.

Among any of the compounds of Formula A described above and below, are compounds or pharmaceutically acceptable salt, N-oxide, racemate or stereoisomer thereof, selected from:

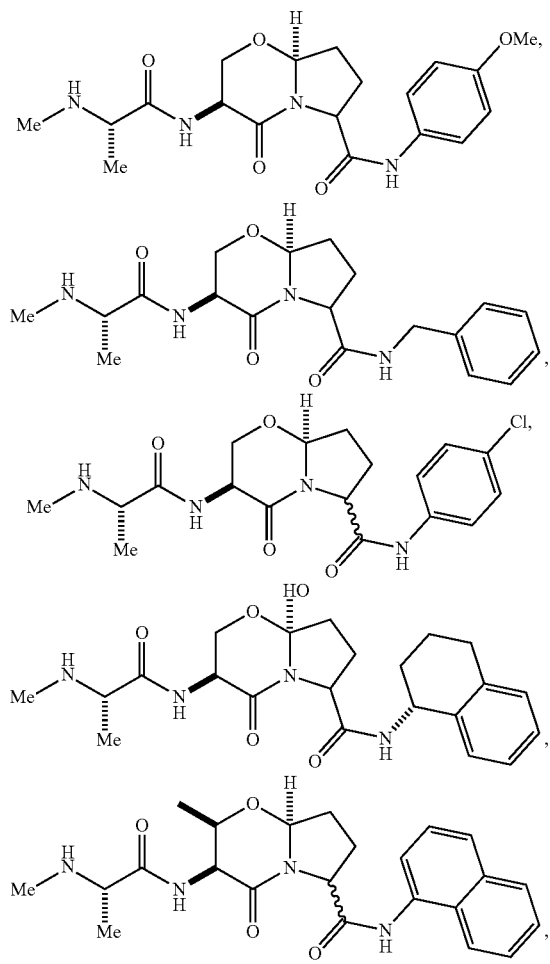

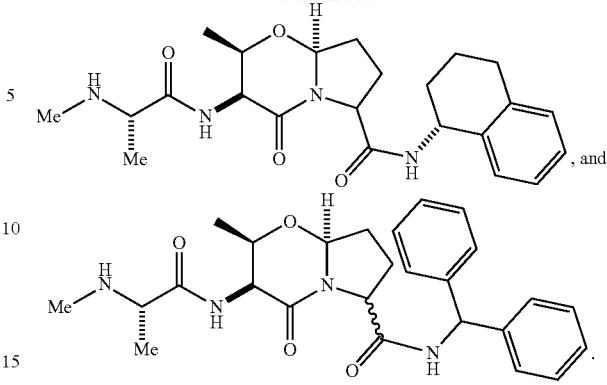

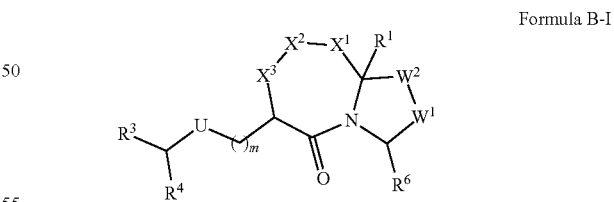

A pharmaceutical composition comprising a compound of Formula A described above or below, or pharmaceutically acceptable salt, N-oxide, racemate or stereoisomer thereof, and a pharmaceutically acceptable carrier.

Formula B—Seven-Five Ring Systems

In one aspect, the IAP antagonist for use in any of the methods, uses, compositions described herein is a Formula B compound. As used herein, Formula B includes compounds of Formula B-I, Formula B-II, Formula B-III-1, Formula B-III-2, Formula B-III-3, Formula B-IV, Formula B-V-1, Formula B-V-2, Formula B-V-3, Formula B-VI-1, Formula B-VI-2, Formula B-VI-3, Formula B-VII-1, Formula B-VII-2, Formula B-VII-3, Formula B-VIII-1, Formula B-VIII-2, Formula B-VIII-3, Formula B-IX-1, Formula B-IX-2, Formula B-X, Formula B-XI-1, Formula B-XI-2, Formula B-XII, Formula B-XIII, Formula B-XIV, Formula B-XV, Formula B-XVI-1, Formula B-XVI-2, Formula B-XVI-3, Formula B-XVI-4, Formula B-XVII-1, Formula B-XVII-2, Formula B-XVIII, Formula B-XIX, Formula B-XX, Formula B-XXI, and Formula B-XXII.

In one aspect, described herein is a compound of Formula B-I, or a pharmaceutically acceptable salt, N-oxide, racemate or stereoisomer thereof, as described in the summary of the invention.

In another aspect, provided herein are compounds having the structure of Formula B-I, pharmaceutically acceptable salt, N-oxide, racemate or stereoisomer thereof:

Formula B-I wherein,
$R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl); when $X^1$ is selected from N—$R^4$, S, S(O) and S(O)$_2$, then $X^2$ is $CR^{2c}R^{2d}$, and $X^3$ is $CR^{2a}R^{2b}$;
or
when $X^1$ is O, then $X^2$ is selected from $CR^{2c}R^{2d}$ and N—$R^4$, and $X^3$ is $CR^{2a}R^{2b}$;

or:
when $X^1$ is $CH_2$, then $X^2$ is selected from O, N—$R^A$, S, S(O), and $S(O)_2$, and $X^3$ is $CR^{2a}R^{2b}$;

or:
$X^1$ is $CR^{2e}R^{2f}$ and $X^2$ is $CR^2CR^{2d}$, and $R^{2e}$ and $R^{2c}$ together form a bond, and $X^3$ is $CR^{2a}R^{2b}$;

or:
$X^1$ and $X^3$ are both $CH_2$ and $X^2$ is C=O, C=C($R^C)_2$, or C=$NR^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:
$X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:
$X^2$ and $X^3$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ is $CR^{2e}R^{2f}$;

$R^A$ is H, $C_1$-$C_6$alkyl, —C(=O)$C_1$-$C_6$alkyl, substituted or unsubstituted aryl, or substituted or unsubstituted heteroaryl;

$W^1$ is O, S, N—$R^A$, or C($R^{8a}$)($R^{8b}$);

$W^2$ is O, S, N—$R^A$, or C($R^{8c}$)($R^{8d}$); provided that $W^1$ and $W^2$ are not both O, or both S;

$R^{2a}$, $R^{2b}$, $R^{2c}$, $R^{2d}$ $R^{2e}$, and $R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$ NH—;

$R^3$ is $C_1$-$C_3$alkyl, or $C_1$-$C_3$fluoroalkyl;

$R^4$ is —$NHR^5$, —N($R^5)_2$, —N($R^5)_3$ or —$OR^5$;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:
$R^3$ and $R^5$ together with the atoms to which they are attached form a substituted or unsubstituted 5-7 membered ring;

or:
$R^3$ is bonded to a nitrogen atom of U to form a substituted or unsubstituted 5-7 membered ring;

$R^6$ is —NHC(=O)$R^7$, —C(=O)$NHR^7$, —NHS(=O)$_2$$R^7$, —S(=O)$_2$$NHR^7$; —NHC(=O)$NHR^7$, —NHS(=O)$_2$$NHR^7$, —($C_1$-$C_3$alkyl)-NHC(=O)$R^7$, —($C_1$-$C_3$alkyl)-C(=O)$NHR^5$, —($C_1$-$C_3$alkyl)-NHS(=O)$_2$$R^7$, —($C_1$-$C_3$alkyl)-S(=O)$_2$$NHR^7$; —($C_1$-$C_3$alkyl)-NHC(=O)$NHR^7$, —($C_1$-$C_3$alkyl)-NHS(=O)$_2$$NHR^7$, substituted or unsubstituted $C_2$-$C_{10}$heterocycloalkyl, or substituted or unsubstituted heteroaryl;

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$, $R^{8b}$, $R^{8c}$, and $R^{8d}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:
$R^{8a}$ and $R^{8d}$ are as defined above, and $R^{8b}$ and $R^{8c}$ together form a bond;

or:
$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, cycloalkyl, heterocycloalkyl, aryl or heteroaryl is substituted with 1-3 $R^9$; and each $R^9$ is independently selected from halogen, —OH, —SH, (C═O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —N($C_1$-$C_4$alkyl)$_2$, —C(═O)OH, —C(═O)$NH_2$, —C(═O)$C_1$-$C_3$alkyl, —S(═O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula B-I described above or below, or pharmaceutically acceptable salt, N-oxide, racemate or stereoisomer thereof, is one group of compounds having the structure of Formula B-II:

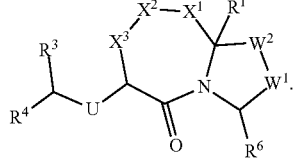

Formula B-II

Among the compounds of Formula B-I described above or below, or pharmaceutically acceptable salt, N-oxide, racemate or stereoisomer thereof, is one group of compounds having the structure of Formula B-III-1, Formula B-III-2 or Formula B-III-3:

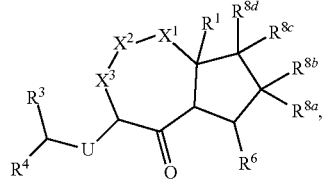

Formula B-III-1

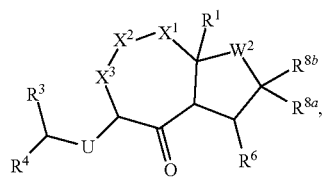

Formula B-III-2

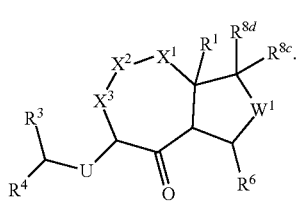

Formula B-III-3

Among the compounds of Formula B-I described above or below, or pharmaceutically acceptable salt, N-oxide, racemate or stereoisomer thereof, is one group of compounds having the structure of Formula B-III-1:

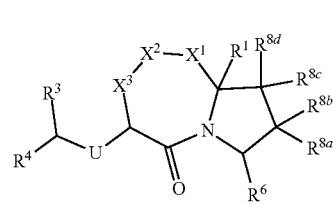

Formula B-III-1

Among the compounds of Formula B-I described above or below, or pharmaceutically acceptable salt, N-oxide, racemate or stereoisomer thereof, is one group of compounds having the structure of Formula B-IV:

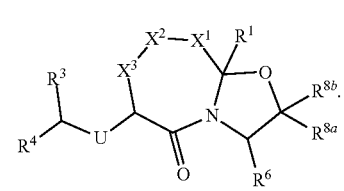

Formula B-IV

Among the compounds of Formula B described above or below, or pharmaceutically acceptable salt, N-oxide, racemate or stereoisomer thereof, is one group of compounds wherein, —U— is —NHC(═O)—, —C(═O)NH—, —NHS(═O)$_2$—, or —S(═O)$_2$NH—.

Among the compounds of Formula B described above or below, or pharmaceutically acceptable salt, N-oxide, racemate or stereoisomer thereof, is one group of compounds wherein, —U— is —NHC(═O)—, or —C(═O)NH—.

Among the compounds of Formula B described above or below, or pharmaceutically acceptable salt, N-oxide, racemate or stereoisomer thereof, is one group of compounds wherein, $R^3$ is $C_1$-$C_3$alkyl.

Among the compounds of Formula B described above or below, or pharmaceutically acceptable salt, N-oxide, racemate or stereoisomer thereof, is one group of compounds wherein, $R^4$ is-$NHR^5$, —N($R^5$)$_2$, or —$N^+(R^5)_3$; and each $R^5$ is independently selected from H, $C_1$-$C_3$alkyl, and —$C_1$-$C_3$alkyl-($C_3$-$C_5$cycloalkyl).

Among the compounds of Formula B described above or below, or pharmaceutically acceptable salt, N-oxide, racemate or stereoisomer thereof, is one group of compounds wherein, —U— is —NHC(=O)—, or —C(=O)NH—;

$R^3$ is $C_1$-$C_3$alkyl;

$R^4$ is -NHR$^5$, —N(R$^5$)$_2$, or —N$^+$(R$^5$)$_3$; and each $R^5$ is independently selected from H, $C_1$-$C_3$alkyl, and —$C_1$-$C_3$alkyl-($C_3$-$C_5$cycloalkyl).

Among the compounds of Formula B described above or below, or pharmaceutically acceptable salt, N-oxide, racemate or stereoisomer thereof, is one group of compounds wherein,

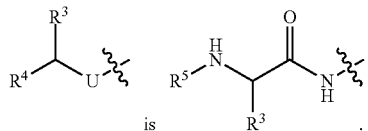

is

Among the compounds of Formula B described above or below, or pharmaceutically acceptable salt, N-oxide, racemate or stereoisomer thereof, is one group of compounds wherein,

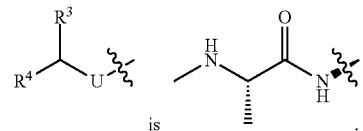

is

Among the compounds of Formula B described above or below, or pharmaceutically acceptable salt, N-oxide, racemate or stereoisomer thereof, is one group of compounds wherein $R^3$ and $R^5$ together with the atoms to which they are attached form a substituted or unsubstituted 5-7 membered ring.

Among the compounds of Formula B described above or below, or pharmaceutically acceptable salt, N-oxide, racemate or stereoisomer thereof, is one group of compounds wherein,

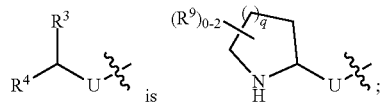

and q is 1, 2 or 3.

Among the compounds of Formula B described above or below, or pharmaceutically acceptable salt, N-oxide, racemate or stereoisomer thereof, is one group of compounds wherein $R^3$ is bonded to a nitrogen atom of U to form a substituted or unsubstituted 5-7 membered ring.

Among the compounds of Formula B described above or below, or pharmaceutically acceptable salt, N-oxide, racemate or stereoisomer thereof, is one group of compounds wherein,

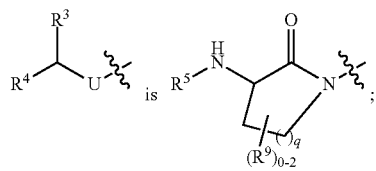

is and q is 1, 2 or 3.

Among the compounds of Formula B described above or below, or pharmaceutically acceptable salt, N-oxide, racemate or stereoisomer thereof, is one group of compounds wherein, $X^1$ is selected from N—$R^A$, S, S(O) and S(O)$_2$; and $X^2$ is CH$_2$.

Among the compounds of Formula B-I described above or below, or pharmaceutically acceptable salt, N-oxide, racemate or stereoisomer thereof, is one group of compounds having the structure of Formula B-V-1, Formula B-V-2, or Formula B-V-3:

Formula B-V-1

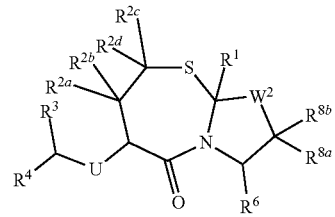

Formula B-V-2

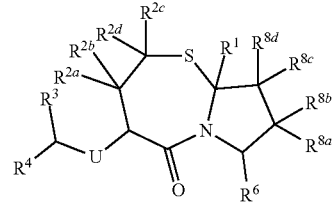

Formula B-V-3

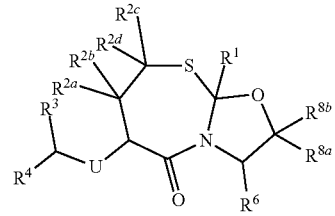

Among the compounds of Formula B-I described above or below, or pharmaceutically acceptable salt, N-oxide, racemate or stereoisomer thereof, is one group of compounds having the structure of Formula B-VI-1, Formula B-VI-2, Formula B-VI-3:

Formula B-VI-1

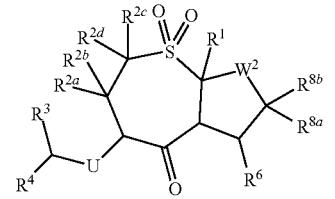

Formula B-VI-2

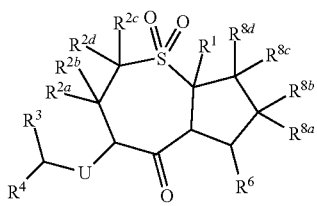

Formula B-VI-3

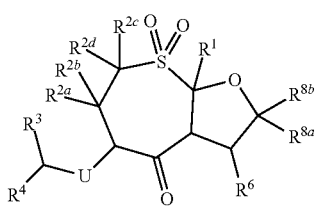

Among the compounds of Formula B-I described above or below, or pharmaceutically acceptable salt, N-oxide, racemate or stereoisomer thereof, is one group of compounds having the structure of Formula B-VII-1, Formula B-VII-2 or Formula B-VII-3

Formula B-VII-1

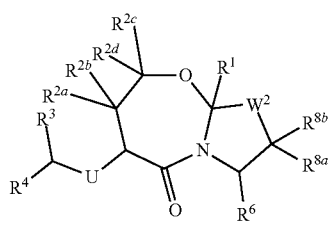

Formula B-VII-2

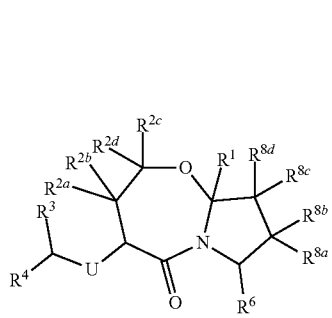

Formula B-VII-3

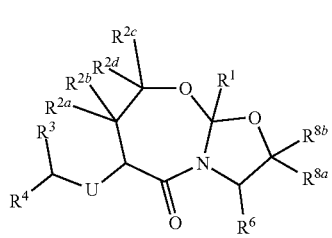

Among the compounds of Formula B-I described above or below, or pharmaceutically acceptable salt, N-oxide, racemate or stereoisomer thereof, is one group of compounds having the structure of Formula B-V-2, Formula B-VI-2, or Formula B-VII-2:

Formula B-V-2

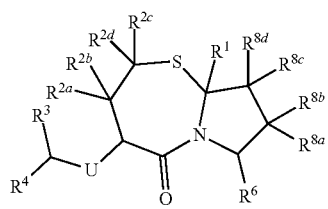

Formula B-VI-2

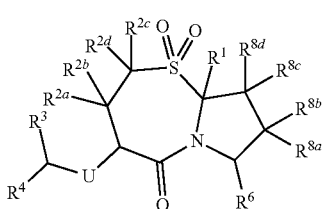

Formula B-VII-2

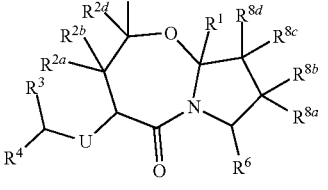

Among the compounds of Formula B-I described above or below, or pharmaceutically acceptable salt, N-oxide, racemate or stereoisomer thereof, is one group of compounds having the structure of Formula B-VIII-1, Formula B-VIII-2, or Formula B-VIII-3:

Formula B-VIII-1

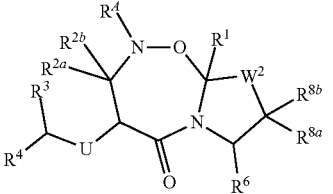

Formula B-VIII-2

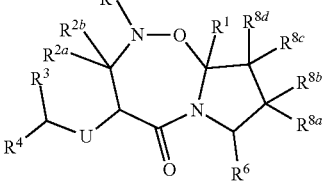

Formula B-VIII-3

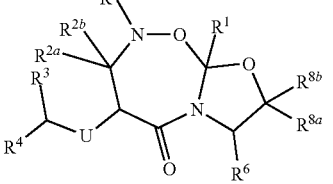

Among the compounds of Formula B-I described above or below, or pharmaceutically acceptable salt, N-oxide, racemate or stereoisomer thereof, is one group of compounds wherein $X^1$ is $CH_2$; and $X^2$ is selected from O, N—$R^4$, S, S(O), and S(O)$_2$.

Among the compounds of Formula B-I described above or below, or pharmaceutically acceptable salt, N-oxide, racemate or stereoisomer thereof, is one group of compounds having the structure of Formula B-IX-1 or Formula B-IX-2:

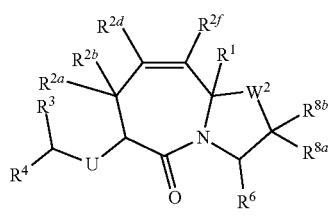

Formula B-IX-1

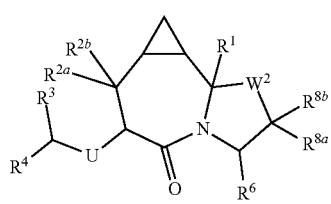

Formula B-IX-2

Among the compounds of Formula B-I described above or below, or pharmaceutically acceptable salt, N-oxide, racemate or stereoisomer thereof, is one group of compounds having the structure of Formula B-X:

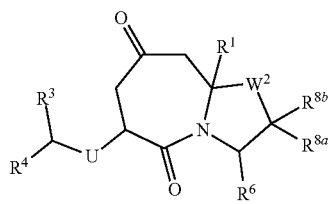

Formula B-X

Among the compounds of Formula B-I described above or below, or pharmaceutically acceptable salt, N-oxide, racemate or stereoisomer thereof, is one group of compounds having the structure of Formula B-XI-1 or Formula B-XI-2:

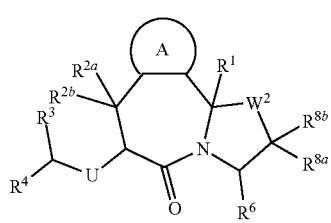

Formula B-XI-1

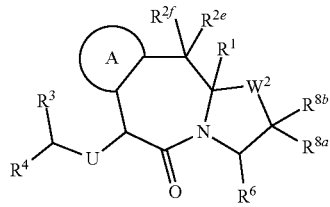

Formula B-XI-2 wherein, ring A is a fused substituted or unsubstituted saturated or partially saturated 3-10 membered cycloalkyl ring, substituted or unsubstituted saturated or partially saturated 3-10 membered heterocycloalkyl ring, substituted or unsubstituted 5-10 membered aryl ring, or substituted or unsubstituted 5-10 membered heteroaryl ring.

Within such a group of compounds are compounds wherein ring A is selected from indolyl and phenyl.

Among the compounds of Formula B-I described above or below, or pharmaceutically acceptable salt, N-oxide, racemate or stereoisomer thereof, is one group of compounds having the structure of Formula B-XI-1:

Among the compounds of Formula B-I described above or below, or pharmaceutically acceptable salt, N-oxide, racemate or stereoisomer thereof, is one group of compounds having the structure of Formula B-XII:

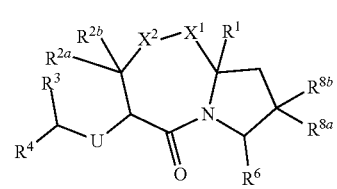

Formula B-XII

Within such a group of compounds are compounds wherein $R^{8a}$ and $R^{8b}$ are independently selected from H and $C_1$-$C_3$alkyl.

Among the compounds of Formula B-I described above or below, or pharmaceutically acceptable salt, N-oxide, racemate or stereoisomer thereof, is one group of compounds having the structure of Formula B-XIII:

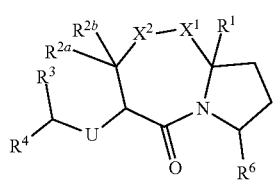

Formula B-XIII

Among the compounds of Formula B-I described above or below, or pharmaceutically acceptable salt, N-oxide, racemate or stereoisomer thereof, is one group of compounds having the structure of Formula B-XIV:

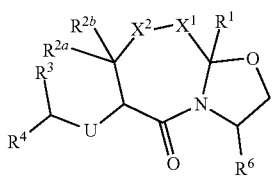

Formula B-XIV

Within the group of compounds of Formula B-XII, B-XIII and B-XIV are compounds wherein $X^1$ is O, S or $S(O)_2$, and $X^2$ is $CH_2$.

Within the group of compounds of Formula B-XII, B-XIII and B-XIV are compounds wherein $X^1$ is O, and $X^2$ is N—$R^A$.

Among the compounds of Formula B described above or below, or pharmaceutically acceptable salt, N-oxide, racemate or stereoisomer thereof, is one group of compounds wherein $X^1$ is O, S or $S(O)_2$, and $X^2$ is $CH_2$;
or $X^1$ is N—$R^A$ and $X^2$ is C=O or $CH_2$;
or $X^1$ and $X^2$ are C and are members of a fused substituted or unsubstituted a fused substituted or unsubstituted 5-10 membered aryl ring, or a fused substituted or unsubstituted 5-10 membered heteroaryl ring;

$R^A$ is H, $C_1$-$C_6$alkyl, or —C(=O)$C_1$-$C_6$alkyl.

Among the compounds of Formula B-I described above or below, or pharmaceutically acceptable salt, N-oxide, racemate or stereoisomer thereof, is one group of compounds wherein $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N.

Within such a group of compounds are compounds having the structure of Formula B-XV:

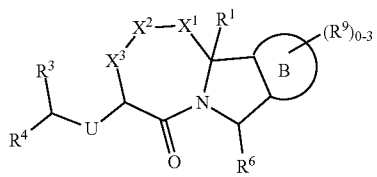

Formula B-XV wherein ring B is an aryl or heteroaryl ring.

In some embodiments, ring B is an aryl. In some embodiments, ring B is phenyl. In some embodiments, ring B is a heteroaryl ring. In some embodiments, ring B is a monocyclic heteroaryl ring or a bicyclic heteroaryl ring. In some embodiments, ring B is a monocyclic heteroaryl ring. In some embodiments, ring B is a bicyclic heteroaryl ring. In some embodiments, ring B is selected from phenyl, pyridinyl and thiophenyl. In some embodiments, ring B is selected from pyridinyl and thiophenyl.

Among the compounds of Formula B-I described above or below, or pharmaceutically acceptable salt, N-oxide, racemate or stereoisomer thereof, is one group of compounds wherein $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N or $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N.

Within such a group are compounds having the structure of Formula B-XVI-1, Formula B-XVI-2, Formula B-XVI-3, or Formula B-XVI-4:

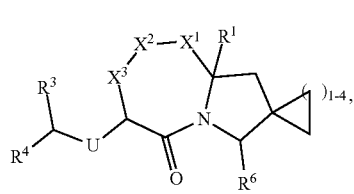

Formula B-XVI-1

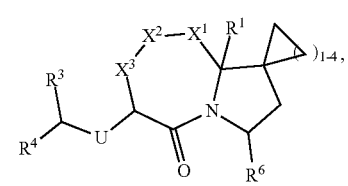

Formula B-XVI-2

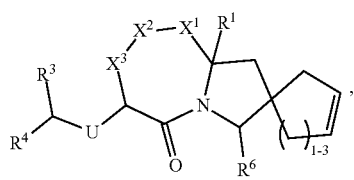

Formula B-XVI-3

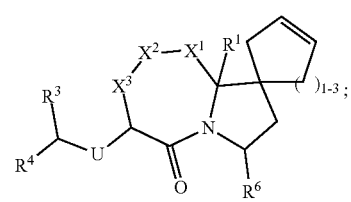

Formula B-XVI-4 or having the structure of Formula B-XVII-1 or Formula B-XVII-2:

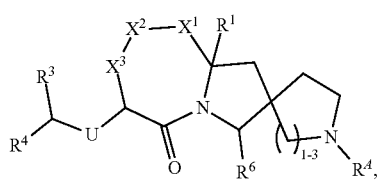

Formula B-XVII-1

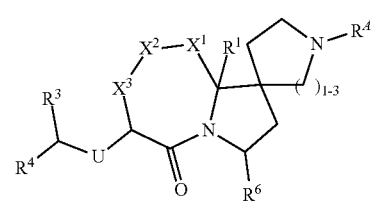

Formula B-XVII-2 wherein $R^A$ is H, $C_1$-$C_3$alkyl or —C(=O)$C_1$-$C_3$alkyl.

Among the compounds of Formula B-I described above or below, or pharmaceutically acceptable salt, N-oxide, racemate or stereoisomer thereof, is one group of compounds wherein $R^{8b}$ and $R^{8c}$ together form a bond.

Within such a group are compounds having the structure of Formula B-XVIII:

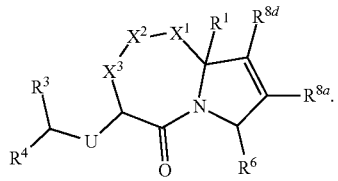

Formula B-XVIII

Among the compounds of Formula B described above or below, or pharmaceutically acceptable salt, N-oxide, racemate or stereoisomer thereof, is one group of compounds having the structure of Formula B-XIX:

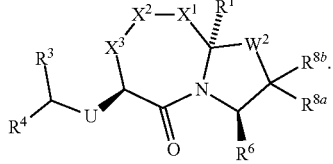

Formula B-XIX

Among the compounds of Formula B described above or below, or pharmaceutically acceptable salt, N-oxide, racemate or stereoisomer thereof, is one group of compounds having the structure of Formula B-XX:

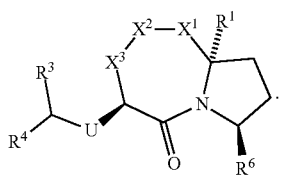

Formula B-XX

Among the compounds of Formula B described above or below, or pharmaceutically acceptable salt, N-oxide, racemate or stereoisomer thereof, is one group of compounds having the structure of Formula B-XXI:

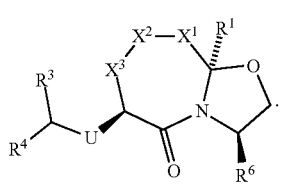

Formula B-XXI

In another aspect, provided herein are compounds having the structure of Formula B-XXII, or pharmaceutically acceptable salt, N-oxide, racemate or stereoisomer thereof:

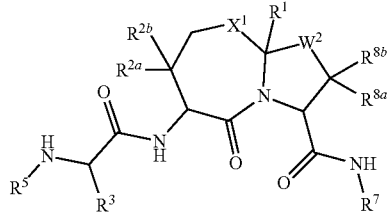

Formula B-XXII wherein, $W^2$ is O, S, or $C(R^{8c})(R^{8d})$;

$R^1$ is H, or $C_1$-$C_6$alkyl;

$X^1$ is O, N—$R^A$, S, S(O), or $S(O)_2$;

$R^A$ is H, $C_1$-$C_6$alkyl, —C(=O)$C_1$-$C_6$alkyl, substituted or unsubstituted aryl, or substituted or unsubstituted heteroaryl;

$R^{2a}$ and $R^{2b}$ are independently selected from H, substituted or unsubstituted $C_1$-$C_6$alkyl, and —C(=O)$R^B$;

$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

$R^3$ is $C_1$-$C_3$alkyl, or $C_1$-$C_3$fluoroalkyl;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$ and $R^{8b}$ are independently selected from H, $C_1$-$C_6$alkyl, and $C_1$-$C_6$fluoroalkyl;

$R^{8c}$ and $R^{8d}$ are independently selected from H, $C_1$-$C_6$alkyl, and $C_1$-$C_6$fluoroalkyl;

where each substituted alkyl, heteroalkyl, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —NH$_2$, —NH($C_1$-$C_4$alkyl), —N($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula B described above or below, or pharmaceutically acceptable salt, N-oxide, racemate or stereoisomer thereof, is one group of compounds wherein, $R^{2a}$, $R^{2b}$ $R^{2c}$, $R^{2d}$, $R^{2e}$, and $R^{2f}$ are independently selected from H, $C_1$-$C_3$alkyl and —C(=O)$R^B$; and $R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl).

Among the compounds of Formula B described above or below, or pharmaceutically acceptable salt, N-oxide, racemate or stereoisomer thereof, is one group of compounds wherein $R^{2a}$, $R^{2b}$ $R^{2c}$, $R^{2d}$, $R^{2e}$, and $R^{2f}$ are independently H or $C_1$-$C_3$ alkyl.

Among the compounds of Formula B described above or below, or pharmaceutically acceptable salt, N-oxide, racemate or stereoisomer thereof, is one group of compounds wherein $R^1$ is H or methyl.

Among the compounds of Formula B described above or below, or pharmaceutically acceptable salt, N-oxide, racemate or stereoisomer thereof, is one group of compounds wherein $R^1$ is H.

Among the compounds of Formula B described above or below, or pharmaceutically acceptable salt, N-oxide, racemate or stereoisomer thereof, is one group of compounds wherein, $R^6$ is —NHC(=O)$R^7$, —C(=O)NHR$^7$, —NHS(=O)$_2$R$^7$, —S(=O)$_2$NHR$^7$; —NHC(=O)NHR$^7$, —NHS(=O)$_2$NHR$^7$, —($C_1$-$C_3$alkyl)-NHC(=O)R$^7$, —($C_1$-$C_3$alkyl)-C(=O)NHR$^5$, —($C_1$-$C_3$alkyl)-NHS(=O)$_2$R$^7$, —($C_1$-$C_3$alkyl)-S(=O)$_2$NHR$^7$; —($C_1$-$C_3$alkyl)-NHC(=O)NHR$^7$, or —($C_1$-$C_3$alkyl)-NHS(=O)$_2$NHR$^7$.

Among the compounds of Formula B described above or below, or pharmaceutically acceptable salt, N-oxide, racemate or stereoisomer thereof, is one group of compounds wherein, $R^6$ is substituted or unsubstituted $C_2$-$C_{10}$heterocycloalkyl, or substituted or unsubstituted heteroaryl.

Among the compounds of Formula B described above or below, or pharmaceutically acceptable salt, N-oxide, racemate or stereoisomer thereof, is one group of compounds wherein, $R^6$ is a substituted or unsubstituted $C_2$-$C_{10}$heterocycloalkyl.

Among the compounds of Formula B described above or below, or pharmaceutically acceptable salt, N-oxide, racemate or stereoisomer thereof, is one group of compounds wherein, $R^6$ is a substituted or unsubstituted heteroaryl.

Among the compounds of Formula B described above or below, or pharmaceutically acceptable salt, N-oxide, racemate or stereoisomer thereof, is one group of compounds wherein, $R^6$ is —C(=O)NHR$^7$, —S(=O)$_2$NHR$^7$, —($C_1$-$C_3$alkyl)-C(=O)NHR$^5$, or —($C_1$-$C_3$alkyl)-S(=O)$_2$NHR$^7$.

Among the compounds of Formula B described above or below, or pharmaceutically acceptable salt, N-oxide, racemate or stereoisomer thereof, is one group of compounds wherein, $R^6$ is —C(=O)NHR$^7$, or —S(=O)$_2$NHR$^7$.

Among the compounds of Formula B described above or below, or pharmaceutically acceptable salt, N-oxide, racemate or stereoisomer thereof, is one group of compounds wherein $R^6$ is —C(=O)NHR$^7$.

Among the compounds of Formula B described above or below, or pharmaceutically acceptable salt, N-oxide, racemate or stereoisomer thereof, is one group of compounds wherein, each $R^7$ is independently selected from a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$-(CH$_2$)$_p$—CH (substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl).

Among the compounds of Formula B described above or below, or pharmaceutically acceptable salt, N-oxide, racemate or stereoisomer thereof, is one group of compounds wherein, $R^7$ is independently selected from a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, and —(CH$_2$)$_p$—CH(substituted or unsubstituted aryl)$_2$.

Among the compounds of Formula B described above or below, or pharmaceutically acceptable salt, N-oxide, racemate or stereoisomer thereof, is one group of compounds wherein, $R^7$ is selected from

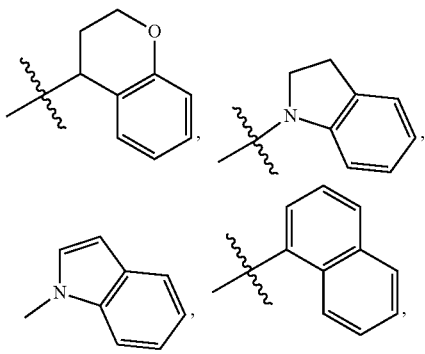

-continued

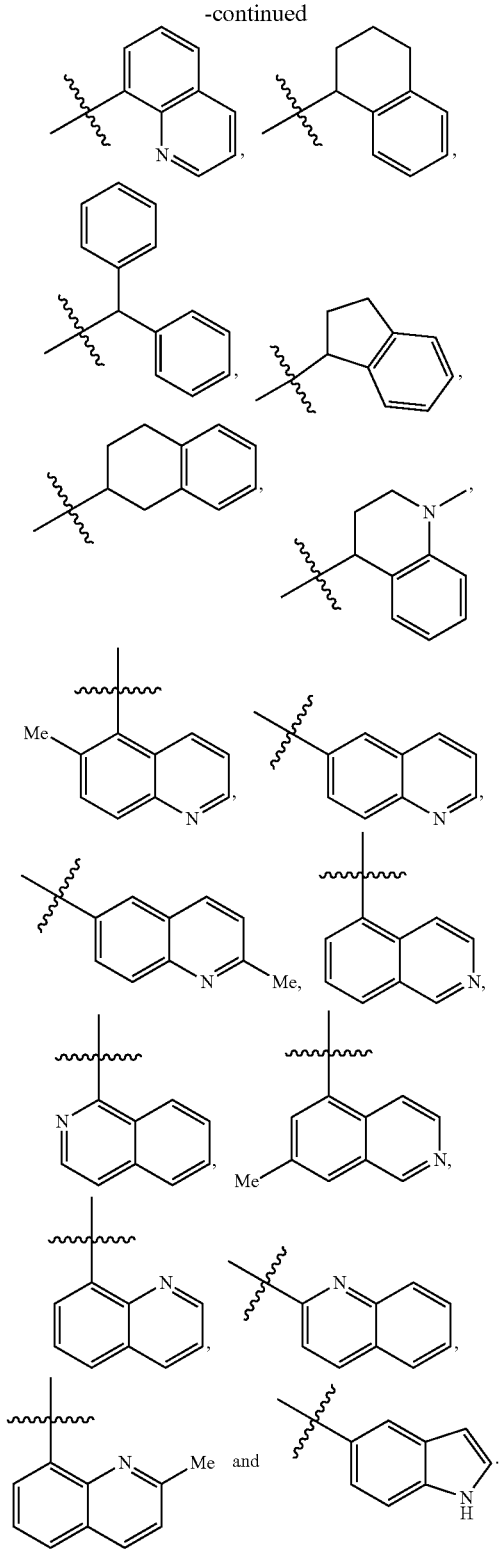

Among the compounds of Formula B described above or below, or pharmaceutically acceptable salt, N-oxide, racemate or stereoisomer thereof, is one group of compounds wherein, $W^2$ is $C(R^{8c})(R^{8d})$;

$R^1$ is H;

$R^{2a}$, $R^{2b}$ are independently selected from H, and $C_1$-$C_3$alkyl;

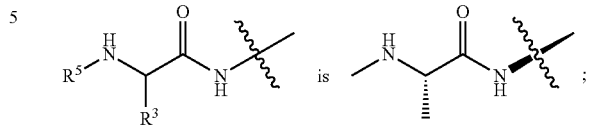

$R^{8a}$, $R^{8b}$, $R^{8c}$, $R^{8d}$ are independently selected from H and $C_1$-$C_3$alkyl.

Any combination of the groups described above or below for the various variables is contemplated herein. Throughout the specification, groups and substituents thereof are chosen by one skilled in the field to provide stable moieties and compounds.

Among the compounds of Formula B described above or below, or pharmaceutically acceptable salt, N-oxide, racemate or stereoisomer thereof, are compounds selected from:

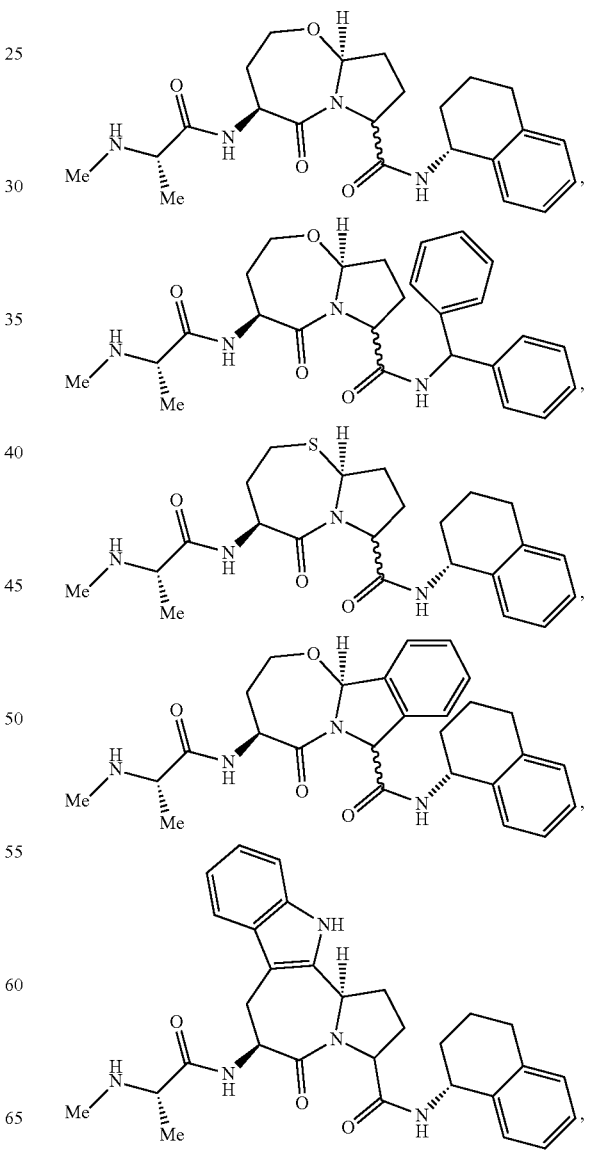

73
-continued
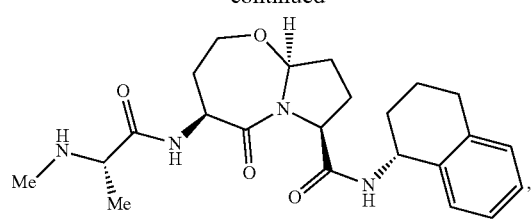
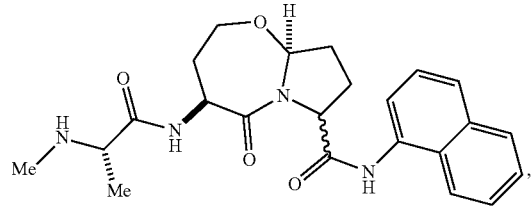
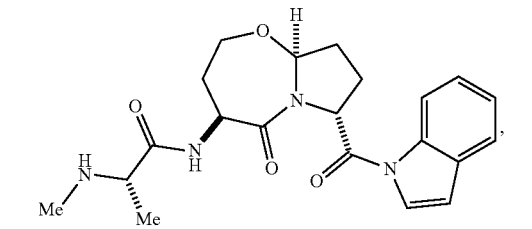
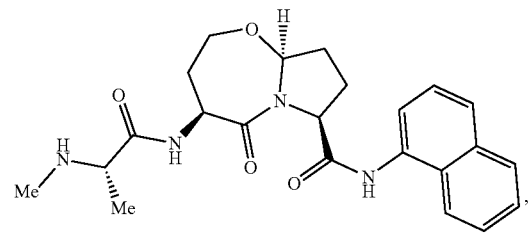
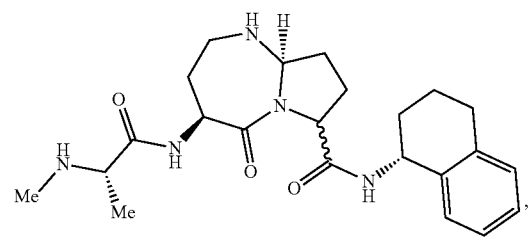
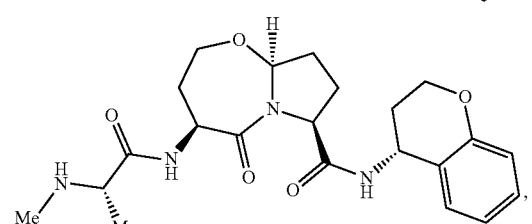
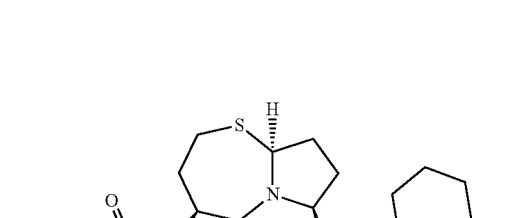
74
-continued
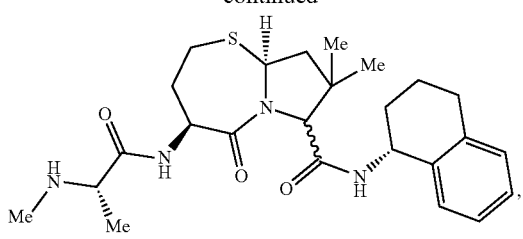
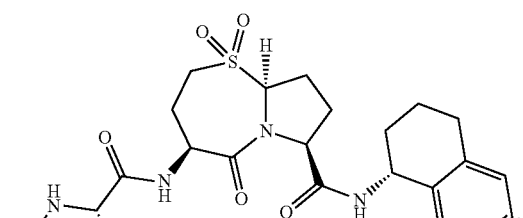
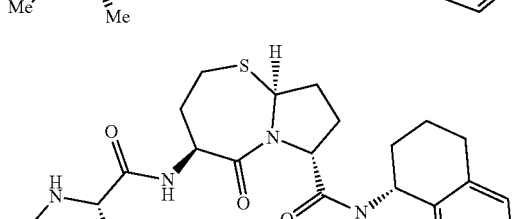
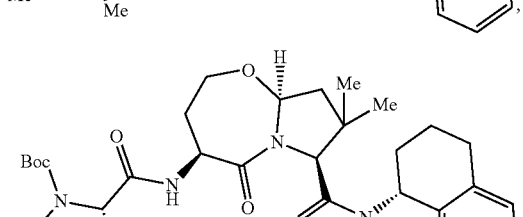
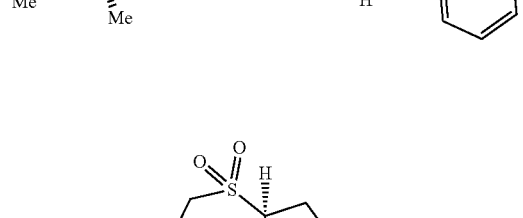
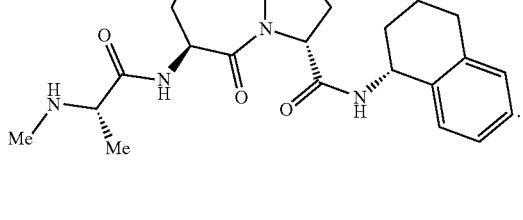
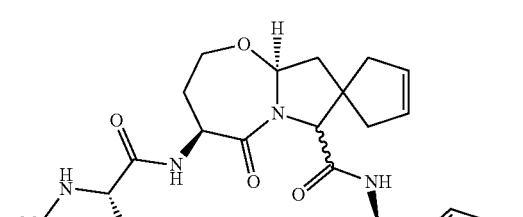

-continued

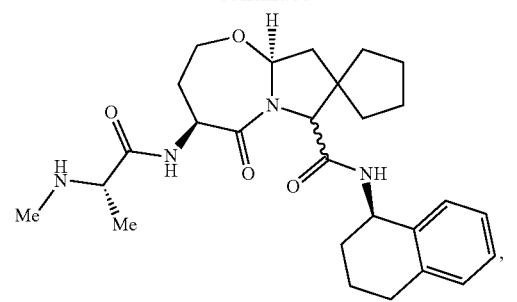

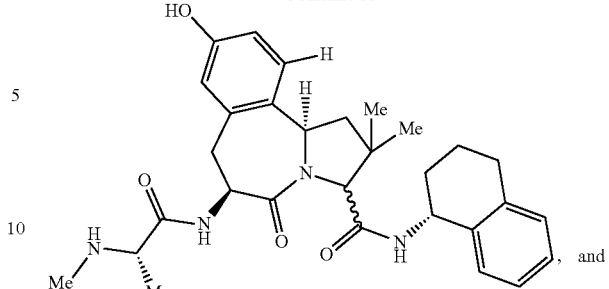

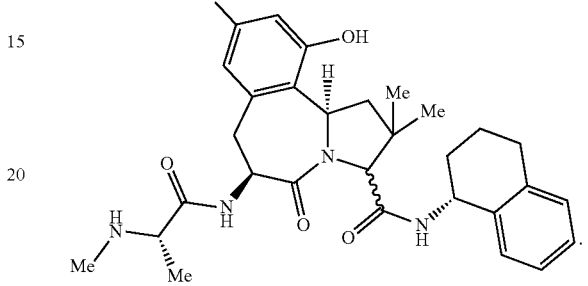

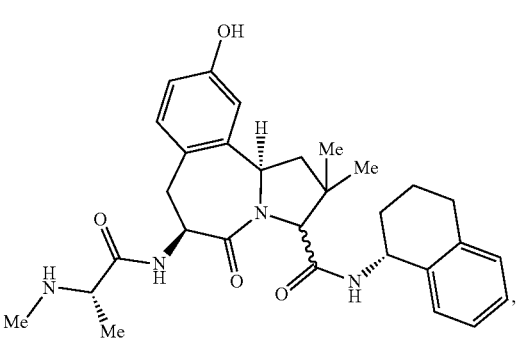

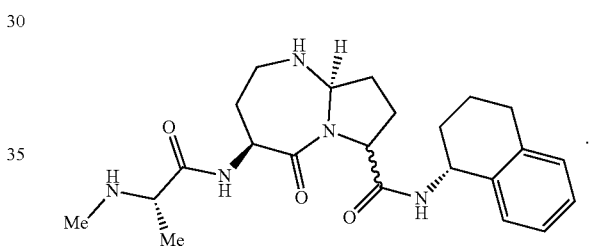

In some embodiments, a compound of Formula B described above or below, or pharmaceutically acceptable salt, N-oxide, racemate or stereoisomer thereof, is

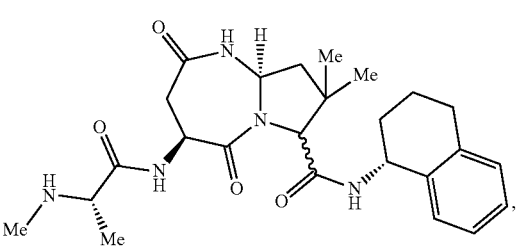

Also provided herein are pharmaceutical compositions comprising a compound of Formula B described above, or pharmaceutically acceptable salt, N-oxide, racemate or stereoisomer thereof, and a pharmaceutically acceptable carrier.

Formula C—Eight-Five Ring Systems

In one aspect, the IAP antagonist for use in any of the methods, uses, compositions described herein is a Formula C compound. As used herein, Formula C includes compounds of Formula C-I, Formula C-II, Formula C-III-1, Formula C-III-2, Formula C-III-3, Formula C-IV, Formula C-V-1, Formula C-V-2, Formula C-V-3, Formula C-VI-1, Formula C-VI-2, Formula C-VI-3, Formula C-VII-1, Formula C-VII-2, Formula C-VII-3, Formula C-VIII-1, Formula C-VIII-2, Formula C-VIII-3, Formula C-IX-1, Formula C-IX-2, Formula C-X-1, Formula C-X-2, Formula C-XI, Formula C-XII, Formula C-XIII, Formula C-XIV, Formula C-XV-1, Formula C-XV-2, Formula C-XV-3, Formula C-XV-4, Formula C-XVI-1, Formula C-XVI-2, Formula C-XVII, Formula C-XVIII, Formula C-XIX, Formula C-XX, and Formula C-XXI.

In one aspect, described herein is a compound of Formula C-I, or a pharmaceutically acceptable salt, N-oxide, racemate or stereoisomer thereof, as described in the summary of the invention.

In another aspect, provided herein are compounds having the structure of Formula C-I, pharmaceutically acceptable salt, N-oxide, racemate or stereoisomer thereof:

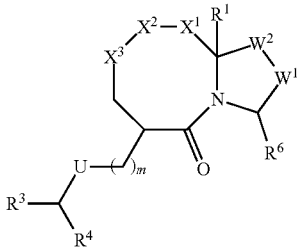

Formula C-I wherein,

R$^1$ is H, C$_1$-C$_6$alkyl, C$_3$-C$_6$cycloalkyl, —C$_1$-C$_6$alkyl-(substituted or unsubstituted C$_3$-C$_6$cycloalkyl), substituted or unsubstituted aryl, substituted or unsubstituted heteroaryl, —C$_1$-C$_6$alkyl-(substituted or unsubstituted aryl), —C$_1$-C$_6$alkyl-(substituted or unsubstituted heteroaryl); when X$^1$ is selected from N—R$^A$, S, S(O) and S(O)$_2$, then X$^2$ is CR$^{2c}$R$^{2d}$, and X$^3$ is CR$^{2a}$R$^{2b}$;

or when X$^1$ is O, then X$^2$ is selected from CR$^{2c}$R$^{2d}$ and N—R$^A$, and X$^3$ is CR$^{2a}$R$^{2b}$;

or:

when X$^1$ is CH$_2$, then X$^2$ is selected from O, N—R$^A$, S, S(O), and S(O)$_2$, and X$^3$ is CR$^{2a}$R$^{2b}$;

or:

X$^1$ is CR$^{2e}$R$^{2f}$ and X$^2$ is CR$^{2c}$R$^{2d}$, and R$^{2e}$ and R$^{2c}$ together form a bond, and X$^3$ is CR$^{2a}$R$^{2b}$;

or:

X$^1$ and X$^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X$^3$ is CR$^{2a}$R$^{2b}$;

or:

X$^2$ and X$^3$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X$^1$ is CR$^{2e}$R$^{2f}$;

R$^A$ is H, C$_1$-C$_6$alkyl, —C(=O)C$_1$-C$_6$alkyl, substituted or unsubstituted aryl, or substituted or unsubstituted heteroaryl;

W$^1$ is O, S, N—R$^A$, or C(R$^{8a}$)(R$^{8b}$); W$^2$ is O, S, N—R$^A$, or C(R$^{8c}$)(R$^{8d}$); provided that W$^1$ and W$^2$ are not both O, or both S;

R$^{2a}$, R$^{2b}$, R$^{2c}$, R$^{2d}$ R$^{2e}$, and R$^{2f}$ are independently selected from H, substituted or unsubstituted C$_1$-C$_6$alkyl, substituted or unsubstituted C$_1$-C$_6$heteroalkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), —C$_1$-C$_6$alkyl-(substituted or unsubstituted heteroaryl) and —C(=O)R$^B$;

R$^B$ is substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), —C$_1$-C$_6$alkyl-(substituted or unsubstituted heteroaryl) or —NR$^D$R$^E$;

R$^D$ and R$^E$ are independently selected from H, substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), or —C$_1$-C$_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

R$^3$ is C$_1$-C$_3$alkyl, or C$_1$-C$_3$fluoroalkyl;

R$^4$ is —NHR$^5$, —N(R$^5$)$_2$, —N$^+$(R$^5$)$_3$ or —OR$^5$;

each R$^5$ is independently selected from H, C$_1$-C$_3$alkyl, C$_1$-C$_3$haloalkyl, C$_1$-C$_3$heteroalkyl and —C$_1$-C$_3$alkyl-(C$_3$-C$_5$cycloalkyl);

or:

R$^3$ and R$^5$ together with the atoms to which they are attached form a substituted or unsubstituted 5-7 membered ring;

or:

R$^3$ is bonded to a nitrogen atom of U to form a substituted or unsubstituted 5-7 membered ring;

R$^6$ is —NHC(=O)R$^7$, —C(=O)NHR$^7$, —NHS(=O)$_2$R$^7$, —S(=O)$_2$NHR$^7$; —NHC(=O)NHR$^7$, —NHS(=O)$_2$NHR$^7$, —(C$_1$-C$_3$alkyl)-NHC(=O)R$^7$, —(C$_1$-C$_3$alkyl)-C(=O)NHR$^5$, —(C$_1$-C$_3$alkyl)-NHS(=O)$_2$R$^7$, —(C$_1$-C$_3$alkyl)-S(=O)$_2$NHR$^7$; —(C$_1$-C$_3$alkyl)-NHC(=O)NHR$^7$, —(C$_1$-C$_3$alkyl)-NHS(=O)$_2$NHR$^7$, substituted or unsubstituted C$_2$-C$_{10}$heterocycloalkyl, or substituted or unsubstituted heteroaryl;

each R$^7$ is independently selected from C$_1$-C$_6$alkyl, C$_1$-C$_6$haloalkyl, C$_1$-C$_6$heteroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_6$alkyl-(substituted or unsubstituted C$_3$-C$_{10}$cycloalkyl), —C$_1$-C$_6$alkyl-(substituted or unsubstituted C$_2$-C$_{10}$heterocycloalkyl), —C$_1$-C$_6$alkyl-(substituted or unsubstituted aryl), —C$_1$-C$_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

R$^{8a}$, R$^{8b}$, R$^{8c}$, and R$^{8d}$ are independently selected from H, C$_1$-C$_6$alkyl, C$_1$-C$_6$fluoroalkyl, C$_1$-C$_6$ alkoxy, C$_1$-C$_6$heteroalkyl, and substituted or unsubstituted aryl;

or:

R$^{8a}$ and R$^{8d}$ are as defined above, and R$^{8b}$ and R$^{8c}$ together form a bond;

or:

R$^{8a}$ and R$^{8d}$ are as defined above, and R$^{8b}$ and R$^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

R$^{8c}$ and R$^{8d}$ are as defined above, and R$^{8a}$ and R$^{8b}$ together with the atoms to which they are attached form a substituted or unsubstituted saturated, or partially saturated 3-7 membered spirocycle or heterospirocycle comprising 1-3 heteroatoms selected from S, O and N;

or:

R$^{8a}$ and R$^{8b}$ are as defined above, and R$^{8c}$ and R$^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, cycloalkyl, heterocycloalkyl, aryl or heteroaryl is substituted with 1-3 R$^9$; and each R$^9$ is independently selected from halogen, —OH, —SH, (C═O), CN, C$_1$-C$_4$alkyl, C$_1$-C$_4$ fluoroalkyl, C$_1$-C$_4$ alkoxy, C$_1$-C$_4$ fluoroalkoxy, —NH$_2$, —NH(C$_1$-C$_4$alkyl), —N(C$_1$-C$_4$alkyl)$_2$, —C(═O)OH, —C(═O)NH$_2$, —C(═O)C$_1$-C$_3$alkyl, —S(═O)$_2$CH$_3$, —NH(C$_1$-C$_4$alkyl)-OH, —NH(C$_1$-C$_4$alkyl)-O—(C$_1$-C$_4$alkyl), —O(C$_1$-C$_4$alkyl)-NH$_2$, —O(C$_1$-C$_4$alkyl)-NH—(C$_1$-C$_4$alkyl), and —O(C$_1$-C$_4$alkyl)-N—(C$_1$-C$_4$alkyl)$_2$, or two R$^9$ together with the atoms to which they are attached form a methylene dioxy or ethylene dioxy ring substituted or unsubstituted with halogen, —OH, or C$_1$-C$_3$alkyl.

Among the compounds of Formula C-I described above or below, or pharmaceutically acceptable salt, N-oxide, racemate or stereoisomer thereof, is one group of compounds having the structure of Formula C-II:

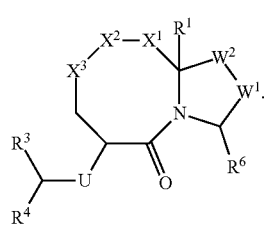

Formula C-II

Among the compounds of Formula C-I described above or below, or pharmaceutically acceptable salt, N-oxide, racemate or stereoisomer thereof, is one group of compounds having the structure of Formula C-III-1, Formula C-III-2 or Formula C-III-3:

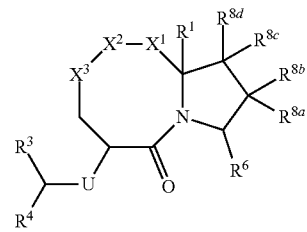

Formula C-III-1

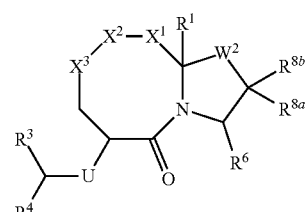

Formula C-III-2

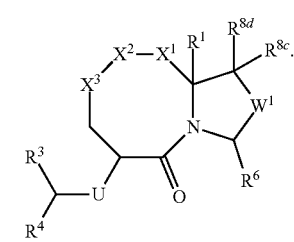

Formula C-III-3

Among the compounds of Formula C-I described above or below, or pharmaceutically acceptable salt, N-oxide, racemate or stereoisomer thereof, is one group of compounds having the structure of Formula C-III-1:

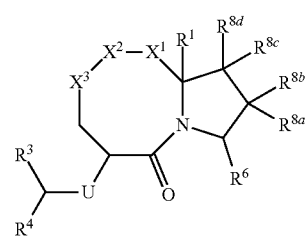

Formula C-III-1

Among the compounds of Formula C-I described above or below, or pharmaceutically acceptable salt, N-oxide, racemate or stereoisomer thereof, is one group of compounds having the structure of Formula C-IV:

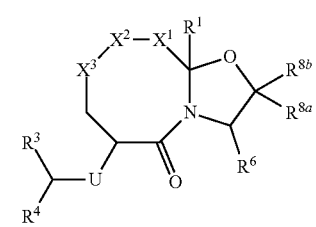

Formula C-IV

Among the compounds of Formula C described above or below, or pharmaceutically acceptable salt, N-oxide, racemate or stereoisomer thereof, is one group of compounds wherein, —U— is —NHC(=O)—, —C(=O)NH—, —NHS(=O)$_2$—, or —S(=O)$_2$NH—.

Among the compounds of Formula C described above or below, or pharmaceutically acceptable salt, N-oxide, racemate or stereoisomer thereof, is one group of compounds wherein, —U— is —NHC(=O)—, or —C(=O)NH—.

Among the compounds of Formula C described above or below, or pharmaceutically acceptable salt, N-oxide, racemate or stereoisomer thereof, is one group of compounds wherein, $R^3$ is $C_1$-$C_3$alkyl.

Among the compounds of Formula C described above or below, or pharmaceutically acceptable salt, N-oxide, racemate or stereoisomer thereof, is one group of compounds wherein, $R^4$ is -NHR$^5$, —N(R$^5$)$_2$, or —N$^+$(R$^5$)$_3$; and each $R^5$ is independently selected from H, $C_1$-$C_3$alkyl, and —$C_1$-$C_3$alkyl-($C_3$-$C_5$cycloalkyl).

Among the compounds of Formula C described above or below, or pharmaceutically acceptable salt, N-oxide, racemate or stereoisomer thereof, is one group of compounds wherein, —U— is —NHC(=O)—, or —C(=O)NH—;

$R^3$ is $C_1$-$C_3$alkyl;

$R^4$ is -NHR$^5$, —N(R$^5$)$_2$, or —N$^+$(R$^5$)$_3$; and each $R^5$ is independently selected from H, $C_1$-$C_3$alkyl, and —$C_1$-$C_3$alkyl-($C_3$-$C_5$cycloalkyl).

Among the compounds of Formula C described above or below, or pharmaceutically acceptable salt, N-oxide, racemate or stereoisomer thereof, is one group of compounds wherein,

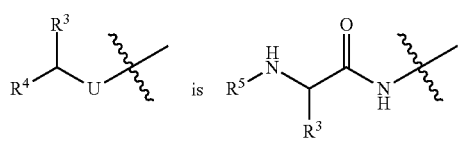

Among the compounds of Formula C described above or below, or pharmaceutically acceptable salt, N-oxide, racemate or stereoisomer thereof, is one group of compounds wherein,

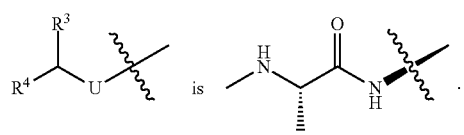

Among the compounds of Formula C described above or below, or pharmaceutically acceptable salt, N-oxide, racemate or stereoisomer thereof, is one group of compounds wherein $R^3$ and $R^5$ together with the atoms to which they are attached form a substituted or unsubstituted 5-7 membered ring.

Among the compounds of Formula C described above or below, or pharmaceutically acceptable salt, N-oxide, racemate or stereoisomer thereof, is one group of compounds, wherein,

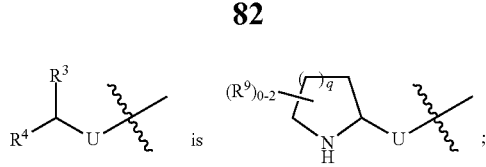

and q is 1, 2 or 3.

Among the compounds of Formula C described above or below, or pharmaceutically acceptable salt, N-oxide, racemate or stereoisomer thereof, is one group of compounds wherein $R^3$ is bonded to a nitrogen atom of U to form a substituted or unsubstituted 5-7 membered ring.

Among the compounds of Formula C described above or below, or pharmaceutically acceptable salt, N-oxide, racemate or stereoisomer thereof, is one group of compounds wherein,

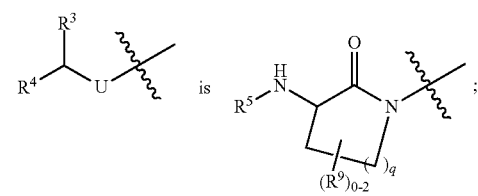

and q is 1, 2 or 3.

Among the compounds of Formula C described above or below, or pharmaceutically acceptable salt, N-oxide, racemate or stereoisomer thereof, is one group of compounds wherein, $X^1$ is selected from N—$R^A$, S, S(O) and S(O)$_2$; and $X^2$ is CH$_2$.

Among the compounds of Formula C-I described above or below, or pharmaceutically acceptable salt, N-oxide, racemate or stereoisomer thereof, is one group of compounds having the structure of Formula C-V-1 or Formula C-V-2 or Formula C-V-3:

Formula C-V-1

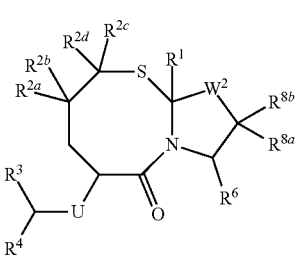

Formula C-V-2

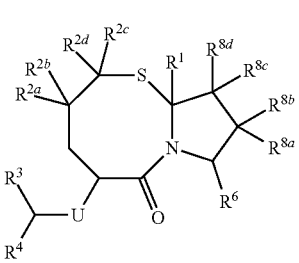

Formula C-V-3

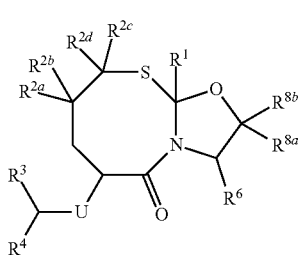

Among the compounds of Formula C-I described above or below, or pharmaceutically acceptable salt, N-oxide, racemate or stereoisomer thereof, is one group of compounds having the structure of Formula C-VI-1 or Formula C-VI-2 or Formula C-VI-3:

Formula C-VI-1

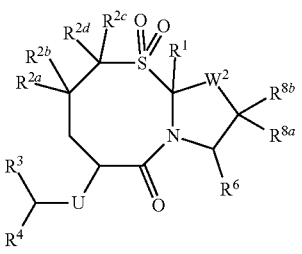

Formula C-VI-2

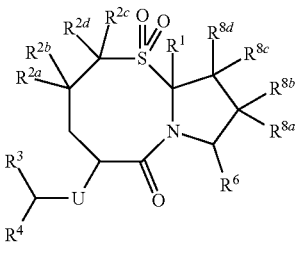

Formula C-VI-3

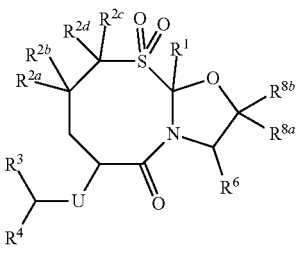

Among the compounds of Formula C-I described above or below, or pharmaceutically acceptable salt, N-oxide, racemate or stereoisomer thereof, is one group of compounds having the structure of Formula C-VII-1 or Formula C-VII-2 or Formula C-VII-3:

Formula C-VII-1

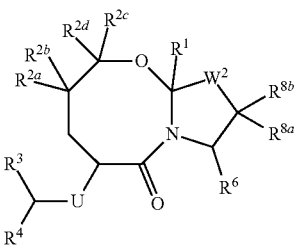

Formula C-VII-2

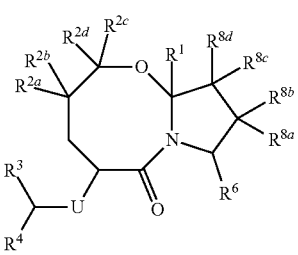

Formula C-VII-3

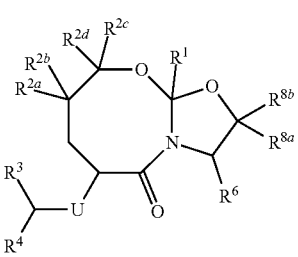

Among the compounds of Formula C-I described above or below, or pharmaceutically acceptable salt, N-oxide, racemate or stereoisomer thereof, is one group of compounds having the structure of Formula C-VIII-1 or Formula C-VIII-2 or Formula C-VIII-3:

Formula C-VIII-1

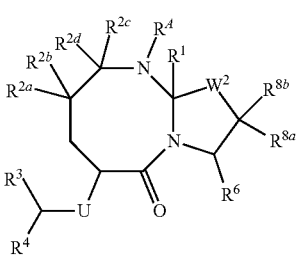

Formula C-VIII-2

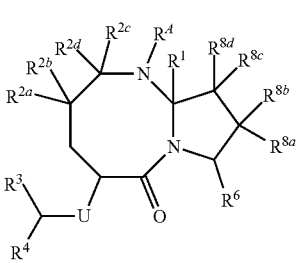

-continued

Formula C-VIII-3

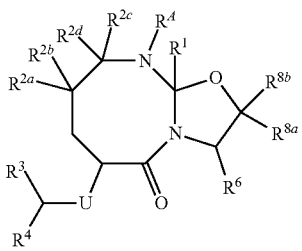

Among the compounds of Formula C-I described above or below, or pharmaceutically acceptable salt, N-oxide, racemate or stereoisomer thereof, is one group of compounds having the structure of Formula C-V-2 or Formula C-VI-2 or Formula C-VII-2 or Formula C-VIII-2:

Formula C-V-2

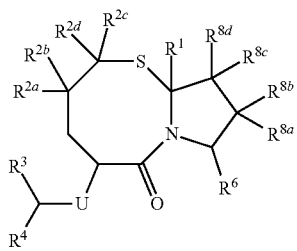

Formula C-VI-2

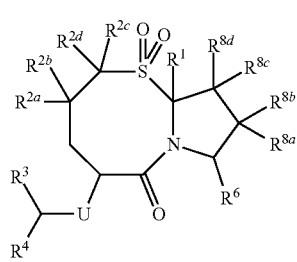

Formula C-VII-2

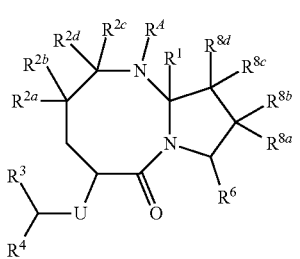

Formula C-VIII-2

Among the compounds of Formula C-I described above or below, or pharmaceutically acceptable salt, N-oxide, racemate or stereoisomer thereof, is one group of compounds wherein $X^1$ is $CH_2$; and
$X^2$ is selected from O, N—$R^A$, S, S(O), and $S(O)_2$.

Among the compounds of Formula C-I described above or below, or pharmaceutically acceptable salt, N-oxide, racemate or stereoisomer thereof, is one group of compounds having the structure of Formula C-IX-1 or Formula C-IX-2:

Formula C-IX-1

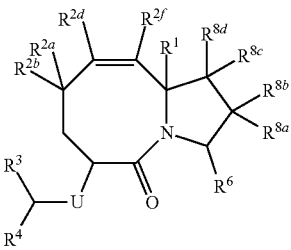

Formula C-IX-2

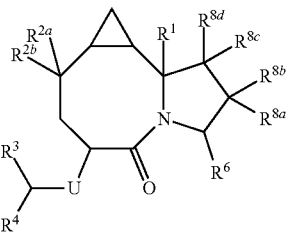

Among the compounds of Formula C-I described above or below, or pharmaceutically acceptable salt, N-oxide, racemate or stereoisomer thereof, is one group of compounds having the structure of Formula C-X-1 or Formula C-X-2:

Formula C-X-1

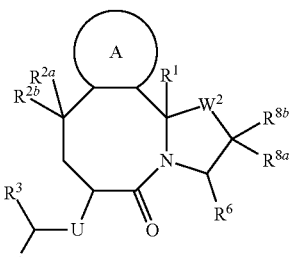

Formula C-X-2

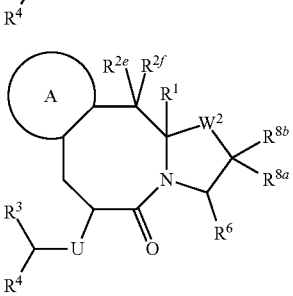

wherein ring A is a fused substituted or unsubstituted saturated or partially saturated 3-10 membered cycloalkyl ring, substituted or unsubstituted saturated or partially saturated 3-10 membered heterocycloalkyl ring, substituted or unsubstituted 5-10 membered aryl ring, or substituted or unsubstituted 5-10 membered heteroaryl ring.

Within such a group of compounds are compounds wherein ring A is selected from indolyl and phenyl.

Among the compounds of Formula C-I described above or below, or pharmaceutically acceptable salt, N-oxide, racemate or stereoisomer thereof, is one group of compounds having the structure of Formula C-XI:

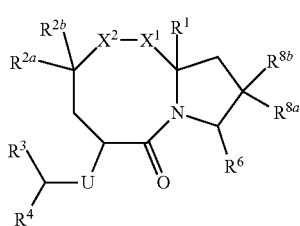

Formula C-XI

Among the compounds of Formula C-I described above or below, or pharmaceutically acceptable salt, N-oxide, racemate or stereoisomer thereof, is one group of compounds having the structure of Formula C-XII:

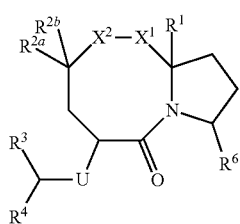

Formula C-XII

Among the compounds of Formula C-I described above or below, or pharmaceutically acceptable salt, N-oxide, racemate or stereoisomer thereof, is one group of compounds having the structure of Formula C-XIII:

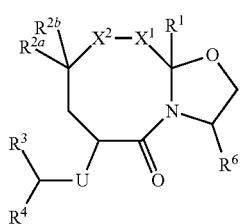

Formula C-XIII

Among the compounds of Formula C-XI, Formula C-XII and Formula C-XIII, is one group of compounds wherein $X^1$ is O, S or $S(O)_2$, and $X^2$ is $CH_2$.

Among the compounds of Formula C-XI, Formula C-XII and Formula C-XIII, is one group of compounds wherein $X^1$ is $N-R^A$, and $X^2CH_2$.

Among the compounds is one group of compounds wherein $R^{2a}$, $R^{2b}$ $R^{2c}$, $R^{2d}$, $R^{2e}$, and $R^{2f}$ are independently H or $C_1$-$C_3$ alkyl; and $R^1$ is H or methyl. Among the compounds is one group of compounds wherein $R^1$ is H.

Among the compounds of Formula C-I described above or below, or pharmaceutically acceptable salt, N-oxide, racemate or stereoisomer thereof, is one group of compounds wherein $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N.

Within such a group of compounds are compounds having the structure of Formula C-XIV:

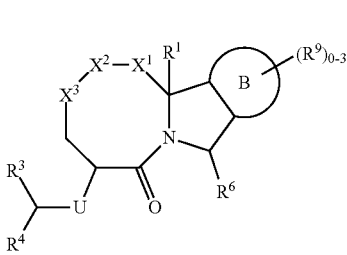

Formula C-XIV where ring B is an aryl or heteroaryl ring.

In some embodiments, ring B is an aryl. In some embodiments, ring B is phenyl. In some embodiments, ring B is a heteroaryl ring. In some embodiments, ring B is a monocyclic heteroaryl ring or a bicyclic heteroaryl ring. In some embodiments, ring B is a monocyclic heteroaryl ring. In some embodiments, ring B is a bicyclic heteroaryl ring. In some embodiments, ring B is selected from phenyl, pyridinyl and thiophenyl. In some embodiments, ring B is selected from pyridinyl and thiophenyl.

Among the compounds of Formula C-I described above or below, or pharmaceutically acceptable salt, N-oxide, racemate or stereoisomer thereof, is one group of compounds wherein $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N; or $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N.

Within such a group of compounds are compounds having the structure of Formula C-XV-1, Formula C-XV-2, Formula C-XV-3, or Formula C-XV-4:

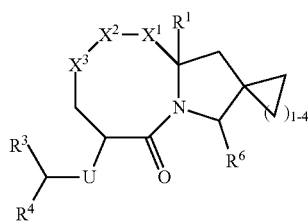

Formula C-XV-1

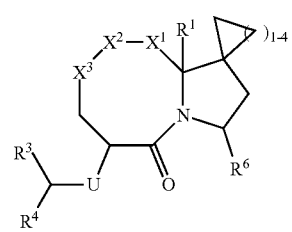

Formula C-XV-2

Formula C-XV-3

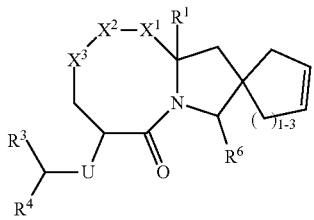

Formula C-XV-4

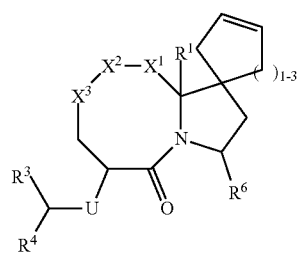

or having the structure of Formula C-XVI-1 or Formula C-XVI-2:

Formula C-XVI-1

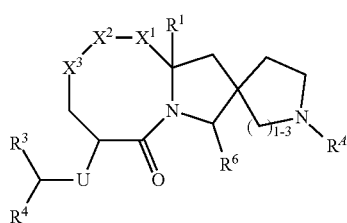

Formula C-XVI-2

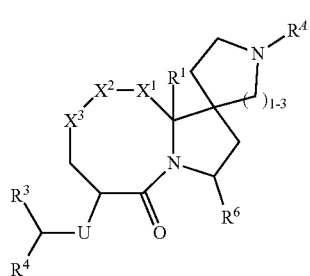

wherein $R^A$ is H, $C_1$-$C_3$alkyl or —C(=O)$C_1$-$C_3$alkyl.

Among the compounds of Formula C-I described above or below, or pharmaceutically acceptable salt, N-oxide, racemate or stereoisomer thereof, is one group of compounds wherein $R^{8b}$ and $R^{8c}$ together form a bond.

Within such a group of compounds are compounds having the structure of Formula C-XVII:

Formula C-XVII

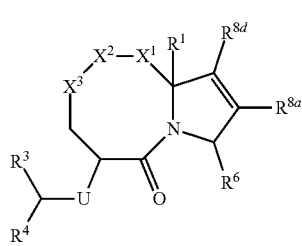

Among the compounds of Formula C described above or below, or pharmaceutically acceptable salt, N-oxide, racemate or stereoisomer thereof, is one group of compounds having the structure of Formula C-XVIII:

Formula C-XVIII

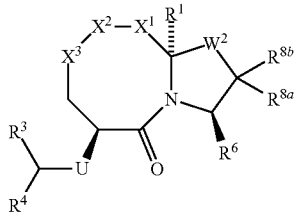

Among the compounds of Formula C described above or below, or pharmaceutically acceptable salt, N-oxide, racemate or stereoisomer thereof, is one group of compounds having the structure of Formula C-XIX:

Formula C-XIX

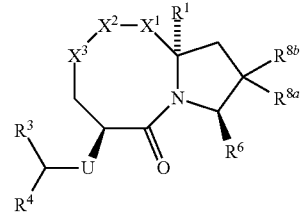

Among the compounds of Formula C described above or below, or pharmaceutically acceptable salt, N-oxide, racemate or stereoisomer thereof, is one group of compounds having the structure of Formula C-XX:

Formula C-XX

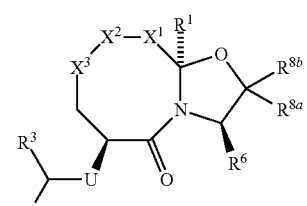

Among the compounds of Formula C described above or below, or pharmaceutically acceptable salt, N-oxide, racemate or stereoisomer thereof, is one group of compounds having the structure of Formula C-XXI, or pharmaceutically acceptable salt, N-oxide, racemate or stereoisomer thereof:

Formula C-XXI

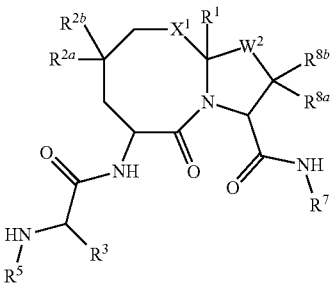

wherein,
$W^2$ is O, S, or $C(R^{8c})(R^{8d})$;
$R^1$ is H, or $C_1$-$C_6$alkyl;
$X^1$ is O, N—$R^A$, S, S(O), or $S(O)_2$;
$R^A$ is H, $C_1$-$C_6$alkyl, —C(=O)$C_1$-$C_6$alkyl, substituted or unsubstituted aryl, or substituted or unsubstituted heteroaryl;
$R^{2a}$ and $R^{2b}$ are independently selected from H, substituted or unsubstituted $C_1$-$C_6$alkyl, and —C(=O)$R^B$;
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^D R^E$;
$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
$R^3$ is $C_1$-$C_3$alkyl, or $C_1$-$C_3$fluoroalkyl;
each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);
p is 0, 1 or 2;
$R^{8a}$ and $R^{8b}$ are independently selected from H, $C_1$-$C_6$alkyl, and $C_1$-$C_6$fluoroalkyl;
$R^{8c}$ and $R^{8d}$ are independently selected from H, $C_1$-$C_6$alkyl, and $C_1$-$C_6$fluoroalkyl;
where each substituted alkyl, heteroalkyl, cycloalkyl, heterocycloalkyl, aryl or heteroaryl is substituted with 1-3 $R^9$; and
each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —N($C_1$-$C_4$alkyl)$_2$, —C(=O)OH, —C(=O)$NH_2$, —C(=O)$C_1$-$C_3$alkyl, —$S(=O)_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula C described above or below, or pharmaceutically acceptable salt, N-oxide, racemate or stereoisomer thereof, is one group of compounds wherein,
$R^{2a}$, $R^{2b}$ $R^{2c}$, $R^{2d}$, $R^{2e}$, and $R^{2f}$ are independently selected from H, $C_1$-$C_3$alkyl and —C(=O)$R^B$; and
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl).

Among the compounds of Formula C described above or below, or pharmaceutically acceptable salt, N-oxide, racemate or stereoisomer thereof, is one group of compounds wherein $R^{2a}$, $R^{2b}$ $R^{2c}$, $R^{2d}$, $R^{2e}$, and $R^{2f}$are independently H or $C_1$-$C_3$ alkyl.

Among the compounds of Formula C described above or below, or pharmaceutically acceptable salt, N-oxide, racemate or stereoisomer thereof, is one group of compounds wherein $R^1$ is H or methyl.

Among the compounds of Formula C described above or below, or pharmaceutically acceptable salt, N-oxide, racemate or stereoisomer thereof, is one group of compounds wherein $R^1$ is H.

Among the compounds of Formula C described above or below, or pharmaceutically acceptable salt, N-oxide, racemate or stereoisomer thereof, is one group of compounds wherein,
$R^6$ is —NHC(=O)$R^7$, —C(=O)$NHR^7$, —$NHS(=O)_2 R^7$, —$S(=O)_2NHR^7$; —NHC(=O)$NHR^7$, —$NHS(=O)_2NHR^7$, —($C_1$-$C_3$alkyl)-NHC(=O)$R^7$, —($C_1$-$C_3$alkyl)-C(=O)$NHR^5$, —($C_1$-$C_3$alkyl)-$NHS(=O)_2 R^7$, —($C_1$-$C_3$alkyl)-$S(=O)_2NHR^7$; —($C_1$-$C_3$alkyl)-NHC(=O)$NHR^7$, or —($C_1$-$C_3$alkyl)-$NHS(=O)_2 NHR^7$.

Among the compounds of Formula C described above or below, or pharmaceutically acceptable salt, N-oxide, racemate or stereoisomer thereof, is one group of compounds wherein,
$R^6$ is substituted or unsubstituted $C_2$-$C_{10}$heterocycloalkyl, or substituted or unsubstituted heteroaryl.

Among the compounds of Formula C described above or below, or pharmaceutically acceptable salt, N-oxide, racemate or stereoisomer thereof, is one group of compounds wherein,
$R^6$ is a substituted or unsubstituted $C_2$-$C_{10}$heterocycloalkyl.

Among the compounds of Formula C described above or below, or pharmaceutically acceptable salt, N-oxide, racemate or stereoisomer thereof, is one group of compounds wherein,
  $R^6$ is a substituted or unsubstituted heteroaryl.

Among the compounds of Formula C described above or below, or pharmaceutically acceptable salt, N-oxide, racemate or stereoisomer thereof, is one group of compounds wherein,
  $R^6$ is —C(=O)NHR$^7$, —S(=O)$_2$NHR$^7$, —(C$_1$-C$_3$alkyl)-C(=O)NHR$^5$, or —(C$_1$-C$_3$alkyl)-S(=O)$_2$NHR$^7$.

Among the compounds of Formula C described above or below, or pharmaceutically acceptable salt, N-oxide, racemate or stereoisomer thereof, is one group of compounds wherein,
  $R^6$ is —C(=O)NHR$^7$, or —S(=O)$_2$NHR$^7$.

Among the compounds of Formula C described above or below, or pharmaceutically acceptable salt, N-oxide, racemate or stereoisomer thereof, is one group of compounds wherein $R^6$ is —C(=O)NHR$^7$.

Among the compounds of Formula C described above or below, or pharmaceutically acceptable salt, N-oxide, racemate or stereoisomer thereof, is one group of compounds wherein,
  each $R^7$ is independently selected from a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_6$alkyl-(substituted or unsubstituted C$_3$-C$_{10}$cycloalkyl), —C$_1$-C$_6$alkyl-(substituted or unsubstituted C$_2$-C$_{10}$heterocycloalkyl, —C$_1$-C$_6$alkyl-(substituted or unsubstituted aryl), —C$_1$-C$_6$alkyl-(substituted or unsubstituted heteroaryl), —(CH$_2$)$_p$—CH(substituted or unsubstituted aryl)$_2$-(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl).

Among the compounds of Formula C described above or below, or pharmaceutically acceptable salt, N-oxide, racemate or stereoisomer thereof, is one group of compounds wherein,
  $R^7$ is independently selected from a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted heteroaryl, and —(CH$_2$)$_p$—CH(substituted or unsubstituted aryl)$_2$.

Among the compounds of Formula C described above or below, or pharmaceutically acceptable salt, N-oxide, racemate or stereoisomer thereof, is one group of compounds wherein,
$R^7$ is selected from

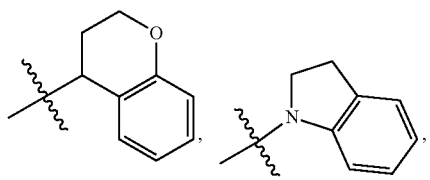

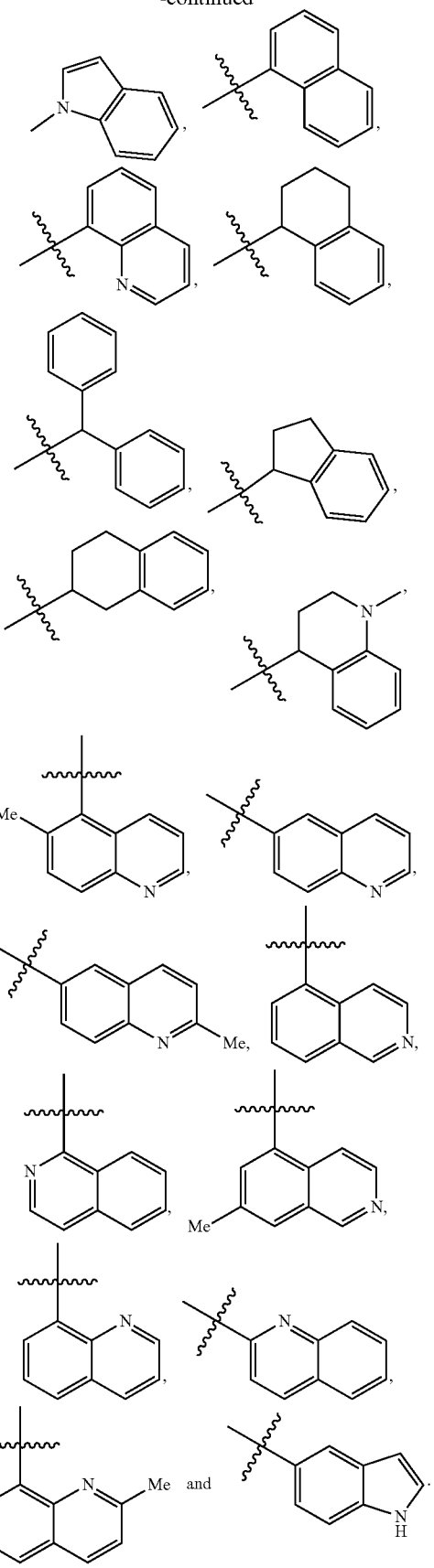

Among the compounds of Formula C described above or below, or pharmaceutically acceptable salt, N-oxide, racemate or stereoisomer thereof, is one group of compounds wherein, $W^2$ is $C(R^{8c})(R^{8d})$;

$R^1$ is H;

$R^{2a}$, $R^{2b}$ are independently selected from H, and $C_1$-$C_3$alkyl;

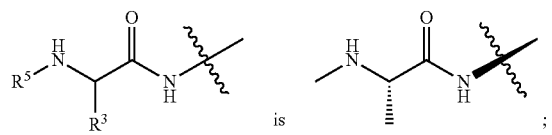

is $R^{8a}$, $R^{8b}$, $R^{8c}$, $R^{8d}$ are independently selected from H and $C_1$-$C_3$alkyl.

Any combination of the groups described above or below for the various variables is contemplated herein. Throughout the specification, groups and substituents thereof are chosen by one skilled in the field to provide stable moieties and compounds.

Among the compounds of Formula C described above or below, or pharmaceutically acceptable salt, N-oxide, racemate or stereoisomer thereof, are compounds selected from:

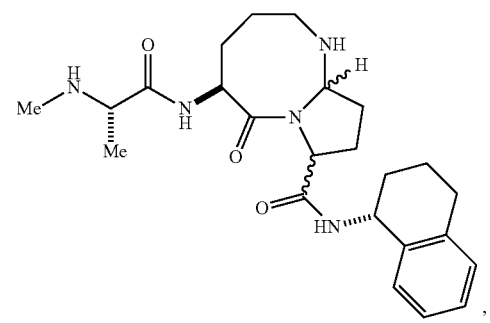

,

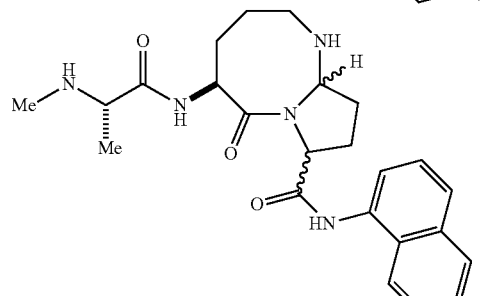

,

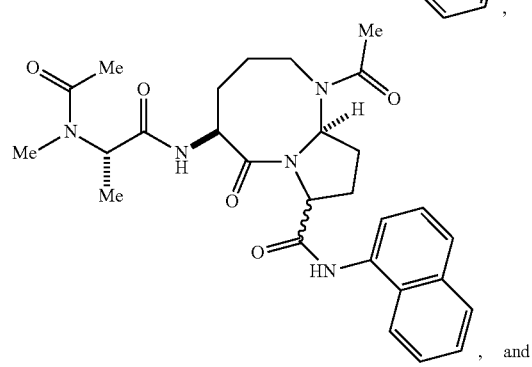

, and

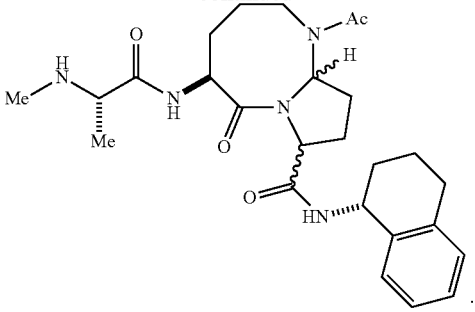

Also provided herein are pharmaceutical composition comprising a compound of Formula C, or pharmaceutically acceptable salt, N-oxide, racemate or stereoisomer thereof, and a pharmaceutically acceptable carrier.

Formula D—Seven-Six Ring Systems

In one aspect, the IAP antagonist for use in any of the methods, uses, compositions described herein is a Formula D compound. As used herein, Formula D includes compounds of Formula D-I, Formula D-II, Formula D-II-1, Formula D-II-2, Formula D-II-3, Formula D-III, Formula D-IV, Formula D-V-1, Formula D-V-2, Formula D-V-3, Formula D-VI-1, Formula D-VI-2, Formula D-VI-3, Formula D-VII-1, Formula D-VII-2, Formula D-VII-3, Formula D-VIII-1, Formula D-VIII-2, Formula D-VIII-3, Formula D-IX-1, Formula D-IX-2, Formula D-X, Formula D-XI-1, Formula D-XI-2, Formula D-XII-1, Formula D-XII-2, Formula D-XIII, Formula D-XIV, Formula D-XV, Formula D-XVI-1, Formula D-XVI-2, Formula D-XVI-3, Formula D-XVI-4, Formula D-XVII-1, Formula D-XVII-2, Formula D-XVIII-1, Formula D-XVIII-2, Formula D-XIX, Formula D-XX, Formula D-XXI and Formula D-XXII.

In one aspect, described herein is a compound of Formula D-I, or a pharmaceutically acceptable salt, N-oxide, racemate or stereoisomer thereof, as described in the summary of the invention.

A compound having the structure of Formula D-I, pharmaceutically acceptable salt, N-oxide, racemate or stereoisomer thereof:

Formula D-I

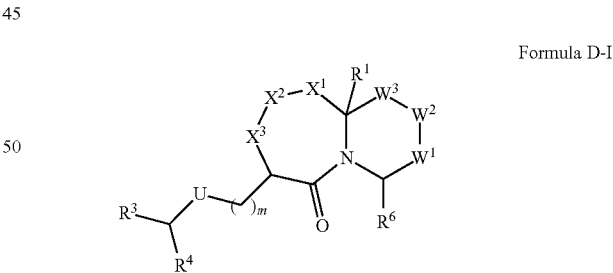

wherein, $R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl); when $X^1$ is selected from N—$R^4$, S, S(O) and $S(O)_2$, then $X^2$ is $CR^{2c}R^{2d}$, and $X^3$ is $CR^{2a}R^{2b}$;

or when $X^1$ is O, then $X^2$ is selected from $CR^{2c}R^{2d}$ and N—$R^4$, and $X^3$ is $CR^{2a}R^{2b}$;

or:
- when $X^1$ is $CH_2$, then $X^2$ is selected from O, N—$R^A$, S, S(O), and S(O)$_2$, and $X^3$ is $CR^{2a}R^{2b}$;

or:
- $X^1$ is $CR^{2e}R^{2f}$ and $X^2$ is $CR^{2c}R^{2d}$, and $R^{2e}$ and $R^{2c}$ together form a bond, and $X^3$ is $CR^{2a}R^{2b}$;

or:
- $X^1$ and $X^3$ are both $CH_2$ and $X^2$ is C=O, C=C($R^C$)$_2$, or C=N$R^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:
- $X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:
- $X^2$ and $X^3$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ is $CR^{2e}R^{2f}$;

$W^1$ is O, S, N—$R^A$, or $C(R^{8a})(R^{8b})$;
$W^2$ is O, S, N—$R^A$, or $C(R^{8c})(R^{8d})$;
$W^3$ is O, S, N—$R^A$, or $C(R^{8e})(R^{8f})$; provided that the ring comprising $W^1$, $W^2$ and $W^3$ does not comprise two adjacent oxygen atoms or sulfur atoms;
$R^A$ is H, $C_1$-$C_6$alkyl, —C(=O)$C_1$-$C_6$alkyl, substituted or unsubstituted aryl, or substituted or unsubstituted heteroaryl;
$R^{2a}$, $R^{2b}$, $R^{2c}$, $R^{2d}$ $R^{2e}$, and $R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;
$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —N$R^D R^E$;
$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;
—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;
$R^3$ is $C_1$-$C_3$alkyl, or $C_1$-$C_3$fluoroalkyl;
$R^4$ is —NH$R^5$, —N($R^5$)$_2$, —N$^+$($R^5$)$_3$ or —O$R^5$;
each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:
- $R^3$ and $R^5$ together with the atoms to which they are attached form a substituted or unsubstituted 5-7 membered ring;

or:
- $R^3$ is bonded to a nitrogen atom of U to form a substituted or unsubstituted 5-7 membered ring;

$R^6$ is —NHC(=O)$R^7$, —C(=O)NH$R^7$, —NHS(=O)$_2$$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^5$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;
$R^{8a}$, $R^{8b}$, $R^{8c}$, $R^{8d}$, $R^{8e}$ and $R^{8f}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:
- $R^{8a}$, $R^{8d}$, $R^{8e}$ and $R^{8f}$ are as defined above, and $R^{8b}$ and $R^{8c}$ together form a bond;

or:
- $R^{8a}$, $R^{8b}$, $R^{8d}$, and $R^{8f}$ are as defined above, and $R^{8c}$ and $R^{8e}$ together form a bond;

or:
- $R^{8a}$, $R^{8d}$, $R^{8e}$ and $R^{8f}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8a}$, $R^{8b}$, $R^{8d}$, and $R^{8f}$ are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$, $R^{8d}$, $R^{8e}$ and $R^{8f}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8e}$ and $R^{8f}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8c}$, and $R^{8d}$ are as defined above, and $R^{8e}$ and $R^{8f}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —$NH(C_1$-$C_4$alkyl), —$N(C_1$-$C_4$alkyl$)_2$, —C(=O)OH, —C(=O)$NH_2$, —C(=O)$C_1$-$C_3$alkyl, —S(=O$)_2CH_3$, —$NH(C_1$-$C_4$alkyl)-OH, —$NH(C_1$-$C_4$alkyl)-O—($C_1$-$C_4$alkyl), —O($C_1$-$C_4$alkyl)-$NH_2$, —O($C_1$-$C_4$alkyl)-NH—($C_1$-$C_4$alkyl), and —O($C_1$-$C_4$alkyl)-N—($C_1$-$C_4$alkyl$)_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula D-I described above or below, or pharmaceutically acceptable salt, N-oxide, racemate or stereoisomer thereof, is one group of compounds having the structure of Formula D-II:

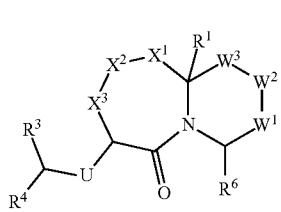

Formula D-II

Among the compounds of Formula D-I described above or below, or pharmaceutically acceptable salt, N-oxide, racemate or stereoisomer thereof, is one group of compounds having the structure of Formula D-II-1, Formula D-II-2, or Formula D-II-3:

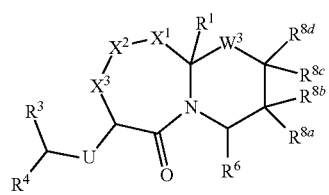

Formula D-II-1

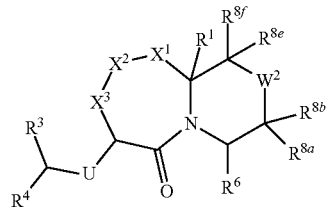

Formula D-II-2

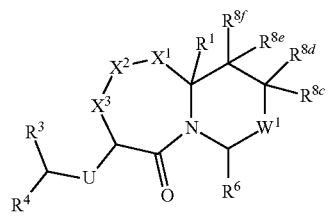

Formula D-II-3

Among the compounds of Formula D-I described above or below, or pharmaceutically acceptable salt, N-oxide, racemate or stereoisomer thereof, is one group of compounds having the structure of Formula D-III:

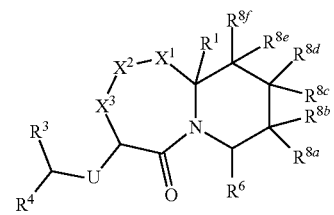

Formula D-III

Among the compounds of Formula D-I described above or below, or pharmaceutically acceptable salt, N-oxide, racemate or stereoisomer thereof, is one group of compounds having the structure of Formula D-IV:

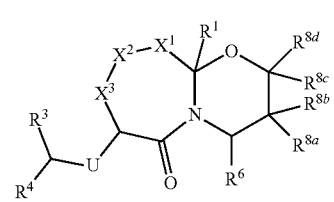

Formula D-IV

Among the compounds of Formula D described above or below, or pharmaceutically acceptable salt, N-oxide, racemate or stereoisomer thereof, is one group of compounds wherein,
—U— is —NHC(=O)—, —C(=O)NH—, —NHS(=O)$_2$—, or —S(=O)$_2$NH—.

Among the compounds of Formula D described above or below, or pharmaceutically acceptable salt, N-oxide, racemate or stereoisomer thereof, is one group of compounds wherein,
—U— is —NHC(=O)—, or —C(=O)NH—.

Among the compounds of Formula D described above or below, or pharmaceutically acceptable salt, N-oxide, racemate or stereoisomer thereof, is one group of compounds wherein,
$R^3$ is $C_1$-$C_3$alkyl.

Among the compounds of Formula D described above or below, or pharmaceutically acceptable salt, N-oxide, racemate or stereoisomer thereof, is one group of compounds wherein,
$R^4$ is -NHR$^5$, —N(R$^5$)$_2$, or —N(R$^5$)$_3$; and
each $R^5$ is independently selected from H, $C_1$-$C_3$alkyl, and —$C_1$-$C_3$alkyl-($C_3$-$C_5$cycloalkyl).

Among the compounds of Formula D described above or below, or pharmaceutically acceptable salt, N-oxide, racemate or stereoisomer thereof, is one group of compounds wherein,
—U— is —NHC(=O)—, or —C(=O)NH—;
$R^3$ is $C_1$-$C_3$alkyl;
$R^4$ is -NHR$^5$, —N(R$^5$)$_2$, or —N(R$^5$)$_3$; and
each $R^5$ is independently selected from H, $C_1$-$C_3$alkyl, and —$C_1$-$C_3$alkyl-($C_3$-$C_5$cycloalkyl).

Among the compounds of Formula D described above or below, or pharmaceutically acceptable salt, N-oxide, racemate or stereoisomer thereof, is one group of compounds wherein,

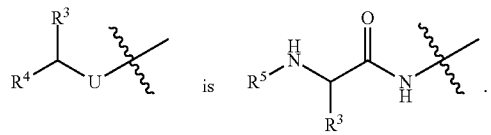

Among the compounds of Formula D described above or below, or pharmaceutically acceptable salt, N-oxide, racemate or stereoisomer thereof, is one group of compounds wherein,

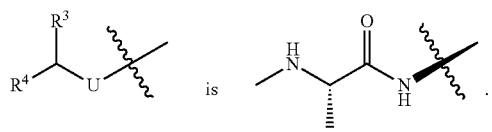

Among the compounds of Formula D described above or below, or pharmaceutically acceptable salt, N-oxide, racemate or stereoisomer thereof, is one group of compounds wherein $R^3$ and $R^5$ together with the atoms to which they are attached form a substituted or unsubstituted 5-7 membered ring.

Among the compounds of Formula D described above or below, or pharmaceutically acceptable salt, N-oxide, racemate or stereoisomer thereof, is one group of compounds wherein,

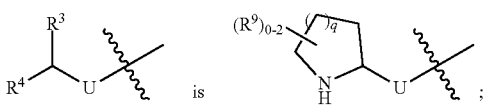

and q is 1, 2 or 3.

Among the compounds of Formula D described above or below, or pharmaceutically acceptable salt, N-oxide, racemate or stereoisomer thereof, is one group of compounds wherein $R^3$ is bonded to a nitrogen atom of U to form a substituted or unsubstituted 5-7 membered ring.

Among the compounds of Formula D described above or below, or pharmaceutically acceptable salt, N-oxide, racemate or stereoisomer thereof, is one group of compounds wherein,

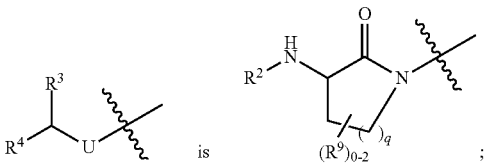

and q is 1, 2 or 3.

Among the compounds of Formula D-I described above or below, or pharmaceutically acceptable salt, N-oxide, racemate or stereoisomer thereof, is one group of compounds wherein,
$X^1$ is selected from N—R$^A$, S, S(O) and S(O)$_2$; and
$X^2$ is CH$_2$.

Among the compounds of Formula D-I described above or below, or pharmaceutically acceptable salt, N-oxide, racemate or stereoisomer thereof, is one group of compounds having the structure of Formula D-V-1, Formula D-V-2, or Formula D-V-3:

Formula D-V-1

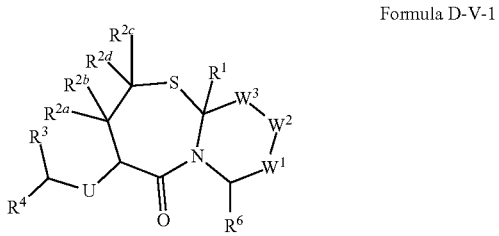

Formula D-V-2

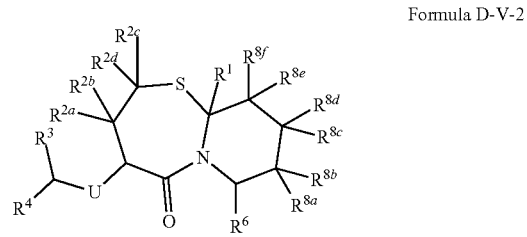

Formula D-V-3

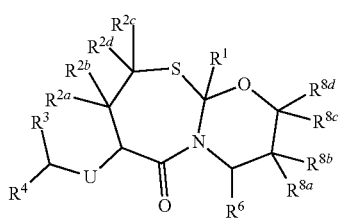

Among the compounds of Formula D-I described above or below, or pharmaceutically acceptable salt, N-oxide, racemate or stereoisomer thereof, is one group of compounds having the structure of Formula D-VI-1, Formula D-VI-2, Formula D-VI-3:

Formula D-VI-1

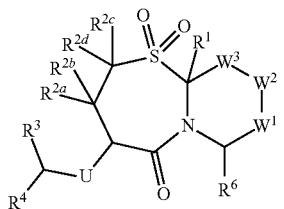

Formula D-VI-2

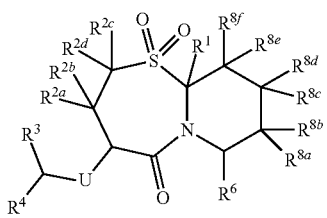

Formula D-VI-3

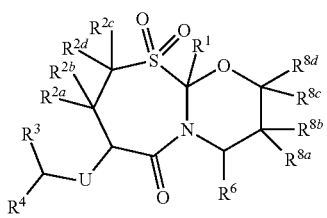

Among the compounds of Formula D-I described above or below, or pharmaceutically acceptable salt, N-oxide, racemate or stereoisomer thereof, is one group of compounds having the structure of Formula D-VII-1, Formula D-VII-2 or Formula D-VII-3

Formula D-VII-1

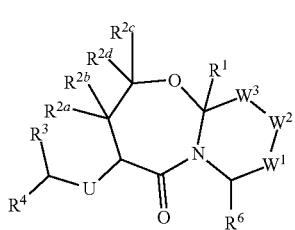

Formula D-VII-2

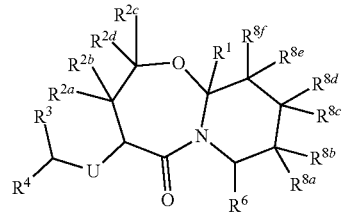

Formula D-VII-3

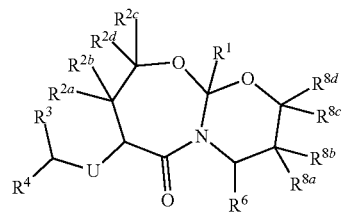

Among the compounds of Formula D-I described above or below, or pharmaceutically acceptable salt, N-oxide, racemate or stereoisomer thereof, is one group of compounds having the structure of Formula D-V-2, Formula D-VI-2, or Formula D-VII-2:

Formula D-V-2

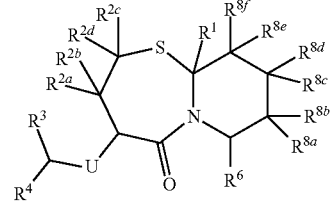

Formula D-VI-2

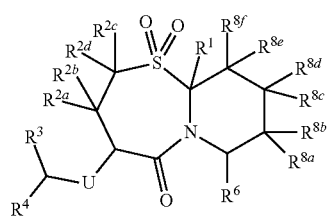

Formula D-VII-2

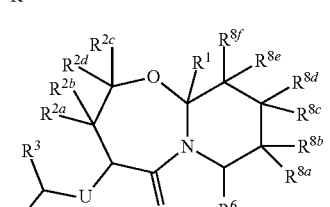

Among the compounds of Formula D-I described above or below, or pharmaceutically acceptable salt, N-oxide, racemate or stereoisomer thereof, is one group wherein $R^1$ is H or methyl; $R^{2a}$, $R^{2b}$, $R^{2c}$, $R^{2d}$, $R^{2e}$ and $R^{2f}$ are independently H or $C_1$-$C_3$ alkyl; $R^{8a}$, $R^{8b}$, $R^{8c}$, $R^{8d}$, $R^{8e}$, and $R^{8f}$ are independently H or $C_1$-$C_3$ alkyl.

Among the compounds of Formula D-I described above or below, or pharmaceutically acceptable salt, N-oxide, racemate or stereoisomer thereof, is one group wherein $R^1$ is H.

Among the compounds of Formula D-I described above or below, or pharmaceutically acceptable salt, N-oxide, racemate or stereoisomer thereof, is one group of compounds having the structure of Formula D-VIII-1, Formula D-VIII-2, or Formula D-VIII-3:

Formula D-VIII-1

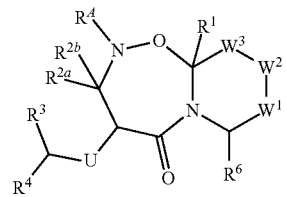

Formula D-VIII-2

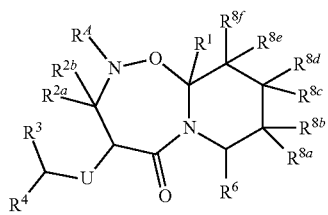

Formula D-VIII-3

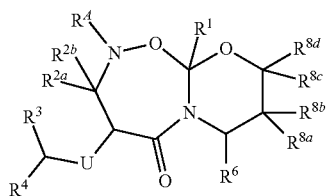

Among the compounds of Formula D-I described above or below, or pharmaceutically acceptable salt, N-oxide, racemate or stereoisomer thereof, is one group of compounds wherein $X^1$ is $CH_2$; and $X^2$ is selected from O, N—$R^4$, S, S(O), and $S(O)_2$.

Among the compounds of Formula D-I described above or below, or pharmaceutically acceptable salt, N-oxide, racemate or stereoisomer thereof, is one group of compounds having the structure of Formula D-IX-1 or Formula D-IX-2:

Formula D-IX-1

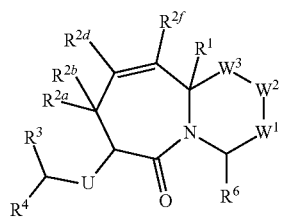

Formula D-IX-2

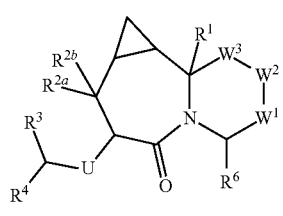

Among the compounds of Formula D-I described above or below, or pharmaceutically acceptable salt, N-oxide, racemate or stereoisomer thereof, is one group of compounds having the structure of Formula D-X:

Formula D-X

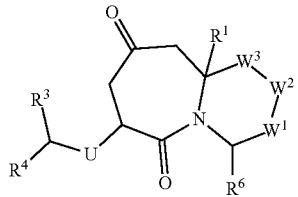

Among the compounds of Formula D-I described above or below, or pharmaceutically acceptable salt, N-oxide, racemate or stereoisomer thereof, is one group of compounds having the structure of Formula D-XI-1 or Formula D-XI-2:

Formula D-XI-1

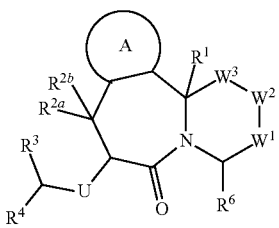

Formula D-XI-2

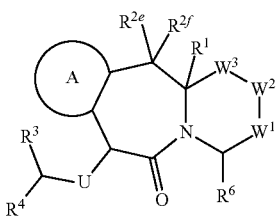

wherein, ring A is a fused substituted or unsubstituted saturated or partially saturated 3-10 membered cycloalkyl ring, substituted or unsubstituted saturated or partially saturated 3-10 membered heterocycloalkyl ring, substituted or unsubstituted 5-10 membered aryl ring, or substituted or unsubstituted 5-10 membered heteroaryl ring.

Within this group of compounds are compounds wherein ring A is selected from indolyl and phenyl.

Among the compounds of Formula D-I described above or below, or pharmaceutically acceptable salt, N-oxide, racemate or stereoisomer thereof, is one group of compounds having the structure of Formula D-XII-1 or Formula D-XII-2:

Formula D-XII-1

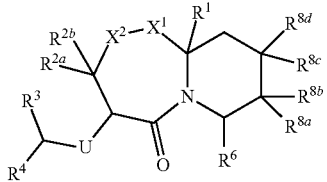

Formula D-XII-2

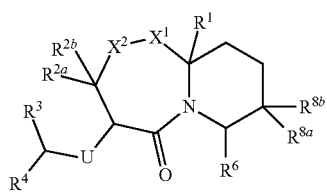

Within such a group of compounds wherein $R^{8a}$ and $R^{8b}$ are independently selected from H and $C_1$-$C_3$alkyl.

Among the compounds of Formula D-I described above or below, or pharmaceutically acceptable salt, N-oxide, racemate or stereoisomer thereof, is one group of compounds having the structure of Formula D-XIII:

Formula D-XIII

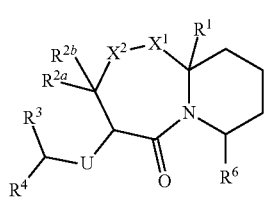

Among the compounds of Formula D-I described above or below, or pharmaceutically acceptable salt, N-oxide, racemate or stereoisomer thereof, is one group of compounds having the structure of Formula D-XIV:

Formula D-XIV

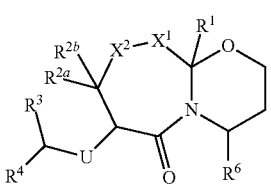

Among the compounds of Formula D-XII, Formula D-XIII and Formula D-XIV are compounds wherein $X^1$ is O, S or $S(O)_2$, and $X^2$ is $CH_2$.

Among the compounds of Formula D-XII, Formula D-XIII and Formula D-XIV are compounds wherein $X^1$ is O, and $X^2$ is N—$R^A$.

Among the compounds of Formula D-I described above or below, or pharmaceutically acceptable salt, N-oxide, racemate or stereoisomer thereof, is one group of compounds wherein $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N.

Within such a group of compounds are compounds having the structure of Formula D-XV:

Formula D-XV

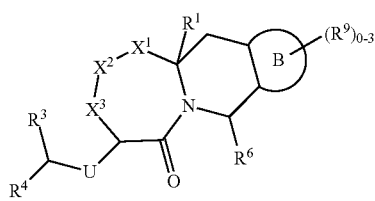

wherein ring B is an aryl or heteroaryl ring.

In some embodiments, ring B is an aryl. In some embodiments, ring B is phenyl. In some embodiments, ring B is a heteroaryl ring. In some embodiments, ring B is a monocyclic heteroaryl ring or a bicyclic heteroaryl ring. In some embodiments, ring B is a monocyclic heteroaryl ring. In some embodiments, ring B is a bicyclic heteroaryl ring. In some embodiments, ring B is selected from phenyl, pyridinyl and thiophenyl. In some embodiments, ring B is selected from pyridinyl and thiophenyl.

Among the compounds of Formula D-I described above or below, or pharmaceutically acceptable salt, N-oxide, racemate or stereoisomer thereof, is one group of compounds wherein $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N or $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N.

Within such a group of compounds are compounds having the structure of Formula D-XVI-1, Formula D-XVI-2, Formula D-XVI-3, or Formula D-XVI-4:

Formula D-XVI-1

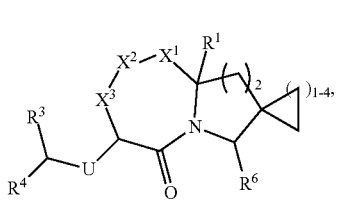

Formula D-XVI-2

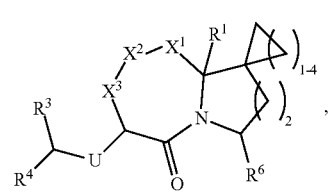

Formula D-XVI-3

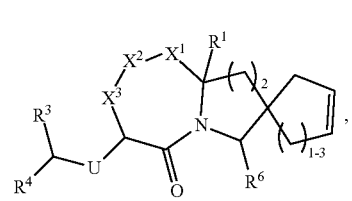

Formula D-XVI-4

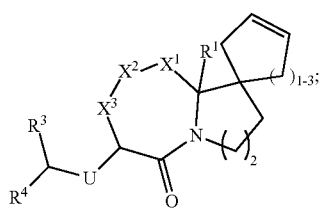

or compounds having the structure of Formula D-XVII-1 or Formula D-XVII-2:

Formula D-XVII-1

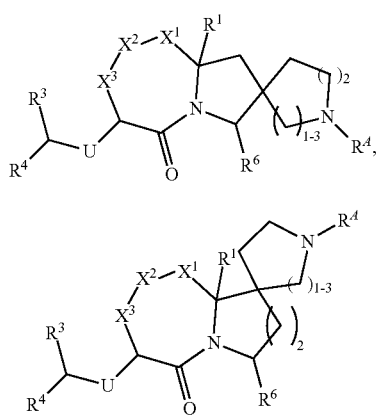

Formula D-XVII-2 wherein $R^A$ is H, $C_1$-$C_3$alkyl or —C(=O)$C_1$-$C_3$alkyl.

Among the compounds of Formula D-I described above or below, or pharmaceutically acceptable salt, N-oxide, racemate or stereoisomer thereof, is one group of compounds wherein $R^{8b}$ and $R^{8c}$ together form a bond.

Among the compounds of Formula D-I described above or below, or pharmaceutically acceptable salt, N-oxide, racemate or stereoisomer thereof, is one group of compounds wherein $R^{8c}$ and $R^{8e}$ together form a bond.

Within such a group of compounds are compounds having the structure of Formula D-XVIII-1 or Formula D-XVIII-2:

Formula D-XVIII-1

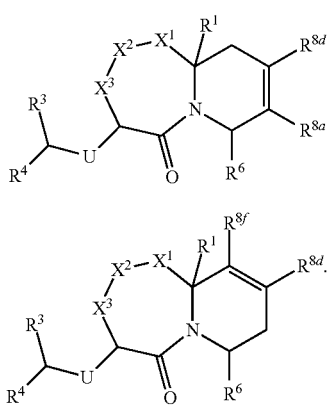

Formula D-XVIII-2

Among the compounds of Formula D described above or below, or pharmaceutically acceptable salt, N-oxide, racemate or stereoisomer thereof, is one group of compounds having the structure of Formula D-XIX:

Formula D-XIX

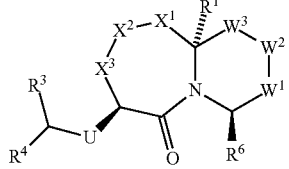

Among the compounds of Formula D described above or below, or pharmaceutically acceptable salt, N-oxide, racemate or stereoisomer thereof, is one group of compounds having the structure of Formula D-XX:

Formula D-XX

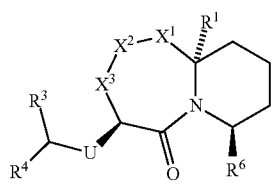

Among the compounds of Formula D described above or below, or pharmaceutically acceptable salt, N-oxide, racemate or stereoisomer thereof, is one group of compounds having the structure of Formula D-XXI:

Formula D-XXI

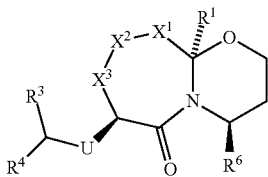

Among the compounds of Formula D described above or below, or pharmaceutically acceptable salt, N-oxide, racemate or stereoisomer thereof, is one group of compounds having the structure of Formula D-XXII, or pharmaceutically acceptable salt, N-oxide, racemate or stereoisomer thereof:

Formula D-XXII

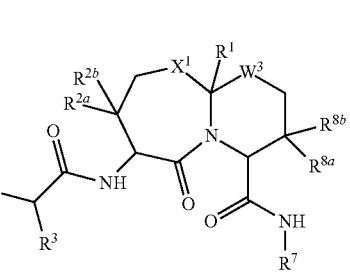

wherein,
$W^3$ is O, S, or C($R^{8e}$)($R^{8f}$);
$R^1$ is H, or $C_1$-$C_6$alkyl;
$X^1$ is O, N—$R^A$, S, S(O), or S(O)$_2$;
$R^A$ is H, $C_1$-$C_6$alkyl, —C(=O)$C_1$-$C_6$alkyl, substituted or unsubstituted aryl, or substituted or unsubstituted heteroaryl;
$R^{2a}$ and $R^{2b}$ are independently selected from H, substituted or unsubstituted $C_1$-$C_6$alkyl, and —C(=O)$R^B$;

$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

$R^3$ is $C_1$-$C_3$alkyl, or $C_1$-$C_3$fluoroalkyl;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$ and $R^{8b}$ are independently selected from H, $C_1$-$C_6$alkyl and $C_1$-$C_6$fluoroalkyl;

$R^{8e}$ and $R^{8f}$ are independently selected from H, $C_1$-$C_6$alkyl and $C_1$-$C_6$fluoroalkyl;

where each substituted alkyl, heteroalkyl, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —N($C_1$-$C_4$alkyl)$_2$, —C(=O)OH, —C(=O)$NH_2$, —C(=O)$C_1$-$C_3$alkyl, —S(=O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula D described above or below, or pharmaceutically acceptable salt, N-oxide, racemate or stereoisomer thereof, is one group of compounds wherein, $R^{2a}$, $R^{2b}$, $R^{2c}$, $R^{2d}$, $R^{2e}$, and $R^{2f}$ are independently selected from H, $C_1$-$C_3$alkyl and —C(=O)$R^B$; and $R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl).

Among the compounds of Formula D described above or below, or pharmaceutically acceptable salt, N-oxide, racemate or stereoisomer thereof, is one group of compounds wherein $R^{2a}$, $R^{2b}$, $R^{2c}$, $R^{2d}$, $R^{2e}$, and $R^{2f}$ are independently H or $C_1$-$C_3$ alkyl.

Among the compounds of Formula D described above or below, or pharmaceutically acceptable salt, N-oxide, racemate or stereoisomer thereof, is one group of compounds wherein, $R^{8a}$, $R^{8b}$, $R^{8c}$, $R^{8d}$, $R^{8e}$, and $R^{8f}$ are independently selected from H, $C_1$-$C_3$alkyl and —C(=O)$R^B$; and $R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl).

Among the compounds of Formula D described above or below, or pharmaceutically acceptable salt, N-oxide, racemate or stereoisomer thereof, is one group of compounds wherein $R^{8a}$, $R^{8b}$, $R^{8c}$, $R^{8d}$, $R^{8e}$, and $R^{8f}$ are independently H or $C_1$-$C_3$ alkyl.

Among the compounds of Formula D described above or below, or pharmaceutically acceptable salt, N-oxide, racemate or stereoisomer thereof, is one group of compounds wherein $R^1$ is H or methyl.

Among the compounds of Formula D described above or below, or pharmaceutically acceptable salt, N-oxide, racemate or stereoisomer thereof, is one group of compounds wherein $R^1$ is H.

Among the compounds of Formula D described above or below, or pharmaceutically acceptable salt, N-oxide, racemate or stereoisomer thereof, is one group of compounds wherein, $R^6$ is —NHC(=O)$R^7$, —C(=O)NH$R^7$, —NHS(=O)$_2R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^5$, —($C_1$-$C_3$alkyl)-NHS(=O)$_2R^7$, —($C_1$-$C_3$alkyl)-S(=O)$_2$NH$R^7$; —($C_1$-$C_3$alkyl)-NHC(=O)NH$R^7$, or —($C_1$-$C_3$alkyl)-NHS(=O)$_2$NH$R^7$.

Among the compounds of Formula D described above or below, or pharmaceutically acceptable salt, N-oxide, racemate or stereoisomer thereof, is one group of compounds wherein, $R^6$ is substituted or unsubstituted $C_2$-$C_{10}$heterocycloalkyl, or substituted or unsubstituted heteroaryl.

Among the compounds of Formula D described above or below, or pharmaceutically acceptable salt, N-oxide, racemate or stereoisomer thereof, is one group of compounds wherein, $R^6$ is a substituted or unsubstituted $C_2$-$C_{10}$heterocycloalkyl.

Among the compounds of Formula D described above or below, or pharmaceutically acceptable salt, N-oxide, racemate or stereoisomer thereof, is one group of compounds wherein, $R^6$ is a substituted or unsubstituted heteroaryl.

Among the compounds of Formula D described above or below, or pharmaceutically acceptable salt, N-oxide, racemate or stereoisomer thereof, is one group of compounds wherein, $R^6$ is —C(=O)NHR$^7$, —S(=O)$_2$NHR$^7$, —(C$_1$-C$_3$alkyl)-C(=O)NHR$^5$, or —(C$_1$-C$_3$alkyl)-S(=O)$_2$NHR$^7$.

Among the compounds of Formula D described above or below, or pharmaceutically acceptable salt, N-oxide, racemate or stereoisomer thereof, is one group of compounds wherein, $R^6$ is —C(=O)NHR$^7$, or —S(=O)$_2$NHR$^7$.

Among the compounds of Formula D described above or below, or pharmaceutically acceptable salt, N-oxide, racemate or stereoisomer thereof, is one group of compounds wherein $R^6$ is —C(=O)NHR$^7$.

Among the compounds of Formula D described above or below, or pharmaceutically acceptable salt, N-oxide, racemate or stereoisomer thereof, is one group of compounds wherein, each $R^7$ is independently selected from a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_6$alkyl-(substituted or unsubstituted C$_3$-C$_{10}$cycloalkyl), —C$_1$-C$_6$alkyl-(substituted or unsubstituted C$_2$-C$_{10}$heterocycloalkyl), —C$_1$-C$_6$alkyl-(substituted or unsubstituted aryl), —C$_1$-C$_6$alkyl-(substituted or unsubstituted heteroaryl), —(CH$_2$)$_p$—CH(substituted or unsubstituted aryl)$_2$-(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl).

Among the compounds of Formula D described above or below, or pharmaceutically acceptable salt, N-oxide, racemate or stereoisomer thereof, is one group of compounds wherein, $R^7$ is independently selected from a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted heteroaryl, and —(CH$_2$)$_p$—CH(substituted or unsubstituted aryl)$_2$.

Among the compounds of Formula D described above or below, or pharmaceutically acceptable salt, N-oxide, racemate or stereoisomer thereof, is one group of compounds wherein, $R^7$ is selected from

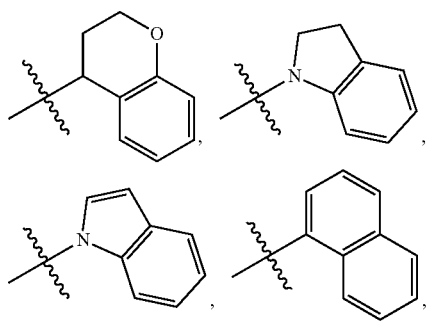

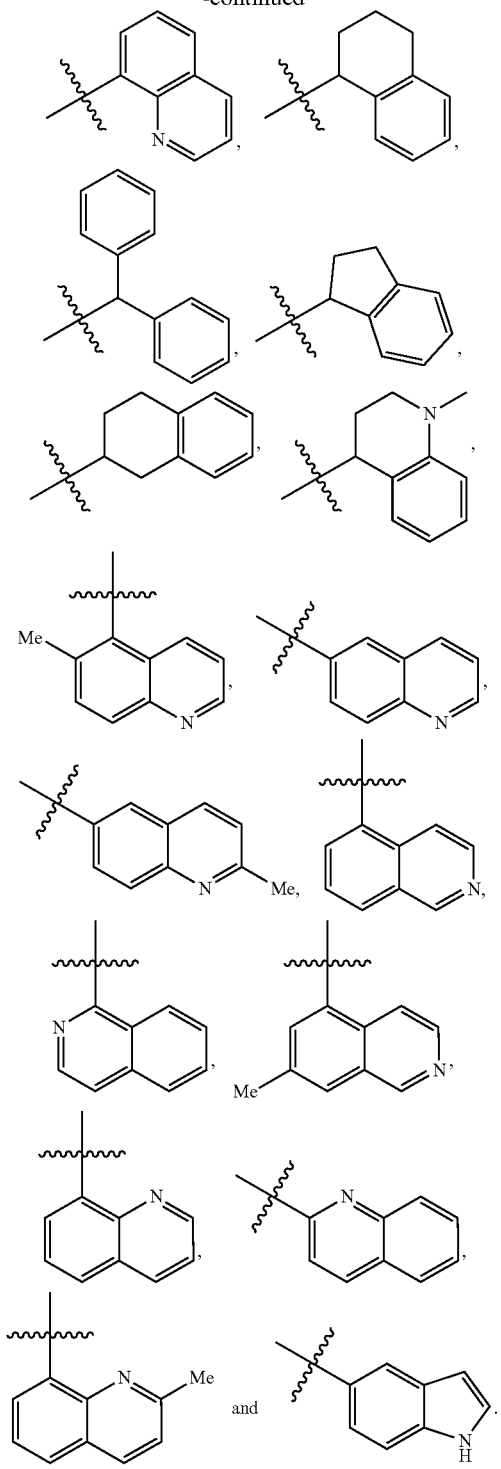

Among the compounds of Formula D described above or below, or pharmaceutically acceptable salt, N-oxide, racemate or stereoisomer thereof, is one group of compounds wherein, $W^3$ is C(R$^{8e}$)(R$^8$);

$R^1$ is H;

$R^{2a}$, $R^{2b}$ are independently selected from H, and C$_1$-C$_3$alkyl;

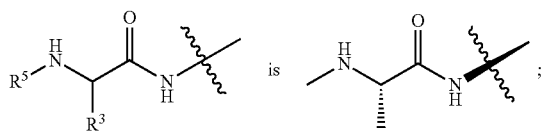 is 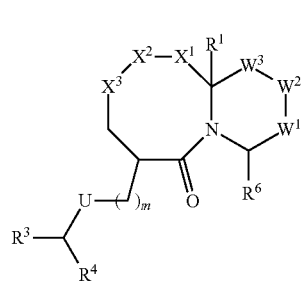

Formula E-I $R^{8a}$, $R^{8b}$, $R^{8e}$, $R^{8f}$ are independently selected from H and $C_1$-$C_3$alkyl.

Any combination of the groups described above or below for the various variables is contemplated herein. Throughout the specification, groups and substituents thereof are chosen by one skilled in the field to provide stable moieties and compounds.

Any combination of the groups described above for the various variables is contemplated herein. Throughout the specification, groups and substituents thereof are chosen by one skilled in the field to provide stable moieties and compounds.

Among the compounds of Formula D described above or below, or pharmaceutically acceptable salt, N-oxide, racemate or stereoisomer thereof, is a compound of structure:

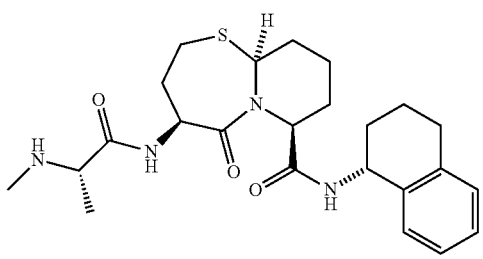

Also provided herein are pharmaceutical composition comprising a compound of Formula D or pharmaceutically acceptable salt, N-oxide, racemate or stereoisomer thereof, and a pharmaceutically acceptable carrier.

Formula E—Eight-Six Ring Systems

In one aspect, the IAP antagonist for use in any of the methods, uses, compositions described herein is a Formula E compound. As used herein, Formula E includes compounds of Formula E-I, Formula E-II, Formula E-II-1, Formula E-II-2, Formula E-II-3, Formula E-III, Formula E-IV, Formula E-V-1, Formula E-V-2, Formula E-V-3, Formula E-VI-1, Formula E-VI-2, Formula E-VI-3, Formula E-VII-1, Formula E-VII-2, Formula E-VII-3, Formula E-VIII-1, Formula E-VIII-2, Formula E-VIII-3, Formula E-IX-1, Formula E-IX-2, Formula E-X-1, Formula E-X-2, Formula E-XI-1, Formula E-XI-2, Formula E-XII, Formula E-XIII, Formula E-XIV, Formula E-XV-1, Formula E-XV-2, Formula E-XV-3, Formula E-XV-4, Formula E-XVI-1, Formula E-XVI-2, Formula E-XVII-1, Formula E-XVII-2, Formula E-XVIII, Formula E-XIX, Formula E-XX, and Formula E-XXI.

In one aspect, described herein is a compound of Formula E-I, or a pharmaceutically acceptable salt, N-oxide, racemate or stereoisomer thereof, as described in the summary of the invention.

In another aspect, provided herein are compounds having the structure of Formula E-I, pharmaceutically acceptable salt, N-oxide, racemate or stereoisomer thereof:

wherein,
$R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl); when $X^1$ is selected from N—$R^A$, S, S(O) and S(O)$_2$, then $X^2$ is $CR^{2c}R^{2d}$, and $X^3$ is $CR^{2a}R^{2b}$;
or when $X^1$ is O, then $X^2$ is selected from $CR^{2c}R^{2d}$ and N—$R^A$, and $X^3$ is $CR^{2a}R^{2b}$;
or:
when $X^1$ is $CH_2$, then $X^2$ is selected from O, N—$R^A$, S, S(O), and S(O)$_2$, and $X^3$ is $CR^{2a}R^{2b}$;
or:
$X^1$ is $CR^{2e}R^{2f}$ and $X^2$ is $CR^2CR^{2d}$, and $R^{2e}$ and $R^{2c}$ together form a bond, and $X^3$ is $CR^{2a}R^{2b}$;
or:
$X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;
or:
$X^2$ and $X^3$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ is $CR^{2e}R^{2f}$;
$R^A$ is H, $C_1$-$C_6$alkyl, —C(=O)$C_1$-$C_6$alkyl, substituted or unsubstituted aryl, or substituted or unsubstituted heteroaryl;
$W^1$ is O, S, N—$R^A$, or $C(R^{8a})(R^{8b})$;
$W^2$ is O, S, N—$R^A$, or $C(R^{8c})(R^{8d})$;
$W^3$ is O, S, N—$R^A$, or $C(R^{8e})(R^{8f})$; provided that the ring comprising $W^1$, $W^2$ and $W^3$ does not comprise two adjacent oxygen atoms or sulfur atoms;
$R^{2a}$, $R^{2b}$, $R^{2c}$, $R^{2d}$ $R^{2e}$, and $R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^D R^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$ NH—;

$R^3$ is $C_1$-$C_3$alkyl, or $C_1$-$C_3$fluoroalkyl;

$R^4$ is —$NHR^5$, —$N(R^5)_2$, —$N^+(R^5)_3$ or —$OR^5$;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ together with the atoms to which they are attached form a substituted or unsubstituted 5-7 membered ring;

or:

$R^3$ is bonded to a nitrogen atom of U to form a substituted or unsubstituted 5-7 membered ring;

$R^6$ is —NHC(=O)$R^7$, —C(=O)NH$R^7$, —NHS(=O)$_2$ $R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^5$, —($C_1$-$C_3$alkyl)-NHS(=O)$_2$ $R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$, $R^{8b}$, $R^{8c}$, $R^{8d}$, $R^{8e}$ and $R^{8f}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$, $R^{8d}$, $R^{8e}$ and $R^{8f}$ are as defined above, and $R^{8b}$ and $R^{8c}$ together form a bond;

or:

$R^{8a}$, $R^{8b}$, $R^{8d}$, and $R^{8f}$ are as defined above, and $R^{8c}$ and $R^{8e}$ together form a bond;

or:

$R^{8a}$, $R^{8d}$, $R^{8e}$ and $R^{8f}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8a}$, $R^{8b}$, $R^{8d}$, and $R^{8f}$ are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$, $R^{8d}$, $R^{8e}$ and $R^{8f}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8e}$ and $R^{8f}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8c}$, and $R^{8d}$ are as defined above, and $R^{8e}$ and $R^{8f}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —NH$_2$, —NH($C_1$-$C_4$alkyl), —N($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula E-I described above or below, or pharmaceutically acceptable salt, N-oxide, racemate or stereoisomer thereof, is one group of compounds having the structure of Formula E-II:

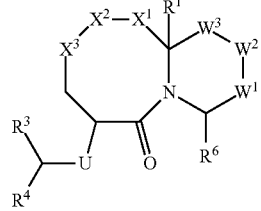
Formula E-II

Among the compounds of Formula E-I described above or below, or pharmaceutically acceptable salt, N-oxide, racemate or stereoisomer thereof, is one group of compounds having the structure of Formula E-II-1, Formula E-II-2, or Formula E-II-3:

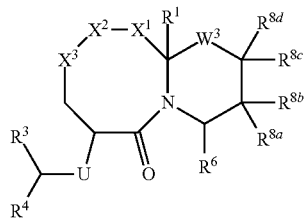
Formula E-II-1

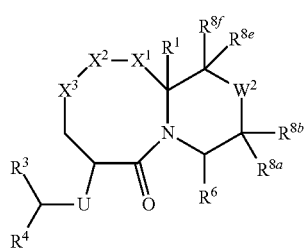
Formula E-II-2

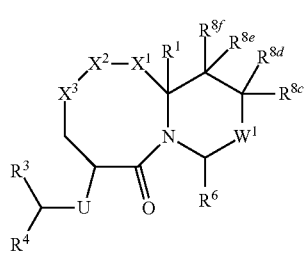
Formula E-II-3

Among the compounds of Formula E-I described above or below, or pharmaceutically acceptable salt, N-oxide, racemate or stereoisomer thereof, is one group of compounds having the structure of Formula E-III:

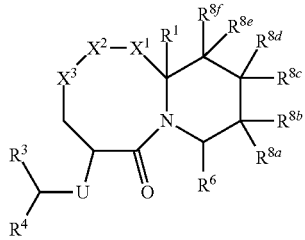
Formula E-III

Among the compounds of Formula E-I described above or below, or pharmaceutically acceptable salt, N-oxide, racemate or stereoisomer thereof, is one group of compounds having the structure of Formula E-IV:

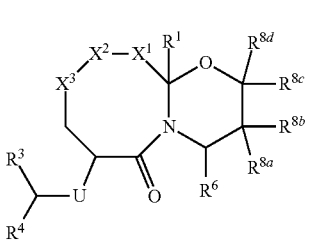
Formula E-IV

Among the compounds of Formula E described above or below, or pharmaceutically acceptable salt, N-oxide, racemate or stereoisomer thereof, is one group of compounds wherein,
—U— is —NHC(=O)—, —C(=O)NH—, —NHS(=O)$_2$—, or —S(=O)$_2$NH—.

Among the compounds of Formula E described above or below, or pharmaceutically acceptable salt, N-oxide, racemate or stereoisomer thereof, is one group of compounds wherein,
—U— is —NHC(=O)—, or —C(=O)NH—.

Among the compounds of Formula E described above or below, or pharmaceutically acceptable salt, N-oxide, racemate or stereoisomer thereof, is one group of compounds wherein,
$R^3$ is $C_1$-$C_3$alkyl.

Among the compounds of Formula E described above or below, or pharmaceutically acceptable salt, N-oxide, racemate or stereoisomer thereof, is one group of compounds wherein,
$R^4$ is -NHR$^5$, —N(R$^5$)$_2$, or —N$^+$(R$^5$)$_3$; and
each $R^5$ is independently selected from H, $C_1$-$C_3$alkyl, and —$C_1$-$C_3$alkyl-($C_3$-$C_5$cycloalkyl).

Among the compounds of Formula E described above or below, or pharmaceutically acceptable salt, N-oxide, racemate or stereoisomer thereof, is one group of compounds wherein,

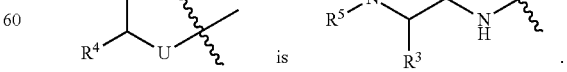

Among the compounds of Formula E described above or below, or pharmaceutically acceptable salt, N-oxide, racemate or stereoisomer thereof, is one group of compounds wherein,

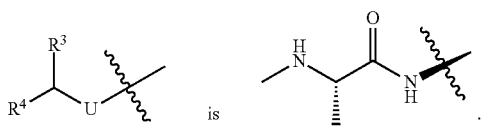 is

Among the compounds of Formula E described above or below, or pharmaceutically acceptable salt, N-oxide, racemate or stereoisomer thereof, is one group of compounds wherein $R^3$ and $R^5$ together with the atoms to which they are attached form a substituted or unsubstituted 5-7 membered ring.

Among the compounds of Formula E described above or below, or pharmaceutically acceptable salt, N-oxide, racemate or stereoisomer thereof, is one group of compounds wherein,

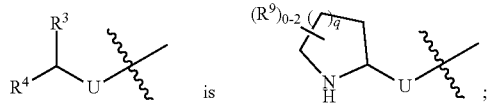

and
q is 1, 2 or 3.

Among the compounds of Formula E described above or below, or pharmaceutically acceptable salt, N-oxide, racemate or stereoisomer thereof, is one group of compounds wherein $R^3$ is bonded to a nitrogen atom of U to form a substituted or unsubstituted 5-7 membered ring.

Among the compounds of Formula E described above or below, or pharmaceutically acceptable salt, N-oxide, racemate or stereoisomer thereof, is one group of compounds wherein,

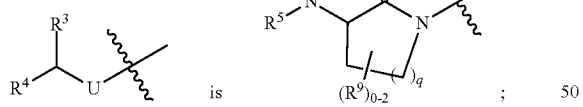

and
q is 1, 2 or 3.

Among the compounds of Formula E-I described above or below, or pharmaceutically acceptable salt, N-oxide, racemate or stereoisomer thereof, is one group of compounds wherein, $X^1$ is selected from N—$R^A$, S, S(O) and S(O)$_2$; and
$X^2$ is CH$_2$.

Among the compounds of Formula E-I described above or below, or pharmaceutically acceptable salt, N-oxide, racemate or stereoisomer thereof, is one group of compounds having the structure of Formula E-V-1 or Formula E-V-2 or Formula E-V-3:

Formula E-V-1
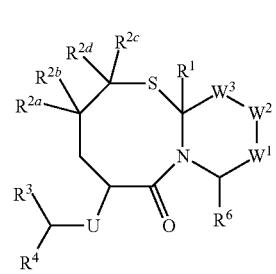

Formula E-V-2
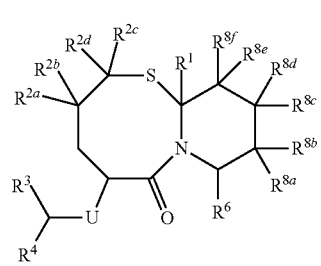

Formula E-V-3
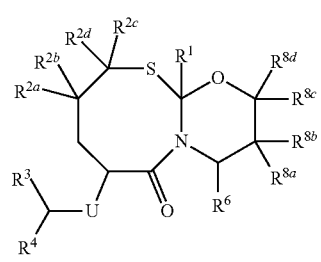

Among the compounds of Formula E-I described above or below, or pharmaceutically acceptable salt, N-oxide, racemate or stereoisomer thereof, is one group of compounds having the structure of Formula E-VI-1 or Formula E-VI-2 or Formula E-VI-3:

Formula E-VI-1
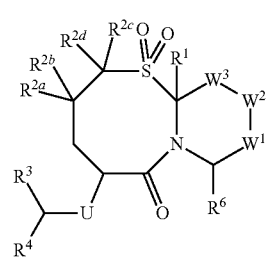

Formula E-VI-2
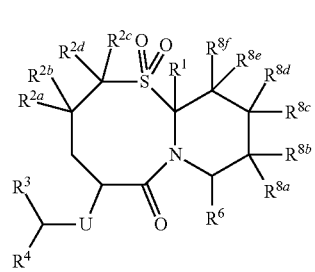

Formula E-VI-3

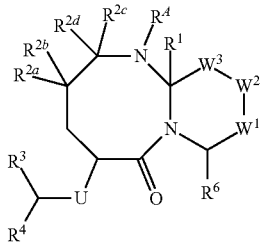

Among the compounds of Formula E-I described above or below, or pharmaceutically acceptable salt, N-oxide, racemate or stereoisomer thereof, is one group of compounds having the structure of Formula E-VII-1 or Formula E-VII-2 or Formula E-VII-3:

Formula E-VII-1

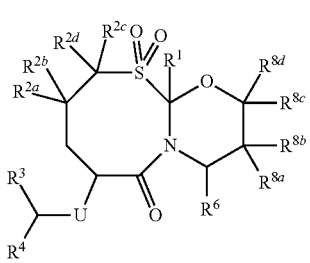

Formula E-VII-2

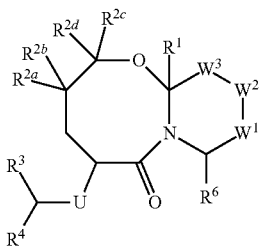

Formula E-VII-3

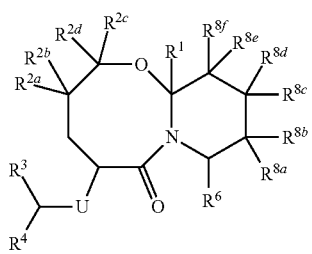

Among the compounds of Formula E-I described above or below, or pharmaceutically acceptable salt, N-oxide, racemate or stereoisomer thereof, is one group of compounds having the structure of Formula E-VIII-1 or Formula E-VIII-2 or Formula E-VIII-3:

Formula E-VIII-3

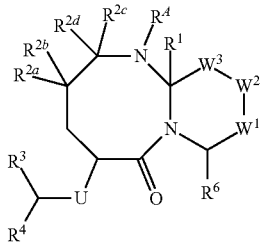

Formula E-VIII-3

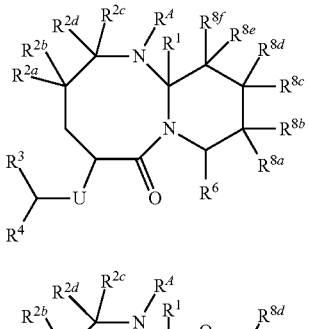

Formula E-VIII-3

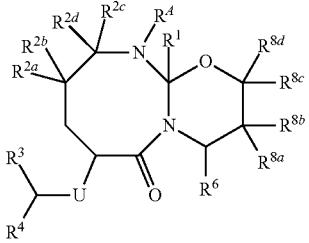

Among the compounds of Formula E described above or below, or pharmaceutically acceptable salt, N-oxide, racemate or stereoisomer thereof, is one group of compounds wherein
$X^1$ is $CH_2$; and
$X^2$ is selected from O, N—$R^A$, S, S(O), and $S(O)_2$.

Among the compounds of Formula E-I described above or below, or pharmaceutically acceptable salt, N-oxide, racemate or stereoisomer thereof, is one group of compounds having the structure of Formula E-IX-1 or Formula E-IX-2:

Formula E-IX-1

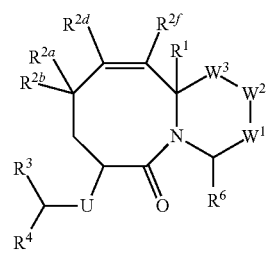

Formula E-IX-2

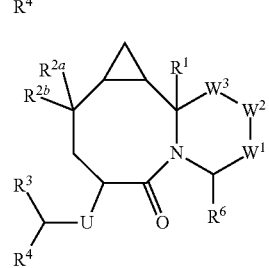

Among the compounds of Formula E-I described above or below, or pharmaceutically acceptable salt, N-oxide, racemate or stereoisomer thereof, is one group of compounds having the structure of Formula E-X-1 or Formula E-X-2:

Formula E-X-1

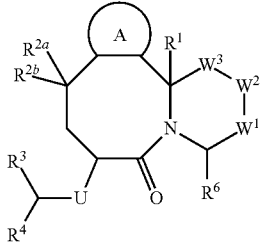

Formula E-X-2

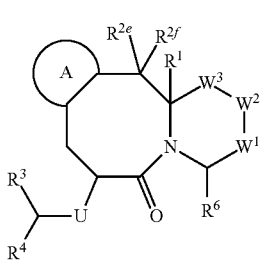

wherein ring A is a fused substituted or unsubstituted saturated or partially saturated 3-10 membered cycloalkyl ring, substituted or unsubstituted saturated or partially saturated 3-10 membered heterocycloalkyl ring, substituted or unsubstituted 5-10 membered aryl ring, or substituted or unsubstituted 5-10 membered heteroaryl ring.

Within such a group of compounds are compounds wherein ring A is selected from indolyl and phenyl.

Among the compounds of Formula E-I described above or below, or pharmaceutically acceptable salt, N-oxide, racemate or stereoisomer thereof, is one group of compounds having the structure of Formula E-XI or Formula E-XI-2:

Formula E-XI-1

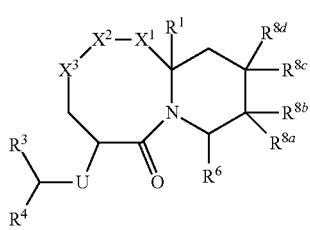

Formula E-XI-2

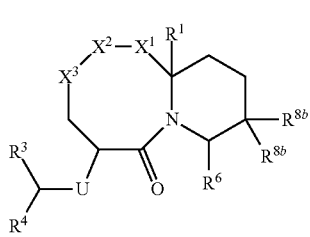

Among the compounds of Formula E-I described above or below, or pharmaceutically acceptable salt, N-oxide, racemate or stereoisomer thereof, is one group of compounds having the structure of Formula E-XII:

Formula E-XII

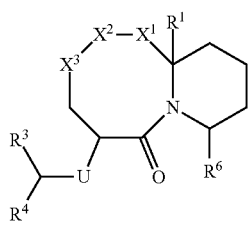

Among the compounds of Formula E-I described above or below, or pharmaceutically acceptable salt, N-oxide, racemate or stereoisomer thereof, is one group of compounds having the structure of Formula E-XIII:

Formula E-XIII

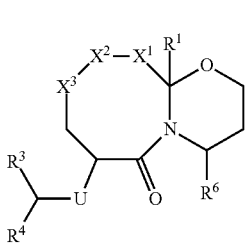

Within the group of compounds of Formula E-XI, Formula E-XII and Formula E-XIII are compounds wherein $X^1$ is O, S or $S(O)_2$, and $X^2$ is $CH_2$.

Within the group of compounds of Formula E-XI, Formula E-XII and Formula E-XIII are compounds wherein $X^1$ is N—$R^A$, and $X^2CH_2$.

Among the compounds of Formula E-I described above or below, or pharmaceutically acceptable salt, N-oxide, racemate or stereoisomer thereof, is one group of compounds wherein $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N.

Within such a group of compounds are compounds having the structure of Formula E-XIV:

Formula E-XIV

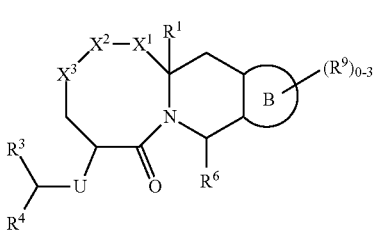

where ring B is an aryl or heteroaryl ring.

In some embodiments, ring B is an aryl. In some embodiments, ring B is phenyl. In some embodiments, ring B is a heteroaryl ring. In some embodiments, ring B is a monocyclic heteroaryl ring or a bicyclic heteroaryl ring. In some embodiments, ring B is a monocyclic heteroaryl ring. In some embodiments, ring B is a bicyclic heteroaryl ring. In some embodiments, ring B is selected from phenyl, pyridinyl and thiophenyl. In some embodiments, ring B is selected from pyridinyl and thiophenyl.

Among the compounds of Formula E-I described above or below, or pharmaceutically acceptable salt, N-oxide, racemate or stereoisomer thereof, is one group of compounds wherein $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N; or $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N.

Within this group are compounds having the structure of Formula E-XV-1, Formula E-XV-2, Formula E-XV-3, or Formula E-XV-4:

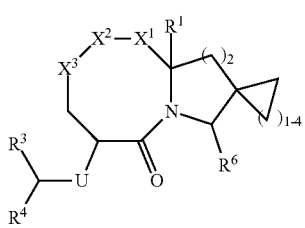

Formula E-XV-1

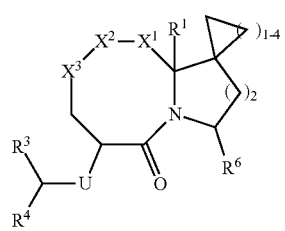

Formula-XV-2

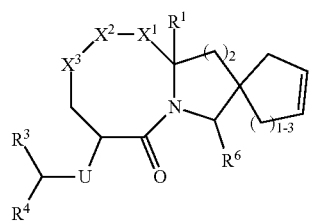

Formla E-XV-3

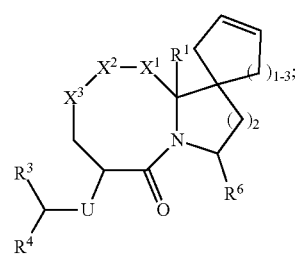

Formula E-XV-4 or Formula E-XVI-1 or Formula E-XVI-2:

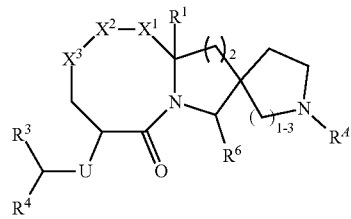

Formula E-XVI-1

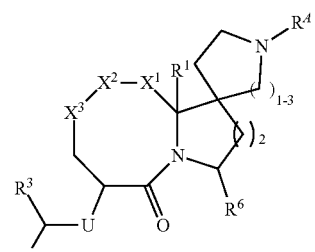

Formula E-XVI-2 wherein $R^A$ is H, $C_1$-$C_3$alkyl or —C(=O)$C_1$-$C_3$alkyl.

Among the compounds of Formula E-I described above or below, or pharmaceutically acceptable salt, N-oxide, racemate or stereoisomer thereof, is one group of compounds wherein $R^{8b}$ and $R^{8c}$ together form a bond.

Among the compounds of Formula E-I described above or below, or pharmaceutically acceptable salt, N-oxide, racemate or stereoisomer thereof, is one group of compounds wherein $R^{8d}$ and $R^{8e}$ together form a bond.

Within this group are compounds having the structure of Formula E-XVII-1 or Formula E-XVII-2:

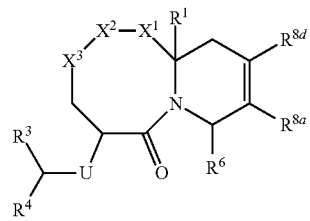

Formula E-XVII-1

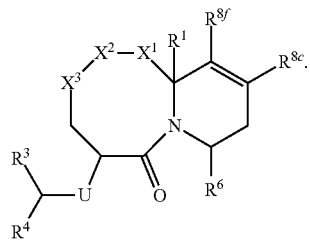

Formula E-XVII-2

Among the compounds of Formula E described above or below, or pharmaceutically acceptable salt, N-oxide, racemate or stereoisomer thereof, is one group of compounds having the structure of Formula E-XVIII:

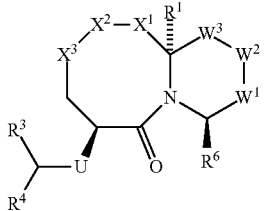

Formula E-XVIII

Among the compounds of Formula E described above or below, or pharmaceutically acceptable salt, N-oxide, racemate or stereoisomer thereof, is one group of compounds having the structure of Formula E-XIX:

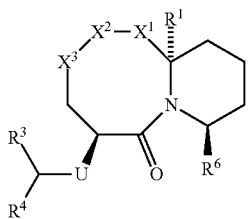

Formula E-XIX

Among the compounds of Formula E described above or below, or pharmaceutically acceptable salt, N-oxide, racemate or stereoisomer thereof, is one group of compounds having the structure of Formula E-XX:

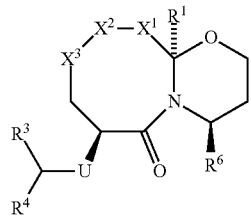

Formula E-XX

Among the compounds of Formula E described above or below, or pharmaceutically acceptable salt, N-oxide, racemate or stereoisomer thereof, is one group of compounds having the structure Formula E-XXI, or pharmaceutically acceptable salt, N-oxide, racemate or stereoisomer thereof:

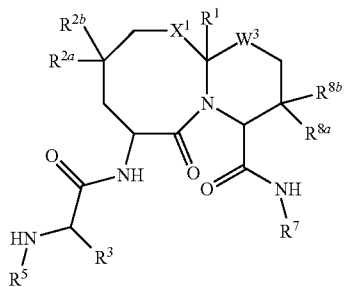

Formula E-XXI wherein,
$W^3$ is O, S, or $C(R^{8e})(R^{8f})$;
$R^1$ is H, or $C_1$-$C_6$alkyl;
$X^1$ is O, N—$R^A$, S, S(O), or $S(O)_2$;
$R^A$ is H, $C_1$-$C_6$alkyl, —C(=O)$C_1$-$C_6$alkyl, substituted or unsubstituted aryl, or substituted or unsubstituted heteroaryl;
$R^{2a}$ and $R^{2b}$ are independently selected from H, substituted or unsubstituted $C_1$-$C_6$alkyl, and —C(=N)$R^B$;
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;
$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
$R^3$ is $C_1$-$C_3$alkyl, or $C_1$-$C_3$fluoroalkyl;
each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);
p is 0, 1 or 2;
$R^{8a}$ and $R^{8b}$ are independently selected from H, $C_1$-$C_6$alkyl, and $C_1$-$C_6$fluoroalkyl;
$R^{8e}$ and $R^{8f}$ are independently selected from H, $C_1$-$C_6$alkyl, and $C_1$-$C_6$fluoroalkyl;
where each substituted alkyl, heteroalkyl, cycloalkyl, heterocycloalkyl, aryl or heteroaryl is substituted with 1-3 $R^9$; and
each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —N($C_1$-$C_4$alkyl)$_2$, —C(=O)OH, —C(=O)$NH_2$, —C(=O)$C_1$-$C_3$alkyl, —S(=O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$, —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula E described above or below, or pharmaceutically acceptable salt, N-oxide, racemate or stereoisomer thereof, is one group of compounds wherein, $R^{2a}$, $R^{2b}$ $R^{2c}$, $R^{2d}$, $R^{2e}$, and $R^{2f}$ are independently selected from H, $C_1$-$C_3$alkyl and —C(=O)$R^B$; and $R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl).

Among the compounds of Formula E described above or below, or pharmaceutically acceptable salt, N-oxide, racemate or stereoisomer thereof, is one group of compounds wherein $R^{2a}$, $R^{2b}$ $R^{2c}$, $R^{2d}$, $R^{2e}$, and $R^{2f}$ are independently H or $C_1$-$C_3$ alkyl.

Among the compounds of Formula E described above or below, or pharmaceutically acceptable salt, N-oxide, racemate or stereoisomer thereof, is one group of compounds wherein $R^1$ is H or methyl.

Among the compounds of Formula E described above or below, or pharmaceutically acceptable salt, N-oxide, racemate or stereoisomer thereof, is one group of compounds wherein $R^1$ is H.

Among the compounds of Formula E described above or below, or pharmaceutically acceptable salt, N-oxide, racemate or stereoisomer thereof, is one group of compounds wherein, $R^6$ is —NHC(=O)$R^7$, —C(=O)NH$R^7$, —NHS(=O)$_2$$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^5$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, or —($C_1$-$C_3$alkyl)-NHS(=O)$_2$NH$R^7$.

Among the compounds of Formula E described above or below, or pharmaceutically acceptable salt, N-oxide, racemate or stereoisomer thereof, is one group of compounds wherein, $R^6$ is substituted or unsubstituted $C_2$-$C_{10}$heterocycloalkyl, or substituted or unsubstituted heteroaryl.

Among the compounds of Formula E described above or below, or pharmaceutically acceptable salt, N-oxide, racemate or stereoisomer thereof, is one group of compounds wherein, $R^6$ is a substituted or unsubstituted $C_2$-$C_{10}$heterocycloalkyl.

Among the compounds of Formula E described above or below, or pharmaceutically acceptable salt, N-oxide, racemate or stereoisomer thereof, is one group of compounds wherein, $R^6$ is a substituted or unsubstituted heteroaryl.

Among the compounds of Formula E described above or below, or pharmaceutically acceptable salt, N-oxide, racemate or stereoisomer thereof, is one group of compounds wherein, $R^6$ is —C(=O)NH$R^7$, —S(=O)$_2$NH$R^7$, —($C_1$-$C_3$alkyl)-C(=O)NH$R^5$, or —($C_1$-$C_3$alkyl)-S(=O)$_2$NH$R^7$.

Among the compounds of Formula E described above or below, or pharmaceutically acceptable salt, N-oxide, racemate or stereoisomer thereof, is one group of compounds wherein, $R^6$ is —C(=O)NH$R^7$, or —S(=O)$_2$NH$R^7$.

Among the compounds of Formula E described above or below, or pharmaceutically acceptable salt, N-oxide, racemate or stereoisomer thereof, is one group of compounds wherein $R^6$ is —C(=O)NH$R^7$.

Among the compounds of Formula E described above or below, or pharmaceutically acceptable salt, N-oxide, racemate or stereoisomer thereof, is one group of compounds wherein, each $R^7$ is independently selected from a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$-(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl).

Among the compounds of Formula E described above or below, or pharmaceutically acceptable salt, N-oxide, racemate or stereoisomer thereof, is one group of compounds wherein, $R^7$ is independently selected from a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, and —(CH$_2$)$_p$—CH(substituted or unsubstituted aryl)$_2$.

Among the compounds of Formula E described above or below, or pharmaceutically acceptable salt, N-oxide, racemate or stereoisomer thereof, is one group of compounds wherein, $R^7$ is selected from

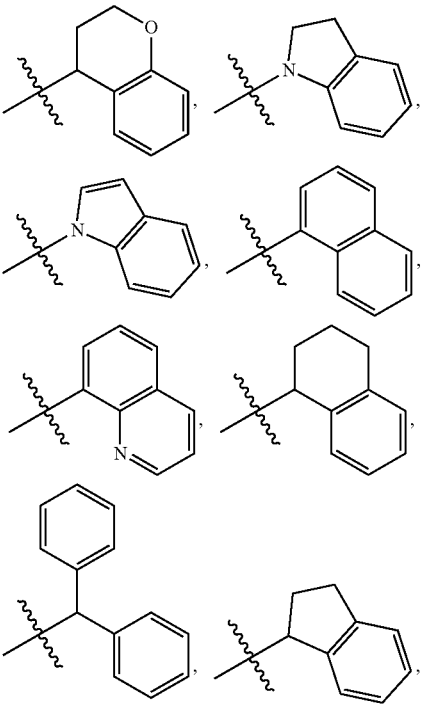

-continued

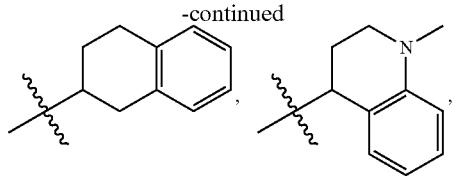

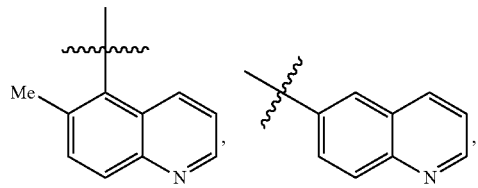

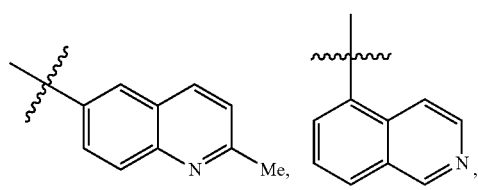

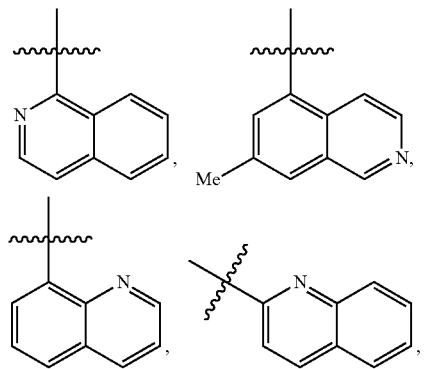

-continued

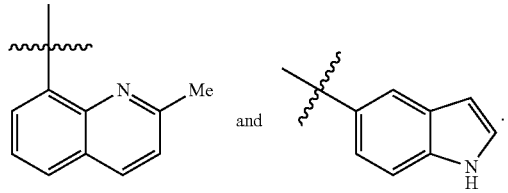

Also provided herein are pharmaceutical compositions comprising a compound of Formula E, or pharmaceutically acceptable salt, N-oxide, racemate or stereoisomer thereof, and a pharmaceutically acceptable carrier.

Also contemplated within the scope of embodiments described herein are dimeric compounds. In one aspect, the IAP antagonist for use in any of the methods, uses, compositions described herein is a Formula F compound. In one aspect, provided herein are compounds of Formula F:

Formula F

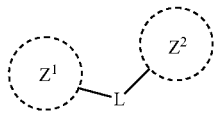

wherein $Z^1$ and $Z^2$ are compounds selected from any one of Formula A, Formula B, Formula C, Formula D or Formula E described above or below; and L is a bridge between the compounds such that a compound of Formula F is a dimeric compound. In some embodiments, L is a bond (e.g., a bond between two aryl groups of $Z^1$ and $Z^2$. In some embodiments, L is a disulfide linkage. In some embodiments, L is an ether, amide or ester linkage. In some embodiments, L is a cycle (e.g., a cyclopropyl ring, a pyrrolidine ring, a phenyl ring). In some embodiments, a compound of Formula F is selected from:

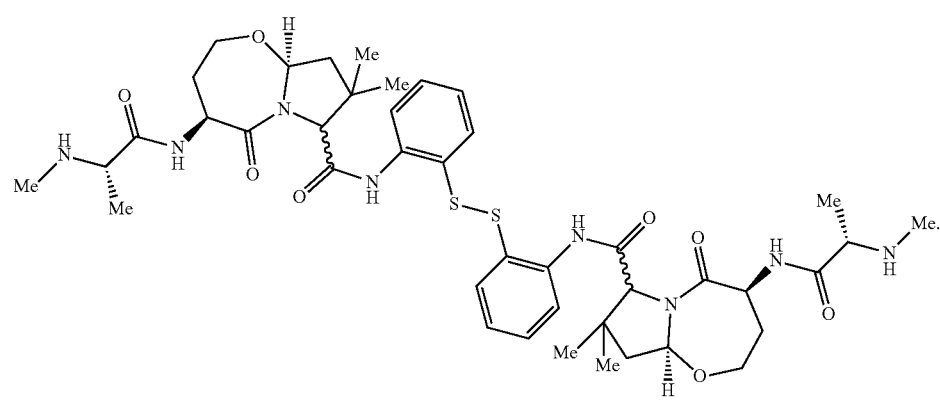 [SMILES: CN[C@@H](C)C(=O)N[C@H]1CCO[C@H]2CC(C)(C)C(C(=O)Nc3ccccc3SSc3ccccc3NC(=O)C3N4C(=O)[C@@H](NC(=O)[C@H](C)NC)CCO[C@H]4CC3(C)C)N2C1=O]

Also contemplated within the scope of embodiments described herein are trimeric compounds. In one aspect, the IAP antagonist for use in any of the methods, uses, compositions described herein is a Formula G compound. In one aspect, provided herein are compounds of Formula G:

Formula G

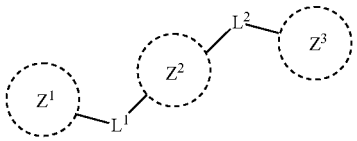

wherein $Z^1$ and $Z^2$ and $Z^3$ are compounds selected from any one of Formula A, Formula B, Formula C, Formula D or Formula E described above or below; and $L^1$ and $L^2$ are a bridges between the compounds such that a compound of Formula G is a trimeric compound. In some embodiments, $L^1$ and $L^2$ are independently selected from a bond (e.g., a bond between two aryl groups of $Z^1$ and $Z^2$ or $Z^3$), a disulfide linkage, an ether, amide or ester linkage and the like.

Any combination of the groups described above or below for the various variables is contemplated herein. Throughout the specification, groups and substituents thereof are chosen by one skilled in the field to provide stable moieties and compounds.

Additional IAP antagonists contemplated for use in any of the methods and compositions described herein include those described in US2008/0269140; U.S. Pat. No. 7,419,975 (LBW242); WO2006/017295; WO2006/069063; U.S. Pat. Nos. 7,345,081; 7,456,209; WO2004/007529; WO2008/073305; WO2007/101347; U.S. Pat. No. 7,244,851; WO2008/128171; U.S. Pat. Nos. 7,309,792; 7,547,724; WO2009/060292; WO2008/134679; WO2007/130626 (SM-164); U.S. Pat. No. 7,517,906; WO2008/128121; Flygare, J. A. and Fairbrother, W. J. *Expert Opin. Ther. Patents* 2010, 20(2), 251-267; and Wang, S. *Curr. Top Microbiol Immunol.* 2011, 348, 89-113; all of which are incorporated by reference for the disclosure of such compounds.

Other IAP antagonists contemplated for use in any of the methods and uses described herein include, but are not limited to, GDC-0152 (Genentech); GDC-0917 (Genentech); LCL161 (Novartis); TL32711 (Tetralogic Pharmaceuticals); AT-406 (Ascenta Therapeutics); and HGS1029 (Human Genome Sciences).

Combination Therapy—Exemplary Therapeutic Agents

Additional therapeutic agents may be used in combination with the IAP antagonists described herein for the treatment of HIV. In some embodiments, additional therapeutic agents are used in combination with IAP antagonists described herein for activating HIV transcription in latently infected cells. In some embodiments, additional therapeutic agents are used in combination with IAP antagonists described herein for reversing HIV latency. In some embodiments, additional therapeutic agents are used in combination with IAP antagonists described herein for reducing HIV reservoirs of latently infected cells. In some embodiments, additional therapeutic agents are used in combination with IAP antagonists to reduce dormant, replication competent HIV. In some embodiments, additional therapeutic agents are used in combination with IAP antagonists to make dormant, replication competent HIV susceptible to immune system clearance. In some embodiments, additional therapeutic agents are used in combination with IAP antagonists to make dormant, replication competent HIV susceptible to the effects of antiretroviral therapy. In some embodiments, the additional therapeutic agents are used in combination with IAP antagonists to eliminate replication competent HIV. In some embodiments, the additional therapeutic agent are used in combination with IAP antagonist to induce long term control of HIV replication and growth in the absence of antiretroviral therapy. In some embodiments, additional therapeutic agents are used in combination with the IAP antagonists described herein for individuals on concomitant antiretroviral therapy.

In some embodiments, a combination treatment regimen encompasses treatment regimens in which administration of an IAP antagonist is initiated prior to, during, or after treatment with a second agent described herein, and continues until any time during treatment with the second agent or after termination of treatment with the second agent. It also includes treatments in which an IAP antagonist and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is an IAP antagonist) are administered in any order or even simultaneously. If administration is simultaneous, the multiple therapeutic agents are, by way of example only, provided in a single, unified form, or in multiple forms (e.g., as a single pill or as two separate pills).

Therapeutic Agents that Activate HIV Transcription

Additional therapeutic agents that can be used in combination with the IAP antagonists described herein include therapeutic agents that activate HIV transcription in latently infected cells. Such compounds are described below and are meant to be exemplary and are not limiting.

HDAC Inhibitors

Histone deacetylase inhibitors (HDAC inhibitors or HDACis) are a class of compounds that inhibit histone deacetylase function. HDACs remove acetyl groups from lysine residues within the histone tail, resulting in reduced transcription with cellular and viral promoters. HDACs are currently classified into the following four groups based on their homology of accessory domains to the following yeast histone deacteylases: RPD3 (Class I), HDA1 (Class II), Sir2 (Class III) and RPD3/HDA1 (Class IV). Class 1 HDACS include RPD3 homologs, HDAC1, 2, 3, and 8 and represent mostly nuclear and ubiquitous enzymes. Class II HDACs are found in the nuclei and cytoplasm and are divided into two classes: class IIa includes HDAC4, 5, 7, and 9; and class IIb includes HDAC 6 and 10. Class IIa HDACs have a large regulatory N-terminal domain whereas class IIb HDACs has two deacetylase domains. Class III HDACs are sirtuins, which are nicotinamide adenine dinucleotide (NAD$^+$)-dependent protein deacetylases, and include SIRT1, 2, 3, 4, 5, 6, and 7. Class IV HDAC consists only of HDAC11, which is related to RPD3 and HDA1. Classes I, II, and III share similar sequence homology and are Zn$^{2+}$ dependent enzymes that can be inhibited by Zn$^{2+}$ chelating compounds.

HDAC inhibition allows for the lysine residues within the histone tail to remain acetylated, which allows for the recruitment of transcriptional activators and facilitates transcription. HDAC inhibitors are classified into four major structural families: short chain aliphatic acids (such as valproic acid, butyric acid, phenylbutyrate), hydroxamic acids (such as trichostatin A, vorinostat, givinostat, panobinostat, oxamflatin, and scriptaid, LBH-589, ITF2357, bellinostat), benzamides (such as entinostat, mocetinostat, tacedinaline), and cyclic tetrapeptides and depsidpeptides (such as trapoxin B, romidespin, and apicidin). The basic structural motif of HDAC inhibitors consists of a cap group for surface recognition, a linker (usually an aliphatic chain), and functional group that interacts with the zinc cation in the HDAC active center. The functional group, or head, can be a hydroxamic acid, a benzamide, a phenylene diamine, a carboxylic acid, an epoxide, or a thiol.

HDACs have been implicated in HIV transcriptional regulation wherein HIV latency is directly regulated by histone deacetylation. Multiple transcription factors, such as Ying-Ying 1 (YY1), late SV40 factor (LSF), COUP-TF interacting protein (CTIP2), c-promotor-binding factor-1 (CBF-1), NF-κB p 50 homodimer, c-myc and Sp1, recruit HDACs (HDAC1, 2, and 3) to the HIV long terminal repeat (LTR) promoter for transcriptional silencing during latency. However, the relative importance of each HDAC for HIV transcriptional silencing during latency remains to be elucidated. Accordingly, inhibition of HDAC would disrupt transcriptional silencing and therefore induce active HIV transcription.

Several HDAC inhibitors have been demonstrated to activate HIV transcription in latently infected cells. The most studied HDAC inhibitor is vorinstat (SAHA). Vorinostat, a class I inhibitor, has been shown to reverse HIV latency in primary CD4$^+$ T cells models of HIV latency and CD4$^+$ T cells isolated from patients on ART. Other HDAC inhibitors that have been examined for reversing HIV latency include valproic acid, givinostat, panobinostat, entinostat, mocetinostat and romidepsin. At this point, it is important to note that most desirable characteristics for the ideal HDAC inhibitor for activating HIV transcription in latently infected cells have yet to be elucidated.

Examples of Class I HDAC inhibitors include and are not limited to taceminaline, givinostat, CUDC-907, vorinostat, entinostat, pracinostat, abexinostat, quinsinostat, romidepsin, mocetinostat, droxinostat, PCI-345051, and tubastatin. Examples of Class II HDAC inhibitors include and are not limited to MC1568, pracinostat, quisinostat, tubastatin, rocilinostat, droxinostat, abexinostat, CUDC-907, pracinostat, abexinostat, quisinostat. Examples of Class IV HDAC inhibitors include and are not limited to quisinostat. Other HDAC inhibitors include and are not limited to APHA Compound 8, BATCP, cambinol, M344, MOCPAC, PTACH, resveratrol, splitomicin, oxamflatin, scriptaid, tacedinaline, apicidin, LBH-589, ITF2357, LAQ-824, FK-228, AN-9 (pivaloylxymethyl butyrate), SK-7041, and SK07068.

Additional HDAC inhibitors include, but are not limited to, NKL 22, ATRA-BA Hybrid, BML-281, Valproic acid, CI-994, MC-1293, Vorinostat, p-Fluoro-SAHA, Oxamflatin, Phenylbutyrate.Na, Apicidin, M344, Scriptaid, NSC-3852, Suberoyl bis-hydroxamic acid, BML-210, Trichostatin A, NCH-51, HNHA, and Droxinostat.

Other Therapeutic Agents that Activate HIV Transcription

In addition to histone deacetylation, non-histone protein modifications have been implicated in HIV transcriptional regulation, such as through the modulation of the nuclear factor-kappa B (NF-κB) pathway. Thus, there are other therapeutic agents that activate HIV transcription in latently infected cells. Other therapeutic agents include those that activate HIV transcription through the NF-κB response via the protein kinase C (PKC) pathway, such as prostatin and bryostatin. Prostatin and bryostatin have been reported to reactivate HIV in cell line models of HIV latency. Other therapeutic agents include those that increase the availability of positive transcription elongation factor b (PTEF-b) at the HIV promoter site, such as small molecule BET (bromodomain and extraterminal) inhibitor JQ1 and disulfiram. BET inhibitor JQ1 has demonstrated an ability to increase HIV production in cell line models of HIV latency. Disulfiram, which activates the Akt pathway and results in the release of PTEF-b at the HIV promoter site, has been identified in a screen for small molecules that reactivate latent HIV.

Other epigenetic modifiers, such as histone methyltransferases and DNA methyltransferases, have also been implicated in HIV transcription. DNA cytosine methylation inhibitor 5-aza-2' deoxycytidine in combination with either prostratin or TNF-α has demonstrated an ability to reactivate latent HIV in J-LAT cell lines. Histone methyltransferase inhibitors, such as Suv39H1 inhibitor chaetocin, EZH2 inhibitor 3-deazaneplanocin A, and G9a inhibitor BIX01294, have been shown to reactivate latent HIV in primary CD4$^+$ T cell model or cell line models of HIV latency.

Additionally, hexamethylbisacetamide (HMBA), has been shown to induce expression of the HIV-1 promoter in the LTR region.

Accordingly, the IAP antagonists described herein may be used in combination with at least one additional therapeutic agent. In some embodiments, the additional therapeutic agent is one that is used in the treatment of HIV. In certain embodiments, the additional therapeutic agent reverses HIV latency. In other embodiments, the additional therapeutic agent reverses HIV latency by activating HIV transcription in latently infected cells. In some embodiments, the additional therapeutic agent activates HIV transcription in latently infected cells. In some embodiments, the additional therapeutic agent activates HIV transcription through the inhibition of histone deacetylase. In some embodiments, the additional therapeutic agent is a HDAC inhibitor. In other embodiments, the HDAC inhibitor is a Class I inhibitor. In some embodiments, the HDAC inhibitor is a hydroxamic acid, a short chain aliphatic acid, a benzamide, a cyclic tetrapeptide, or a cyclic depsidpeptide. In other embodiments, the HDAC inhibitor is vorinostat, valproic acid, belinostat, panobinostat, givinostat, entinostat, or entinostat. In certain embodiments, the HDAC inhibitor is vorinostat.

In other embodiments, the additional therapeutic agent activates HIV transcription through the NF-κB pathway or through increasing the availability of PTEF-b. In some embodiments, the additional therapeutic agent is prostatin or bryostatin. In other embodiments, the additional therapeutic agent activates HIV transcription through inhibition of histone methyltransferases or DNA methyltransferases. In some embodiments, the additional therapeutic agent is HMBA.

Additional therapeutic agents that can be employed in combination with IAP antagonists include therapeutic agents that activate HIV transcription in latently infected cells. Examples include, but are limited to, HDAC inhibitors, such as trichostatin A, panobinostat, bellinostat, taceminaline, givinostat, CUDC-907, vorinostat, entinostat, pracinostat, abexinostat, quinsinostat, romidepsin, trapoxin B, mocetinostat, droxinostat, PCI-345051, tubastatin, MC1568, rocilinostat, APHA Compound 8, BATCP, cambinol, M344, MOCPAC, PTACH, resveratrol, splitomicin, oxamflatin, scriptaid, tacedinaline, apicidin, LBH-589, ITF2357, LAQ-824, FK-228, AN-9 (pivaloylxymethyl butyrate), SK-7041, SK07068; compounds that activate the NF-κB response via the protein kinase C (PKC) pathway or increase the availability of positive transcription elongation factor b, such as prostatin, bryostatin, BET inhibitor JQ1, disulfiram; DNA methyltransferases inhibitors, such as 5-aza-2' deoxycytidine, Histone methyltransferase inhibitors, such as Suv39H1 inhibitor chaetocin, EZH2 inhibitor 3-deazaneplanocin A, and G9a inhibitor BIX01294; or any combination thereof.

Therapeutic Agents that Inhibit HIV Replication

Additional therapeutic agents that can be used in combination with the IAP antagonists described herein include therapeutic agents that inhibit or limit active HIV replication. The "shock and kill" strategy for treating HIV requires the following in order to reduce dormant, replication competent HIV and the HIV reservoirs in the body: reversal of HIV latency through activating HIV transcription in latently infected cells and inhibition of the active HIV replication to eliminate the reactivated virus. In some embodiments, the additional therapeutic agent inhibits active HIV replication. In some embodiments, the additional therapeutic agent inhibits active HIV replication by inhibiting a specific stage of the HIV life cycle. In some embodiments, the additional therapeutic agent is an antiretroviral drug. Discussed below are examples of additional therapeutic agents that inhibit active HIV replication and are meant to be exemplary and are not limiting.

Antiretroviral Therapy (ART)

Antiretroviral therapy (ART) is the main type of treatment for HIV and uses a combination of different kinds of medication to keep HIV from growing and multiplying in the body. Other synonyms for antiretroviral therapy include, but are not limited to, combination therapy, combined antiretroviral therapy, and highly active antiretroviral therapy (HAART). These medications used in ART are typically antiretroviral drugs, which are drugs used in the treatment of HIV infection because they act against the retrovirus HIV. ART is effective at targeting active viral replication and reducing the viral load, the amount of HIV in the blood, to near undetectable levels, but ART does not eradicate the virus because it does not target latently infected cells, wherein the virus has integrated into the genome of the host and has become indistinguishable from the host's DNA. These latently infected cells are primarily resting CD4$^+$ T lymphocytes but can also include follicular dendritic cells, hematopoietic stem cells, and cells in certain anatomical structures of the human body that are inaccessible to ART drugs. Because latently infected cells can become active and start viral replication upon discontinuation of ART, it is important that individuals adhere and remain on antiretroviral therapy for the remainder of their lives. The usual regimen for ART consists of taking a combination of three different antiretroviral drugs from two different classes. Currently, there are five different classes of antiretroviral drugs with each class describing the specific stage of the HIV life cycle that is targeted by the drug. The five classes are nucleoside/nucleotide reverse transcriptase inhibitors (NRTIs), non-nucleoside reverse transcriptase inhibitors (NNRTIs), protease inhibitors (PIs), entry/fusion inhibitors, and integrase inhibitors.

Nucleoside/nucleotide reverse transcriptase inhibitors (NRTIs) are nucleoside/nucleotide analogues that block HIV reverse transcription by interfering with the viral DNA synthesis. NRTIs are analogues of the naturally occurring deoxynucleotides that are required for viral DNA synthesis but lack the 3'-hydroxyl group on the deoxyribose moiety necessary to form a bond with the next incoming deoxynucleotide. Thus, viral DNA synthesis is terminated upon incorporation of a NRTI. Because NRTIs compete with the natural deoxynucleotides for incorporation into the viral DNA chain, NRTIs are also considered as competitive substrate inhibitors. Examples of NRTIs include and are not limited to zidovudine (azidothymidine, AZT, ZDV), abacavir (ABC), lamivudine (2',3'-dideoxy-3'-thiacytidine, 3TC), emtricitabine (FTC), tenofovir (TDF), zalcitabine (2'-3'-dideoxycytidine, dideoxycytidine, ddC), didanosine (2',3'-dideoxyinosine, ddI), stavudine (2',3'-didehydro-2',3'-dideoxythymidine, d4T), entecavir (ETV), and adefovir. Further examples include Combivir® (zidovudine+lamivudine, AZT+3TC); Emtriva® (emtricitabine, FTC); Epivir® (lamivudine, 3TC); Epzicom® (Livexa, abacavir+lamivudine, ABC+3TC); Retrovir® (zidovudine, AZT, ZDV); Trizivir® (abacavir+zidovudine+lamivudine, ABC+AZT+3TC); Truvada® (tenofovir DF+emtricitabine, TDF+FTC); Videx® and videx EC® (didanosine, ddI); Viread® (tenofovir disoproxil fumarate, TDF); Zerit® (stavudine, d4T); Ziagen® (abacavir, ABC); Amadoxovir® (AMDX, DAPD); and tenofovir alafenamide fumarate (TAF).

Non-nucleoside reverse transcriptase inhibitors (NNRTIs) targets viral DNA synthesis by inhibiting reverse transcriptase through binding to the allosteric site. Examples of NNRTIs include and are not limited to nevirapine, efavirenz, etravirine, rilpivirine, and delavirdine. Further examples include Edurant® (rilpivirine, RPV, TMC-278); Intelence® (etravirine, ETR, TMC-125); Rescriptor® (delavirdine, DLV); Sustiva® (Stocrin, efavirenz, EFV); Viramune® and viramune XR® (nevirapine, NVP), and lersivirine (UK-453061).

Protease inhibitors (PIs) target viral protease, which are involved with producing smaller individual proteins digesting longer protein chains. These smaller individual proteins are required for the assembly of new virus particles. Examples of HIV protease inhibitors include and are not limited to lopinavir, indinavir, nelfinavir, amprenavir, ritonavir, darunavir, atazanavir, fosamprenavir, saquinavir, and tipranavir. Further examples include Aptivus® (tipranavir, TPV), Crixivan® (indinavir, IDV), Invirase® (saquinavir, SQV), Kaletra® (Aluvia, lopinavir/ritonavir, LPV/r), Lexiva® (Telzir, fosamprenavir, FPV), Norvir® (ritonavir, RTV), Prezista® (darunavir, DRV), Reyataz® (atazanavir, ATV) and Viracept® (nelfinavir, NFV).

Entry/fusion inhibitors interfere with the binding, fusion, and entry of HIV into the host cell by targeting key proteins involved in the entry process, such as receptor proteins. Examples of entry/fusion inhibitors include and are not limited to maraviroc and enfuvirtide. Further examples include Fuzeon® (enfuvirtide, ENF, T-20), Selzentry® (Celsentri, maraviroc, UK-427, 857), cenicriviroc (TBR-652, TAK-652), ibalizumab (TNX-355) and PRO140.

Integrase inhibitors or integrase nuclear strand transfer inhibitors (INSTIs) target the viral enzyme integrase, which is involved in the incorporation, or integration, of viral DNA into the DNA of the infected cells. Examples of integrase inhibitors include and are not limited to raltegravir, elvitegravir, and dolutegravir. Further examples include Isentress® (raltegravir, MK-0518), Tivicay® (dolutegravir, S/GSK-572) and elvitegravir (GS-9137).

In addition to the different classes of antiretroviral therapy drugs that are mentioned, a further advancement in ART are fixed-dose combinations, or multi-class combination products, wherein the combinations of two or more medications from one or more different classes are combined into a single pill with specific fixed doses. Fixed-dose combinations have increased the ease of adhering to antiretroviral therapy by simplifying the complex regimen, which also increases the overall effectiveness of ART. Examples of fixed-dose combinations include and are not limited to Combivir® (lamivudine/zidovudine), Trizivir® (abacavir/lamivudine/zidovudine), Keletra® (lopinavir/ritonavir), Epzicom® (abacavir/lamivudine), Truvada® (tenofovir/emtricitabine), Atripla® (emtricitabine/tenofovir/efavirenz), Complera® (emtricitabine/rilpivirine/tenofovir), Stribild® (elvitegravir/cobicistat/emtricitabine/tenofovir), and "572-Trii" (dolutegravir+abacavir+lamivudine or DTG+ABC+3TC).

Accordingly, the IAP antagonists described herein may be used in combination with at least one additional therapeutic agent. In some embodiments, the additional therapeutic agent inhibits active HIV replication. In other embodiments, the additional therapeutic agent inhibits any stage of the HIV life cycle. In some embodiments, the additional therapeutic agent inhibits HIV reverse transcriptase, HIV protease, HIV receptor proteins, HIV integrase. In other embodiments, the additional therapeutic agent inhibits the binding and fusion of HIV into cells, HIV reverse transcription, HIV integration, or HIV virus assembly. In other embodiments, the additional therapeutic agent is an antiretroviral drug. In other embodiments, the additional therapeutic agent is a nucleoside/nucleotide reverse transcriptase inhibitor (NRTI), non-nucleoside reverse transcriptase inhibitor (NNRTI), protease inhibitor (PI), entry/fusion inhibitor, integrase inhibitor, a fixed-dose combination, or any combination thereof. In some embodiments, the nucleoside/nucleotide reverse transcriptase inhibitor is zidovudine (azidothymidine, AZT, ZDV), abacavir (ABC), lamivudine (2',3'-dideoxy-3'-thiacytidine, 3TC), emtricitabine (FTC), tenofovir (TDF), zalcitabine (2'-3'-dideoxycytidine, dideoxycytidine, ddC), didanosine (2',3'-dideoxyinosine, ddl), stavudine (2',3'-didehydro-2',3'-dideoxythymidine, d4T), entecavir (ETV), or adefovir. In other embodiments, the non-nucleoside reverse transcriptase inhibitor is nevirapine, efavirenz, etravirine, rilpivirine, or delavirdine. In some embodiments, the protease inhibitor is lopinavir, indinavir, nelfinavir, amprenavir, ritonavir, darunavir, atazanavir, fosamprenavir, saquinavir, or tipranavirl. In other embodiments, the entry/fusion inhibitor is maraviroc, or enfuvirtide. In some embodiments, the integrase inhibitor is raltegravir, elvitegravir, or dolutegravir. In other embodiments, the fixed-dose combination is Combivir®, Trizivir®, Keletra®, Epzicom®, Truvada®, Atripla®, Complera®, Stribild®, or "572-Trii".

In some embodiments, therapeutic agents that can be employed in combination with IAP antagonists, include therapeutic agents that inhibit active HIV replication. Examples include, but are not limited to, nucleoside/nucleotide reverse transcriptase inhibitors (NRTIs), such as zidovudine (azidothymidine, AZT, ZDV); abacavir (ABC); lamivudine (2',3'-dideoxy-3'-thiacytidine, 3TC); emtricitabine (FTC); tenofovir (TDF); zalcitabine (2'-3'-dideoxycytidine, dideoxycytidine, ddC); didanosine (2',3'-dideoxyinosine, ddl); stavudine (2',3'-didehydro-2',3'-dideoxythymidine, d4T); entecavir (ETV); adefovir; Combivir® (zidovudine+lamivudine, AZT+3TC); Emtriva® (emtricitabine, FTC); Epivir® (lamivudine, 3TC); Epzicom® (Livexa, abacavir+lamivudine, ABC+3TC); Retrovir® (zidovudine, AZT, ZDV); Trizivir® (abacavir+zidovudine+lamivudine, ABC+AZT+3TC); Truvada® (tenofovir DF+emtricitabine, TDF+FTC); Videx® and videx EC® (didanosine, ddl); Viread® (tenofovir disoproxil fumarate, TDF); Zerit® (stavudine, d4T); Ziagen® (abacavir, ABC); amadoxovir (AMDX, DAPD); tenofovir alafenamide fumarate (TAF); non-nucleoside reverse transcriptase inhibitors (NNRTIs), such as nevirapine; efavirenz; etravirine; rilpivirine; delavirdine; Edurant® (rilpivirine, RPV, TMC-278); Intelence® (etravirine, ETR, TMC-125); Rescriptor® (delavirdine, DLV); Sustiva® (Stocrin, efavirenz, EFV); Viramune® and viramune XR® (nevirapine, NVP), lersivirine (UK-453061); protease inhibitors (PIs), such as lopinavir; indinavir; nelfinavir; amprenavir; ritonavir; darunavir; atazanavir; fosamprenavir; saquinavir; tipranavir; Aptivus® (tipranavir, TPV); Crixivan® (indinavir, IDV); Invirase® (saquinavir, SQV); Kaletra® (Aluvia, lopinavir/ritonavir, LPV/r); Lexiva® (Telzir, fosamprenavir, FPV); norvir (ritonavir, RTV); Prezista® (darunavir, DRV); Reyataz® (atazanavir, ATV); Viracept® (nelfinavir, NFV); entry/fusion inhibitors, such as maraviroc; enfuvirtide; Fuzeon® (enfuvirtide, ENF, T-20); Selzentry® (Celsentri, maraviroc, UK-427, 857); Cenicriviroc® (TBR-652, TAK-652); ibalizumab (TNX-355); PRO140; integrase inhibitors, such as raltegravir; elvitegravir; dolutegravir; Isentress® (raltegravir, MK-0518); Tivicay® (dolutegravir, S/GSK-572); elvitegravir (GS-9137); fixed dosed combinations, such as Combivir® (lamivudine/zidovudine), Trizivir® (abacavir/lamivudine/zidovudine), Kelatra® (lopinavir/ritonavir), Epzicom® (abacavir/lamivudine), Truvada® (tenofovir/emtricitabine), Atripla® (emtricitabine/tenofovir/efavirenz), Complera® (emtricitabine/rilpivirine/tenofovir), Stribild® (elvitegravir/cobicistat/emtricitabine/tenofovir), "572-Trii" (dolutegravir+abacavir+lamivudine or DTG+ABC+3TC) or any combination thereof.

Methods of Use

Provided herein are methods of activating HIV transcription in latently infected cells in an individual in need of comprising administration of a therapeutically effective amount of at least one inhibitor of apoptosis proteins (IAP) antagonist. Provided herein are methods of reversing HIV latency in an individual in need of comprising administration of a therapeutically effective amount of at least one IAP antagonist. Provided herein are methods of reducing HIV reservoirs in latently infected cells in an individual in need of comprising administration of a therapeutically effective amount of at least one IAP antagonist. Provided herein are methods of reducing dormant, replication competent HIV in an individual in need of comprising administration of a therapeutically effective amount of at least one IAP antagonist. Provided herein are methods of making dormant, replication competent HIV susceptible to immune system clearance in an individual in need of comprising administration of a therapeutically effective amount of at least one IAP antagonist. Provided herein are methods of making dormant, replication competent HIV susceptible to the effects of antiretroviral therapy in an individual in need of comprising administration of a therapeutically effective amount of at least one IAP antagonist. Provided herein are methods of eliminating replication competent HIV in an individual in need of comprising administration of a therapeutically effective amount of at least one IAP antagonist. Provided herein are methods of inducing long term control of HIV replication and growth in the absence of antiretroviral therapy in an individual in need of comprising administration of a therapeutically effective amount of at least one IAP antagonist.

In some embodiments of any one of the methods described herein, the method further comprises administration of at least one additional therapeutic agent in addition to the IAP antagonist. In some embodiments, the additional therapeutic agent is used in the treatment of HIV. In further embodiments, the additional therapeutic agent activates HIV transcription in latently infected cells or inhibits active HIV replication. In some embodiments, the additional therapeutic agent that activates HIV transcription in latently infected cells is a histone deacetylase inhibitor. In other embodiments, the additional therapeutic agent inhibits active HIV replication. In some embodiments, the additional therapeutic agent that inhibits active HIV replication is an antiretroviral drug. In some embodiments, the additional therapeutic agent is a nucleoside/nucleotide reverse transcriptase inhibitor (NRTI), non-nucleoside reverse transcriptase inhibitor (NNRTI), protease inhibitors (PI), entry/fusion inhibitor, integrase inhibitor, fixed dose combination or any combination thereof.

In certain embodiments of any one of the methods described herein, the latently infected cells are CD4$^+$ T cells. In certain embodiments of any one of the methods described herein, the individuals in need thereof are on concomitant antiretroviral therapy. In certain embodiments of any one of the methods described herein, the IAP antagonist is used in combination with antiretroviral therapy.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

Formation of Covalent Linkages by Reaction of an Electrophile with a Nucleophile The compounds described herein can be modified using various electrophiles and/or nucleophiles to form new functional groups or substituents. Table IA entitled "Examples of Covalent Linkages and Precursors Thereof" lists selected non-limiting examples of covalent linkages and precursor functional groups which yield the covalent linkages. Table IA may be used as guidance toward the variety of electrophiles and nucleophiles combinations available that provide covalent linkages. Precursor functional groups are shown as electrophilic groups and nucleophilic groups.

TABLE I

Examples of Covalent Linkages and Precursors Thereof

| Covalent Linkage Product | Electrophile | Nucleophile |
| --- | --- | --- |
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Alkyl amines | sulfonate esters | amines/anilines |
| hioethers | sulfonate esters | Thiols |
| Sulfonamides | sulfonyl halides | amines/anilines |
| Sulfonate esters | sulfonyl halides | phenols/alcohols |

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd⁰-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

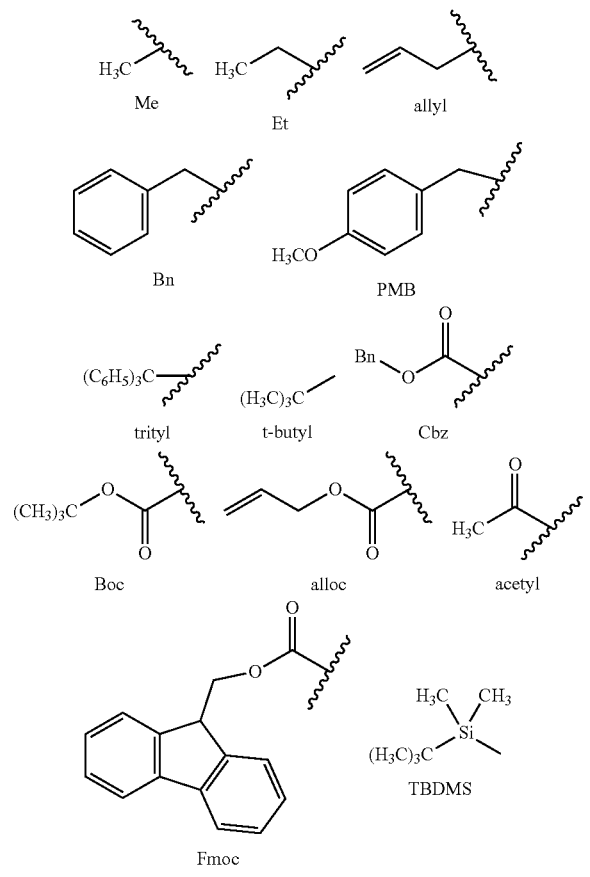

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Synthesis of Compounds of Formula A

In some embodiments, a compound of Formula A-I is synthesized as shown below in Scheme 1 and in the Chemistry Examples section:

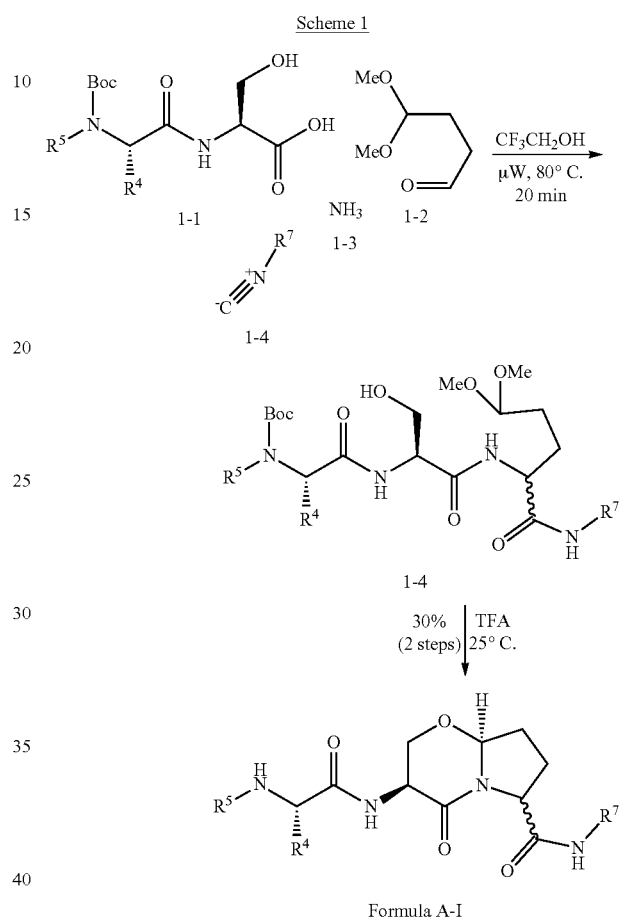

Starting with a compound of Formula 1-1, a four component Ugi reaction provides a compound of Formula 1-2, which is then cyclized and deprotected to provide a compound of Formula A-I.

In a further embodiment, compounds of Formula A-I are synthesized starting with compound 1-6 as shown in Scheme 2 below:

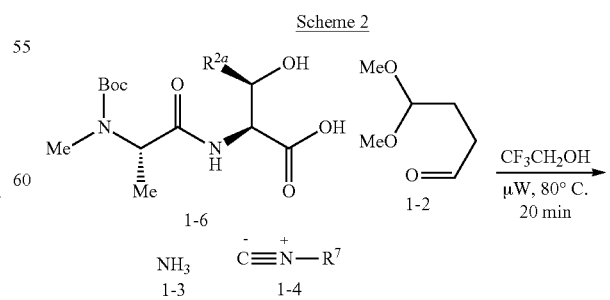

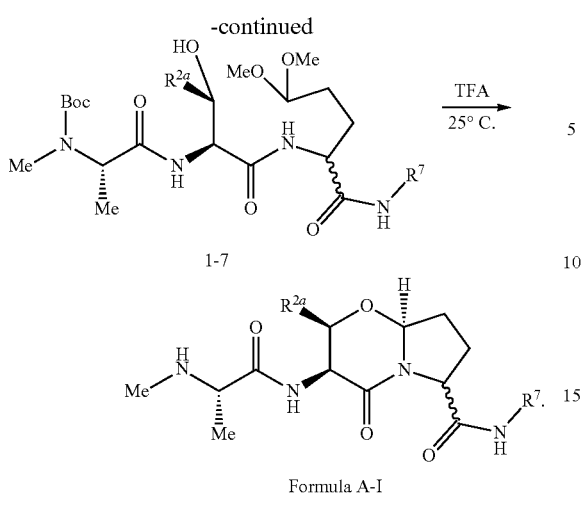

Table 1-1 shows data for certain compounds of Formula A-I.

TABLE 1-1

| Product | $R^{2a}$ | $R^2$ | Yield (2 steps) | XIAP BIR1/2 $K_i$ (μM) | XIAP BIR3 $K_i$ (μM) |
|---|---|---|---|---|---|
| 7a | H | benzyl | 30% | C | B |
| 7b | H | 4-chlorobenzyl | 69% | C | B |
| 7c | H | (R)-tetrahydronaphthyl | 67% | C | A |
| 7d | Me | (R)-tetrahydronaphthyl | 79%* | C | A |
| 7e | Me | 1-naphthyl | 63% | C | B |
| 7f | Me | diphenylmethyl | 46% | C | B |

KEY:
A = ≤25 micromolar;
B = >25 and ≤50 micromolar;
C = >50 micromolar

Other compounds that are useful for the Ugi reaction shown above or below include and are not limited to:

Synthesis of Compounds of Formula B

In some embodiments, a compound of Formula B-I is synthesized as shown below in Scheme 3:

Scheme 3

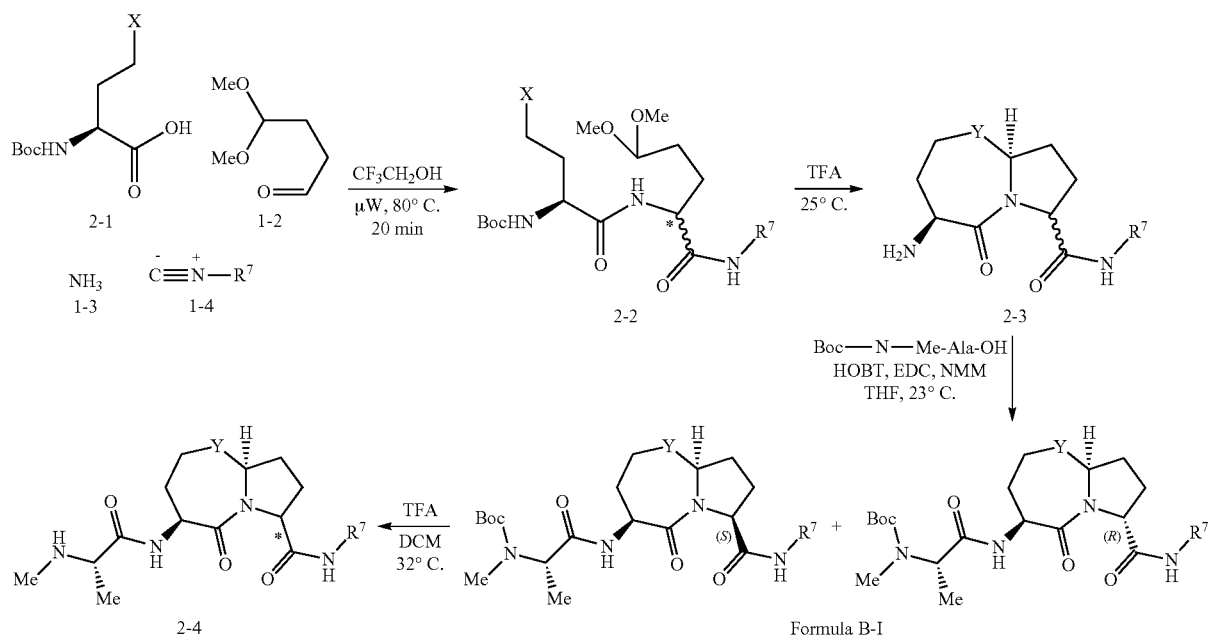

Starting with a compound of Formula 2-1, a four component Ugi reaction provides a compound of Formula 2-2. X is a protected thiol, or protected hydroxyl, or N—R$^A$ as described herein. The compound of Formula 2-2 is cyclized and a reaction with a protected alanine provides a compound of Formula B-I as a mixture of diastereomers. The mixture of diastereomers is separated by silica gel chromatography to provide a compound of Formula B-I having the structure 2-4. Where Y is S, the sulfur atom is optionally oxidized.

Figure 1B:
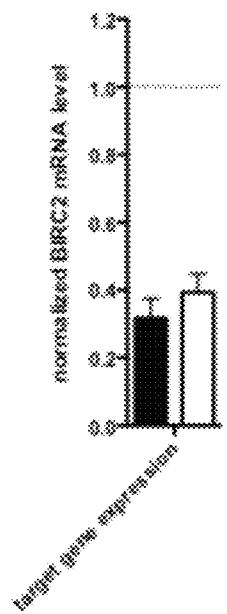
FIG. 1B shows that the cell viability of the siRNA-treated cells was verified.
Figure 1C:
FIG. 1C shows that all values were normalized to a non-targeting control siRNA.

Table 2-1 and below and FIG. 1A-1C show certain data for compounds of Formula B:

TABLE 2-1

| Product | Y | R$^1$ | Yield (4 steps) | XIAP BIR1/2 K$_i$ (μM) | XIAP BIR3 K$_i$ (μM) | ML-IAP K$_i$ (μM) |
|---|---|---|---|---|---|---|
| 16a | O | (R)-tetrahydronaphthalenyl | 44% | C | A | A |
| 16b | O | naphthalenyl | 36% | A | A | — |
| 16c | S | (R)-tetrahydronaphthalenyl | 47% | C | A | A |
| 16d | O | diphenylmethyl | ND | C | A | A |

TABLE 2-1-continued

| Product | Y | R[1] | Yield (4 steps) | XIAP BIR1/2 $K_i$ (μM) | XIAP BIR3 $K_i$ (μM) | ML-IAP $K_i$ (μM) |
|---|---|---|---|---|---|---|
| 16e | O |  | 41% | C | B | — |

KEY:
A = ≤25 micromolar;
B >25 and ≤50 micromolar;
C >50 micromolar

In an alternative embodiment, compounds of Formula B-XV are synthesized according to Scheme 4 shown below.

Scheme 4

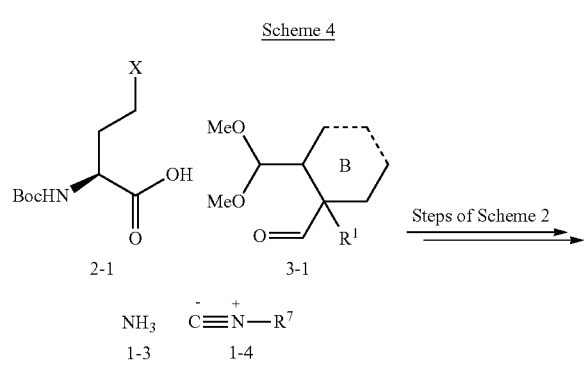

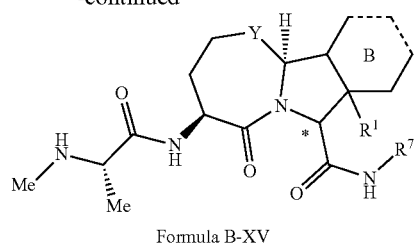

Formula B-XV

Starting with a compound of Formula 2-1, a four component Ugi reaction comprising a compound of Formula 3-1 followed by cyclization and a reaction with a protected alanine as shown in Scheme 3 provides a compound of Formula B-XV. Table 2-2 below shows certain data for compounds of Formula B-XV:

TABLE 2-2

| Product | Structure | Yield (4 steps) | XIAP BIR1/2 $K_i$ (μM) | XIAP BIR3 $K_i$ (μM) | ML-IAP $K_i$ (μM) |
|---|---|---|---|---|---|
| 17a | 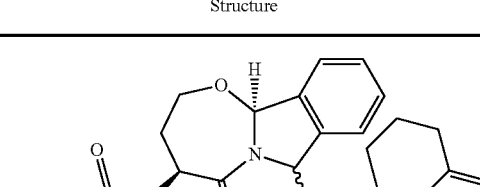 | 43% | C | A | A |
| 17b | 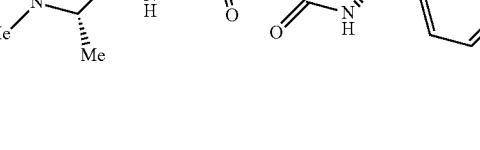 | 49% | A | A | A |

TABLE 2-2-continued

| Product | Structure | Yield (4 steps) | XIAP BIR1/2 $K_i$ (µM) | XIAP BIR3 $K_i$ (µM) | ML-IAP $K_i$ (µM) |
|---|---|---|---|---|---|
| 17c | 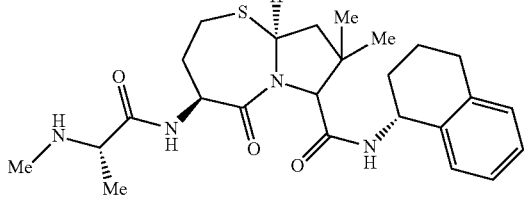 | 60% | A | A | A |

KEY:
A = ≤25 micromolar;
B >25 and ≤50 micromolar;
C >50 micromolar

It will be understood that the reactions shown in Schemes 1-4 above are illustrative and are also applicable to synthesis of compounds of Formula C, Formula D and Formula E, and such disclosure is contemplated within the scope of embodiments described herein. Synthesis of compounds of Formula C, Formula D and Formula E is shown in further detail in the Chemistry Examples section.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —NH₂ radical.
"Cyano" or "nitrile" refers to the —CN radical.
"Hydroxy" or "hydroxyl" refers to the —OH radical.
"Nitro" refers to the —NO₂ radical.
"Oxo" refers to the =O substituent.
"Thioxo" refers to the =S substituent.
"Alkyl" refers to a straight or branched hydrocarbon chain radical, having from one to thirty carbon atoms, and which is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarily. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, and the like. Unless stated otherwise specifically in the specification, an alkyl group may be optionally substituted as described below. "Alkylene" or "alkylene chain" refers to a straight or branched divalent hydrocarbon chain linking the rest of the molecule to a radical group.

"Alkoxy" refers to a radical of the formula —OR$_a$ where R$_a$ is an alkyl radical as defined. Unless stated otherwise specifically in the specification, an alkoxy group may be optionally substituted as described below.

"Heteroalkylene" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —OCH₂CH₂OMe, —OCH₂CH₂OCH₂CH₂NH₂, or —OCH₂CH₂OCH₂CH₂OCH₂CH₂N(Me)₂. Representative heteroalkylene groups include, but are not limited to —OCH₂CH₂O—, —OCH₂CH₂OCH₂CH₂O—, or —OCH₂CH₂OCH₂CH₂OCH₂CH₂O—.

"Alkylamino" refers to a radical of the formula —NHR$_a$ or —NR$_a$R$_a$ where each R$_a$ is, independently, an alkyl radical as defined above. Unless stated otherwise specifically in the specification, an alkylamino group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Carboxy" refers to —CO₂H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

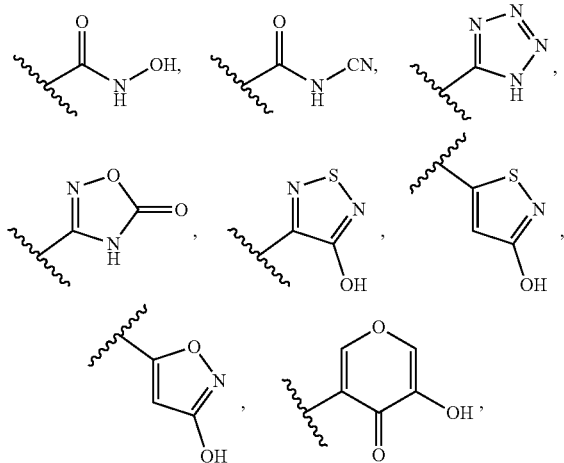

and the like.

"Cycloalkyl" refers to a stable, non-aromatic, monocyclic or polycyclic carbocyclic ring, which may include fused or bridged ring systems, which is saturated or unsaturated, and attached to the rest of the molecule by a single bond. Representative cycloalkyls include, but are not limited to, cycloaklyls having from three to fifteen carbon atoms, from three to ten carbon atoms, from three to eight carbon atoms, from three to six carbon atoms, from three to five carbon atoms, or three to four carbon atoms. Monocyclic cyclcoalkyl radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and 7,7-dimethyl-bicyclo[2.2.1]heptanyl. Unless otherwise stated specifically in the specification, a cycloalkyl group may be optionally substituted. Illustrative examples of cycloalkyl groups include, but are not limited to, the following moieties:

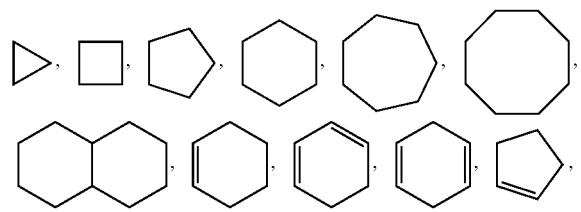

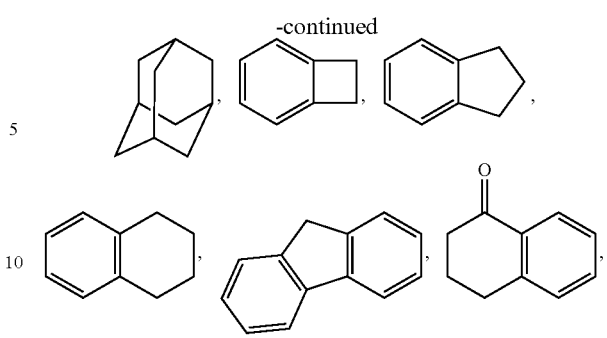

and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Perhalo" or "perfluoro" refers to a moiety in which each hydrogen atom has been replaced by a halo atom or fluorine atom, respectively.

"Heterocyclyl" or "heterocyclic ring" or "hetercycloalkyl" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted. Illustrative examples of heterocycloalkyl groups, also referred to as non-aromatic heterocycles, include:

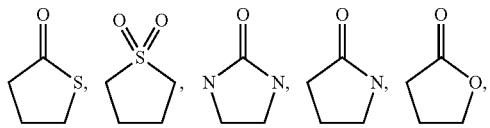

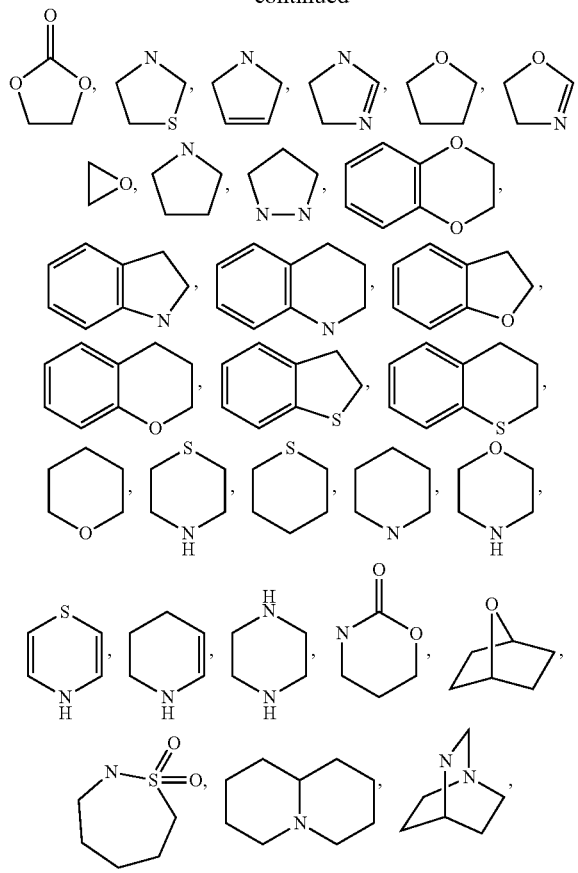

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups (i.e., alkyl, alkylene, alkoxy, alkoxyalkyl, alkylcarbonyl, alkyloxycarbonyl, alkylamino, amidyl, amidinylalkyl, amidinylalkylcarbonyl, aminoalkyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, guanidinylalkyl, guanidinylalkylcarbonyl, haloalkyl, heterocyclyl and/or heteroaryl), may be further functionalized wherein at least one hydrogen atom is replaced by a bond to a non-hydrogen atom substituent. Unless stated specifically in the specification, a substituted group may include one or more substituents selected from: oxo, —CO$_2$H, nitrile, nitro, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, trialkylammonium (—N$^+$R$_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with —C(=O)R$_g$, —C(=O)OR$_g$, —CH$_2$SO$_2$R$_g$, —CH$_2$SO$_2$NR$_g$R$_h$, —SH, —SR$_g$ or —SSR$_g$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen or sulfur atoms. For example, an alkyl group may be substituted with one or more internal oxygen atoms to form an ether or polyether group. Similarly, an alkyl group may be substituted with one or more internal sulfur atoms to form a thioether, disulfide, etc. Amidyl moieties may be substituted with up to 2 halo atoms, while other groups above may be substituted with one or more halo atoms. With the exception of alkyl groups, all other groups may also be substituted with amino or monoalklyamino. With the exception of alkyl and alkylcarbonyl groups, all other groups may also be substituted with guanidinyl or amidynyl. Optional substitutents for any of the above groups also include arylphosphoryl, for example —$R_aP(Ar)_3$ wherein $R_a$ is an alkylene and Ar is aryl moiety, for example phenyl.

An "effective amount" or "therapeutically effective amount" refers to an amount of a compound administered to a subject (e.g. a mammal, such as a human), either as a single dose or as part of a series of doses, which is effective to produce a desired therapeutic effect.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

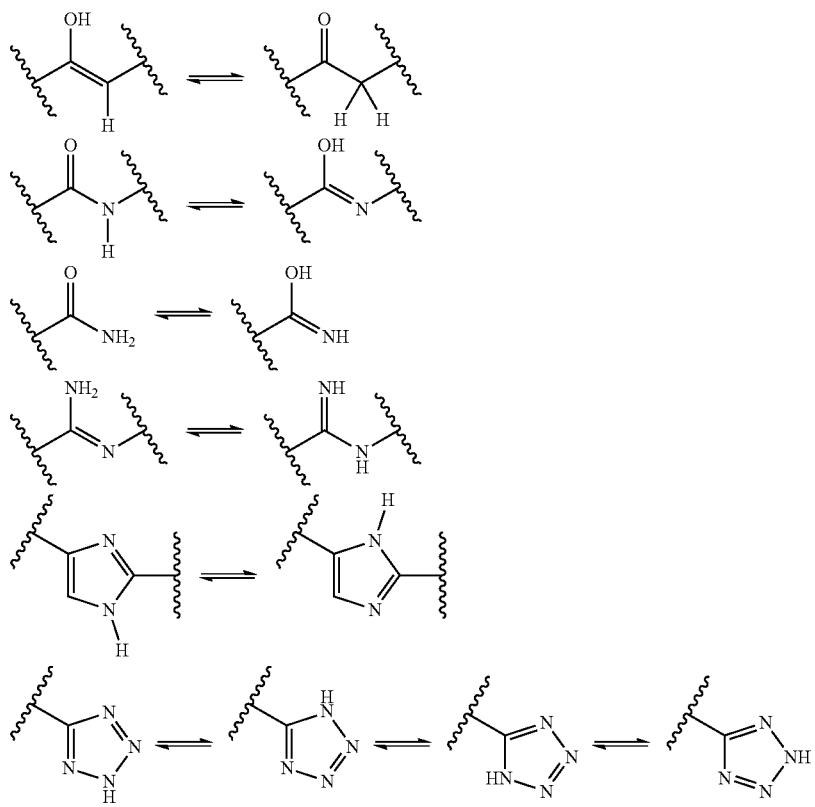

"Treatment" of a subject (e.g. a mammal, such as a human) includes any type of intervention used in an attempt to alter the natural course of the subject. In some embodiments, treatment includes administration of a pharmaceutical composition, subsequent to the initiation of a pathologic event or contact with an etiologic agent and includes stabilization of the condition (e.g., condition does not worsen, e.g., cancer does not metastasize and the like) or alleviation of the condition (e.g., reduction in tumor size, remission of cancer, absence of symptoms of autoimmune disease and the like). In other embodiments, treatment also includes prophylactic treatment (e.g., administration of a composition described herein when an individual is suspected to be suffering from a condition described herein).

As used herein, "subject", "individual" and "patient" are used interchangeably. None of the terms imply that a medical professional is required for the administration of the compounds disclosed herein.

As used herein, HIV latency is used to describe a state wherein HIV infected cells are not actively producing HIV, such as undergoing active HIV transcription. The term is not to be confused with "clinical latency", which is used to describe a stage during the incubation period wherein HIV is reproducing at very low levels and it still active.

As used herein, HIV reservoir is used the population of latently infected HIV cells. As CD4+ T cells are the major target of HIV, the latently infected CD4+ T cells, or resting memory cells, are the major component of the HIV reservoir. Synonyms for HIV reservoir include, but are not limited to, latent reservoir and HIV latent reservoir.

As used herein, antiretroviral therapy or ART is used to describe the combination of antiretroviral drugs that inhibit the ability of HIV to replicate and multiply in the body. Synonyms include, but are not limited to, "the cocktail", antiretrovirals (ARVs), highly active antiretroviral therapy (HAART), combination antiretroviral therapy (CART).

As used herein, antiretroviral drugs are used to describe drugs that target the retrovirus HIV. The classes of antiretroviral drugs are grouped by specific life of the HIV virus that is targeted by the drug and include, but are not limited to, entry inhibitors, fusion inhibitors, nucleotide/nucleoside reverse transcriptase inhibitors, non-nucleoside reverse transcriptase inhibitors, integrase inhibitors, protease inhibitors, and fixed dosed combinations.

Administration and Pharmaceutical Composition

In general, the compounds of this invention will be administered in a therapeutically effective amount by any of the accepted modes of administration for agents that serve similar utilities. Therapeutically effective amounts of compounds of inhibitors of apopotosis (IAP) antagonists, such those of Formula A, Formula B, Formula C, Formula D, Formula E, Formula F or Formula G, may range from about 0.01 to about 500 mg per kg patient body weight per day, which can be administered in single or multiple doses. Preferably, the dosage level will be about 0.1 to about 250 mg/kg per day; more preferably about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions are preferably provided in the form of tablets containing about 1.0 to about 1000 milligrams of the active ingredient, particularly about 1.0, 5.0, 10, 15, 20, 25, 50, 75, 100, 150, 200, 250, 300, 400, 500, 600, 750, 800, 900, and 1000 milligrams of the active ingredient. The actual amount of the compound of this invention, i.e., the active ingredient, will depend upon numerous factors such as the severity of the disease to be treated, the age and relative health of the subject, the potency of the compound being utilized, the route and form of administration, and other factors.

In general, compounds of this invention will be administered as pharmaceutical compositions by any one of the following routes: oral, systemic (e.g., intranasal, suppository, intrapulmonary), or parenteral (e.g., intramuscular, intravenous, intrathecal, or intraperitoneal) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, inhibitor of apoptosis proteins (IAP) antagonists, such as a compound of Formula A, Formula B, Formula C, Formula D, Formula E, Formula F or Formula G in combination with at least one pharmaceutically acceptable excipient. The compositions may further comprise at least one additional therapeutic agent. Such additional therapeutic agents include those that activate HIV transcription of latently infected cells, those that are used in the treatment of HIV, or those that inhibit active HIV replication. Acceptable excipients are non-toxic, aid administration, and do not adversely affect the therapeutic benefit of the compound of Formula A, Formula B, Formula C, Formula D, Formula E, Formula F or Formula G. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt %) basis, from about 0.01-99.99 wt % of a compound of Formula A, Formula B, Formula C, Formula D, Formula E, Formula F or Formula G based on the total formulation, with the balance being one or more suitable pharmaceutical excipients. Preferably, the compound is present at a level of about 1-80 wt %.

The compounds of the present invention may be used in combination with one or more other drugs in the treatment of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention also include those that contain one or more other active ingredients, in addition to a compound of the present invention.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound of the present invention. The weight ratio of the compound of the present invention to the second active ingredient may be varied and will depend upon the effective dose of each ingredient. Generally, an effective dose of each will be used.

In the case wherein the patient's status does improve, upon the doctor's discretion the administration of a compound described herein is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms.

CHEMISTRY EXAMPLES

The following examples are intended to illustrate but not limit the disclosed embodiments. All solvents were used as purchased from commercial sources or dried over 4 Å molecular sieves prior to use in the case of moisture sensitive reactions. Reactions conducted under microwave irradiation were performed in a CEM Discover microwave reactor using either CEM 10 mL reaction vessels or a ChemGlass heavy wall pressure vessel (100 mL, 38 mm×190 mm). Reaction progress was monitored by reverse-phase HPLC and/or thin-layer chromatography (TLC). High resolution mass spectrometry was performed using ESI-TOFMS, EI-MS (reference: perfluorokerosene) and APCI-MS. TLC was performed using silica gel 60 F254 pre-coated plates (0.25 mm). Flash chromatography was performed using silica gel (32-63 μm particle size) or aluminum oxide (activated, basic, ~150 mesh size). All products were purified to homogeneity by TLC analysis (single spot, unless stated otherwise), using a UV lamp and/or iodine and/or CAM or basic KMnO$_4$ for detection purposes. NMR spectra were recorded on 400 MHz and 500 MHz spectrometers at ambient temperature. $^1$H and $^{13}$C NMR chemical shifts are reported as δ using residual solvent as an internal standard; CDCl$_3$: 7.26, 77.16 ppm; CD$_3$OD: 3.31, 49.00 ppm; DMSO-d6: 2.50, 39.52 ppm, CD$_3$CN: 1.94 ($^1$H), 1.32 ($^{13}$C) ppm. Abbreviations used: alanine (Ala), 1-hydroxybenzotriazole (HOBT), N-methylmorpholine (NMM), N-(3-dimethylaminopropyl)-N'-ethylcarbodiimide (EDC), palladium on carbon (Pd-C), dichloromethane (DCM), diethyl ether (Et$_2$O), ethyl acetate (EtOAc), 2,2,2-trifluoroethanol (TFE), methanol (MeOH), homoserine (HSer), tetrahydrofuran (THF), trifluoroacetic acid (TFA), diisobutylaluminum hydride (DIBAL).

Example 1: Preparation of (S)-benzyl 3-(benzyloxy)-2-((S)-2-((tert-butoxycarbonyl)(methyl)amino)propanamido)propanoate

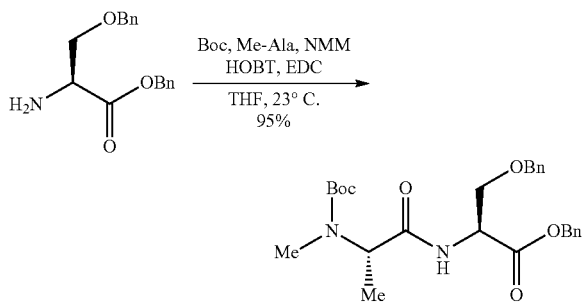

To a solution of the serine derivative (1.74 g, 3.80 mmol, 1.0 equiv), Boc-N-Me-Ala-OH (773 mg, 3.80 mmol, 1.0 equiv), HOBT.xH$_2$O (641 mg, 4.18 mmol, 1.1 equiv) and NMM (1.25 mL, 11.4 mmol, 3 equiv) in THF (45 mL) at 0° C. was added EDC.HCl (766 mg, 3.99 mmol, 1.05 equiv). After 30 min the cold bath was removed. The solution stirred for 14 h and then was quenched with saturated aqueous NaHCO$_3$ (50 mL), extracted with ethyl acetate (2×40 mL), dried over sodium sulfate and then concentrated in vacuo. The resultant oil was purified by flash chromatography on silica gel (5:1→4:1→3:1 hexanes/EtOAc) to yield the product (1.70 g, 95%). R$_f$=0.20 (5:1 hexanes/EtOAc). $^1$H NMR (400 MHz, CDCl$_3$) δ: 7.34-7.27 (m, 8H), 7.19 (dd, 2H, J=2.0, 8.0 Hz), 5.18 (q, 2H, J=12.0 Hz), 4.79-4.74 (m, 1H), 4.45 (q, 2H, J=12.0 Hz), 3.89 (dd, 1H, J=3.2, 9.6 Hz), 3.66 (dd, 1H, J=3.2, 9.6 Hz), 2.75 (s, 3H), 1.45 (s, 9H), 1.34 (t, 3H, J=7.2 Hz); $^{13}$C NMR (100 MHz, CDCl$_3$) δ: 171.6, 170.0, 137.5, 135.4, 128.7, 128.5, 128.5, 128.3, 127.9, 127.7, 73.4, 69.8, 67.4, 52.9, 30.0, 28.4, 13.9; HRMS calcd for C$_{26}$H$_{34}$N$_2$O$_6$Na: 493.23091, found 493.23211.

Example 2: Preparation of (S)-2-((S)-2-((tert-butoxycarbonyl)(methyl)amino)propanamido)-3-hydroxypropanoic Acid

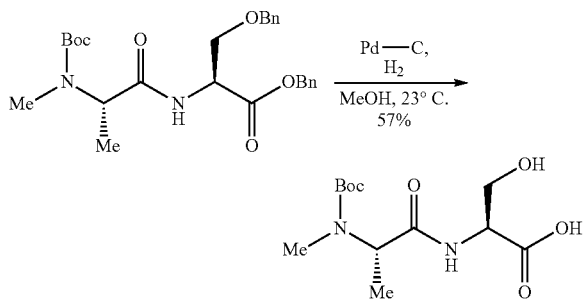

To a solution of benzyl ester (1.70 g, 3.61 mmol, 1.0 equiv) in methanol (25 mL) was added 10 wt % Pd-C (100 mg). A balloon of $H_2$ was applied for 16 h, then the mixture was filtered through Celite with DCM and concentrated in vacuo. The resultant oil was purified by flash chromatography on silica gel (1:1 hexanes/EtOAc→100% DCM→5% MeOH/DCM) to yield the product (591 mg, 57%). $^1$H NMR (400 MHz, CD$_3$OD) δ: 4.41 (t, 1H, J=3.6 Hz), 3.91 (dd, 1H, J=4.4, 10.8 Hz), 3.83 (dd, 1H, J=4.0, 11.2 Hz), 3.35-3.34 (m, 1H), 2.86 (s, 3H), 1.47 (s, 9H), 1.38 (d, 3H, J=6.8 Hz); $^{13}$C NMR (100 MHz, CD$_3$CN) δ: 207.9, 173.1, 172.4, 81.0, 62.6, 55.4, 30.9, 28.5. HRMS calcd for $C_{12}H_{22}N_2O_6Na$: 313.1370, found 313.1371.

Example 3: Preparation of (2S,3R)-benzyl 3-(benzyloxy)-2-((S)-2-((tert-butoxycarbonyl)(methyl)amino)propanamido)butanoate

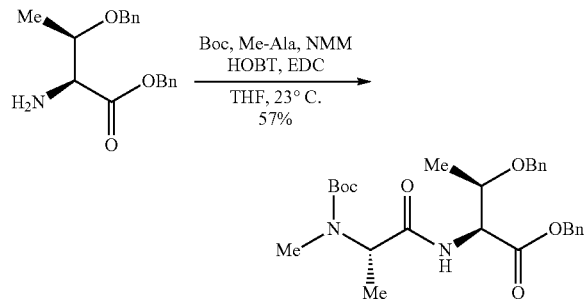

Same procedure as Example 1 using threonine derivative (4.65 g, 11.9 mmol, 1.0 equiv), Boc-N-Me-Ala-OH (2.43 g, 11.9 mmol, 1.0 equiv), HOBT.xH$_2$O (2.19 g, 14.3 mmol, 1.1 equiv), NMM (3.94 mL, 35.8 mmol, 3 equiv) and EDC.HCl (2.75 g, 14.3 mmol, 1.05 equiv) in THF (100 mL). The resultant oil was purified by flash chromatography on silica gel (5:1→4:1→2:1 hexanes/EtOAc) to yield the product (3.32 g, 57%). R$_f$=0.26 (5:1 hexanes/ethyl acetate). $^1$H NMR (400 MHz, CDCl$_3$) δ: 7.31-7.25 (m, 8H), 7.17-7.15 (m, 2H), 5.14 (d, 1H, J=6.0 Hz), 5.06 (d, 1H, J=6.0 Hz), 4.67 (dd, 1H, J=2.4, 9.2 Hz), 4.48 (d, 1H, J=12.0 Hz), 4.27 (d, 1H, J=12.0 Hz), 4.15 (qd, 1H, J=2.0, 6.0 Hz), 2.79 (s, 3H), 1.60 (s, 1H), 1.42 (s, 9H), 1.35 (d, 3H, J=7.2 Hz), 1.16 (d, 3H, 6.4 Hz); $^{13}$C NMR (100 MHz, CDCl$_3$) δ: 172.2, 170.4, 135.5, 128.7, 128.7, 128.5, 128.5, 128.5, 128.4, 127.8, 127.8, 74.3, 70.9, 67.3, 56.8, 28.4, 16.4. HRMS calcd for $C_{27}H_{36}N_2O_6Na$: 507.2466, found 507.2468.

Example 4: Preparation of (2S,3R)-2-((S)-2-((tert-butoxycarbonyl)(methyl)amino)propanamido)-3-hydroxybutanoic Acid

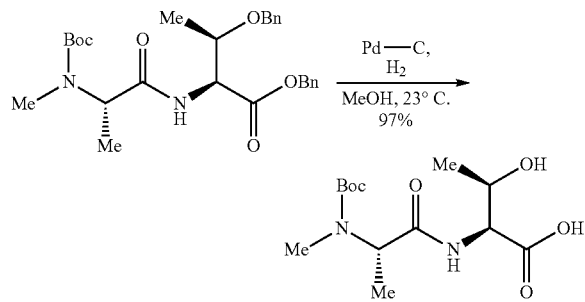

Same procedure as Example 2 using benzyl ester (3.306 g, 6.82 mmol, 1.0 equiv) and 10 wt % Pd-C (150 mg) in methanol (50 mL). The resultant oil was sufficiently pure as a crude product (2.01 g, 97%). $^1$H NMR (400 MHz, CD$_3$OD) δ: 7.44 (bs, 1H), 4.70 (bs, 1H), 4.40-4.36 (m, 1H), 4.33 (dd, 1H, J=2.8, 6.4 Hz), 2.87 (s, 3H), 1.48 (s, 9H), 1.39 (d, 3H, J=7.2 Hz), 1.18 (d, 3H, J=6.4 Hz); $^{13}$C NMR (100 MHz, CD$_3$OD) δ: 174.7, 173.7, 157.5, 81.9, 68.2, 59.0, 55.7, 30.9, 28.6, 20.7, 14.9. HRMS calcd for $C_{13}H_{24}N_2O_6Na$: 327.15266, found 327.15236.

Example 5: 4,4-Dimethoxybutanal

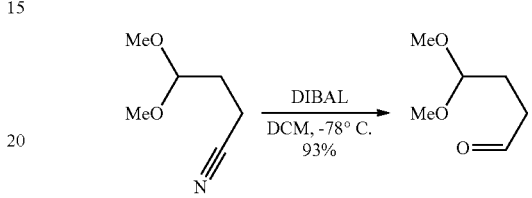

To a solution of nitrile (1.2 g, 9.29 mmol, 1.0 equiv) in DCM (75 mL) at −78° C. under N$_2$ was added 1.1 M DIBAL in cyclohexane (23.23 mL, 10.2 mmol, 1.1 equiv). After 3 h at −78° C., the mixture was slowly warmed to r.t. and quenched with sat. aq. NH$_4$Cl (25 mL) and Rochelle salt (25 mL). Reaction progress was monitored by TLC (vanillin stain). After stirring for 1 h, the mixture was extracted with DCM (3×20 mL). The organics were then washed with brine (30 mL), dried over Na$_2$SO$_4$, filtered and concentrated in vacuo to yield a colorless, relatively volatile liquid product (1.14 g, 93%) which was sufficiently pure to use without further purification. The analytical data match those previously reported: Griesbaum, K.; Jung, I. C.; Mertens, H. *J. Org. Chem.* 1990, 55, 6024.

Example 6: 4,4-Dimethoxy-2,2-dimethylbutanenitrile

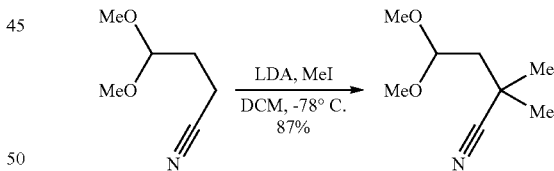

To a solution of diisopropylamine (4.77 mL, 34.1 mmol, 2.2 equiv) in THF (50 mL) at −10° C. under N$_2$ was added 1.5 M n-BuLi in hexanes (22.7 mL, 34.1 mmol, 2.2 equiv). After 30 min the mixture was cooled to −78° C. and a solution of nitrile (2.0 g, 15.5 mmol, 1.0 equiv) in THF (10 mL) was added. After 1 h iodomethane (2.12 mL, 34.1 mmol, 2.2 equiv) was added. The mixture was slowly warmed to 0° C. and kept there for 14 h, at which time it was quenched with sat. aq. NH$_4$Cl (40 mL) and extracted with EtOAc (3×20 mL). The organics were dried over Na$_2$SO$_4$, filtered and concentrated in vacuo. The resultant oil was purified by flash chromatography on silica gel (5:1→3:1 hexanes/EtOAc) to yield the product (2.105 g, 87%) as a yellow oil. R$_f$=0.49 (3:1 hexanes/EtOAc). $^1$H NMR (400 MHz, CDCl$_3$) δ: 4.60 (t, 1H, J=5.6 Hz), 3.37 (s, 6H), 1.83

(d, 2H, J=4.4 Hz), 1.39 (s, 6H); $^{13}$C NMR (100 MHz, CDCl$_3$) δ: 124.7, 102.4, 53.3, 43.0, 30.0, 27.5

Example 7: Preparation of 4,4-dimethoxy-2,2-dimethylbutanal

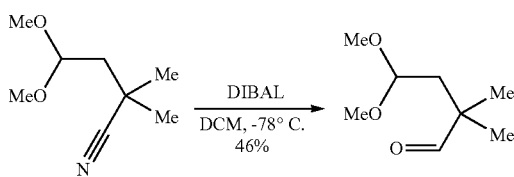 [SMILES: COC(CC(C)(C)C#N)OC ; COC(CC(C)(C)C=O)OC]

Same procedure as Example 5 using the nitrile derivative (500 mg, 3.18 mmol, 1.0 equiv) in DCM (25 mL) and 1.1 M DIBAL in cyclohexane (3.18 mL, 10.2 mmol, 1.1 equiv). The resultant oil was purified by flash chromatography on silica gel (9:1 hexanes/EtOAc) to yield the product (232 mg, 46%) as a colorless, relatively volatile oil. R$_f$=0.39 (7:1 hexanes/EtOAc).

Example 8: Preparation of 2-(diethoxymethyl)benzaldehyde

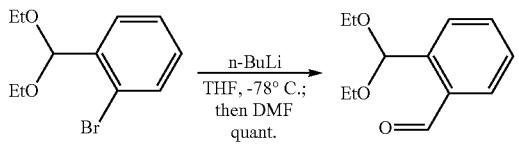

To a solution of aryl bromide (1.94 g, 7.49 mmol, 1.0 equiv) in THF (20 mL) at −78° C. under N$_2$ was added 1.5 M n-BuLi in hexanes (7.49 mL, 11.2 mmol, 1.5 equiv). After 30 min DMF (869 µL, 11.2 mmol, 1.5 equiv) was added. The mixture was slowly warmed to r.t. over 4 h, at which time it was quenched with sat. aq. NH$_4$Cl (40 mL) and extracted with EtOAc (3×20 mL). The organics were dried over Na$_2$SO$_4$, filtered and concentrated in vacuo. The resultant oil was purified by flash chromatography on silica gel (95:4:1 hexanes/EtOAc/Et$_3$N) to yield the product (2.105 g, 87%) as a yellow oil. R$_f$=0.46 (3:1 hexanes/EtOAc). The analytical data match those previously reported: Ueda, M.; Kawai, S.; Hayashi, M.; Naito, T.; Miyata, O. *J Org. Chem.* 2010, 75, 914.

Example 9: N-(Naphthalen-1-yl)formamide

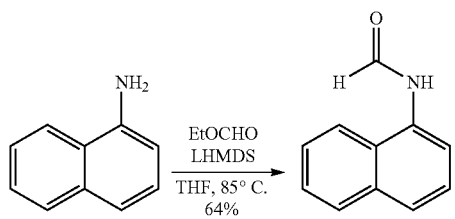 [SMILES: Nc1cccc2ccccc12 ; O=CNc1cccc2ccccc12]

To a mixture of 1-naphthylamine (6.0 g, 41.9 mmol, 1.0 equiv) and ethyl formate (6.74 mL, 83.8 mmol, 2 equiv) in THF (200 mL) was added 1 M LHMDS in THF (75.4 mL, 75.4 mmol, 1.8 equiv). The mixture was heated to 85° C. for 14 h and then concentrated. The resulting solid was filtered and rinsed with hexanes to yield the product. The filtrate was concentrated and the filtration procedure was repeated for a second batch of product to yield overall the product (3.05 g, 64%) as a brown solid and a 2:1 mixture of rotational isomers. R$_f$=0.10 (5:1 hexanes/ethyl acetate). $^1$H NMR (400 MHz, CDCl$_3$) δ: 8.65-8.61 (m, 2H), 8.45 (bs, 1H), 8.04-7.99 (m, 2H), 7.92-7.85 (m, 2H), 7.80 (d, 1H, J=8.4 Hz), 7.73 (d, 1H, J=8.0 Hz), 7.63-7.51 (m, 3H), 7.50-7.44 (m, 2H), 7.32 (d, 1H, J=7.6 Hz); $^{13}$C NMR (100 MHz, CDCl$_3$) δ: 164.1, 159.7, 134.4, 134.2, 132.2, 131.1, 129.0, 128.7, 127.9, 127.2, 127.2, 127.2, 127.0, 126.7, 126.4, 126.3, 125.9, 125.7, 121.4, 121.0, 120.5, 119.3. HRMS calcd for C$_{11}$H$_9$NO: 171.0679, found 171.0681.

Example 10: Preparation of 1-isocyanonaphthalene

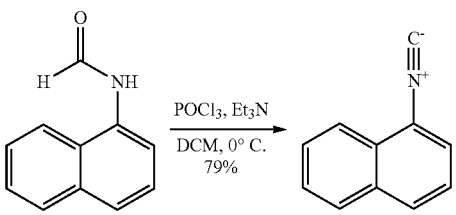

To a solution of formamide derivative (1.048 g, 6.12 mmol, 1.0 equiv) in DCM (20 mL) at 0° C. was added Et$_3$N (4.33 mL, 31.2 mmol, 5.1 equiv) followed by phosphorus oxychloride (841 µL, 9.18 mmol, 1.5 equiv). The mixture was warmed to 23° C. and stirred for 2 h, at which time it was poured into a mixture of saturated NaHCO$_3$ (40 mL) and 1 M NaOH (20 mL) and extracted with DCM (3×20 mL). The organics were dried over Na$_2$SO$_4$, filtered and concentrated in vacuo. The resultant oil was purified by flash chromatography on silica gel (1:1 hexanes/DCM) to yield the product (740 mg, 79%) as a brown oil which was stored at 0° C. R$_f$=0.72 (3:1 hexanes/EtOAc). $^1$H NMR (400 MHz, CDCl$_3$) δ: 8.19 (d, 1H, J=8.4 Hz), 7.90 (d, 2H, J=8.0 Hz), 7.68 (t, 1H, J=7.6 Hz), 7.61 (t, 2H, J=7.2 Hz), 7.45 (td, 1H, J=2.4, 8.4 Hz); $^{13}$C NMR (100 MHz, CDCl$_3$) δ: 167.3, 133.7, 129.9, 128.5, 128.2, 128.1, 127.6, 125.1, 124.7, 123.1. HRMS calcd for C$_{11}$H$_8$N: 154.06513, found 154.06671.

Example 11: Preparation of N-benzhydrylformamide

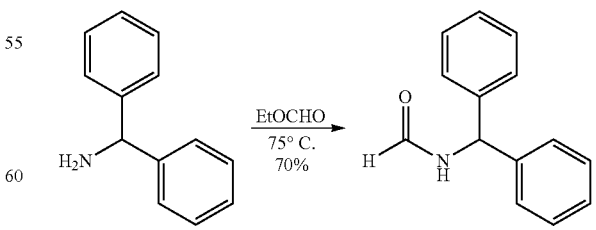

A mixture of benzhydrylamine (4.0 g, 21.8 mmol, 1.0 equiv) and ethyl formate (2.0 mL, 24.9 mmol, 1.14 equiv) was heated to 75° C. for 14 h. Ethyl acetate was added and the mixture was triturated by sonication, then filtered and rinsed with Et$_2$O to yield the product (3.24 g, 70%) as a white solid. The compound exists as a mixture of rotational isomers. R$_f$=0.29 (3:1 hexanes/EtOAc). $^1$H NMR (400 MHz, CDCl$_3$) δ: 8.15 (s, 1H), 7.34-7.19 (m, 10H), 6.69 (d, 1H, J=6.0 Hz), 6.27 (d, 1H, J=8.4 Hz); $^{13}$C NMR (100 MHz, CDCl$_3$) δ: 160.4, 141.0, 128.8, 127.7, 127.5, 55.7. HRMS calcd for C$_{14}$H$_{14}$NO: 212.10699, found 212.100748.

Example 12: Preparation of (isocyanomethylene)dibenzene

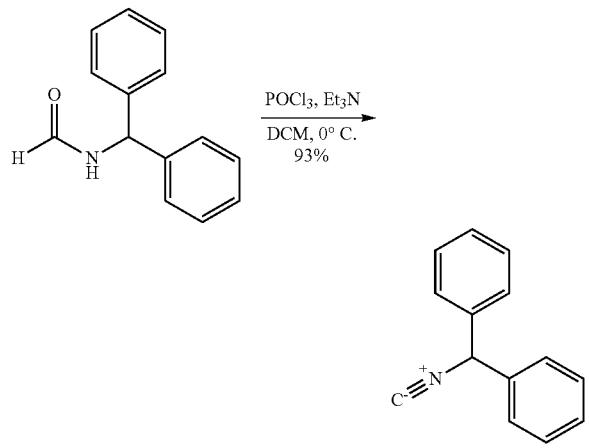

To a solution of formamide derivative (1.727 g, 8.17 mmol, 1.0 equiv) in DCM (35 mL) at 0° C. was added Et$_3$N (5.79 mL, 41.7 mmol, 5.1 equiv) followed by phosphorus oxychloride (1.12 mL, 12.3 mmol, 1.5 equiv). The mixture was warmed to 23° C. and stirred for 18 h, at which time it was poured into a mixture of saturated NaHCO$_3$ (50 mL) and 1 M NaOH (20 mL) and extracted with DCM (3×30 mL). The organics were dried over Na$_2$SO$_4$, filtered and concentrated in vacuo. The resultant oil was purified by flash chromatography on silica gel (DCM-5:1 DCM/EtOAc) to yield the product (1.467 g, 93%) as an orange solid which was stored at 0° C. R$_f$=0.73 (7:1 hexanes/EtOAc). $^1$H NMR (400 MHz, CDCl$_3$) δ: 7.41-7.33 (m, 10H), 5.92 (s, 1H); $^{13}$C NMR (100 MHz, CDCl$_3$) δ: 158.5, 137.7, 129.1, 128.6, 126.7, 77.2, 62.1. HRMS calcd for C$_{14}$H$_{11}$NNa: 216.07837, found 216.07971.

Example 13: Preparation of (R)—N-(1,2,3,4-tetrahydronaphthalen-1-yl)formamide

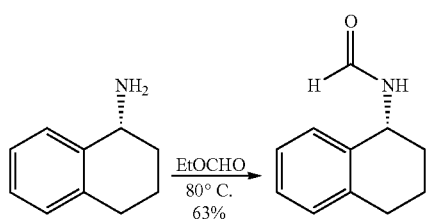 [SMILES: "EtOCHO" ; N[C@@H]1CCCc2ccccc21 ; O=CN[C@@H]1CCCc2ccccc21]

A mixture of (R)-(−)-1,2,3,4-tetrahydro-1-naphthylamine (10.0 g, 67.9 mmol, 1 equiv) and ethyl formate (6.23 mL, 77.4 mmol, 1.14 equiv) was heated to 80° C. for 14 h. Hexanes was added and the mixture was triturated by sonication, then filtered and rinsed with hexanes to yield the product (7.44 g, 63%) as a tan solid. R$_f$=0.22 (3:1 hexanes/EtOAc). $^1$H NMR (400 MHz, CDCl$_3$) δ: 8.23 (s, 1H), 7.29-7.25 (m, 1H), 7.23-7.16 (m, 2H), 7.13-7.08 (m, 1H), 5.82 (bs, 1H), 5.28 (dd, 1H, J=5.2, 14.0 Hz), 2.85-2.73 (m, 2H), 2.15-2.03 (m, 1H), 1.88-1.81 (m, 3H); $^{13}$C NMR (100 MHz, CDCl$_3$) δ: 160.5, 137.7, 136.1, 129.4, 128.8, 127.6, 126.5, 46.4, 30.3, 29.3, 20.0. HRMS calcd for C$_{11}$H$_{13}$NONa: 198.0889, found 198.0890.

Example 14: Preparation of (R)-1-isocyano-1,2,3,4-tetrahydronaphthalene

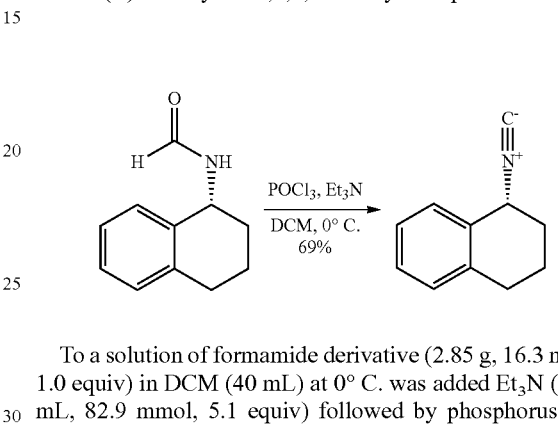

To a solution of formamide derivative (2.85 g, 16.3 mmol, 1.0 equiv) in DCM (40 mL) at 0° C. was added Et$_3$N (11.51 mL, 82.9 mmol, 5.1 equiv) followed by phosphorus oxychloride (2.23 mL, 24.4 mmol, 1.5 equiv). The mixture was warmed to 23° C. and stirred for 2 h, at which time it was poured into saturated NaHCO$_3$ (200 mL) and extracted with DCM (2×100 mL). The organics were dried over Na$_2$SO$_4$, filtered and concentrated in vacuo. The resultant oil was purified by flash chromatography on silica gel (3:1→1:1 hexanes/DCM) to yield the product (1.76 g, 69%) as a brown oil which was stored at 0° C. R$_f$=0.59 (5:1 hexanes/EtOAc). $^1$H NMR (400 MHz, CDCl$_3$) δ: 7.45-7.43 (m, 1H), 7.26-7.23 (m, 2H), 7.14-7.11 (m, 1H), 4.83 (app. s, 1H), 2.92-2.84 (m, 1H), 2.80-2.72 (m, 1H), 2.18-2.12 (m, 2H), 2.11-2.01 (m, 1H), 1.87-1.78 (m, 1H); $^{13}$C NMR (100 MHz, CDCl$_3$) δ: 155.2, 136.5, 132.1, 129.5, 128.6, 128.6, 126.7, 52.6, 30.7, 28.6, 19.4. HRMS calcd for C$_{11}$H$_{12}$N: 158.0964, found 158.0966.

Example 15: Preparation of 1-(2,2-dimethoxyethyl)-2-isocyanobenzene

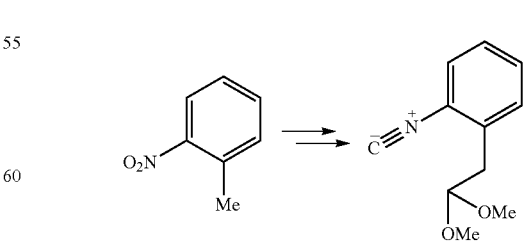

The isocyanide was prepared according to the established literature procedure; see Gilley, C. B.; Buller, M. J.; Kobayashi, Y. *Org. Lett.* 2007, 9, 3631.

Example 16: General Synthetic Scheme for the Preparation of 6,5-Heterobicyclic Compounds Described Below

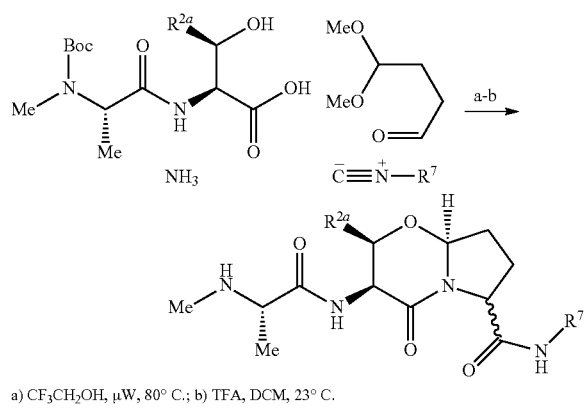

a) CF₃CH₂OH, μW, 80° C.; b) TFA, DCM, 23° C.

Example 17: Preparation of (3S,8aS)—N-benzyl-3-((S)-2-(methylamino)propanamido)-4-oxohexahydro-2H-pyrrolo[2,1-b][1,3]oxazine-6-carboxamide

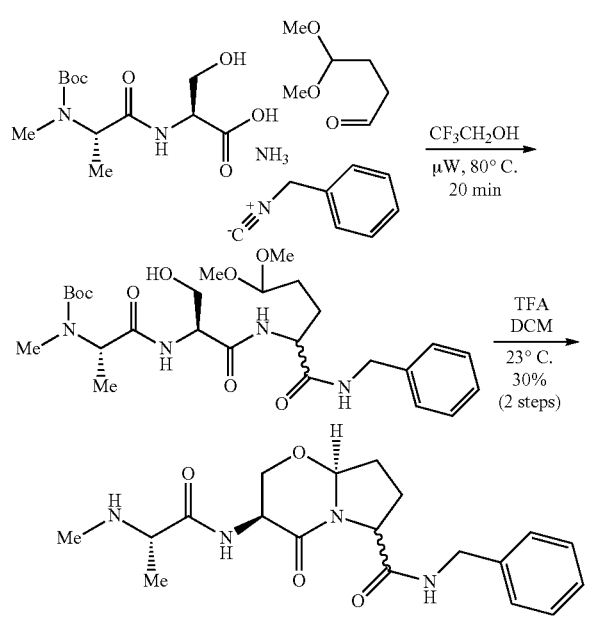

A mixture of carboxylic acid (93 mg, 0.320 mmol, 1.0 equiv), aldehyde (44 mg, 0.336 mmol, 1.05 equiv), benzyl isocyanide (38 mg, 0.320 mmol, 1.0 equiv) and 7 M ammonia in MeOH (92 μL, 0.641 mmol, 2.0 equiv) in TFE (3 mL) was stirred under microwave irradiation at a set temperature of 80° C. for 20 min. The mixture was then transferred to a round bottom flask and concentrated in vacuo, then 1 M NaOH (15 mL) was added and the mixture was extracted with DCM (3×7 mL). The organics were dried over Na₂SO₄, filtered and concentrated in vacuo. The resultant oil was combined with TFA (147 μL, 1.92 mmol, 6 equiv) in DCM (5 mL) and stirred at 23° C. for 14 h. The mixture was concentrated in vacuo and purified by flash chromatography on basic alumina (3:1 hexanes/EtOAc-DCM-7% MeOH/DCM) to yield the product as a 1:1 diastereomixture of the the free base (36 mg, 30% over 2 steps). Some of the material was further purified by preparative scale HPLC for use in biological assays. ¹H NMR (400 MHz, CD₃OD) δ: 8.51 (bs, 1H), 7.33-7.28 (m, 8H), 7.26-7.21 (m, 2H), 5.23 (t, 1H, J=5.2 Hz), 5.16 (dd, 1H, J=5.2, 8.4 Hz), 4.68 (dd, 1H, J=3.2, 6.4 Hz), 4.61-4.56 (m, 2H), 4.48 (d, 1H, J=15.2 Hz), 4.42-4.33 (m, 4H), 4.28 (dd, 1H, J=6.4, 11.6 Hz), 4.24 (dd, 1H, J=6.0, 11.6 Hz), 4.01 (dd, 1H, J=3.2, 11.6 Hz), 3.92 (dd, 1H, J=3.2, 11.6 Hz), 3.69 (q, 2H, J=6.8 Hz), 2.61 (s, 3H), 2.60 (s, 3H), 2.41-2.29 (m, 2H), 2.26-2.16 (m, 2H), 1.94-1.82 (m, 2H), 1.49 (d, 3H, J=7.2 Hz), 1.47 (d, 3H, J=7.2 Hz); ¹³C NMR (100 MHz, CD₃OD) δ: 173.6, 173.4, 167.9, 167.1, 139.7, 139.7, 129.5, 129.5, 128.4, 128.4, 128.2, 128.2, 91.1, 90.9, 71.7, 70.8, 60.7, 59.8, 58.8, 44.2, 44.0, 32.3, 32.2, 32.2, 31.2, 27.2, 26.7, 16.8, 16.7. HRMS calcd for $C_{19}H_{27}N_4O_4$: 375.2027, found 375.2028.

Example 18: Preparation of (3S,8aS)—N-(4-chlorophenyl)-3-((S)-2-(methylamino)propanamido)-4-oxohexahydro-2H-pyrrolo[2,1-b][1,3]oxazine-6-carboxamide

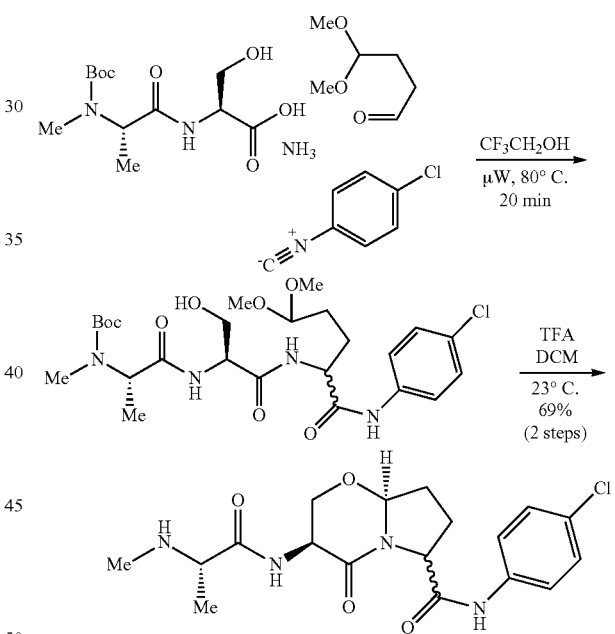

Same procedure as Example 17 with carboxylic acid (105 mg, 0.362 mmol, 1.0 equiv), aldehyde (50 mg, 0.380 mmol, 1.05 equiv), isocyanide (50 mg, 0.362 mmol, 1.0 equiv) and 7 M ammonia in MeOH (103 μL, 0.723 mmol, 2.0 equiv) in TFE (3 mL). The resultant oil was combined with TFA (166 μL, 2.17 mmol, 6 equiv) in DCM (5 mL) and stirred at 23° C. for 14 h. The mixture was concentrated in vacuo and purified by flash chromatography on basic alumina (3:1 hexanes/EtOAc→DCM→7% MeOH/DCM) to yield the product as a 1:1 diastereomixture of the free base (98 mg, 69% over 2 steps). ¹H NMR (400 MHz, CDCl₃) δ: 8.53 (bs, 1H), 7.58 (d, 2H, J=3.2 Hz), 7.57 (d, 2H, J=3.6 Hz), 7.32 (d, 2H, J=2.0 Hz), 7.30 (d, 2H, J=3.6 Hz), 5.29 (dd, 1H, J=5.2, 7.2 Hz), 5.21 (dd, 1H, J=4.8, 6.8 Hz), 4.71-4.68 (m, 2H), 4.66-4.63 (m, 1H), 4.49 (d, 1H, J=8.8 Hz), 4.31 (dd, 1H, J=6.8, 11.6 Hz), 4.26 (dd, 1H, J=6.4, 11.6 Hz), 4.01 (dd, 1H, J=2.8, 11.6 Hz), 3.94 (dd, 1H, J=2.8, 11.6 Hz), 3.62 (q, 1H, J=6.8 Hz), 3.60 (q, 1H, J=6.8 Hz), 2.56 (s, 6H), 2.47-2.35 (m, 2H), 2.30-2.25 (m, 2H), 2.13-2.07 (m, 2H), 2.02-1.87 (m, 2H), 1.45 (d, 3H, J=7.2 Hz), 1.43 (d, 3H, J=7.2 Hz); $^{13}$C NMR (100 MHz, CDCl$_3$) δ: 171.8, 171.6, 167.8, 167.3, 138.5, 138.2, 130.5, 130.3, 129.8, 129.8, 122.8, 122.5, 91.0, 90.9, 71.4, 70.9, 61.1, 60.3, 59.0, 32.6, 32.6, 32.3, 31.3, 27.1, 26.7, 17.2, 17.0. HRMS calcd for $C_{18}H_{24}C_1N_4O_4$: 395.1481, found 395.1479.

Example 19: Preparation of (3S,8aS)-3-((S)-2-(methylamino)propanamido)-4-oxo-N—((R)-1,2,3,4-tetrahydronaphthalen-1-yl)hexahydro-2H-pyrrolo[2,1-b][1,3]oxazine-6-carboxamide

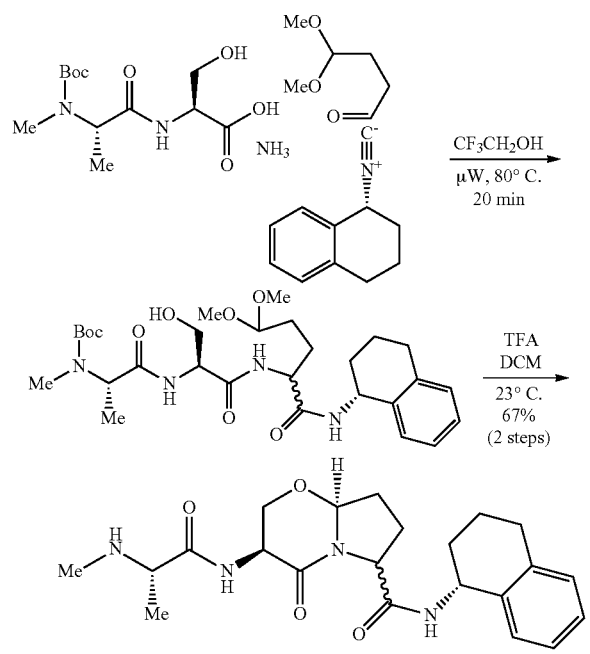

Same procedure as Example 17 with carboxylic acid (97 mg, 0.334 mmol, 1.0 equiv), aldehyde (46 mg, 0.351 mmol, 1.05 equiv), isocyanide (53 mg, 0.334 mmol, 1.0 equiv) and 7 M ammonia in MeOH (97 μL, 0.668 mmol, 2.0 equiv) in TFE (3 mL). The resultant oil was combined with TFA (177 μL, 1.55 mmol, 6 equiv) in DCM (5 mL) and stirred at 23° C. for 14 h. The mixture was concentrated in vacuo and purified by flash chromatography on basic alumina (3:1 hexanes/EtOAc→DCM→7% MeOH/DCM) to yield the product as the free base (72 mg, 67% over 2 steps). Some of the material was further purified by preparative scale HPLC for use in biological assays. $^1$H NMR (400 MHz, CDCl$_3$) δ: 8.51 (s, 1H), 7.40-7.36 (m, 1H), 7.17-7.06 (m, 7H), 5.24 (dd, 1H, J=4.8, 6.4 Hz), 5.17 (dd, 1H, J=4.8, 8.0 Hz), 5.10-5.04 (m, 2H), 4.66-4.62 (m, 2H), 4.57 (t, J=8.0 Hz), 4.35 (d, 1H, J=7.6 Hz), 4.27 (dd, 1H, J=6.4, 11.6 Hz), 4.24 (dd, 1H, J=6.0, 12.0 Hz), 3.76-3.65 (m, 2H), 2.87-2.72 (m, 4H), 2.63 (s, 3H), 2.61 (s, 3H), 2.43-2.31 (m, 2H), 2.28-2.17 (m, 2H), 2.05-1.88 (m, 7H), 1.86-1.74 (m, 5H), 1.52 (d, 3H, J=7.2 Hz), 1.49 (d, 3H, J=7.2 Hz); $^{13}$C NMR (100 MHz, CDCl$_3$) δ: 206.6, 172.9, 171.7, 167.7, 167.0, 138.7, 138.5, 137.6, 137.6, 130.1, 129.9, 129.7, 129.3, 128.2, 128.1, 127.2, 127.2, 127.1, 91.1, 91.0, 71.6, 70.9, 60.8, 59.8, 58.9, 58.8, 58.8, 32.3, 32.3, 32.2, 31.3, 31.3, 31.2, 30.2, 30.2, 27.2, 26.8, 21.8, 21.5, 16.8, 16.7. HRMS calcd for $C_{22}H_{30}N_4O_4Na$: 437.21593, found 437.20535.

Example 20: Preparation of (2R,3S,8aS)-2-methyl-3-((S)-2-(methylamino)propanamido)-4-oxo-N—((R)-1,2,3,4-tetrahydronaphthalen-1-yl)hexahydro-2H-pyrrolo[2,1-b][1,3]oxazine-6-carboxamide

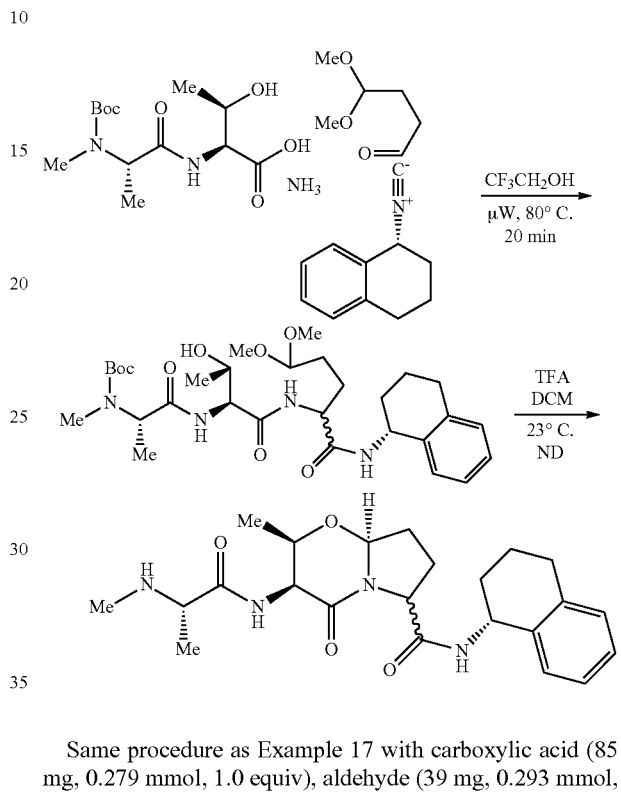

Same procedure as Example 17 with carboxylic acid (85 mg, 0.279 mmol, 1.0 equiv), aldehyde (39 mg, 0.293 mmol, 1.05 equiv), isocyanide (44 mg, 0.279 mmol, 1.0 equiv) and 7 M ammonia in MeOH (80 μL, 0.559 mmol, 2.0 equiv) in TFE (3 mL). The resultant oil was combined with TFA (128 μL, 1.67 mmol, 6 equiv) in DCM (5 mL) and stirred at 23° C. for 14 h. The mixture was concentrated in vacuo and purified by flash chromatography on basic alumina (3:1 hexanes/EtOAc→DCM→7% MeOH/DCM) to yield the product as a slightly impure free base (94 mg, yield not calculated). Some of the material was further purified by preparative scale HPLC for use in biological assays. $^1$H NMR (400 MHz, DMSO-d6) δ: 8.28 (d, 1H, J=8.8 Hz), 8.26 (d, 1H, J=8.8 Hz), 8.24 (s, 2H), 8.18 (d, 1H, J=8.8 Hz), 8.00 (d, 1H, J=8.8 Hz), 7.28 (d, 1H, J=7.2 Hz), 7.16-7.06 (m, 6H), 5.25 (t, 1H, J=5.6 Hz), 5.20 (dd, 1H, J=5.2, 7.6 Hz), 4.99-4.92 (m, 2H), 4.60 (dd, 1H, J=5.6, 8.4 Hz), 4.50 (dd, 1H, J=5.2, 8.4 Hz), 4.46 (t, 1H, J=7.2 Hz), 4.34-4.27 (m, 2H), 4.24 (t, 2H, J=8.4 Hz), 3.13 (q, 1H, J=6.8 Hz), 3.09 (q, 1H, J=6.8 Hz), 2.76-2.70 (m, 3H), 2.24 (s, 3H), 2.22 (s, 3H), 1.93-1.80 (m, 6H), 1.80-1.60 (m, 6H), 1.17 (d, 3H, J=6.8 Hz), 1.15 (d, 3H, J=6.8 Hz), 1.07 (d, 3H, J=6.4 Hz), 1.00 (d, 3H, J=6.4 Hz); $^{13}$C NMR (100 MHz, DMSO-d6) δ: 174.1, 170.3, 169.9, 165.7, 165.2, 137.6, 137.4, 137.0, 136.9, 128.7, 128.5, 128.3, 127.7, 126.7, 126.6, 125.8, 125.7, 99.5, 87.7, 87.6, 73.4, 72.6, 59.2, 58.8, 58.7, 57.9, 50.5, 50.3, 46.6, 46.5, 34.0, 33.7, 30.7, 30.0, 29.9, 28.8, 28.8, 26.0, 25.7, 20.5, 18.9, 18.7, 16.5. HRMS calcd for $C_{23}H_{32}N_4O_4Na$: 451.23158, found 451.23286.

Example 21: Preparation of (2R,3S,8aS)-2-methyl-3-((S)-2-(methylamino)propanamido)-N-(naphthalen-1-yl)-4-oxohexahydro-2H-pyrrolo[2,1-b][1,3]oxazine-6-carboxamide

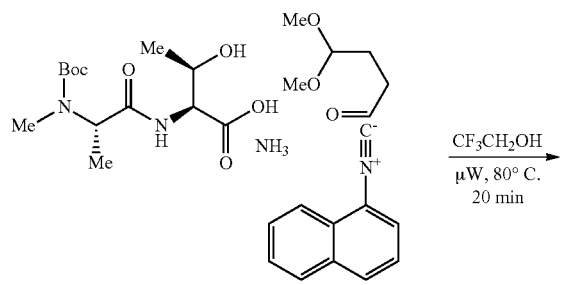

Same procedure as Example 17 with carboxylic acid (100 mg, 0.328 mmol, 1.0 equiv), aldehyde (46 mg, 0.344 mmol, 1.05 equiv), isocyanide (50 mg, 0.328 mmol, 1.0 equiv) and 7 M ammonia in MeOH (94 µL, 0.657 mmol, 2.0 equiv) in TFE (3 mL). The resultant oil was combined with TFA (151 µL, 1.97 mmol, 6 equiv) in DCM (5 mL) and stirred at 23° C. for 14 h. The mixture was concentrated in vacuo and purified by flash chromatography on basic alumina (1:1 hexanes/EtOAc→DCM→7% MeOH/DCM) to yield the product as the free base (88 mg, 63% over 2 steps). Some of the material was further purified by preparative scale HPLC for use in biological assays. $^1$H NMR (400 MHz, CD$_3$OD) δ: 8.53 (bs, 1H), 8.13-8.09 (m, 1H), 8.05 (d, 1H, J=6.8 Hz), 7.92-7.87 (m, 2H), 7.81 (t, 2H, J=6.4 Hz), 7.56-7.46 (m, 8H), 5.29 (dd, 1H, J=5.2, 8.0 Hz), 5.21 (dd, 1H, J=4.8, 8.4 Hz), 4.83 (t, 1H, J=8.4 Hz), 4.71-4.67 (m, 2H), 4.62 (d, 1H, J=4.0 Hz), 4.36-4.24 (m, 2H), 3.70 (q, 1H, J=6.8 Hz), 3.65 (q, 1H, J=6.8 Hz), 2.59 (s, 3H), 2.52 (s, 3H), 2.42-2.32 (m, 2H), 2.31-2.18 (m, 2H), 2.16-2.02 (m, 2H), 1.96-1.85 (m, 1H), 1.50 (d, 3H, J=6.8 Hz), 1.38 (d, 3H, J=7.2 Hz), 1.24 (t, 6H, J=6.8 Hz); $^{13}$C NMR (100 MHz, CD$_3$OD) δ: 173.3, 173.2, 172.7, 172.4, 168.3, 167.5, 135.7, 135.7, 134.0, 133.7, 130.6, 129.3, 129.2, 128.2, 128.1, 127.5, 127.4, 127.3, 127.2, 126.4, 126.4, 124.6, 124.3, 124.1, 123.8, 91.0, 90.9, 76.3, 75.7, 60.6, 59.5, 59.1, 58.9, 52.8, 52.5, 32.6, 32.4, 32.2, 31.2, 26.7, 26.2, 17.3, 17.2, 16.7. HRMS calcd for C$_{23}$H$_{29}$N$_4$O$_4$: 425.2183, found 425.2181.

Example 22: Preparation of (2R,3S,8bS)—N-benzhydryl-2-methyl-3-((S)-2-(methylamino)propanamido)-4-oxohexahydro-2H-pyrrolo[2,1-b][1,3]oxazine-6-carboxamide.

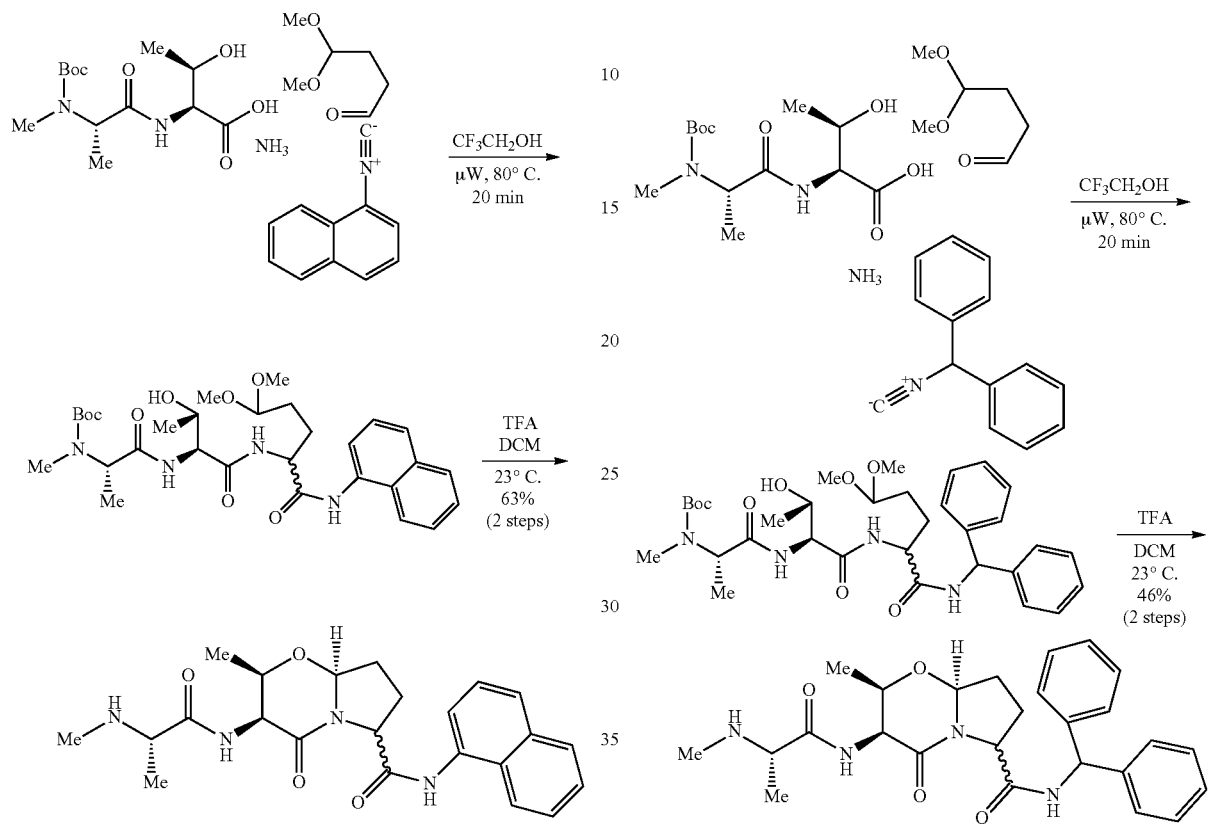

Same procedure as Example 17 with carboxylic acid (105 mg, 0.345 mmol, 1.0 equiv), aldehyde (47 mg, 0.362 mmol, 1.05 equiv), isocyanide (67 mg, 0.345 mmol, 1.0 equiv) and 7 M ammonia in MeOH (99 µL, 0.690 mmol, 2.0 equiv) in TFE (3 mL). The resultant oil was combined with TFA (159 µL, 2.07 mmol, 6 equiv) in DCM (5 mL) and stirred at 23° C. for 14 h. The mixture was concentrated in vacuo and purified by flash chromatography on basic alumina (1:1 hexanes/EtOAc→DCM→7% MeOH/DCM) to yield the product as the free base (73 mg, 46% over 2 steps). $^1$H NMR (400 MHz, CD$_3$OD) δ: 7.38-7.18 (m, 20H), 6.17 (s, 1H), 6.15 (s, 1H), 5.21 (dd, 1H, J=5.2, 8.0 Hz), 5.13 (dd, 1H, J=4.8, 8.8 Hz), 4.66 (t, 1H, J=7.6 Hz), 4.62 (d, 1H, J=4.4 Hz), 4.56 (d, 1H, J=4.4 Hz), 4.47 (d, 1H, J=8.4 Hz), 4.28 (dd, 1H, J=4.4, 6.4 Hz), 4.22 (dd, 1H, J=4.4, 6.4 Hz), 3.25 (q, 1H, J=6.8 Hz), 3.21 (q, 1H, J=6.8 Hz), 2.36 (s, 3H), 2.30 (s, 3H), 2.39-2.25 (m, 2H), 2.19-2.12 (m, 2H), 2.06-1.86 (m, 4H), 1.85-1.79 (m, 2H), 1.31 (d, 3H, J=6.8 Hz), 1.26 (d, 3H, J=7.2 Hz), 1.20 (d, 3H, J=6.4 Hz), 1.18 (d, 3H, J=6.4 Hz); $^{13}$C NMR (100 MHz, CD$_3$OD) δ: 176.8, 176.6, 173.0, 172.7, 168.0, 167.6, 143.0, 142.8, 142.6, 142.6, 129.7, 129.6, 129.5, 129.4, 128.9, 128.8, 128.7, 128.6, 128.5, 128.5, 128.3, 128.1, 90.7, 90.6, 76.3, 75.5, 60.4, 60.3, 60.0, 59.2, 58.5, 58.4, 52.5, 52.2, 34.2, 34.1, 32.1, 31.1, 29.5, 26.7, 26.1, 19.2, 19.1, 16.8, 16.7. HRMS calcd for C$_{26}$H$_{32}$N$_4$O$_4$Na: 487.23158, found 487.23308.

Example 23: General Synthetic Scheme for the Preparation of 7,5-heterobicyclic Smac Peptidomimetics

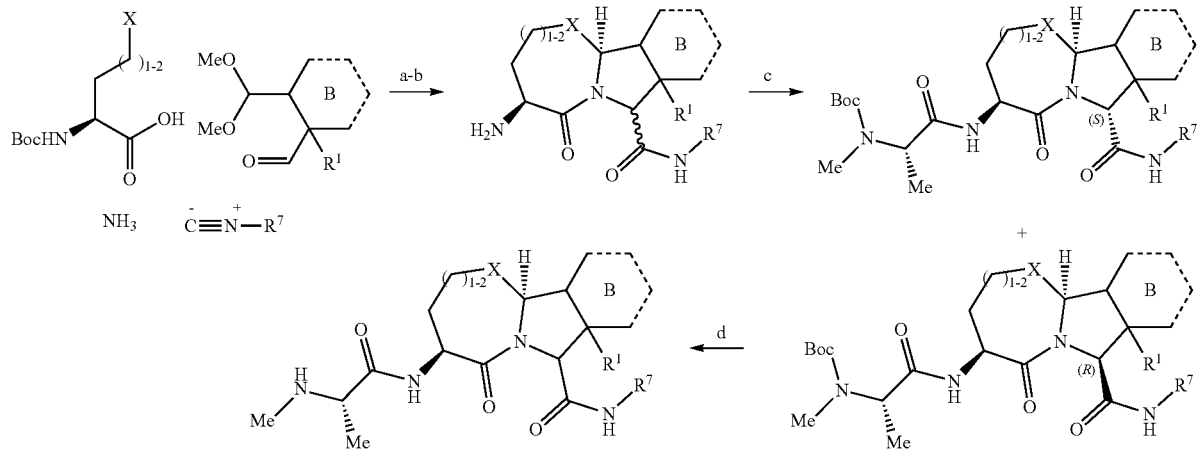

a) CF₃CH₂OH, μW, 80° C.; b) TFA, DCM, 23° C.;
c) Boc-N-Me-Ala-OH, EDC, NMM, HOBT, THF, 23° C.; d) TFA, DCM

Example 24: Preparation of (4S,9aS)-4-amino-5-oxo-N—((R)-1,2,3,4-tetrahydronaphthalen-1-yl)octahydropyrrolo[2,1-b][1,3]oxazepine-7-carboxamide

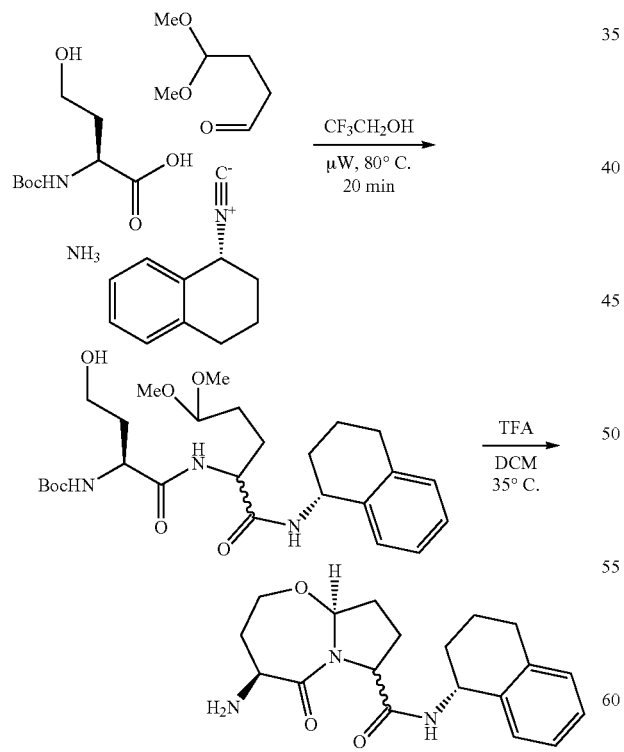

A mixture of Boc-N-HSer-OH (318 mg, 1.45 mmol, 1.0 equiv), aldehyde (201 mg, 1.52 mmol, 1.05 equiv), isocyanide (228 mg, 1.45 mmol, 1.0 equiv) and 7 M ammonia in MeOH (414 μL, 2.90 mmol, 2.0 equiv) in TFE (5 mL) was stirred under microwave irradiation at a set temperature of 80° C. for 20 min. The mixture was then transferred to a round bottom flask and concentrated in vacuo, then 1 M NaOH (15 mL) was added and the mixture was extracted with DCM (3×7 mL). The organics were dried over Na₂SO₄, filtered and concentrated in vacuo. The resultant oil was combined with TFA (834 μL, 10.9 mmol, 8 equiv) in DCM (5 mL) and stirred at 35° C. for 14 h. The mixture was concentrated in vacuo and the crude product used without further purification in the next step.

Example 25: Preparation of tert-butyl methyl((2S)-1-oxo-1-(((4S,9aS)-5-oxo-7-(((R)-1,2,3,4-tetrahydronaphthalen-1-yl)carbamoyl)octahydropyrrolo[2,1-b][1,3]oxazepin-4-yl)amino)propan-2-yl)carbamate

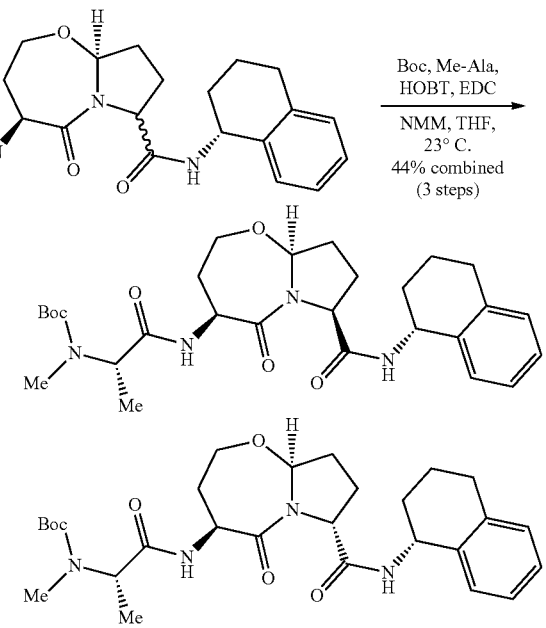

To a solution of amine (622 mg, 1.36 mmol, 1.0 equiv), Boc-N-Me-Ala-OH (276 mg, 1.36 mmol, 1.0 equiv), HOBT.xH$_2$O (229 mg, 1.50 mmol, 1.1 equiv) and NMM (598 µL, 5.44 mmol, 4 equiv) in THF (15 mL) at 0° C. was added EDC.HCl (274 mg, 1.43 mmol, 1.05 equiv). After 30 min the cold bath was removed. The solution stirred for 14 h and then was quenched with saturated aqueous NaHCO$_3$ (25 mL), extracted with ethyl acetate (2×20 mL), dried over sodium sulfate and then concentrated in vacuo. The resultant oil was purified by flash chromatography on silica gel (2:1→1:1→1:3 hexanes/EtOAc) to yield, after 3 steps, partially separated diastereomers S-isomer (30 mg, 4%, ~3:1 d.r.) and R-isomer (40 mg, 5%, ~3:1 d.r.), along with unseparated R+S isomers (267 mg, 35%). Data for S-isomer: R$_f$=0.40 (1:3 hexanes/EtOAc). $^1$H NMR (400 MHz, CDCl$_3$) δ: 7.23-7.05 (m, 4H), 6.84 (d, 1H, J=8.0 Hz), 5.22 (t, 1H, J=6.4 Hz), 5.18-5.08 (m, 1H), 4.69 (dd, 1H, J=5.6, 10.8 Hz), 4.62 (d, 1H, J=7.6 Hz), 4.13-4.03 (m, 1H), 3.95 (q, 1H, J=12.8 Hz), 2.75 (s, 3H), 2.80-2.74 (m, 1H), 2.47-2.37 (m, 1H), 2.17-1.89 (m, 4H), 1.88-1.69 (m, 5H), 1.43 (s, 9H), 1.32 (d, 3H, J=7.2 Hz); $^{13}$C NMR (100 MHz, CDCl$_3$) δ: 171.4, 169.9, 169.8, 137.6, 137.3, 136.9, 136.7, 129.3, 129.2, 128.6, 128.3, 27.4, 127.3, 126.4, 126.2, 90.3, 90.0, 70.7, 70.6, 61.1, 60.6, 53.1, 52.6, 47.7, 47.7, 33.3, 32.7, 32.5, 30.2, 30.1, 29.8, 29.3, 29.3, 28.4, 28.4, 25.9, 20.5, 20.1. Data for R-isomer: R$_f$=0.55 (1:3 hexanes/EtOAc). $^1$H NMR (400 MHz, CDCl$_3$) δ: 7.24-7.11 (m, 4H), 7.11-7.05 (m, 1H), 6.69 (bs, 1H), 5.21 (d, 1H, J=5.6 Hz), 5.10 (q, 1H, J=6.8 Hz), 4.75 (dd, 1H, J=7.6, 11.6 Hz), 4.55 (d, 1H, J=8.0 Hz), 4.47 (t, 1H, J=8.8 Hz), 4.01 (d, 1H, J=12.8 Hz), 3.97 (t, 1H, J=12.4 Hz), 2.82-2.75 (m, 2H), 2.77 (s, 3H), 2.45- 2.33 (m, 1H), 2.32-2.24 (m, 1H), 2.24-2.13 (m, 2H), 2.06-1.93 (m, 3H), 1.84-1.76 (m, 2H), 1.74-1.64 (m, 5H), 1.45 (s, 9H), 1.34 (d, 3H, J=6.8 Hz); $^{13}$C NMR (100 MHz, CDCl$_3$) δ: 172.1, 171.0, 169.8, 137.6, 136.7, 129.3, 128.6, 127.4, 126.4, 90.0, 70.6, 66.0, 61.2, 53.2, 47.8, 33.3, 32.7, 30.2, 29.3, 28.5, 25.8, 20.2, 14.0. HRMS calcd for C$_{28}$H$_{40}$N$_4$O$_6$: 551.2840, found 551.2838.

Example 26: Preparation of (4S,7S,9aS)-4-((S)-2-(methylamino)propanamido)-5-oxo-N—((R)-1,2,3,4-tetrahydronaphthalen-1-yl)octahydropyrrolo[2,1-b][1,3]oxazepine-7-carboxamide

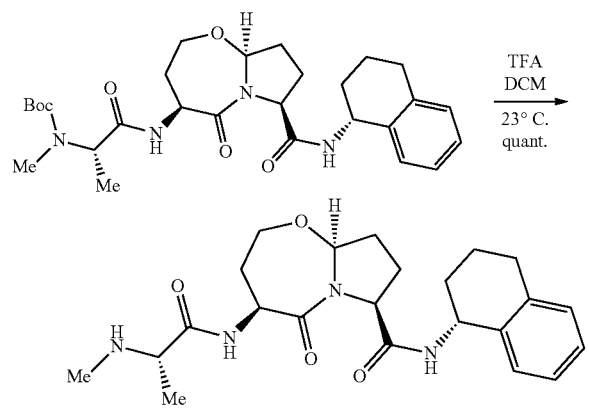

To a solution of carbamate (30 mg, 0.057 mmol, 1 equiv, ~7:3 d.r.) in DCM (2 mL) was added TFA (35 µL, 0.454 mmol, 8 equiv). After stirring for 20 h at 23° C., the solution was concentrated. The product was eluted through a short plug (~400 mg) of Silicyle® TMA-chloride ion exchange resin with MeOH to yield product.HCl (26 mg, quantitative) as the major diastereomer (~7:3). $^1$H NMR (400 MHz, CD$_3$OD) δ: 7.38-7.35 (m, 1H), 7.15-7.06 (m, 3H), 5.41-5.38 (m, 1H), 5.09-5.03 (m, 1H), 4.42 (t, 1H, J=6.4 Hz), 4.15 (dt, 1H, J=2.8, 12.8 Hz), 4.04-3.96 (m, 1H), 3.95-3.89 (m, 1H), 2.86-2.71 (m, 2H), 2.67 (s, 3H), 2.32-2.25 (m, 1H), 2.12 (q, 2H, J=7.2 Hz), 2.06-1.96 (m, 2H), 1.94-1.85 (m, 1H), 1.85-1.74 (m, 2H), 1.58 (d, 3H, J=7.2 Hz); $^{13}$C NMR (100 MHz, CD$_3$OD) δ: 173.4, 172.7, 172.7, 172.2, 169.6, 169.3, 138.6, 138.5, 137.8, 137.7, 130.0, 130.0, 129.6, 129.2, 128.2, 128.1, 127.1, 91.0, 71.3, 71.2, 62.4, 62.4, 58.4, 58.3, 54.4, 54.2, 34.0, 33.6, 33.3, 33.2, 31.8, 31.3, 31.2, 30.2, 30.2, 28.2, 28.0, 21.7, 21.6, 16.4, 16.4. HRMS calcd for C$_{23}$H$_{33}$N$_4$O$_4$: 429.2496, found 429.2495.

Example 27: Preparation of (4S,9aS)-4-amino-N-(naphthalen-1-yl)-5-oxooctahydropyrrolo[2,1-b][1,3]oxazepine-7-carboxamide

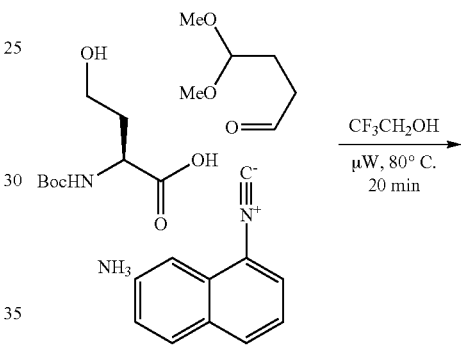

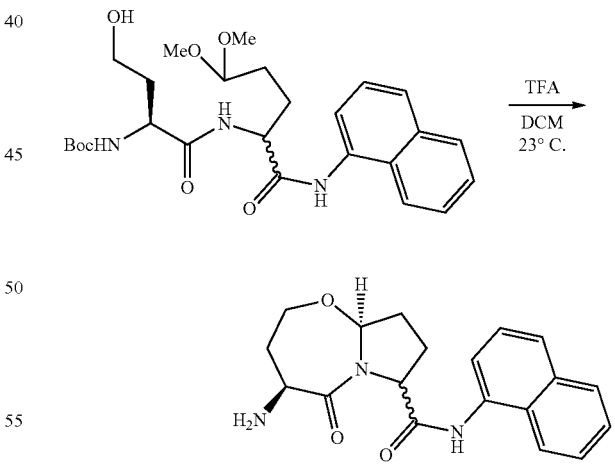

Same procedure as Example 24 with Boc-N-HSer-OH (150 mg, 0.684 mmol, 1.0 equiv), aldehyde (95 mg, 0.718 mmol, 1.05 equiv), isocyanide (105 mg, 0.684 mmol, 1.0 equiv) and 7 M ammonia in MeOH (195 µL, 1.37 mmol, 2.0 equiv) in TFE (4 mL). The resultant oil was combined with TFA (314 µL, 4.10 mmol, 6 equiv) in DCM (5 mL) and stirred at 23° C. for 14 h. The mixture was concentrated in vacuo and the crude product used without further purification in the next step.

Example 28: Preparation of tert-butyl methyl((2S)-1-(((4S,9aS)-7-(naphthalen-1-ylcarbamoyl)-5-oxooctahydropyrrolo[2,1-b][1,3]oxazepin-4-yl)amino)-1-oxopropan-2-yl)carbamate

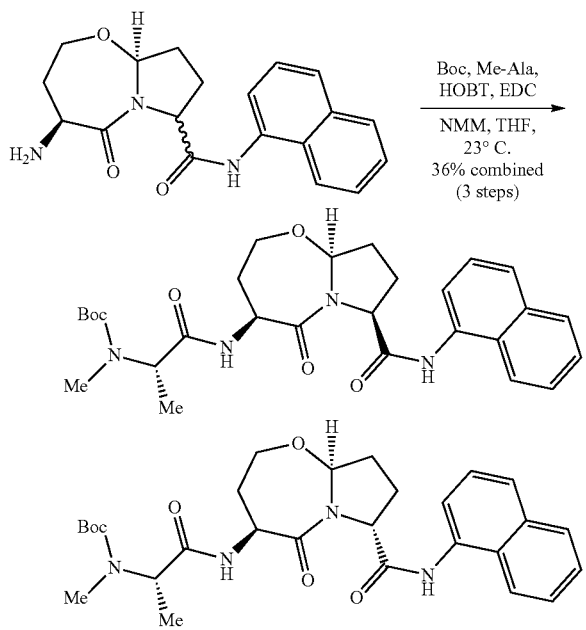

Same procedure as Example 25 above using amine derivative (209 mg, 0.615 mmol, 1.0 equiv), Boc-N-Me-Ala-OH (125 mg, 0.615 mmol, 1.0 equiv), HOBT.xH$_2$O (104 mg, 0.677 mmol, 1.1 equiv), NMM (338 µL, 3.08 mmol, 5 equiv [to soak up xs TFA]) and EDC.HCl (124 mg, 0.646 mmol, 1.05 equiv) in THF (10 mL). The resultant oil was purified by flash chromatography on silica gel (2:1→1:1→1:3 hexanes/EtOAc) to yield, after 3 steps, S-isomer (43 mg, 12%, ~6:1 d.r.) and R-isomer (37 mg, 10%, ~6:1 d.r.), along with unseparated mixture (49 mg, 14%). Data for S-isomer: R$_f$=0.33 (1:3 hexanes/EtOAc). $^1$H NMR (400 MHz, CDCl$_3$) □: 9.11 (s, 1H), 8.10 (d, 1H, J=7.6 Hz), 7.98 (d, 1H, J=8.8 Hz), 7.86 (d, 1H, J=8.0 Hz), 7.67 (d, 1H, J=8.4 Hz), 7.56-7.44 (m, 3H), 7.32 (s, 1H), 5.33 (t, 1H, J=6.4 Hz), 4.90 (d, 1H, J=6.4 Hz), 4.81 (dd, 1H, J=5.2, 10.4 Hz), 4.19 (dt, 1H, J=2.8, 12.8 Hz), 4.07-3.98 (m, 1H), 2.78 (s, 3H), 2.59-2.46 (m, 2H), 2.32-2.21 (m, 1H), 2.01-1.91 (m, 3H), 1.85-1.74 (m, 1H), 1.44 (s, 9H), 1.36 (d, 3H, J=6.8 Hz); $^{13}$C NMR (100 MHz, CDCl$_3$) □: 172.1, 171.4, 169.1, 168.5, 134.1, 132.7, 128.9, 126.6, 126.5, 126.0, 125.9, 125.5, 120.7, 119.8, 90.7, 70.8, 61.2, 52.8, 32.8, 32.6, 30.2, 28.5, 28.4, 25.6. Data for R-isomer: R$_f$=0.42 (1:3 hexanes/EtOAc). $^1$H NMR (400 MHz, CDCl$_3$) δ: 9.47 (s, 1H), 8.03 (d, 1H, J=7.2 Hz), 7.94 (d, 1H, J=7.6 Hz), 7.82 (d, 1H, J=7.6 Hz), 7.63 (d, 1H, J=8.0 Hz), 7.55 (s, 1H), 7.50-7.40 (m, 2H), 7.31 (s, 1H), 5.21 (s, 1H), 4.96 (d, 1H, J=7.6 Hz), 4.85-4.78 (m, 1H), 4.43 (t, 1H, J=8.8 Hz), 4.14 (d, 1H, J=12.8 Hz), 3.99 (t, 1H, J=12.0 Hz), 2.79 (s, 3H), 2.61-2.53 (m, 1H), 2.26-2.14 (m, 1H), 2.11-1.97 (m, 2H), 1.90-1.78 (m, 1H), 1.46 (s, 9H), 1.34 (d, 3H, J=7.2 Hz); $^{13}$C NMR (100 MHz, CDCl$_3$) δ: 175.0, 173.3, 172.4, 168.5, 134.1, 132.8, 128.7, 126.5, 126.1, 125.8, 125.4, 121.0, 119.5, 90.3, 70.6, 65.9, 61.6, 53.2, 49.2, 33.6, 32.5, 30.3, 30.3, 28.5, 28.5, 28.4, 24.6. HRMS calcd for C$_{28}$H$_{36}$N$_4$O$_6$Na: 547.25271, found 547.25362.

Example 29: Preparation of (4S,7S,9aS)-4-((S)-2-(methylamino)propanamido)-N-(naphthalen-1-yl)-5-oxooctahydropyrrolo[2,1-b][1,3]oxazepine-7-carboxamide

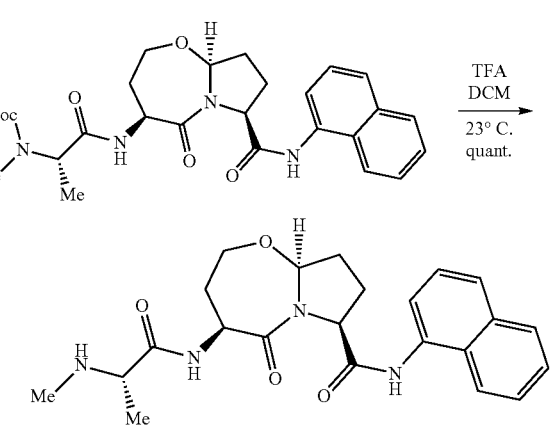

To a solution of carbamate (12 mg, 0.023 mmol, 1 equiv, ~6:1 d.r.) in DCM (1 mL) was added TFA (14 µL, 0.183 mmol, 8 equiv). After stirring for 20 h at 23° C., the solution was concentrated to yield product.TFA (12 mg, quantitative) as the major diastereomer. $^1$H NMR (400 MHz, CD$_3$OD) δ: 8.12-8.08 (m, 1H), 7.92-7.88 (m, 1H), 7.79 (d, 1H, J=8.4 Hz), 7.67 (dd, 1H, J=1.2, 7.2 Hz), 7.56-7.45 (m, 3H), 5.48 (q, 1H, J=2.8 Hz), 4.99 (d, 1H, J=12.0 Hz), 4.75 (t, 2H, J=6.8 Hz), 4.21 (dt, 1H, J=2.8, 12.4 Hz), 4.10-4.00 (m, 1H), 3.96-3.87 (m, 1H), 2.68 (s, 3H), 2.44-2.29 (m, 2H), 2.22-2.07 (m, 2H), 1.83 (dd, 1H, J=2.0, 14.4 Hz), 1.60 (d, 3H, J=6.8 Hz); $^{13}$C NMR (100 MHz, CD$_3$OD) δ: 172.9, 172.5, 169.7, 135.7, 134.0, 129.9, 127.3, 127.2, 126.5, 123.5, 91.1, 71.4, 62.8, 58.4, 54.3, 49.0, 33.8, 33.4, 31.8, 28.1, 16.4. HRMS calcd for C$_{23}$H$_{28}$N$_4$O$_4$Na: 447.20028, found 447.20189.

Example 30: Preparation of (4S,9aS)-4-amino-7-(1H-indole-1-carbonyl)hexahydropyrrolo[2,1-b][1,3]oxazepin-5(2H)-one

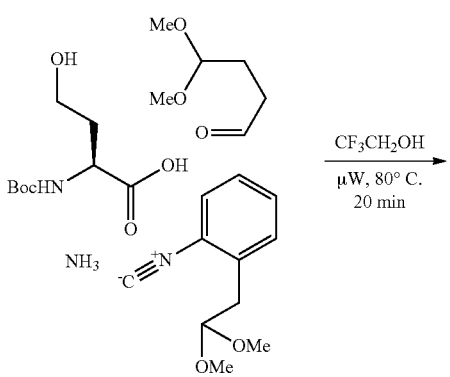

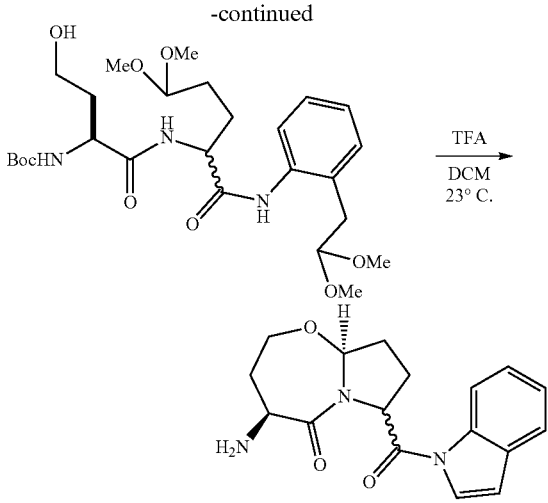

Same procedure as Example 24 with Boc-N-HSer-OH (313 mg, 1.43 mmol, 1.0 equiv), aldehyde (198 mg, 1.50 mmol, 1.05 equiv), isocyanide (273 mg, 1.43 mmol, 1.0 equiv) and 7 M ammonia in MeOH (408 µL, 2.85 mmol, 2.0 equiv) in TFE (5 mL). The resultant oil was combined with TFA (1.09 mL, 14.3 mmol, 10 equiv) in DCM (5 mL) and stirred at 23° C. for 14 h. The mixture was concentrated in vacuo and the crude product used without further purification in the next step.

Example 31: Preparation of tert-Butyl ((2S)-1-(((4S,9aS)-7-(1H-indole-1-carbonyl)-5-oxooctahydropyrrolo[2,1-b][1,3]oxazepin-4-yl)amino)-1-oxopropan-2-yl)(methyl)carbamate soak up xs TFA]) and EDC.HCl (288 mg, 1.50 mmol, 1.05 equiv) in THF (15 mL). The resultant oil was purified by flash chromatography on silica gel (2:1→1:1→1:4 hexanes/EtOAc) to yield, after 3 steps, S-isomer (150 mg, 21%) and R-isomer (144 mg, 20%). Data for S-isomer: $R_f$=0.27 (1:3 hexanes/EtOAc). $^1$H NMR (400 MHz, CDCl$_3$) δ: 8.51 (d, 1H, J=8.4 Hz), 7.57 (d, 1H, J=8.0 Hz), 7.50 (d, 1H, J=4.0 Hz), 7.35 (t, 1H, J=8.4 Hz), 7.28 (t, 1H, J=7.6 Hz), 7.16 (s, 1H), 6.69 (d, 1H, J=3.6 Hz), 5.35 (dd, 1H, J=3.6, 6.4 Hz), 5.28 (dd, 1H, J=4.8, 8.0 Hz), 4.80 (dd, 1H, J=6.0, 10.8 Hz), 4.75-4.65 (m, 1H), 4.31 (dt, 1H, J=3.2, 12.8 Hz), 4.12 (q, 1H, J=7.2 Hz), 4.05 (t, 1H, J=13.2 Hz), 2.76 (s, 3H), 2.44-2.31 (m, 2H), 2.30-2.19 (m, 2H), 2.05-1.98 (m, 2H), 1.42 (s, 9H), 1.34 (d, 3H, J=7.2 Hz); $^{13}$C NMR (100 MHz, CDCl$_3$) δ: 171.1, 170.8, 168.8, 135.9, 130.2, 125.3, 124.0, 124.0, 120.8, 117.0, 110.0, 89.7, 80.6, 80.6, 77.2, 70.8, 64.3, 60.4, 59.7, 53.0, 32.6, 30.3, 28.3, 28.3, 28.3, 27.2, 21.0. Data for R-isomer: $R_f$=0.50 (1:3 hexanes/EtOAc). $^1$H NMR (400 MHz, CDCl$_3$) δ: 8.38 (s, 1H), 7.57 (d, 1H, J=7.6 Hz), 7.49 (d, 1H, J=4.0 Hz), 7.35 (t, 1H, J=7.2 Hz), 7.28 (d, 1H, J=7.6 Hz), 7.18 (s, 1H), 6.71 (d, 1H, J=3.6 Hz), 5.44-5.39 (m, 2H), 4.88 (dd, 1H, J=5.6, 11.2 Hz), 4.75-4.69 (m, 1H), 4.47 (t, 2H, J=8.8 Hz), 4.31-4.24 (m, 1H), 4.17 (dt, 1H, J=3.2, 12.8 Hz), 4.13-4.04 (m, 1H), 3.72-3.66 (m, 1H), 3.56-3.48 (m, 1H), 2.79 (s, 3H), 2.66-2.54 (m, 1H), 2.37 (sept, 1H, J=6.8 Hz), 2.21-2.06 (m, 4H), 1.81 (qd, 1H, J=3.6, 14.0 Hz), 1.67-1.58 (m, 1H), 1.43 (s, 9H), 1.33 (d, 3H, J=7.2 Hz); $^{13}$C NMR (100 MHz, CDCl$_3$) δ: 172.3, 171.1, 168.7, 135.8, 130.2, 125.4, 124.1, 123.8, 121.0, 116.7, 110.3, 89.6, 70.7, 65.8, 60.0, 53.0, 49.1, 33.1, 32.2, 30.4, 28.4, 28.4, 28.4, 26.9. HRMS calcd for $C_{26}H_{34}N_4O_6Na$: 521.2371, found 521.2372.

Example 32: Preparation of (S)—N-((4S,7S,9aS)-7-(1H-indole-1-carbonyl)-5-oxooctahydropyrrolo[2,1-b][1,3]oxazepin-4-yl)-2-(methylamino)propanamide

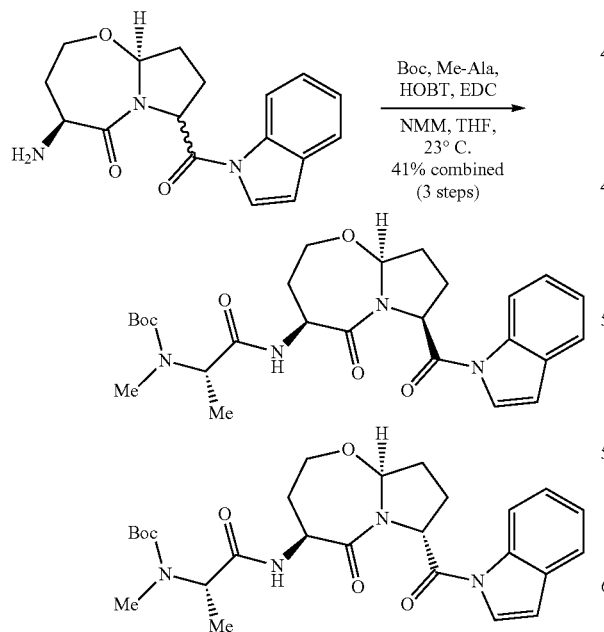

Same procedure as Example 25 above using crude amine (611 mg, 1.43 mmol, 1.0 equiv), Boc-N-Me-Ala-OH (291 mg, 1.43 mmol, 1.0 equiv), HOBT.xH$_2$O (241 mg, 1.57 mmol, 1.1 equiv), NMM (786 µL, 7.15 mmol, 5 equiv [to Same procedure as Example 29 above using carbamate (52 mg, 0.104 mmol, 1 equiv) and TFA (64 µL, 0.834 mmol, 8 equiv) in DCM (2 mL). After stirring for 20 h at 23° C., the solution was concentrated to yield product.TFA (53 mg, quantitative) as a single diastereomer. $^1$H NMR (400 MHz, CD$_3$OD) δ: 8.39 (d, 1H, J=8.0 Hz), 7.84 (d, 1H, J=4.0 Hz), 7.58 (d, 1H, J=7.2 Hz), 7.33-7.24 (m, 2H), 6.73 (d, 1H, J=4.0 Hz), 5.50-5.46 (m, 1H), 5.34 (t, 1H, J=6.8 Hz), 4.26 (dt, 1H, J=3.2, 12.4 Hz), 4.10-4.02 (m, 1H), 3.92-3.84 (m, 2H), 2.65 (s, 3H), 2.28 (qd, 1H, J=3.6, 12.4 Hz), 2.19-2.05 (m, 2H), 1.86 (d, 1H, J=14.0 Hz), 1.55 (dd, 2H, J=4.0, 7.2 Hz), 1.50 (d, 3H, J=7.2 Hz); $^{13}$C NMR (100 MHz, CD$_3$OD) δ: 172.2, 171.0, 169.6, 137.2, 131.9, 126.0, 126.0, 125.0, 122.0, 117.4, 110.7, 90.9, 71.4, 61.5, 58.3, 54.4, 49.0, 33.7, 33.2, 31.7, 28.3, 16.3. HRMS calcd for $C_{21}H_{26}N_4O_4Na$: 421.18463, found 421.18593.

Example 33: Preparation of (S)—N-((4S,7R,9aS)-7-(1H-Indole-1-carbonyl)-5-oxooctahydropyrrolo[2,1-b][1,3]oxazepin-4-yl)-2-(methylamino)propanamide

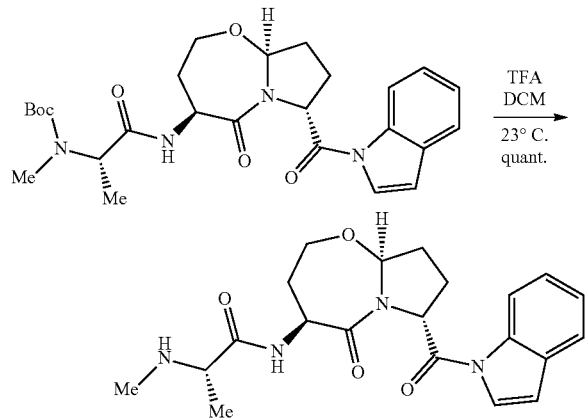

Same procedure as Example 29 above using carbamate (51 mg, 0.102 mmol, 1 equiv) and TFA (117 μL, 1.02 mmol, 10 equiv) in DCM (2 mL). After stirring for 20 h at 23° C., the solution was concentrated to yield product.TFA (52 mg, quantitative) as a single diastereomer. $^1$H NMR (400 MHz, CDCl$_3$) δ: 8.34 (d, 1H, J=8.0 Hz), 7.85 (d, 1H, J=4.0 Hz), 7.59 (d, 1H, J=6.8 Hz), 7.34-7.24 (m, 2H), 6.75 (d, 1H, J=4.0 Hz), 5.57-5.53 (m, 2H), 5.09 (dd, 1H, J=2.0, 11.2 Hz), 4.67 (dd, 1H, J=9.2, 10.8 Hz), 4.46 (td, 1H, J=1.6, 8.8 Hz), 4.35-4.27 (m, 1H), 4.19 (dt, 1H, J=2.8, 12.4 Hz), 4.12-4.04 (m, 1H), 3.90 (t, 2H, J=6.8 Hz), 3.74-3.66 (m, 1H), 2.68 (s, 3H), 2.62-2.53 (m, 2H), 2.39-2.27 (m, 2H), 2.07 (dd, 2H, J=7.2, 13.2 Hz), 1.93-1.87 (m, 1H), 1.55 (d, 3H, J=7.2 Hz); $^{13}$C NMR (100 MHz, CD$_3$OD) δ: 176.8, 172.5, 171.1, 170.4, 169.4, 137.1, 131.9, 126.1, 125.9, 125.1, 122.0, 117.4, 111.0, 90.9, 71.3, 67.2, 61.5, 58.4, 58.2, 54.3, 50.2, 34.1, 33.2, 31.8, 31.8, 29.2, 27.9, 16.3, 16.2. HRMS calcd for $C_{21}H_{27}N_4O_4$: 399.2027, found 399.2028.

Example 34: Preparation of (4S,7S,9aS)-4-amino-5-oxo-N-((R)-1,2,3,4-tetrahydronaphthalen-1-yl)octahydropyrrolo[2,1-b][1,3]thiazepine-7-carboxamide

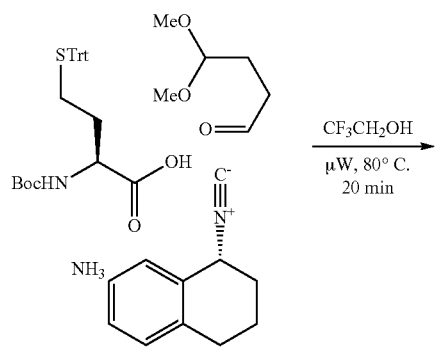

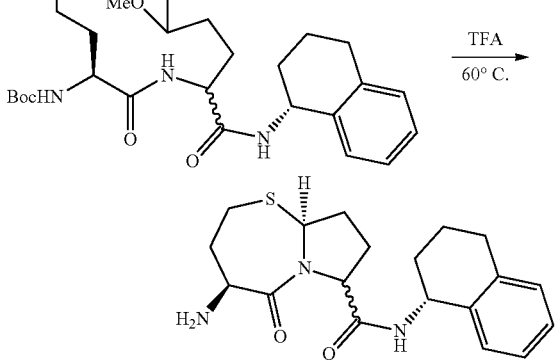

Same procedure as Example 24 with Boc-N-HCys(Trt)-OH (665 mg, 1.39 mmol, 1.0 equiv), aldehyde (193 mg, 1.46 mmol, 1.05 equiv), isocyanide (219 mg, 1.39 mmol, 1.0 equiv) and 7 M ammonia in MeOH (398 μL, 2.78 mmol, 2.0 equiv) in TFE (5 mL). The resultant oil was combined with TFA (1.07 mL, 13.9 mmol, 10 equiv) in DCM (5 mL) and stirred at 60° C. for 6 h. The mixture was concentrated in vacuo, then partially purified (trityl byproduct removed and more polar product(s) collected) by flash chromatography on basic alumina (3:1 hexanes/EtOAc→DCM→7% MeOH/DCM) to yield semi-pure product.

Example 35: Preparation of tert-Butyl methyl((2S)-1-oxo-1-(((4S,9aS)-5-oxo-7-(((R)-1,2,3,4-tetrahydronaphthalen-1-yl)carbamoyl)octahydropyrrolo[2,1-b][1,3]thiazepin-4-yl)amino)propan-2-yl)carbamate

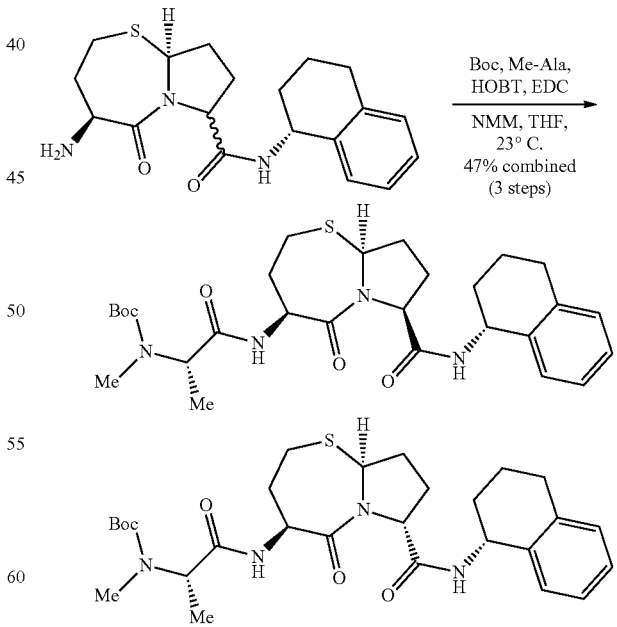

Same procedure as Example 25 above using crude amine (658 mg, 1.39 mmol, 1.0 equiv), Boc-N-Me-Ala-OH (282 mg, 1.39 mmol, 1.0 equiv), HOBT.xH$_2$O (234 mg, 1.39 mmol, 1.1 equiv), NMM (917 μL, 8.34 mmol, 6 equiv [to soak up xs TFA]) and EDC.HCl (280 mg, 1.46 mmol, 1.05 equiv) in THF (18 mL). The resultant oil was purified by flash chromatography on silica gel (1:1→1:2→1:3 hexanes/EtOAc) to yield, after 3 steps, S-isomer (121 mg, 16%, ~3:1 d.r.) and R-isomer (100 mg, 13%, ~3:1 d.r.) along with unseparated mixture (136 mg, 18%). Data for S-isomer: $R_f$=0.27 (1:3 hexanes/EtOAc). $^1$H NMR (400 MHz, CDCl$_3$) δ: 7.32 (d, 1H, J=7.6 Hz), 7.25-7.21 (m, 1H), 7.16-7.04 (m, 4H), 5.17 (q, 1H, J=7.2 Hz), 5.08 (t, 1H, J=7.2 Hz), 4.74 (d, 1H, J=8.0 Hz), 4.53 (dd, 1H, J=6.0, 10.8 Hz), 3.35-3.22 (m, 1H), 2.76 (s, 3H), 2.63-2.46 (m, 1H), 2.20 (d, 1H, J=12.8 Hz), 2.12-1.98 (m, 2H), 1.92-1.71 (m, 5H), 1.59 (q, 1H, J=12.4 Hz), 1.43 (s, 9H), 1.31 (d, 3H, J=7.2 Hz); $^{13}$C NMR (100 MHz, CDCl$_3$) δ: 171.3, 169.6, 169.3, 137.3, 129.2, 129.1, 128.8, 127.2, 126.1, 62.3, 61.8, 52.8, 47.6, 33.0, 32.1, 30.4, 30.2, 29.3, 28.4, 28.4, 26.5, 20.5. Data for R-isomer: $R_f$=0.44 (1:3 hexanes/EtOAc). $^1$H NMR (400 MHz, CDCl$_3$) δ: 7.22-7.12 (m, 4H), 7.09-7.04 (m, 1H), 6.62 (bs, 1H), 5.28 (d, 1H, J=7.6 Hz), 5.09 (d, 1H, J=6.4 Hz), 4.66-4.56 (m, 2H), 3.32 (t, 1H, J=12.0 Hz), 2.87-2.68 (m, 3H), 2.75 (s, 3H), 2.35-2.19 (m, 3H), 2.08-1.96 (m, 2H), 1.85-1.69 (m, 5H), 1.45 (s, 9H), 1.29 (d, 3H, J=7.2 Hz); $^{13}$C NMR (100 MHz, CDCl$_3$) δ: 170.9, 169.6, 137.6, 136.6, 129.3, 128.6, 127.4, 126.3, 63.8, 61.3, 53.5, 47.7, 33.7, 31.7, 30.1, 29.3, 28.5, 28.4, 20.1. HRMS calcd for C$_{28}$H$_{40}$N$_4$O$_5$SNa: 567.26116, found 567.26151.

Example 36: Preparation of (4S,7S,9aS)-4-((S)-2-(methylamino)propanamido)-5-oxo-N-((R)-1,2,3,4-tetrahydronaphthalen-1-yl)octahydropyrrolo[2,1-b][1,3]thiazepine-7-carboxamide

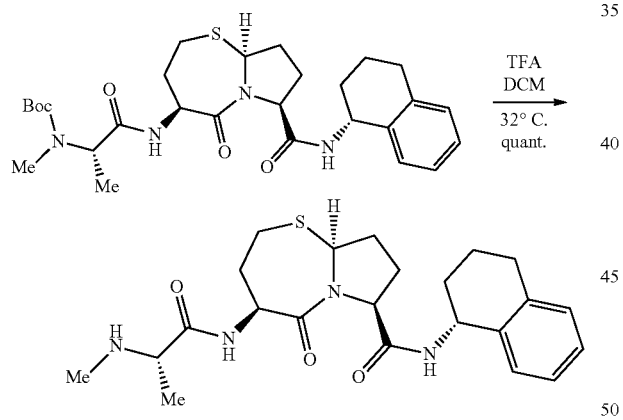

Same procedure as Example 24 using carbamate (90 mg, 0.165 mmol, 1 equiv, ~3:1 d.r.) and TFA (126 μL, 1.65 mmol, 10 equiv) in DCM (4 mL). After stirring for 20 h at 32° C., the solution was concentrated. The product was eluted through a short plug (~500 mg) of Silicyle® TMA-chloride ion exchange resin with MeOH to yield product.HCl (79 mg, quantitative) as the major diastereomer. $^1$H NMR (400 MHz, CD$_3$OD) δ: 7.39-7.34 (m, 1H), 7.17-7.05 (m, 4H), 5.46-5.39 (m, 1H), 5.07 (t, 1H, J=6.8 Hz), 4.77 (dd, 1H, J=2.0, 11.2 Hz), 4.57 (dd, 1H, J=5.2, 7.6 Hz), 3.94-3.87 (m, 1H), 3.29-3.21 (m, 1H), 3.02 (ddd, 1H, J=2.8, 6.0, 14.4 Hz), 2.82-2.75 (m, 2H), 2.66 (s, 3H), 2.60-2.49 (m, 1H), 2.25-2.17 (m, 2H), 2.15- 2.09 (m, 1H), 2.05-1.95 (m, 2H), 1.95-1.74 (m, 4H), 1.53 (d, 3H, J=7.2 Hz); $^{13}$C NMR (100 MHz, CD$_3$OD) δ: 172.3, 171.9, 169.5, 138.7, 138.5, 137.6, 137.3, 130.2, 130.0, 129.9, 129.5, 128.4, 128.3, 127.2, 127.1, 63.9, 63.4, 63.1, 58.4, 58.3, 55.1, 54.2, 54.1, 34.1, 33.3, 31.8, 31.8, 31.3, 31.0, 30.1, 30.1, 28.8, 28.5, 21.5, 21.1, 16.4, 16.3. HRMS calcd for C$_{23}$H$_{33}$N$_4$O$_3$S: 445.2268, found 445.2267.

Example 37: Preparation of (4S,7R,9aS)-4-((S)-2-(methylamino)propanamido)-5-oxo-N-((R)-1,2,3,4-tetrahydronaphthalen-1-yl)octahydropyrrolo[2,1-b][1,3]thiazepine-7-carboxamide

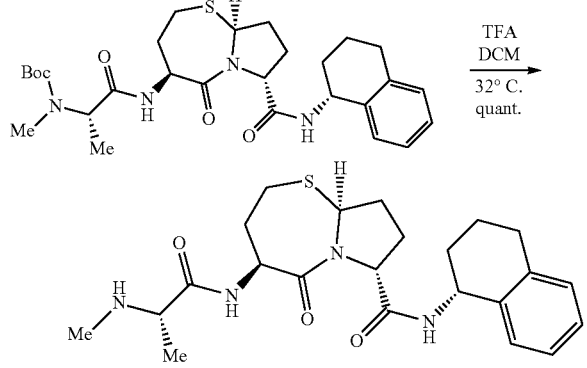

Same procedure as Example 24 using carbamate (24 mg, 0.0441 mmol, 1 equiv, ~3:1 d.r.) and TFA (34 μL, 0.441 mmol, 10 equiv) in DCM (2 mL). After stirring for 20 h at 32° C., the solution was concentrated. The product was eluted through a short plug (~500 mg) of Silicyle® TMA-chloride ion exchange resin with MeOH to yield product.HCl (21 mg, quantitative) as the major diastereomer. $^1$H NMR (400 MHz, CD$_3$OD) δ: 7.16-7.08 (m, 4H), 5.51 (d, 1H, J=7.2 Hz), 5.08-5.03 (m, 1H), 4.83 (s, 1H), 4.57 (d, 1H, J=8.8 Hz), 3.93 (q, 1H, J=7.2 Hz), 3.37-3.34 (m, 1H), 2.90 (ddd, 1H, J=2.8, 5.6, 12.0 Hz), 2.82-2.75 (m, 2H), 2.66 (s, 3H), 2.60-2.50 (m, 1H), 2.49-2.39 (m, 2H), 2.26-2.19 (m, 1H), 2.10-1.89 (m, 6H), 1.86-1.74 (m, 4H), 1.46 (d, 3H, J=6.8 Hz); $^{13}$C NMR (100 MHz, CD$_3$OD) δ: 173.3, 172.3, 169.0, 138.7, 137.8, 130.0, 129.8, 129.2, 128.7, 128.1, 127.1, 64.6, 62.4, 58.3, 54.6, 53.8, 34.2, 33.7, 32.1, 31.8, 31.2, 30.3, 29.6, 21.7, 16.4. HRMS calcd for C$_{23}$H$_{33}$N$_4$O$_3$S: 445.2268, found 445.2267.

Example 38: Preparation of (4S,11bS)-4-amino-5-oxo-N-((R)-1,2,3,4-tetrahydronaphthalen-1-yl)-2,3,4,5,7,11b-hexahydro-[1,3]oxazepino[2,3-a]isoindole-7-carboxamide

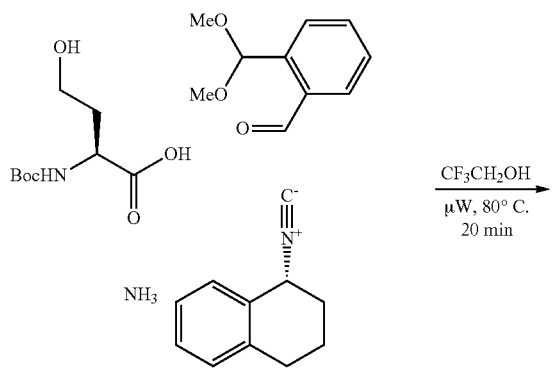

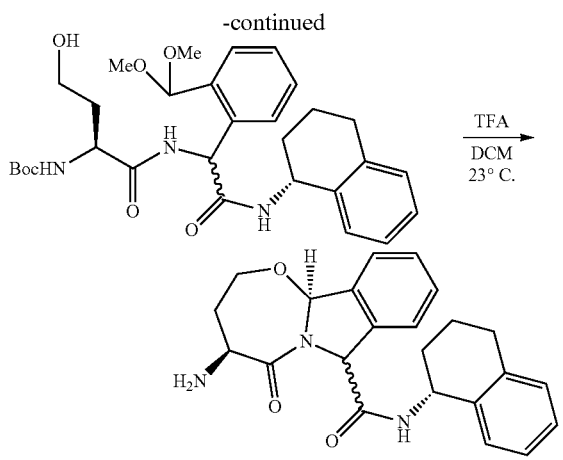

Same procedure as Example 24 with Boc-N-HSer-OH (175 mg, 0.800 mmol, 1.0 equiv), aldehyde (144 mg, 0.800 mmol, 1.0 equiv), isocyanide (126 mg, 0.800 mmol, 1.0 equiv) and 7 M ammonia in MeOH (229 μL, 1.60 mmol, 2.0 equiv) in TFE (4 mL). The resultant oil was combined with TFA (490 μL, 6.40 mmol, 8 equiv) in DCM (3 mL) and stirred at 23° C. for 14 h. The mixture was concentrated in vacuo and the crude product used without further purification in the next step.

Example 39: Preparation of tert-Butyl methyl((2S)-1-oxo-1-(((4S,11bS)-5-oxo-7-(((R)-1,2,3,4-tetrahydronaphthalen-1-yl)carbamoyl)-2,3,4,5,7,11b-hexahydro-[1,3]oxazepino[2,3-a]isoindol-4-yl)amino)propan-2-yl)carbamate

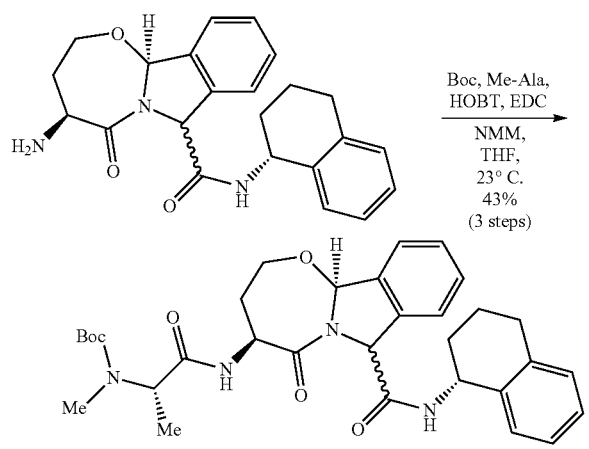

Same procedure as Example 25 using crude amine (323 mg, 0.640 mmol, 1.0 equiv), Boc-N-Me-Ala-OH (130 mg, 0.640 mmol, 1.0 equiv), HOBT.xH$_2$O (108 mg, 0.704 mmol, 1.1 equiv), NMM (281 μL, 2.56 mmol, 4 equiv) and EDC.HCl (129 mg, 0.672 mmol, 1.05 equiv) in THF (12 mL). The resultant oil was purified by flash chromatography on silica gel (3:1→1:1→1:2 hexanes/EtOAc) to yield, after 3 steps, the unseparated diastereomixture (200 mg, 43%). By NMR, one of the diastereomers seems to exist as a pair of rotational isomers. $R_f$=0.18 (1:1 hexanes/EtOAc). $^1$H NMR (400 MHz, CDCl$_3$) δ: 7.56 (d, 1H, J=7.6 Hz), 7.47 (q, 1H, J=4.4 Hz), 7.44-7.39 (m, 5H), 7.38-7.34 (m, 1H), 7.32-7.27 (m, 1H), 7.18-7.14 (m, 3H), 7.10-7.06 (m, 1H), 7.03 (d, 1H, J=7.2 Hz), 6.90 (d, 1H, J=7.2 Hz), 6.74 (d, 1H, J=7.6 Hz), 6.44-6.36 (m, 3H), 6.21 (s, 1H), 5.50 (bs, 2H), 5.17-5.10 (m, 1H), 5.03 (dd, 1H, J=8.0, 14.4 Hz), 4.88-4.80 (m, 2H), 4.72-4.66 (m, 1H), 4.44 (td, 2H, J=8.8 Hz), 4.31-4.15 (m, 5H), 2.80 (s, 3H), 2.79 (s, 3H), 2.77 (s, 3H), 2.71 (t, 4H, J=6.4 Hz), 2.22-2.08 (m, 3H), 2.06-1.98 (m, 2H), 1.86-1.73 (m, 5H), 1.71-1.61 (m, 2H), 1.48 (s, 9H), 1.46 (s, 9H), 1.35 (d, 3H, J=7.2 Hz), 1.34 (d, 3H, J=7.2 Hz), 1.33 (d, 3H, J=7.2 Hz); $^{13}$C NMR (100 MHz, CDCl$_3$) δ: 175.0, 172.4, 170.5, 168.3, 168.1, 137.7, 137.2, 136.8, 136.5, 136.5, 135.9, 135.7, 135.7, 135.2, 130.7, 130.5, 129.4, 129.3, 129.0, 128.7, 127.8, 127.4, 127.2, 126.4, 126.2, 125.0, 125.0, 122.9, 122.3, 122.3, 92.0, 91.5, 71.4, 71.4, 66.7, 66.5, 65.9, 53.3, 52.8, 49.2, 47.9, 47.7, 30.3, 29.3, 29.2, 28.5, 28.4, 28.4, 20.4, 20.2. HRMS calcd for C$_{32}$H$_{41}$N$_4$O$_6$Na: 599.28401, found 599.28561.

Example 40: Preparation of (4S,11bS)-4-((S)-2-(Methylamino)propanamido)-5-oxo-N-((R)-1,2,3,4-tetrahydronaphthalen-1-yl)-2,3,4,5,7,11b-hexahydro-[1,3]oxazepino[2,3-a]isoindole-7-carboxamide

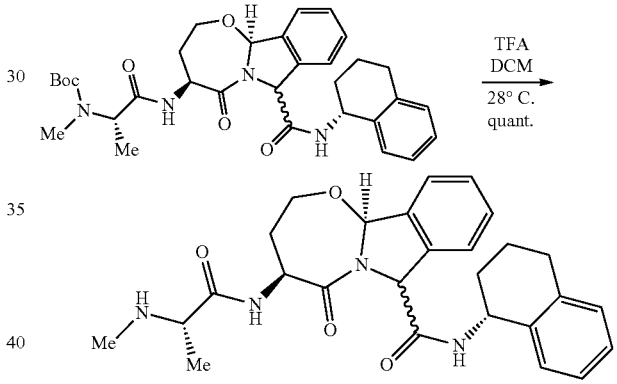

Same procedure as Example 29 using carbamate (38 mg, 0.066 mmol, 1 equiv) and TFA (40 μL, 0.527 mmol, 8 equiv) in DCM (2 mL). After stirring for 20 h at 28° C., the solution was concentrated to yield product.TFA (38 mg, quantitative) as a 1:1 diastereomixture. Data for the 1:1 diastereomixture: $^1$H NMR (400 MHz, CD$_3$OD) δ: 7.53-7.45 (m, 7H), 7.39-7.35 (m, 1H), 7.26 (d, 1H, J=7.2 Hz), 7.16-7.07 (d, 2H, J=2.0 Hz), 6.53 (d, 1H, J=1.6 Hz), 6.47 (s, 1H), 5.57 (d, 1H, J=1.6 Hz), 5.47 (s, 1H), 5.11-5.03 (m, 3H), 4.66 (dd, 1H, J=9.2, 11.2 Hz), 4.46 (td, 1H, J=2.0, 9.2 Hz), 4.35-4.27 (m, 4H), 3.97 (q, 1H, J=6.8 Hz), 3.88 (q, 1H, J=7.2 Hz), 2.89-2.74 (m, 3H), 2.70 (s, 3H), 2.69 (s, 3H), 2.62-2.54 (m, 1H), 2.33 (tt, 1H, J=1.6, 10.8 Hz), 2.02-1.92 (m, 6H), 1.85-1.76 (m, 3H), 1.62 (d, 3H, J=7.2 Hz), 1.55 (d, 3H, J=7.2 Hz), 1.54 (d, 3H, J=7.2 Hz); $^{13}$C NMR (100 MHz, CD$_3$OD) δ: 176.8, 172.2, 172.0, 171.0, 170.5, 170.4, 169.7, 169.2, 162.8, 162.4, 138.7, 138.6, 138.5, 138.4, 137.7, 137.5, 136.9, 136.6, 131.3, 131.3, 130.3, 130.2, 130.1, 130.0, 129.7, 129.5, 128.2, 128.2, 127.1, 126.3, 123.2, 123.2, 101.3, 93.2, 92.4, 72.1, 72.0, 67.3, 67.2, 66.9, 58.4, 58.4, 58.2, 54.6, 54.4, 50.2, 34.2, 33.5, 31.8, 31.8, 31.4, 31.0, 30.2, 30.2, 29.2, 21.6, 21.4, 16.4, 16.4, 16.2. HRMS calcd for C$_{27}$H$_{33}$N$_4$O$_4$: 477.2496, found 477.2493.

Example 41: Preparation of (4S,9aS)-4-Amino-8,8-dimethyl-5-oxo-N-((R)-1,2,3,4-tetrahydronaphthalen-1-yl)octahydropyrrolo[2,1-b][1,3]oxazepine-7-carboxamide

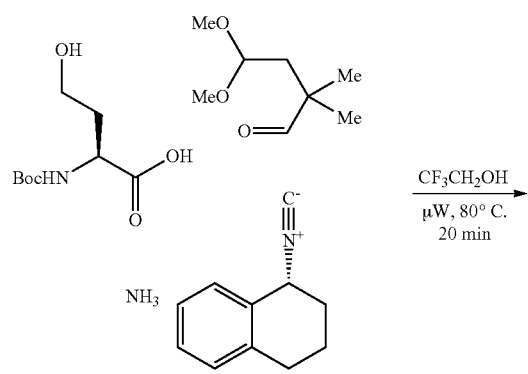

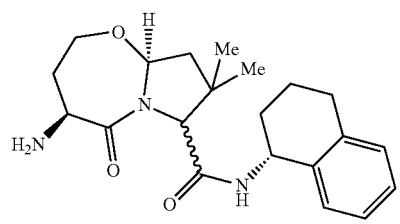

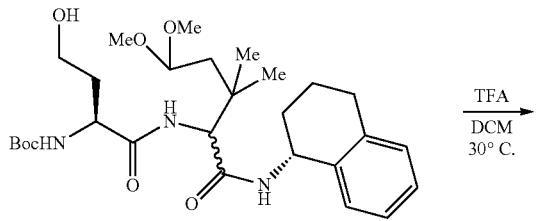

Same procedure as Example 24 with Boc-N-HSer-OH (157 mg, 0.718 mmol, 1.0 equiv), aldehyde (144 mg, 0.718 mmol, 1.0 equiv), isocyanide (113 mg, 0.718 mmol, 1.0 equiv) and 7 M ammonia in MeOH (205 μL, 1.44 mmol, 2.0 equiv) in TFE (4 mL). The resultant oil was combined with TFA (473 μL, 7.18 mmol, 10 equiv) in DCM (4 mL) and stirred at 30° C. for 14 h. The mixture was concentrated in vacuo and the crude product used without further purification in the next step.

Example 42: tert-Butyl ((S)-1-(((4S,7S,9aS)-8,8-dimethyl-5-oxo-7-(((R)-1,2,3,4-tetrahydronaphthalen-1-yl)carbamoyl)octahydropyrrolo[2,1-b][1,3]oxazepin-4-yl)amino)-1-oxopropan-2-yl)(methyl)carbamate

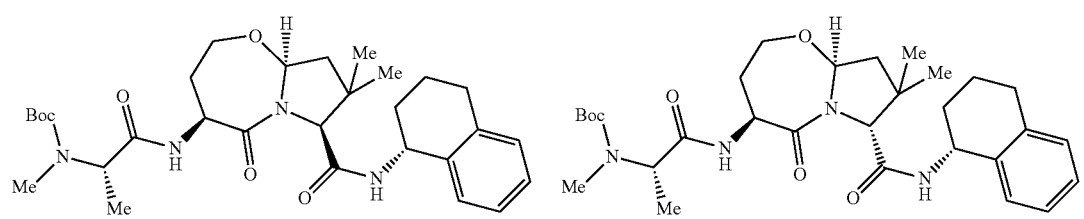

Same procedure as Example 25 using crude amine (270 mg, 0.555 mmol, 1.0 equiv), Boc-N-Me-Ala-OH (113 mg, 0.555 mmol, 1.0 equiv), HOBT.xH$_2$O (93 mg, 0.610 mmol, 1.1 equiv), NMM (366 µL, 3.33 mmol, 6 equiv [to soak up xs TFA]) and EDC.HCl (112 mg, 0.582 mmol, 1.05 equiv) in THF (10 mL). The resultant oil was purified by flash chromatography on silica gel (3:1→1:1→1:3 hexanes/EtOAc) to yield, after 3 steps, S-isomer (29 mg, 7%, >10:1 d.r.) along with unseparated mixture (168 mg, 42%). Data for S-isomer: R$_f$=0.30 (1:1 hexanes/EtOAc). $^1$H NMR (400 MHz, CDCl$_3$) δ: 7.29-7.25 (m, 2H), 7.17-7.12 (m, 2H), 7.09-7.05 (m, 1H), 6.72 (d, 1H, J=8.0 Hz), 5.24 (t, 1H, J=5.6 Hz), 5.16 (dd, 1H, J=5.6, 6.8 Hz), 4.70 (dd, 1H, J=5.6, 11.2 Hz), 4.16 (s, 1H), 4.05-3.98 (m, 1H), 3.93 (q, 1H, J=12.4 Hz), 2.79 (s, 3H), 2.78-2.73 (m, 2H), 2.19 (dd, 1H, J=6.8, 14.0 Hz), 2.06-1.96 (m, 2H), 1.88 (dd, 1H, J=6.0, 14.0 Hz), 1.87-1.69 (m, 5H), 1.66-1.60 (m, 1H), 1.47 (s, 9H), 1.34 (d, 3H, J=7.2 Hz), 1.18 (s, 3H), 1.07 (s, 3H); $^{13}$C NMR (100 MHz, CDCl$_3$) δ: 170.7, 168.8, 137.3, 136.7, 136.6, 129.2, 128.9, 127.4, 126.4, 89.3, 89.2, 70.9, 70.7, 52.6, 47.5, 46.1, 39.6, 30.2, 29.7, 29.2, 28.5, 28.4, 23.8, 21.2, 19.9, 14.3, 14.0. Data for R-isomer: R$_f$=0.39 (1:3 hexanes/EtOAc). HRMS calcd for C$_{30}$H$_{44}$N$_4$O$_6$Na: 579.3153, found 579.3155.

Example 43: Preparation of (4S,7S,9aS)-8,8-Dimethyl-4-((S)-2-(methylamino)propanamido)-5-oxo-N-((R)-1,2,3,4-tetrahydronaphthalen-1-yl)octahydropyrrolo[2,1-b][1,3]oxazepine-7-carboxamide

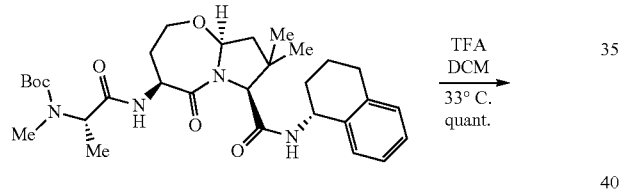

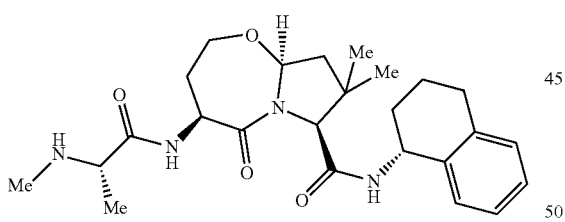

Same procedure as Example 29 using carbamate (25 mg, 0.045 mmol, 1 equiv, 8:3 d.r.) and TFA (35 µL, 0.449 mmol, 10 equiv) in DCM (1 mL). After stirring for 20 h at 33° C., the solution was concentrated to yield product.TFA (25 mg, quantitative) as the major diastereomer. $^1$H NMR (400 MHz, CD$_3$OD) δ: 8.15 (d, 1H, J=8.4 Hz), 7.32 (d, 1H, J=6.4 Hz), 7.17-7.07 (m, 3H), 5.44 (t, 1H, J=6.4 Hz), 5.10 (q, 1H, J=6.8 Hz), 4.14 (dt, 1H, J=3.2, 12.0 Hz), 4.08 (s, 1H), 3.99-3.91 (m, 2H), 2.80 (p, 2H, J=6.0 Hz), 2.68 (s, 3H), 2.20 (dd, 1H, J=6.4, 13.2 Hz), 2.08-1.96 (m, 3H), 1.89-1.77 (m, 4H), 1.58 (d, 3H, J=7.2 Hz); $^{13}$C NMR (100 MHz, CD$_3$OD) δ: 172.2, 171.5, 169.6, 138.5, 137.6, 130.1, 129.7, 128.3, 127.1, 117.5, 114.6, 90.5, 71.7, 71.3, 58.4, 54.2, 47.0, 40.1, 33.2, 31.8, 31.4, 30.1, 29.3, 24.2, 21.4, 16.3. HRMS calcd for C$_{25}$H$_3$N$_4$O$_4$: 457.2809, found 457.2811.

Example 44: Preparation of (4S,7S,9aS)-4-Amino-8,8-dimethyl-5-oxo-N-((R)-1,2,3,4-tetrahydronaphthalen-1-yl)octahydropyrrolo[2,1-b][1,3]thiazepine-7-carboxamide

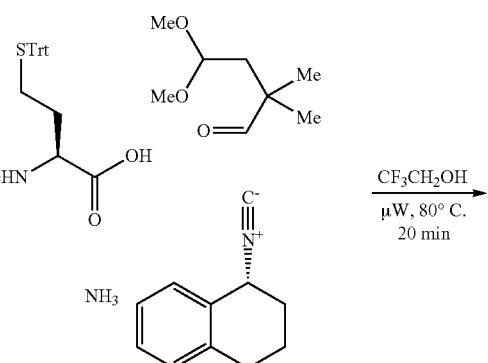

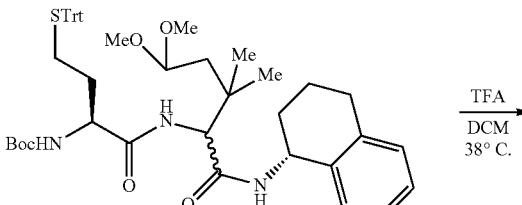

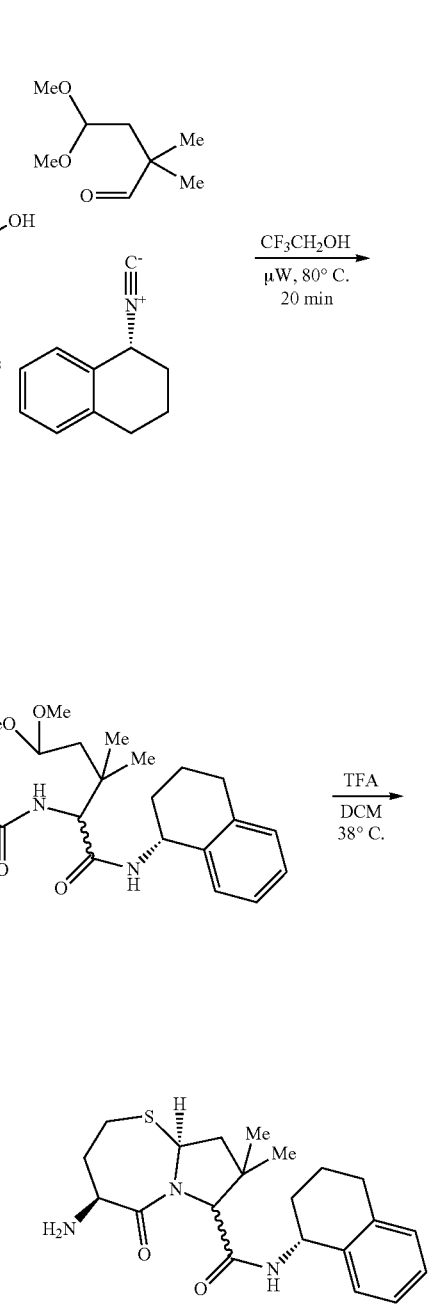

Same procedure as Example 24 with Boc-N-HCys(Trt)-OH (500 mg, 1.05 mmol, 1.0 equiv), aldehyde (176 mg, 1.10 mmol, 1.05 equiv), isocyanide (165 mg, 1.05 mmol, 1.0 equiv) and 7 M ammonia in MeOH (299 µL, 2.09 mmol, 2.0 equiv) in TFE (5 mL). The resultant oil was combined with TFA (804 µL, 10.5 mmol, 10 equiv) in DCM (5 mL) and stirred at 38° C. for 14 h. The mixture was concentrated in vacuo, then partially purified (trityl byproduct removed and more polar product(s) collected) by flash chromatography on basic alumina (3:1 hexanes/EtOAc→DCM→7% MeOH/DCM) to yield semi-pure product.

Example 45: Preparation of tert-butyl ((2S)-1-(((4S, 9aS)-8,8-dimethyl-5-oxo-7-(((R)-1,2,3,4-tetrahydronaphthalen-1-yl)carbamoyl)octahydropyrrolo[2,1-b][1,3]thiazepin-4-yl)amino)-1-oxopropan-2-yl)(methyl)carbamate

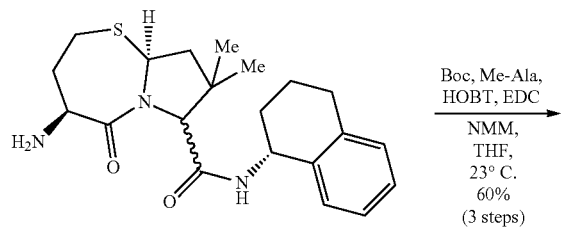

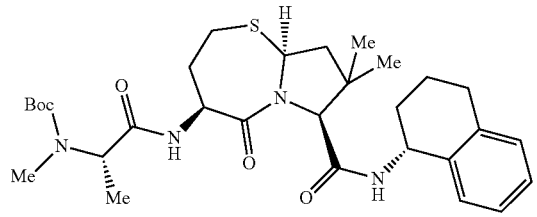

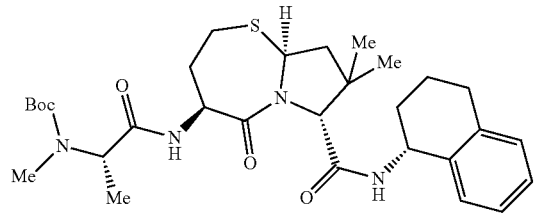

Same procedure as Example 25 using amine (387 mg, 0.998 mmol, 1.0 equiv), Boc-N-Me-Ala-OH (202 mg, 0.998 mmol, 1.0 equiv), HOBT.xH₂O (168 mg, 1.10 mmol, 1.1 equiv), NMM (329 µL, 2.99 mmol, 3 equiv) and EDC.HCl (201 mg, 1.05 mmol, 1.05 equiv) in THF (10 mL). The resultant oil was purified by flash chromatography on silica gel (3:1→1:1→1:3 hexanes/EtOAc) to yield, after 3 steps, S-isomer (12 mg, 2%) and R-isomer (47 mg, 8%), along with unseparated mixture (300 mg, 50%) and unreacted Boc-protected starting material (59 mg, 12%) left over from the previous reaction. Data for diastereomixture: $^1$H NMR (400 MHz, CD₃OD) δ: 7.32-7.28 (m, 1H), 7.18-7.11 (m, 6H), 7.10-7.06 (m, 2H), 5.49 (d, 1H, J=9.2 Hz), 5.41 (q, 1H, J=8.0 Hz), 5.09 (t, 1H, J=6.0 Hz), 5.03 (t, 1H, J=6.0 Hz), 5.03 (t, 1H, J=12.0 Hz), 4.69-4.57 (m, 4H), 4.24 (d, 1H, J=12.4 Hz), 4.19-4.16 (m, 1H), 3.31 (d, 2H, J=2.0 Hz), 3.29-3.21 (m, 2H), 2.86 (s, 6H), 2.81 (s, 3H), 2.80-2.75 (m, 2H), 2.68-2.56 (m, 1H), 2.31-2.20 (m, 3H), 2.02-1.75 (m, 13H), 1.48 (s, 18H), 1.37 (d, 3H, J=7.6 Hz), 1.32 (d, 3H, J=7.2 Hz), 1.15 (s, 3H), 1.13 (s, 3H); $^{13}$C NMR (100 MHz, CD₃OD) δ: 172.7, 171.8, 171.4, 138.8, 138.5, 137.4, 137.4, 130.2, 130.1, 130.0, 130.0, 129.8, 129.8, 128.5, 128.3, 128.2, 127.2, 73.3, 73.3, 63.9, 61.9, 61.7, 54.8, 54.2, 54.1, 47.6, 47.2, 40.9, 40.9, 40.8, 33.8, 33.2, 32.2, 31.3, 31.2, 31.1, 30.8, 30.2, 30.1, 28.7, 28.7, 28.7, 25.3, 23.9, 21.3, 21.0. Data for S-isomer: $R_f$=0.24 (1:1 hexanes/EtOAc). Data for R-isomer: $R_f$=0.38 (1:1 hexanes/EtOAc). $^1$H NMR (400 MHz, CDCl₃) δ: 7.34-7.29 (m, 1H), 7.20-7.12 (m, 3H), 7.08 (d, 1H, J=7.2 Hz), 6.00 (d, 1H, J=8.8 Hz), 5.33 (d, 1H, J=8.8 Hz), 5.14-5.07 (m, 1H), 4.57-4.47 (m, 1H), 4.06-4.02 (m, 1H), 3.28 (t, 1H, J=12.8 Hz), 2.85-2.79 (m, 2H), 2.76 (s, 3H), 2.34-2.26 (m, 1H), 2.01-1.90 (m, 2H), 1.87-1.73 (m, 6H), 1.47 (s, 9H), 1.35 (s, 3H), 1.30 (d, 3H, J=7.2 Hz), 1.25-1.20 (m, 1H), 1.15 (s, 3H); $^{13}$C NMR (100 MHz, CDCl₃) δ: 171.5, 170.6, 170.6, 169.3, 137.9, 136.3, 129.4, 129.1, 129.0, 127.5, 126.3, 73.0, 62.8, 53.9, 47.8, 46.5, 39.9, 39.8, 33.3, 32.7, 30.6, 30.1, 29.3, 28.5, 28.5, 24.6, 19.8. HRMS calcd for C₃₀H₄₄N₄O₅S: 595.2925, found 595.2922.

Example 46: Preparation of (4S,9aS)-8,8-dimethyl-4-((S)-2-(methylamino)propanamido)-5-oxo-N-((R)-1,2,3,4-tetrahydronaphthalen-1-yl)octahydropyrrolo[2,1-b][1,3]thiazepine-7-carboxamide

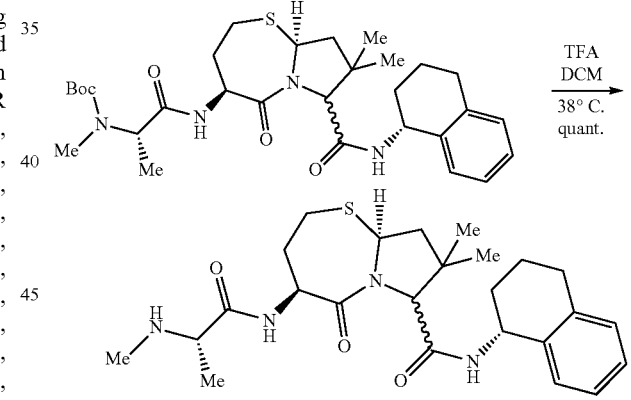

Same procedure as Example 24 using carbamate (62 mg, 0.108 mmol, 1 equiv) and TFA (66 µL, 0.866 mmol, 8 equiv) in DCM (3 mL). After stirring for 20 h at 38° C., the solution was concentrated. The product was eluted through a short plug (~500 mg) of Silicyle® TMA-chloride ion exchange resin with MeOH to yield product.HCl (54 mg, quantitative) as a 1:1 diastereomixture. $^1$H NMR (400 MHz, CD₃OD) δ: 7.34-7.27 (m, 2H), 7.18-7.06 (m, 7H), 5.54-5.45 (m, 1H), 5.41 (t, 1H, J=8.0 Hz), 5.11-5.06 (m, 1H), 5.06-5.01 (m, 1H), 4.77-4.71 (m, 2H), 4.23 (s, 1H), 4.16 (s, 1H), 3.97-3.89 (m, 2H) 3.29-3.19 (m, 2H), 2.93-2.84 (m, 2H), 2.78 (dd, 4H, J=6.4, 12.8 Hz), 2.68 (s, 6H), 2.32-2.21 (m, 3H), 2.01-1.75 (m, 12H), 1.55 (d, 3H, J=7.2 Hz), 1.54-1.50 (m, 2H), 1.47 (d, 3H, J=6.8 Hz), 1.40-1.37 (m, 2H), 1.16 (s, 6H), 1.14 (s, 3H), 1.13 (s, 3H); $^{13}$C NMR (100 MHz, CD₃OD) δ: 172.4, 172.3, 171.8, 171.4, 169.3, 168.9, 138.8, 138.5, 137.4, 137.4, 130.1, 130.1, 129.8, 128.3, 127.1, 127.0, 73.4, 63.8, 61.8, 58.3, 55.1, 54.4, 40.9, 40.9, 40.7, 33.6, 32.1, 31.8, 31.7, 31.3, 31.1, 30.9, 30.2, 30.1, 28.7, 23.9, 21.3, 21.0, 16.3, 16.2. HRMS calcd for $C_{25}H_{37}N_4O_3S$: 473.2581, found 473.2579.

Example 47: Preparation of (4S,7S,9aS)-4-((S)-2-((tert-Butoxycarbonyl)(methyl)amino)propanamido)-5-oxooctahydropyrrolo[2,1-b][1,3]oxazepine-7-carboxylic Acid

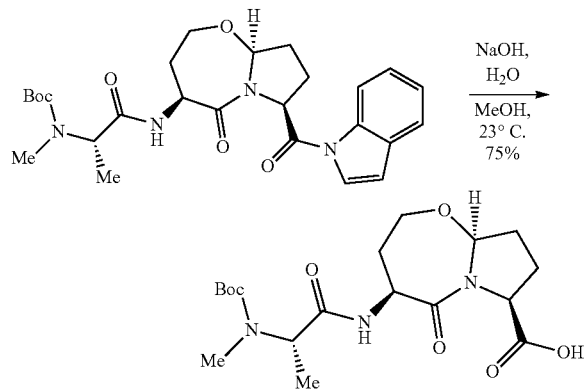

To a solution of amide (142 mg, ~0.285 mmol, 1.0 equiv) in MeOH (6 mL) was added 1M NaOH (1 mL). After stirring for 3 h, the methanol was removed in vacuo. Then EtOAc (10 mL) and 1 M NaOH (8 mL) were added and an extraction was performed, with the organic layer being discarded. The aqueous layer was acidified with 3M HCl to pH≤2 and then extracted with DCM (3×5 mL). The organics were dried over sodium sulfate, filtered and concentrated in vacuo. The resultant oil was purified by flash chromatography on silica gel (1:3 hexanes/EtOAc→DCM→5% MeOH/DCM) to yield the product as a colorless oil (85 mg, 75%). $R_f$=0.17 (7% MeOH/DCM). $^1$H NMR (400 MHz, CDCl$_3$) δ: 7.30 (bs, 1H), 5.22 (m, 1H), 4.77 (t, 1H, J=8.0 Hz), 4.52-4.46 (m, 1H), 4.14 (d, 1H, J=12.8 Hz), 3.95 (t, 1H, J=12.0 Hz), 2.78 (s, 3H), 2.32-2.18 (m, 2H), 2.13-2.02 (m, 2H), 2.00-1.85 (m, 2H), 1.44 (s, 9H), 1.33 (d, 3H, J=7.2 Hz); $^{13}$C NMR (100 MHz, CDCl$_3$) δ: 171.5, 171.5, 156.2, 156.1, 89.8, 80.8, 80.7, 70.7, 59.7, 52.9, 32.7, 30.4, 30.4, 28.4, 28.4, 26.5, 26.5, 14.2. HRMS calcd for $C_{18}H_{29}N_3O_7Na$: 422.18977, found 422.19015.

Example 48: Preparation of tert-butyl ((S)-1-(((4S,7S,9aS)-7-((R)-chroman-4-ylcarbamoyl)-5-oxooctahydropyrrolo[2,1-b][1,3]oxazepin-4-yl)amino)-1-oxopropan-2-yl)(methyl)carbamate

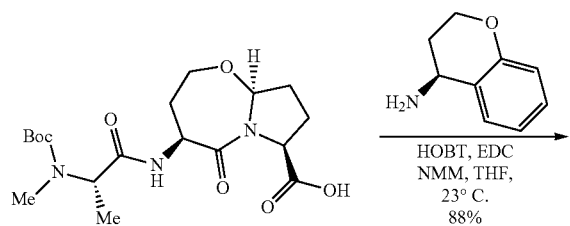

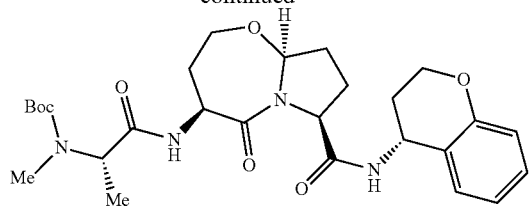

To a solution of carboxylic acid (50 mg, 0.125 mmol, 1.0 equiv), (R)-chroman-4-ylamine.HCl (23 mg, 0.125 mmol, 1.0 equiv), HOBT.xH$_2$O (21 mg, 0.138 mmol, 1.1 equiv) and NMM (41 μL, 0.376 mmol, 3 equiv) in THF (5 mL) at 0° C. was added EDC.HCl (25 mg, 0.131 mmol, 1.05 equiv). After 30 min the cold bath was removed. The solution stirred for 14 h and then was quenched with saturated aqueous NaHCO$_3$ (15 mL), extracted with ethyl acetate (2×10 mL), dried over sodium sulfate and then concentrated in vacuo. The resultant oil was purified by flash chromatography on silica gel (1:3 hexanes/EtOAc) to yield the product (58 mg, 88%). $R_f$=0.11 (1:2 hexanes/EtOAc). $^1$H NMR (400 MHz, CDCl$_3$) δ: 7.16-7.10 (m, 3H), 6.91 (d, 1H, J=7.2 Hz), 6.86-6.77 (m, 2H), 5.22 (t, 1H, J=6.0 Hz), 5.12 (q, 1H, J=6.8 Hz), 4.68 (dd, 1H, J=6.0, 11.2 Hz), 4.59 (d, 1H, J=7.2 Hz), 4.22 (td, 1H, J=2.8, 7.2 Hz), 4.15-4.08 (m, 1H), 4.06-4.01 (m, 1H), 3.92 (t, 1H, J=12.4 Hz), 2.74 (s, 3H), 2.41-2.37 (m, 2H), 2.25-2.17 (m, 1H), 2.16-2.07 (m, 1H), 2.02 (dd, 1H, J=2.8, 7.2 Hz), 1.95-1.84 (m, 2H), 1.61-1.45 (m, 1H), 1.42 (s, 9H), 1.31 (d, 3H, J=7.2 Hz); $^{13}$C NMR (100 MHz, CDCl$_3$) δ: 171.5, 170.1, 155.0, 129.3, 128.9, 122.3, 120.7, 117.2, 90.2, 77.2, 70.6, 63.6, 60.5, 52.6, 43.8, 32.7, 32.5, 30.2, 29.0, 28.4, 25.9. HRMS calcd for $C_{27}H_{38}N_4O_7Na$: 553.26327, found 553.26399.

Example 49: Preparation of (4S,7S,9aS)—N-((R)-chroman-4-yl)-4-((S)-2-(methylamino)propanamido)-5-oxooctahydropyrrolo[2,1-b][1,3]oxazepine-7-carboxamide

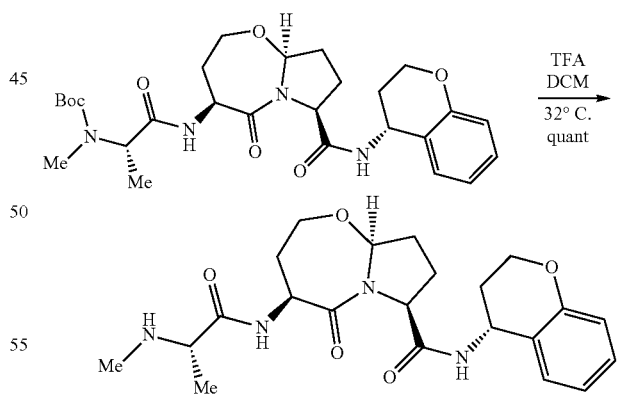

To a solution of carbamate (58 mg, 0.109 mmol, 1 equiv) in DCM (2 mL) was added TFA (83 μL, 1.09 mmol, 10 equiv). After stirring for 20 h at 32° C., the solution was concentrated. The product was eluted through a short plug (~500 mg) of Silicyle® TMA-chloride ion exchange resin with MeOH to yield product.HCl (51 mg, quantitative). $^1$H NMR (400 MHz, CD$_3$OD) δ: 7.33 (d, 1H, J=7.6 Hz), 7.13 (t, 1H, J=8.4 Hz), 6.86 (t, 1H, J=7.2 Hz), 6.76 (d, 1H, J=8.0 Hz), 5.39 (dd, 1H, J=3.6, 6.8 Hz), 5.08 (t, 1H, J=6.0 Hz), 4.40 (d, 1H, J=6.8 Hz), 4.26-4.12 (m, 3H), 4.03-3.89 (m, 2H), 2.67 (s, 3H), 2.33-2.24 (m, 1H), 2.14-1.97 (m, 6H), 1.81 (dd, 1H, J=2.0, 14.0 Hz), 1.58 (d, 3H, J=6.8 Hz); $^{13}$C NMR (100 MHz, CD$_3$OD) δ: 172.9, 172.2, 169.6, 156.4, 130.5, 130.0, 123.5, 121.6, 117.8, 91.0, 71.3, 64.6, 62.3, 58.4, 54.2, 49.0, 44.9, 33.6, 33.3, 31.8, 30.2, 28.0, 16.4. HRMS calcd for C$_{22}$H$_{31}$N$_4$O$_5$: 431.2289, found 431.2286.

Example 50: Preparation of (4S,7R,9aS)-4-((S)-2-((tert-butoxycarbonyl)(methyl)amino)propanamido)-5-oxooctahydropyrrolo[2,1-b][1,3]oxazepine-7-carboxylic Acid

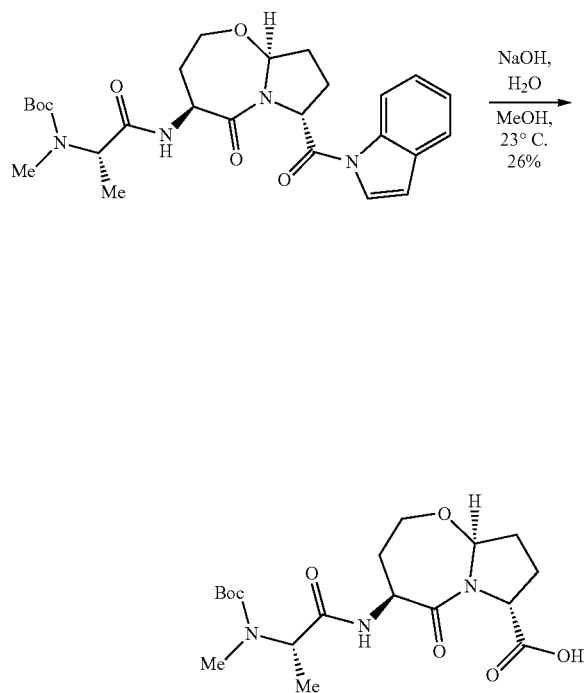

To a solution of amide (105 mg, 0.211 mmol, 1.0 equiv) in MeOH (4 mL) was added 1M NaOH (1 mL). After stirring for 3 h, the methanol was removed in vacuo. HPLC analysis of the crude reaction mixture revealed that the R-isomer didn't react as cleanly as the S-isomer (Example 47). Then DCM (10 mL) and 1 M NaOH (8 mL) were added and an extraction was performed, with the organic layer being discarded. The aqueous layer was acidified with 3M HCl to pH≤2 and then extracted with DCM (3×5 mL). The organics were dried over sodium sulfate, filtered and concentrated in vacuo. The resultant oil was purified by flash chromatography on silica gel (1:3 hexanes/EtOAc→DCM→5% MeOH/DCM) to yield the product as a colorless oil (22 mg, 26%). R$_f$=0.14 (7% MeOH/DCM). $^1$H NMR (400 MHz, CDCl$_3$) δ: 5.25 (d, 1H, J=6.8 Hz), 4.83 (dd, 1H, J=5.6, 9.6 Hz), 4.65 (d, 1H, J=8.8 Hz), 4.14-4.09 (m, 1H), 4.0 (t, 1H, J=12.0 Hz), 2.79 (s, 3H), 2.41-2.31 (m, 1H), 2.27-2.11 (m, 2H), 2.06-1.96 (m, 1H), 1.78 (qd, 1H, J=3.6, 12.0 Hz), 1.46 (s, 9H), 1.33 (d, 3H, J=7.6 Hz); $^{13}$C NMR (100 MHz, CDCl$_3$) δ: 173.9, 172.0, 171.3, 89.6, 80.9, 70.7, 60.6, 59.8, 53.1, 33.0, 32.5, 30.5, 28.5, 26.1, 21.2, 14.3, 14.1. HRMS calcd for C$_{18}$H$_{29}$N$_3$O$_7$Na: 422.18977, found 422.19015.

Example 51: Preparation of tert-butyl ((S)-1-(((4S,7R,9aS)-7-((R)-chroman-4-ylcarbamoyl)-5-oxooctahydropyrrolo[2,1-b][1,3]oxazepin-4-yl)amino)-1-oxopropan-2-yl)(methyl)carbamate

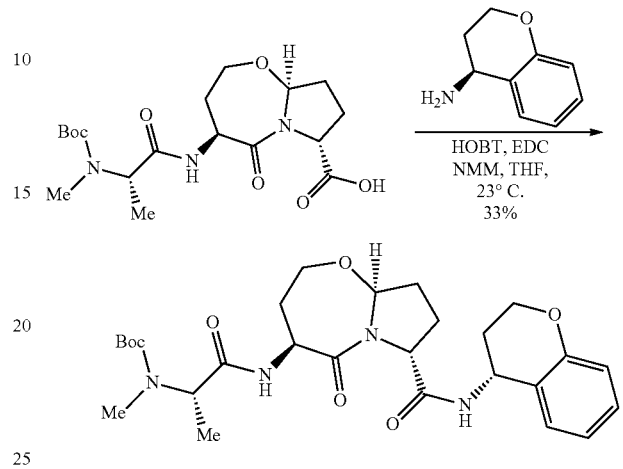

To a solution of carboxylic acid (21 mg, 0.0053 mmol, 1.0 equiv), (R)-chroman-4-ylamine.HCl (10 mg, 0.0053 mmol, 1.0 equiv), HOBT.xH$_2$O (9 mg, 0.0058 mmol, 1.1 equiv) and NMM (17 µL, 0.0158 mmol, 3 equiv) in THF (3 mL) at 0° C. was added EDC.HCl (11 mg, 0.0055 mmol, 1.05 equiv). After 30 min the cold bath was removed. The solution stirred for 14 h and then was quenched with saturated aqueous NaHCO$_3$ (10 mL), extracted with ethyl acetate (2×10 mL), dried over sodium sulfate and then concentrated in vacuo. The resultant oil was purified by flash chromatography on silica gel (1:1→1:3 hexanes/EtOAc) to yield the product (9 mg, 33%). $^1$H NMR (400 MHz, CDCl$_3$) δ: 7.20-7.12 (m, 3H), 6.89 (t, 1H, J=7.6 Hz), 6.82 (d, 1H, J=8.4 Hz), 5.23-5.19 (m, 1H), 5.12-5.05 (m, 1H), 4.79-4.71 (m, 1H), 4.55 (d, 1H, J=8.0 Hz), 4.26-4.19 (m, 1H), 4.15-4.06 (m, 2H), 3.97 (t, 1H, J=12.0 Hz), 2.77 (s, 3H), 2.39-2.26 (m, 1H), 2.24-2.13 (m, 2H), 2.07-2.00 (m, 1H), 1.99-1.91 (m, 2H), 1.80-1.70 (m, 2H), 1.44 (s, 9H), 1.34 (d, 3H, J=7.2 Hz); $^{13}$C NMR (100 MHz, CDCl$_3$) δ: 172.3, 171.1, 169.9, 155.2, 129.4, 129.3, 122.0, 120.9, 117.3, 90.1, 70.6, 63.4, 61.1, 53.1, 43.8, 33.4, 32.7, 32.1, 29.8, 29.1, 28.5, 25.6, 22.8, 14.3. HRMS calcd for C$_{27}$H$_{38}$N$_4$O$_7$Na: 553.26327, found 553.26399.

Example 52: Preparation of (4S,7R,9aS)—N-((R)-chroman-4-yl)-4-((S)-2-(methylamino)propanamido)-5-oxooctahydropyrrolo[2,1-b][1,3]oxazepine-7-carboxamide

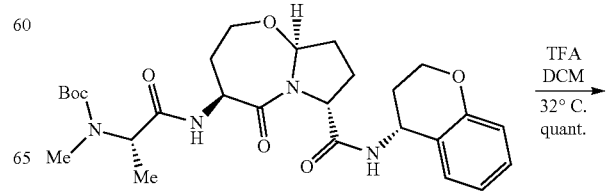

-continued

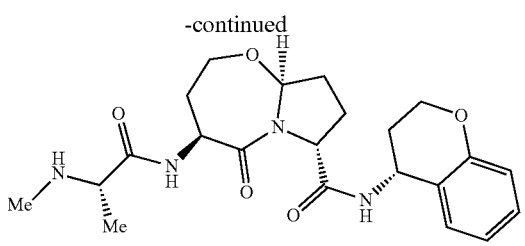

To a solution of carbamate (58 mg, 0.109 mmol, 1 equiv) in DCM (2 mL) was added TFA (83 μL, 1.09 mmol, 10 equiv). After stirring for 20 h at 32° C., the solution was concentrated to yield product.TFA (51 mg, quantitative). $^1$H NMR (400 MHz, CD$_3$OD) δ: 8.43 (d, 1H, J=8.0 Hz), 7.15-7.09 (m, 2H), 6.85 (t, 1H, J=8.0 Hz), 6.78-6.73 (m, 1H), 5.40 (d, 2H, J=5.6 Hz), 5.10-5.04 (m, 1H), 4.99 (dd, 1H, J=2.4, 11.2 Hz), 4.53 (d, 1H, J=9.2 Hz), 4.21 (t, 2H, J=5.2 Hz), 4.14 (dt, 1H, J=3.2, 13.2 Hz), 4.05-3.96 (m, 1H), 3.91 (q, 1H, J=7.2 Hz), 2.67 (s, 3H), 2.44-2.31 (m, 1H), 2.30-2.18 (m, 1H), 2.16-2.07 (m, 1H), 2.04-1.95 (m, 3H), 1.93-1.81 (m, 2H), 1.52 (d, 3H, J=6.8 Hz); $^{13}$C NMR (100 MHz, CD$_3$OD) δ: 173.5, 172.7, 169.3, 156.5, 130.2, 129.9, 123.5, 121.6, 117.9, 91.1, 71.2, 64.6, 62.3, 58.3, 54.4, 44.9, 34.0, 33.3, 31.8, 30.1, 28.2, 16.4. HRMS calcd for C$_{22}$H$_{30}$N$_4$O$_5$Na: 453.21084, found 453.21280.

Example 53: Preparation of (S)-ethyl 2-((S)-2-(((benzyloxy)carbonyl)(methyl)amino)propanamido)-3-(1H-indol-3-yl)propanoate

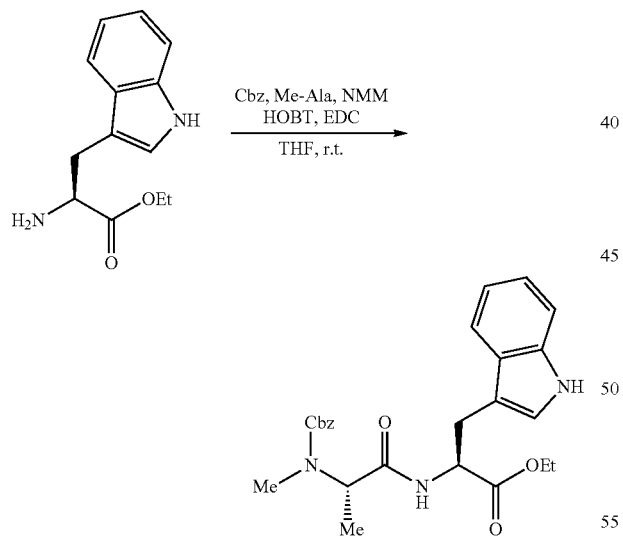

To a solution of tryptophan derivative (600 mg, 2.23 mmol, 1.0 equiv), Boc-N-Me-Ala-OH (530 mg, 2.23 mmol, 1.0 equiv), HOBT.xH$_2$O (376 mg, 2.46 mmol, 1.1 equiv) and NMM (736 μL, 6.70 mmol, 3 equiv) in THF (15 mL) at 0° C. was added EDC.HCl (449 mg, 2.34 mmol, 1.05 equiv). After 30 min the cold bath was removed. The solution was stirred for 14 h and then quenched with saturated aqueous NaHCO$_3$ (20 mL), extracted with ethyl acetate (2×20 mL), dried over sodium sulfate and then concentrated in vacuo. The resultant oil was purified by flash chromatography on silica gel (3:1→1:1 hexanes/EtOAc) to yield the product (790 mg, 79%). LCMS calcd for M+H: 452.22, found 452.22.

Example 54: Preparation of (S)-2-((S)-2-(((benzyloxy)carbonyl)(methyl)amino)propanamido)-3-(1H-indol-3-yl)propanoic acid (88)

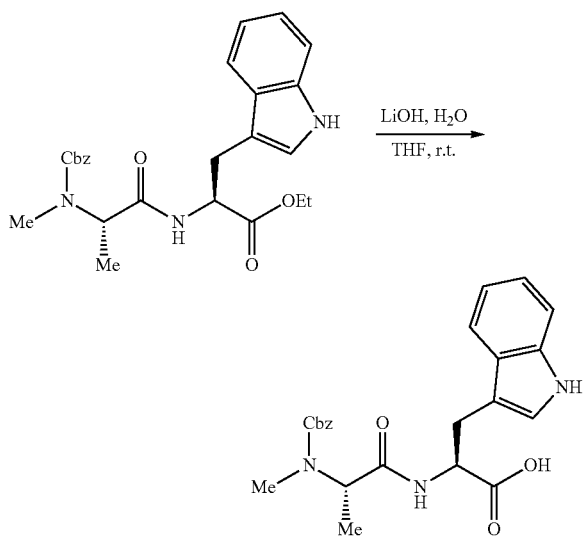

To a solution of ester (790 mg, 1.75 mmol, 1.0 equiv) in THF (12 mL) and H$_2$O (3 mL) was added LiOH (84 mg, 3.50 mmol, 2 equiv). After stirring for 3 h, Et$_2$O (10 mL) and 1 M NaOH (8 mL) were added and an extraction was performed, with the organic layer being discarded. The aqueous layer was acidified with 3M HCl to pH≤2 and then extracted with DCM (3×8 mL). The combined organics were dried over sodium sulfate, filtered and concentrated in vacuo. The resultant oil was purified by flash chromatography on silica gel (DCM-5% MeOH/DCM) to yield the product as a colorless oil (574 mg, 78%). LCMS calcd for M+H: 424.19, found 424.18.

Example 55: Preparation of Benzyl ((2S)-1-(((2S)-1-((5,5-dimethoxy-1-oxo-1-(((R)-1,2,3,4-tetrahydronaphthalen-1-yl)amino)pentan-2-yl)amino)-3-(H-indol-3-yl)-1-oxopropan-2-yl)amino)-1-oxopropan-2-yl)(methyl)carbamate

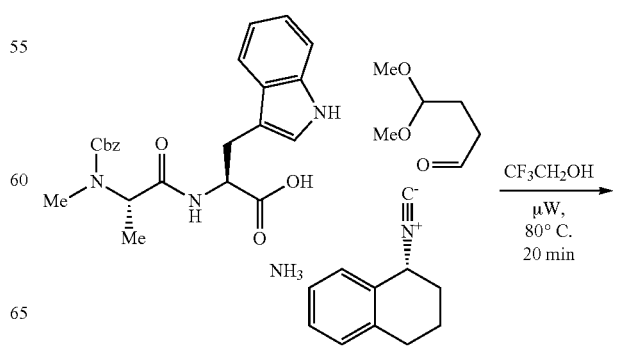

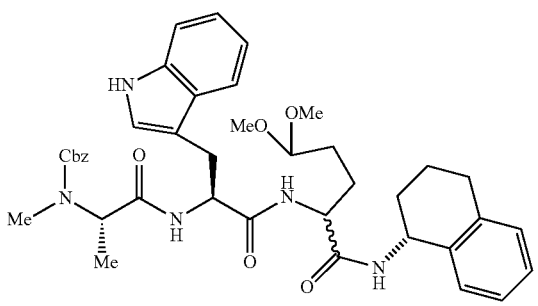

A mixture of carboxylic acid (104 mg, 0.246 mmol, 1.0 equiv), aldehyde (34 mg, 0.258 mmol, 1.0 equiv), isocyanide (39 mg, 0.246 mmol, 1.0 equiv) and 7 M ammonia in MeOH (70 µL, 0.491 mmol, 2.0 equiv) in TFE (3 mL) was stirred under microwave irradiation at a set temperature of 80° C. for 20 min. The mixture was then transferred to a round bottom flask and concentrated in vacuo, then 1 M NaOH (15 mL) was added and the mixture was extracted with DCM (3×7 mL). The organics were dried over $Na_2SO_4$, filtered and concentrated in vacuo. The resultant oil was used without further purification in the next step. LCMS calcd for M+H: 712.37, found 712.34.

Example 56: Preparation of Benzyl Methyl((S)-1-oxo-1-(((3S,6S,12bR)-5-oxo-3-(((R)-1,2,3,4-tetrahydronaphthalen-1-yl)carbamoyl)-1,2,3,5,6,7,12,12b-octahydropyrrolo[1',2':1,2]azepino[3,4-b]indol-6-yl)amino)propan-2-yl)carbamate

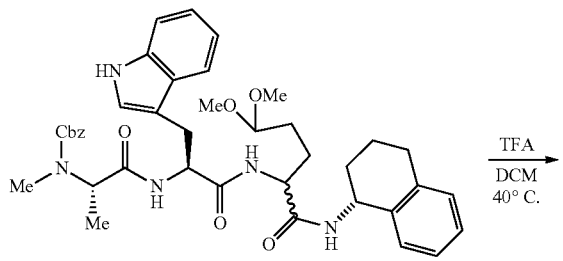

To a solution of dimethyl acetal (166 mg, 0.233 mmol, 1 equiv) in DCM (4 mL) was added TFA (143 µL, 1.87 mmol, 8 equiv). After stirring for 20 h at 23° C., the solution was concentrated and then purified by flash chromatography on silica gel (1:1→1:2 hexanes/EtOAc) to yield S-isomer (18 mg, 11%), R-isomer (38 mg, 24%) and a mixture of the two isomers (10 mg, 6%). LCMS calcd for M+H: 648.32, found 648.30.

Example 57: Preparation of (3S,6S,12bR)-6-((S)-2-(methylamino)propanamido)-5-oxo-N-((R)-1,2,3,4-tetrahydronaphthalen-1-yl)-1,2,3,5,6,7,12,12b-octahydropyrrolo[1',2': 1,2]azepino[3,4-b]indole-3-carboxamide

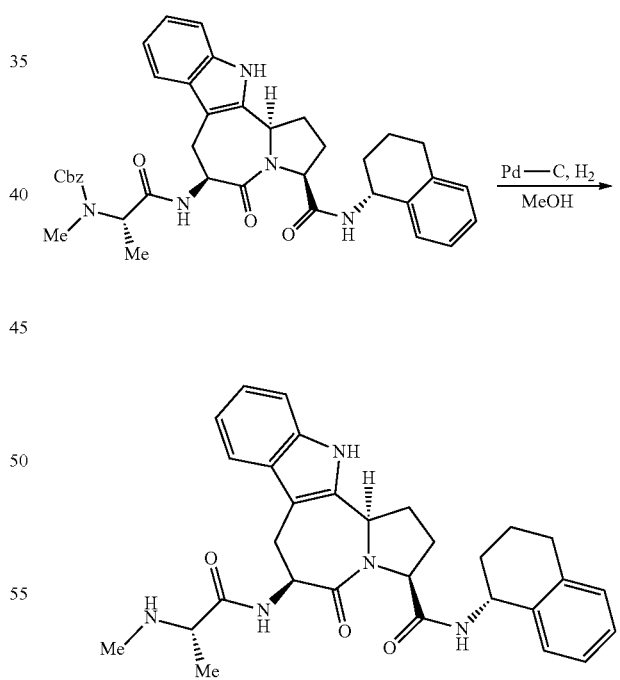

To a solution of carbamate (16 mg, 0.0247 mmol, 1.0 equiv) in methanol (4 mL) was added 10 wt % Pd-C (5 mg). A balloon of $H_2$ was applied for 16 h, then the mixture was filtered through Celite with DCM and concentrated in vacuo. The resultant oil was purified by preparative scale HPLC to yield the product (6 mg, 43%). LCMS calcd for M+H: 514.28, found 514.28.

Example 58: Preparation of tert-butyl ((S)-1-(((4S,7S,9aS)-1,1-dioxido-5-oxo-7-(((R)-1,2,3,4-tetrahydronaphthalen-1-yl)carbamoyl)octahydropyrrolo[2,1-b][1,3]thiazepin-4-yl)amino)-1-oxopropan-2-yl)(methyl)carbamate

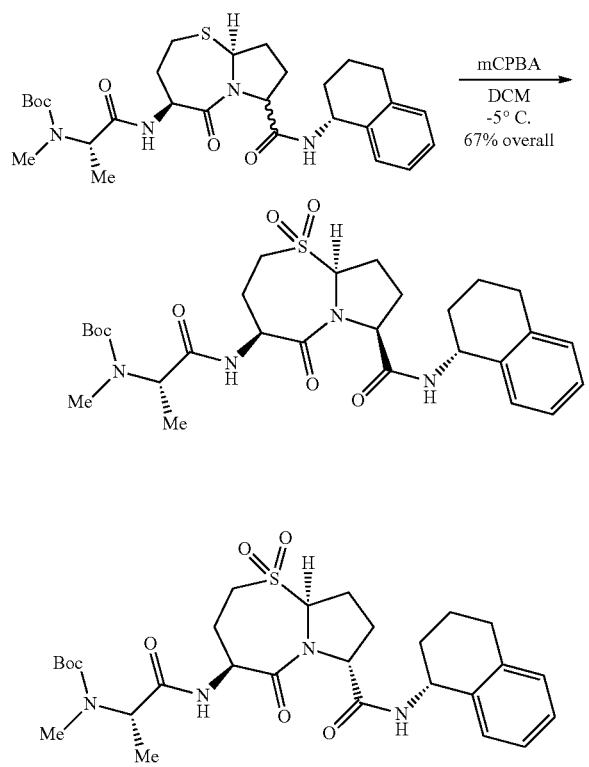

To a solution of sulfide (48 mg, 0.0881 mmol, 1.0 equiv) in DCM (4 mL) at −5° C. was added mCPBA (75% purity, 45 mg, 0.194, 2.2 equiv). After 10 minutes the cold bath was removed and the reaction stirred at 23° C. for 3 h, then concentrated. The crude product was purified by flash chromatography on silica gel (3:1→1:1→1:2 hexanes/EtOAc) to yield S-isomer (15 mg, 21%) and R-isomer (32 mg, 46%). LCMS calcd for M+H: 577.27, found 577.29.

Example 59: Preparation of (4S,7S,9aS)-4-((S)-2-(methylamino)propanamido)-5-oxo-N-((R)-1,2,3,4-tetrahydronaphthalen-1-yl)octahydropyrrolo[2,1-b][1,3]thiazepine-7-carboxamide 1,1-dioxide

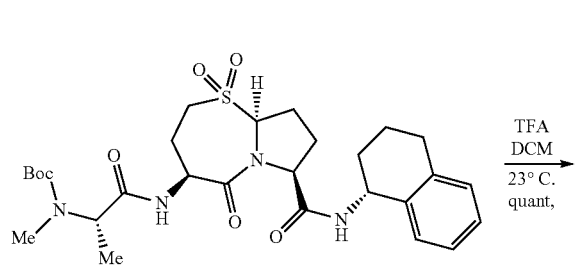

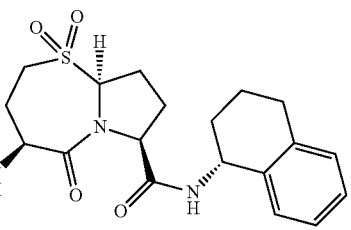

To a solution of carbamate (15 mg, 0.026 mmol, 1 equiv) in DCM (2 mL) was added TFA (16 μL, 0.208 mmol, 8 equiv). After stirring for 20 h at 32° C., the solution was concentrated to yield product.TFA (15 mg, quantitative). LCMS calcd for M+H: 477.22, found 477.23.

Example 60: Preparation of N,N'-(disulfanediylbis(2,1-phenylene))diformamide

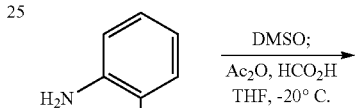

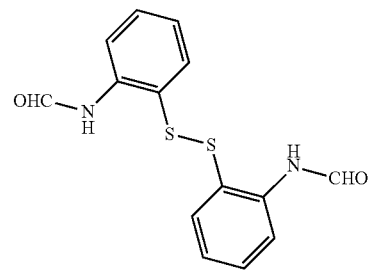

The disulfide was prepared according to the established literature procedure; see Hyvl, J., Srogl, J. *Eur. J. Org. Chem.* 2010, 2849-2851.

Example 61: Preparation of 1,2-bis(2-isocyanophenyl)disulfane

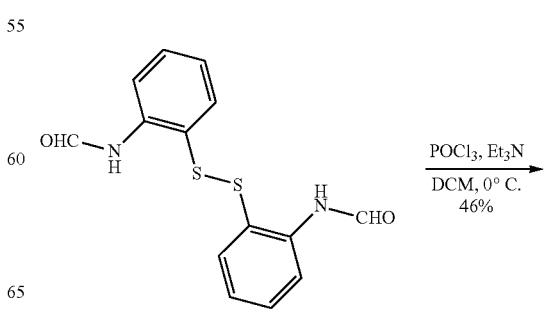

207

-continued

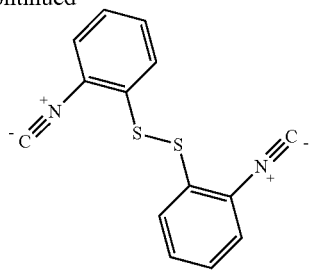

To a solution of formamide (2.41 g, 7.92 mmol, 1.0 equiv) in DCM (40 mL) at 0° C. was added Et₃N (5.60 mL, 40.4 mmol, 5.1 equiv) followed by phosphorus oxychloride (1.09 mL, 11.9 mmol, 1.5 equiv). The mixture was warmed to 23° C. and stirred for 2 h, at which time it was poured into saturated NaHCO₃ (200 mL) and extracted with DCM (2×100 mL). The organics were dried over Na₂SO₄, filtered and concentrated in vacuo. The resultant oil was purified by flash chromatography on silica gel (5:1 hexanes/EtOAc) to yield the product (980 mg, 46%) which was stored at 0° C. Rf=0.38 (5:1 hexanes/EtOAc). LCMS calcd for M+H: 269.02, found 269.01.

Example 62: Preparation of (4S,4'S,9aS,9a'S)—N,N'-(disulfanediylbis(2,1-phenylene))bis(4-amino-8,8-dimethyl-5-oxooctahydropyrrolo[2,1-b][1,3]oxazepine-7-carboxamide)

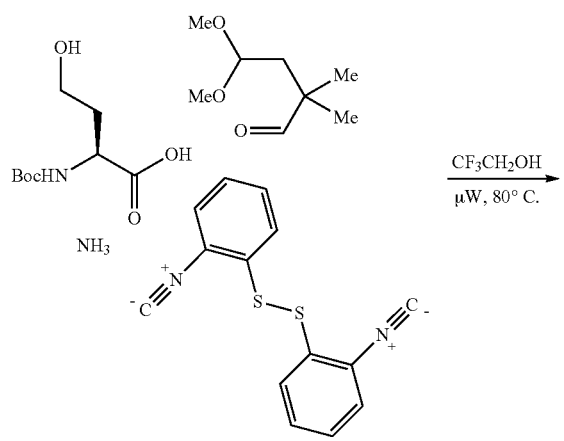

208

-continued

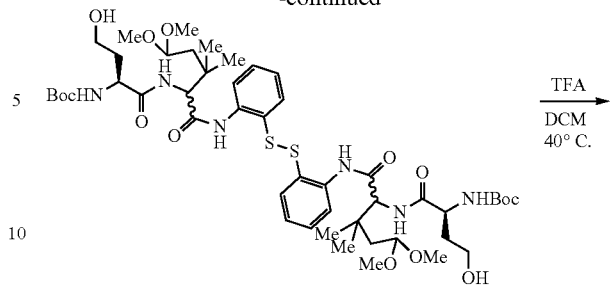

Same procedure as Example 24 with Boc-N-HSer-OH (159 mg, 0.725 mmol, 2.0 equiv), aldehyde (122 mg, 0.762 mmol, 2.1 equiv), isocyanide (97 mg, 0.363 mmol, 1.0 equiv) and 7 M ammonia in MeOH (207 µL, 1.45 mmol, 4.0 equiv) in TFE (5 mL). The resultant oil was combined with TFA (302 µL, 3.95 mmol, 16 equiv) in DCM (5 mL) and stirred at 40° C. for 14 h. The mixture was concentrated in vacuo, then partially purified by flash chromatography on basic alumina (3:1 hexanes/EtOAc→DCM→7% MeOH/DCM), to yield semi-pure product. LCMS calcd for M+H: 697.28, found 697.28.

Example 63: Preparation of (S,4S,4'S,9aS,9a'S)—N,N'-(disulfanediylbis(2,1-phenylene))bis(8,8-dimethyl-4-((S)-2-(methylamino)propanamido)-5-oxooctahydropyrrolo[2,1-b][1,3]oxazepine-7-carboxamide)

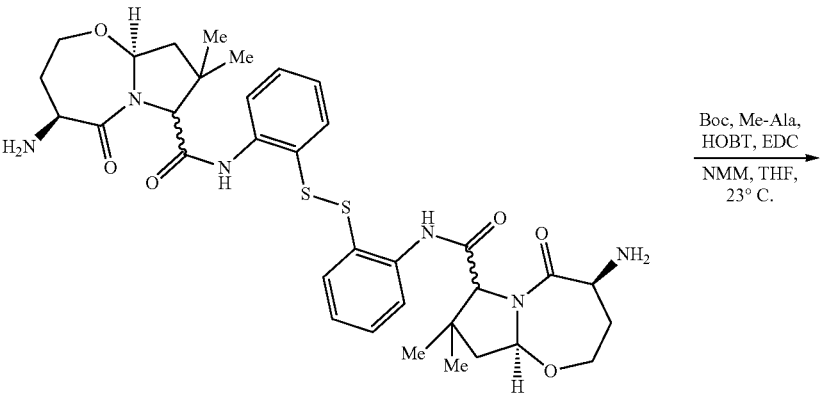

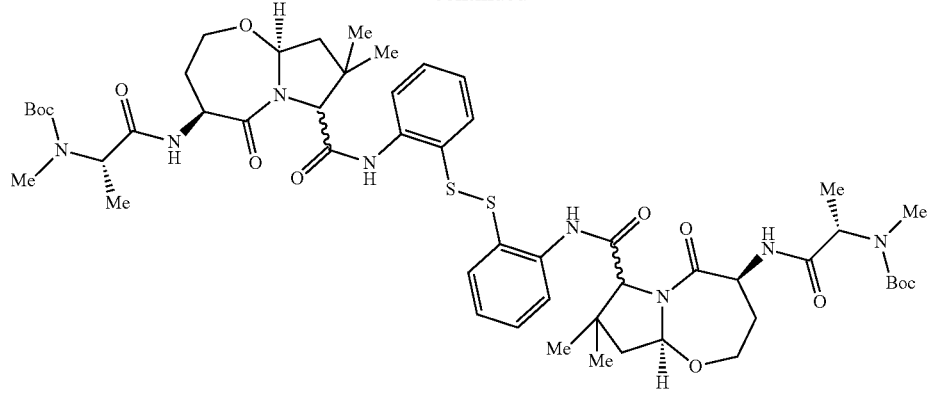

Same procedure as Example 25 using bis-amine (69 mg, 0.099 mmol, 1.0 equiv), Boc-N-Me-Ala-OH (40 mg, 0.198 mmol, 2.0 equiv), HOBT.xH$_2$O (33 mg, 0.218 mmol, 2.2 equiv), NMM (65 μL, 0.594 mmol, 6 equiv) and EDC.HCl (40 mg, 0.208 mmol, 2.1 equiv) in THF (5 mL). The resultant oil was purified by flash chromatography on silica gel (3:1→1:1→1:3 hexanes/EtOAc) to yield the product (32 mg, overall yield not determined). LCMS calcd for M+H: 1067.49, found 1067.60.

Example 64: Preparation of methyl (S,4S,4'S,9aS, 9a'S)—N,N'-(disulfanediylbis(2,1-phenylene))bis(8, 8-dimethyl-4-((S)-2-(methylamino)propanamido)-5-oxooctahydropyrrolo[2,1-b][1,3]oxazepine-7-carboxamide)

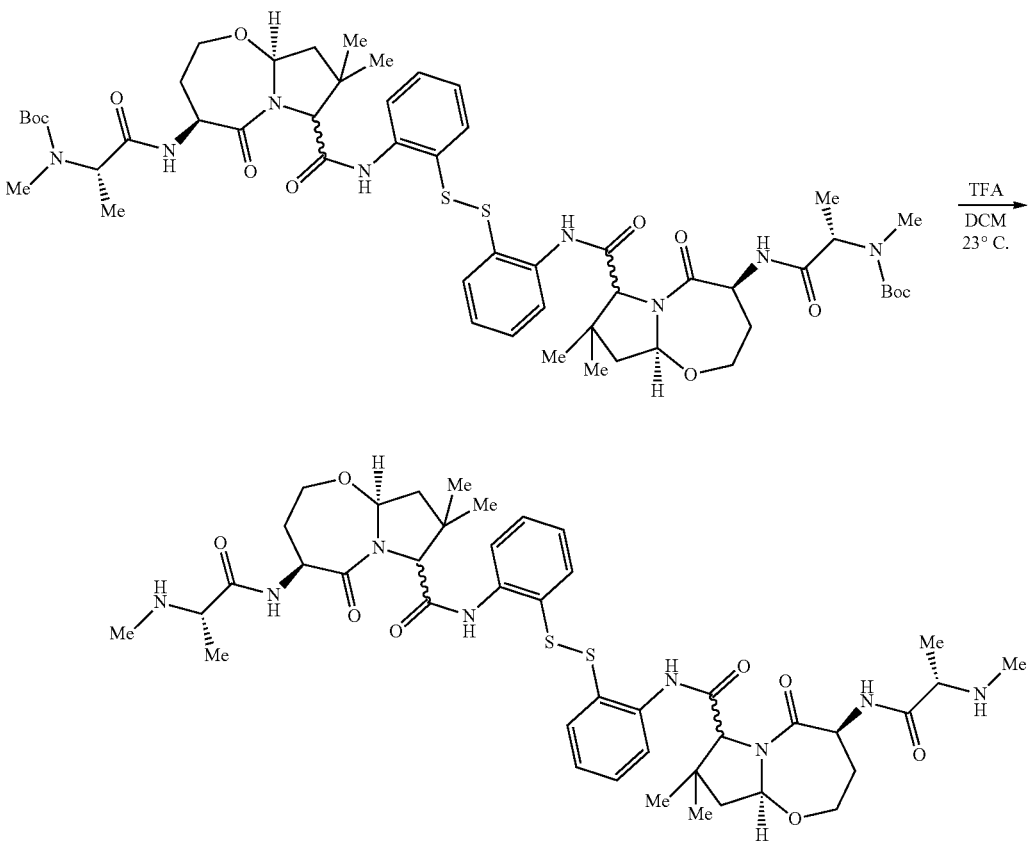

To a solution of carbamate (10 mg, 9.37 μmol. 1 equiv) in DCM (2 mL) was added TFA (7 μL. 93.7 μmol, 10 equiv) The mixture was stirred for 16 h, then concentrated in vacuo to give the product·TFA (9.5 mg, 95%). LCMS ealcd for [M+CF$_3$CO$_2$H]/2+Na:570.18. found 570.25.

Example 65: Preparation of (4S, 10aS)-4-amino-5-oxo-N-((R)-1,2,3,4-tetrahydronaphthalen-1-yl)octahydro-2H-pyrido [2,1-b][1,3]thiazepine-7-carboxamide

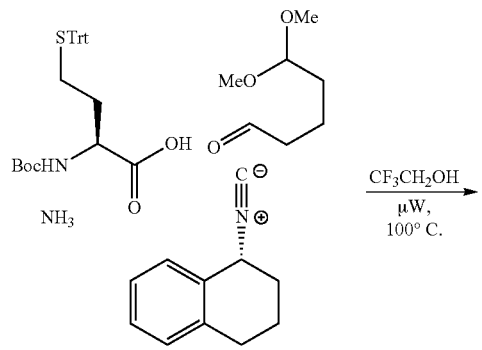

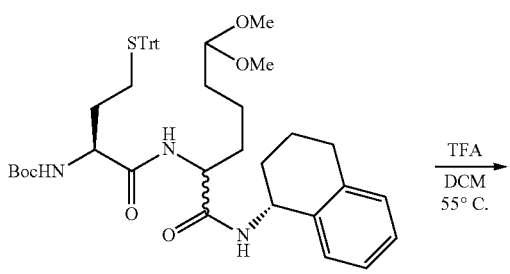

A mixture of Boc-N-HCys(Trt)-OH (250 mg, 0.523 mmol, 1.0 equiv), aldehyde (80 mg, 0.550 mmol, equiv) in TFE (4 mL) was stirred under microwave irradiation at a set temperature of 100° C. for 20 min. The mixture was then transferred to a round bottom flask and concentrated in vacuo, then 1 M NaOH (15 mL) was added and the mixture was extracted with DCM (3×7 mL). The combined organics were dried over $Na_2SO_4$, filtered and concentrated in vacuo. The resultant oil was combined with TFA (401 µL, 5.23 mmol, 10 equiv) in DCM (5 mL) and stirred at 55° C. for 14 h. The mixture was concentrated in vacuo, then partially purified by flash chromatography on basic alumina (3:1 hexanes/EtOAc→DCM→7% MeOH/DCM), to yield semi-pure product. LCMS calcd for M+H: 374.19, found 374.21.

Example 66: Preparation of tert-butyl methyl((2S)-1-oxo-1-(((4S,10aS)-5-oxo-7-(((R)-1,2,3,4-tetrahydronaphthalen-1-yl)carbamoyl)octahydro-2H-pyrido [2,1-b][1,3]thiazepin-4-yl)amino)propan-2-yl)carbamate

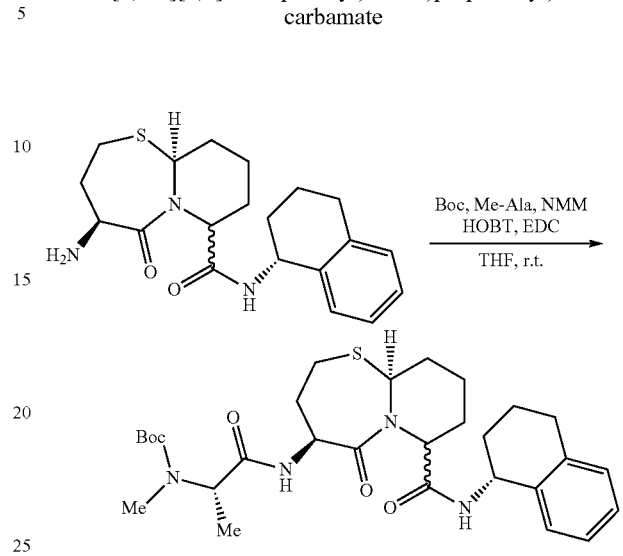

Same procedure as Example 25 using amine (156 mg, 0.418 mmol, 1.0 equiv), Boc-N-Me-Ala-OH (85 mg, 0.418 mmol, 1.0 equiv), HOBT.xH$_2$O (70 mg, 0.459 mmol, 1.1 equiv), NMM (138 µL, 1.25 mmol, 3 equiv) and EDC.HCl (84 mg, 0.439 mmol, 1.05 equiv) in THF (6 mL). The resultant oil was purified by flash chromatography on silica gel (3:1→2:1→1:1→1:3 hexanes/EtOAc) to yield, after 3 steps, the product (102 mg, 43% overall). LCMS calcd for M+H: 559.30, found 559.32.

Example 67: Preparation of (4S,10aS)-4-((S)-2-(methylamino)propanamido)-5-oxo-N-((R)-1,2,3,4-tetrahydronaphthalen-1-yl)octahydro-2H-pyrido[2,1-b][1,3]thiazepine-7-carboxamide

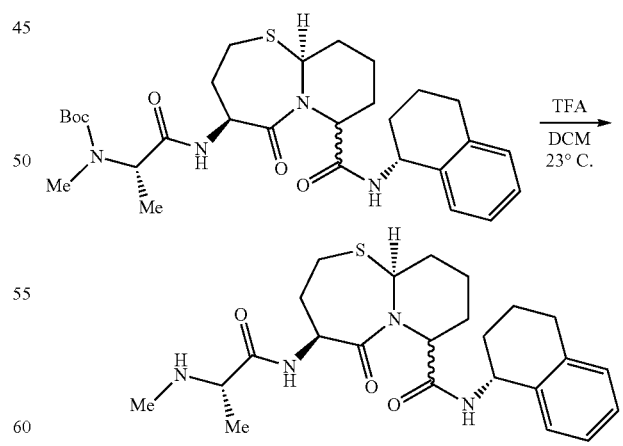

To a solution of carbamate (41 mg, 0.0734 mmol, 1 equiv) in DCM (2 mL) was added TFA (56 µL, 0.734 mmol, 10 equiv). The mixture was stirred for 16 h, then concentrated in vacuo to give the product.TFA (42 mg, quantitative). LCMS calcd for M+H: 459.24, found 459.28.

Example 68: Preparation of tert-butyl ((6S,9aS)-5-oxo-3-(((R)-1,2,3,4-tetrahydronaphthalen-1-yl)carbamoyl)hexahydro-2H-oxazolo[2,3-b][1,3]oxazepin-6-yl)carbamate

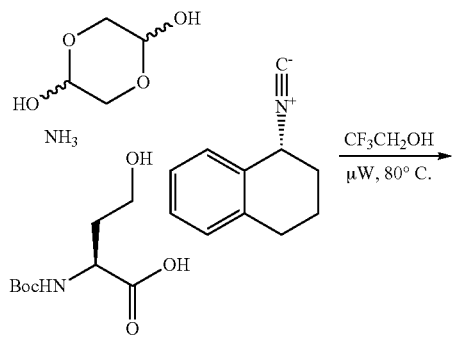

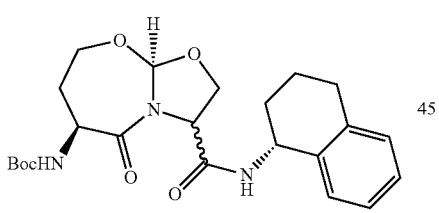

A mixture of Boc-N-HSer-OH (150 mg, 0.684 mmol, 1.0 equiv), glycolaldehyde dimer (41 mg, 0.342 mmol, 0.5 equiv), isocyanide (108 mg, 0.684 mmol, 1.0 equiv) and 7 M ammonia in MeOH (293 μL, 2.05 mmol, 3.0 equiv) in TFE (4 mL) was stirred under microwave irradiation at a set temperature of 80° C. for 20 min. The mixture was then transferred to a round bottom flask and concentrated in vacuo, then 1 M NaOH (15 mL) was added and the mixture was extracted with DCM (3×7 mL). The organics were dried over Na₂SO₄, filtered and concentrated in vacuo. The resultant oil was combined with trimethyl orthoformate (89 μL, 0.808 mmol, 2 equiv) and TsOH·H₂O (23 mg, 0.121 mmol, 0.3 equiv) in PhH (5 mL) and stirred at 90° C. for 10 h. The mixture was concentrated in vacuo and the crude product will be processed as described in preceding examples. LCMS calcd for M+H: 446.23, found 446.23.

Example 69: Preparation of (6S,11bR)-6-amino-10-hydroxy-2,2-dimethyl-5-oxo-N-((R)-1,2,3,4-tetrahydronaphthalen-1-yl)-2,3,5,6,7,11b-hexahydro-1H-benzo[c]pyrrolo[1,2-a]azepine-3-carboxamide

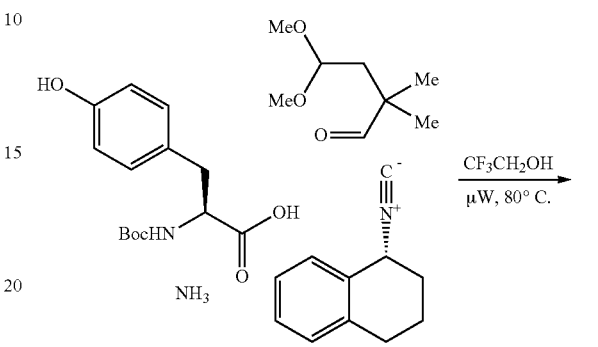

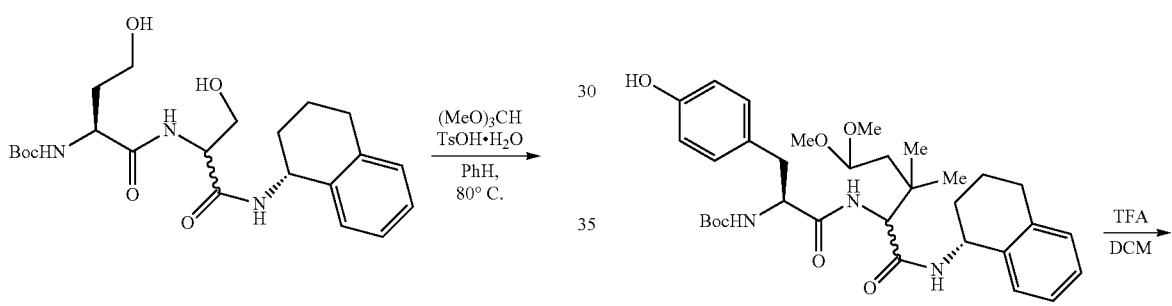

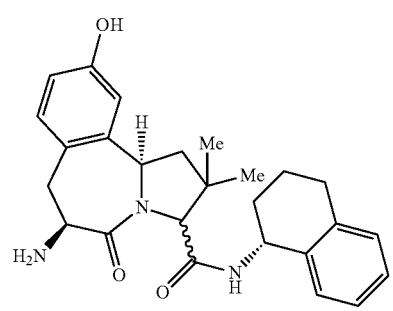

Same procedure as Example 24 with Boc-Tyr-OH (346 mg, 1.23 mmol, 1.0 equiv), aldehyde (197 mg, 1.23 mmol, 1.0 equiv), isocyanide (193 mg, 1.23 mmol, 1.0 equiv) and 7 M ammonia in MeOH (351 μL, 2.46 mmol, 2.0 equiv) in TFE (4 mL). The resultant oil was combined with TFA (575 μL, 7.51 mmol, 8 equiv) in DCM (5 mL) and stirred at 35° C. for 14 h. The mixture was concentrated in vacuo and the crude product used without further purification in the next step.

Example 70: Preparation of tert-butyl ((2S)-1-(((6S,11bR)-10-hydroxy-2,2-dimethyl-5-oxo-3-(((R)-1,2,3,4-tetrahydronaphthalen-1-yl)carbamoyl)-2,3,5,6,7,11b-hexahydro-1H-benzo[c]pyrrolo[1,2-a]azepin-6-yl)amino)-1-oxopropan-2-yl)(methyl)carbamate

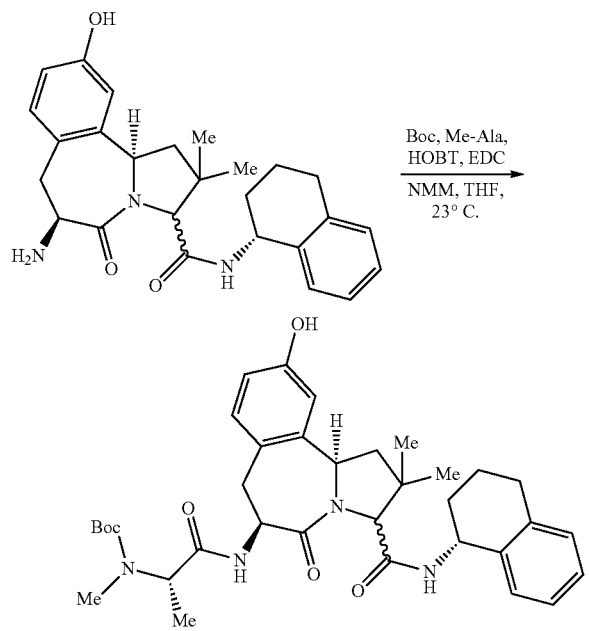

Same procedure as Example 25 using crude amine (406 mg, 0.939 mmol, 1.0 equiv), Boc-N-Me-Ala-OH (191 mg, 0.939 mmol, 1.0 equiv), HOBT·xH₂O (158 mg, 1.03 mmol, 1.1 equiv), NMM (310 μL, 2.82 mmol, 3 equiv and EDC·HCl (189 mg, 0.986 mmol, 1.05 equiv) in THF (10 mL). The resultant oil was purified by flash chromatography on silica gel (3:1→1:1→1:3 hexanes/EtOAc with <5% DCM in all eluant to dissolve) to yield, after 3 steps the unseparated diastereomixture (250 mg, slightly impure). LCMS calcd for M+H: 619.35, found 619.16.

Example 71: Preparation of (6S,11bR)-10-hydroxy-2,2-dimethyl-6-((S)-2-(methylamino)propanamido)-5-oxo-N-((R)-1,2,3,4-tetrahydronaphthalen-1-yl)-2,3,5,6,7,11b-hexahydro-1H-benzo[c]pyrrolo[1,2-a]azepine-3-carboxamide

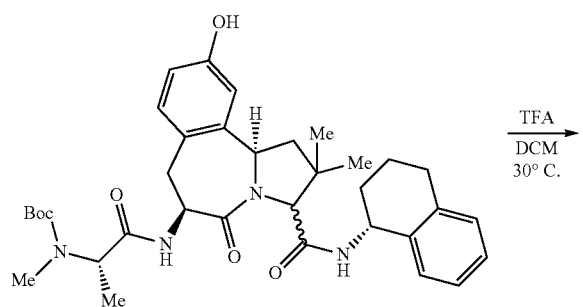

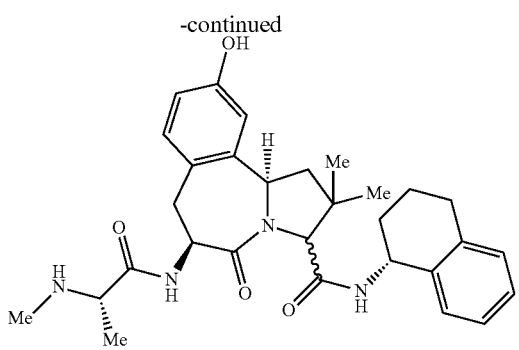

To a solution of carbamate (47 mg, 0.0760 mmol, 1 equiv) in DCM (2 mL) was added TFA (47 μL, 0.608 mmol, 8 equiv). The mixture was stirred for 16 h at 40° C., then concentrated in vacuo to give the product.TFA (42 mg, quantitative). The product was purified by reverse phase HPLC. LCMS calcd for M+H: 519.30, found 519.07.

Example 72: Preparation of (4S,9aR)-4-amino-8,8-dimethyl-2,5-dioxo-N-((R)-1,2,3,4-tetrahydronaphthalen-1-yl)octahydro-1H-pyrrolo[1,2-a][1,3]diazepine-7-carboxamide Same procedure as Example 24 with Boc-Asn-OH (290 mg, 1.25 mmol, 1.0 equiv), aldehyde (200 mg, 1.25 mmol, 1.0 equiv), isocyanide (196 mg, 1.25 mmol, 1.0 equiv) and 7 M ammonia in MeOH (357 μL, 2.50 mmol, 2.0 equiv) in TFE (4 mL). The resultant oil was combined with TFA (635 μL, 8.30 mmol, 8 equiv) in DCM (5 mL) and stirred at 35° C. for 14 h. The mixture was concentrated in vacuo and the crude product used without further purification in the next step.

Example 73: Preparation of tert-butyl ((2S)-1-(((4S, 9aR)-8,8-dimethyl-2,5-dioxo-7-(((R)-1,2,3,4-tetrahydronaphthalen-1-yl)carbamoyl)octahydro-1H-pyrrolo[1,2-a][1,3]diazepin-4-yl)amino)-1-oxopropan-2-yl)(methyl)carbamate

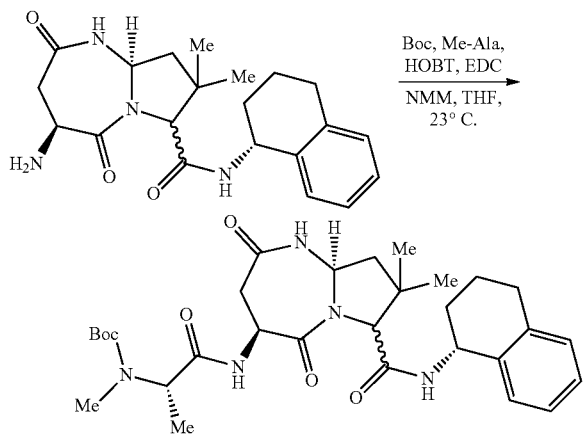

Same procedure as Example 25 using crude amine (398 mg, 1.03 mmol, 1.0 equiv), Boc-N-Me-Ala-OH (210 mg, 1.03 mmol, 1.0 equiv), HOBT.xH$_2$O (174 mg, 1.14 mmol, 1.1 equiv), NMM (341 µL, 3.11 mmol, 3 equiv and EDC.HCl (208 mg, 1.09 mmol, 1.05 equiv) in THF (10 mL). The resultant oil was purified by flash chromatography on silica gel (1:1→1:3 hexanes/EtOAc→DCM→3:1 DCM/EtOAc→EtOAc) to yield, after 3 steps the unseparated diastereomixture (300 mg, slightly impure). LCMS calcd for M+H: 570.33, found 570.14.

Example 74: Preparation of (4S,9aR)-8,8-dimethyl-4-((S)-2-(methylamino)propanamido)-2,5-dioxo-N-((R)-1,2,3,4-tetrahydronaphthalen-1-yl)octahydro-1H-pyrrolo[1,2-a][1,3]diazepine-7-carboxamide

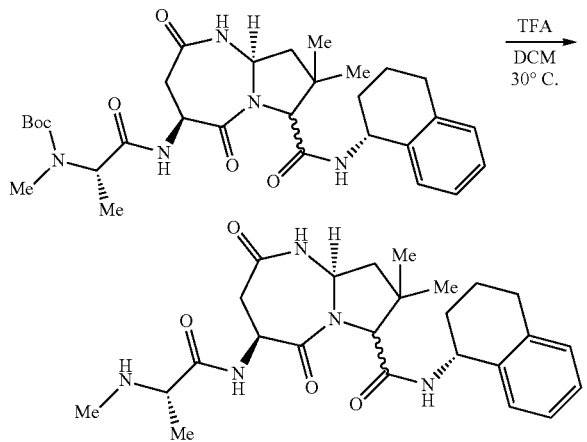

To a solution of carbamate (58 mg, 0.102 mmol, 1 equiv) in DCM (2 mL) was added TFA (62 µL, 0.814 mmol, 8 equiv). The mixture was stirred for 16 h at 23° C., then concentrated in vacuo to give the product.TFA, which was purified by reverse phase HPLC to give 17 mg of a polar isomer and 7 mg of a less polar isomer. LCMS calcd for M+H: 470.28, found 470.36.

Example 75: Preparation of (6S,11bR)-6-amino-9-hydroxy-2,2-dimethyl-5-oxo-N-((R)-1,2,3,4-tetrahydronaphthalen-1-yl)-2,3,5,6,7,11b-hexahydro-1H-benzo[c]pyrrolo[1,2-a]azepine-3-carboxamide and (6S,11bR)-6-amino-11-hydroxy-2,2-dimethyl-5-oxo-N-((R)-1,2,3,4-tetrahydronaphthalen-1-yl)-2,3,5,6,7,11b-hexahydro-1H-benzo[c]pyrrolo[1,2-a]azepine-3-carboxamide

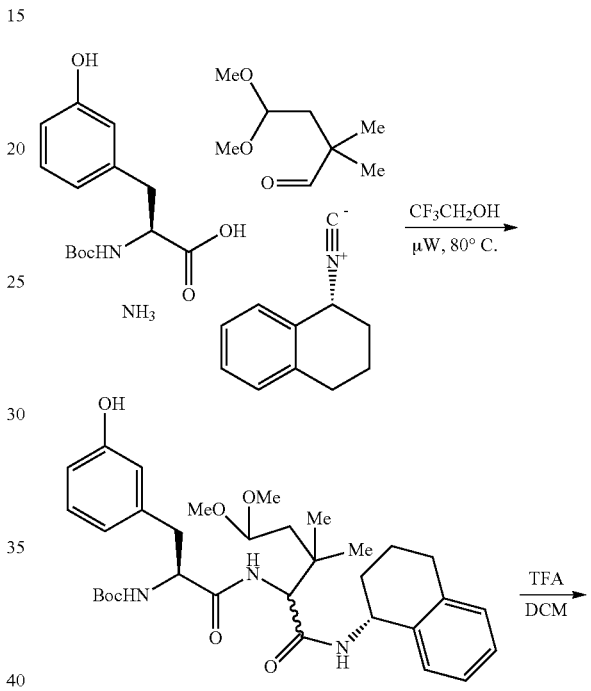

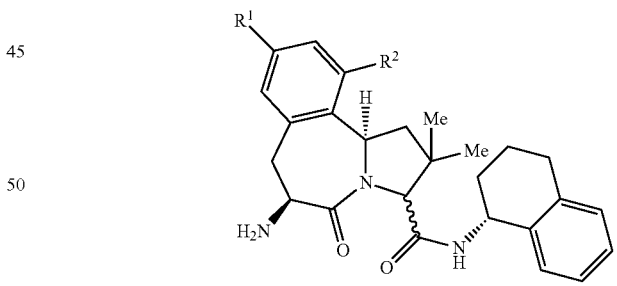

two isomers: R$^1$ or R$^2$ = OH
other substituent = H

Same procedure as Example 24 with Boc-m-Tyr-OH (306 mg, 1.09 mmol, 1.0 equiv), aldehyde (192 mg, 1.20 mmol, 1.0 equiv), isocyanide (171 mg, 1.09 mmol, 1.0 equiv) and 7 M ammonia in MeOH (311 µL, 2.18 mmol, 2.0 equiv) in TFE (4 mL). The resultant oil was combined with TFA (625 µL, 8.16 mmol, 8 equiv) in DCM (5 mL) and stirred at 23° C. for 14 h. The mixture was concentrated in vacuo and the crude product used without further purification in the next step.

Example 76: Preparation of tert-butyl ((2S)-1-(((6S,11bR)-9-hydroxy-2,2-dimethyl-5-oxo-3-(((R)-1,2,3,4-tetrahydronaphthalen-1-yl)carbamoyl)-2,3,5,6,7,11b-hexahydro-1H-benzo[c]pyrrolo[1,2-a]azepin-6-yl)amino)-1-oxopropan-2-yl)(methyl)carbamate and tert-butyl ((2S)-1-(((6S,11bR)-11-hydroxy-2,2-dimethyl-5-oxo-3-(((R)-1,2,3,4-tetrahydronaphthalen-1-yl)carbamoyl)-2,3,5,6,7,11b-hexahydro-1H-benzo[c]pyrrolo[1,2-a]azepin-6-yl)amino)-1-oxopropan-2-yl)(methyl)carbamate Example 77: Preparation of (6S,11bR)-9-hydroxy-2,2-dimethyl-6-((S)-2-(methylamino)propanamido)-5-oxo-N-((R)-1,2,3,4-tetrahydronaphthalen-1-yl)-2,3,5,6,7,11b-hexahydro-1H-benzo[c]pyrrolo[1,2-a]azepine-3-carboxamide and (6S,111bR)-11-hydroxy-2,2-dimethyl-6-((S)-2-(methylamino)propanamido)-5-oxo-N-((R)-1,2,3,4-tetrahydronaphthalen-1-yl)-2,3,5,6,7,11b-hexahydro-1H-benzo[c]pyrrolo[1,2-a]azepine-3-carboxamide

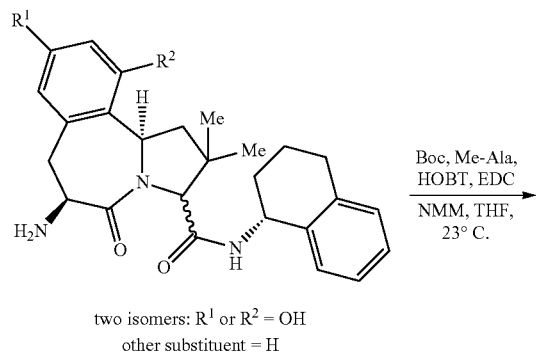

two isomers: $R^1$ or $R^2$ = OH
other substituent = H

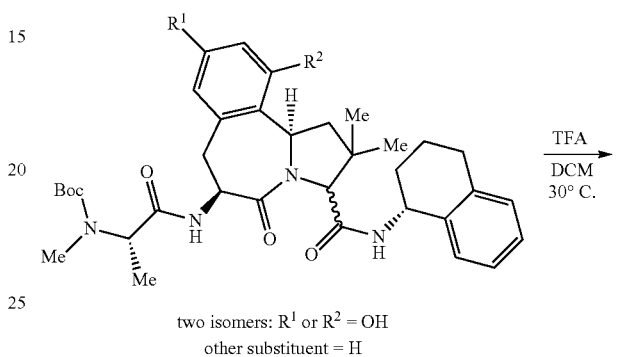

two isomers: $R^1$ or $R^2$ = OH
other substituent = H

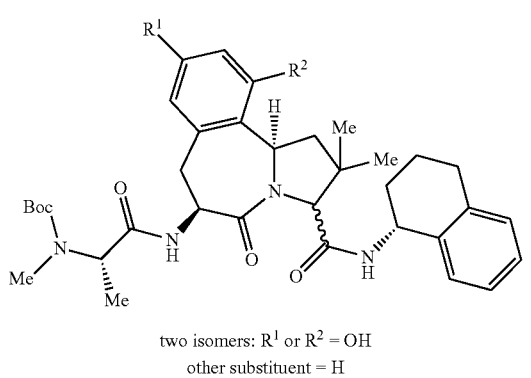

two isomers: $R^1$ or $R^2$ = OH
other substituent = H

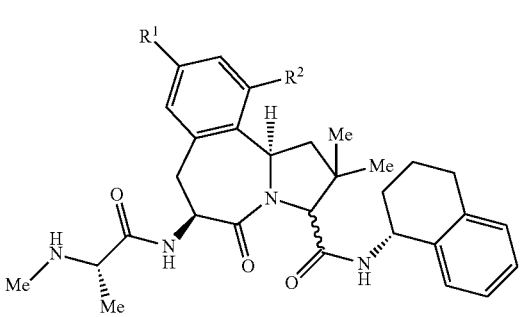

two isomers: $R^1$ or $R^2$ = OH
other substituent = H

Same procedure as Example 25 using crude amine (442 mg, 1.02 mmol, 1.0 equiv), Boc-N-Me-Ala-OH (207 mg, 1.02 mmol, 1.0 equiv), HOBT.xH$_2$O (172 mg, 1.12 mmol, 1.1 equiv), NMM (337 µL, 3.06 mmol, 3 equiv and EDC.HCl (205 mg, 1.07 mmol, 1.05 equiv) in THF (10 mL). The resultant oil was purified by flash chromatography on silica gel (3:1→1:1→1:3 hexanes/EtOAc→7% MeOH/DCM, all eluant with <5% DCM to dissolve) to yield, after 3 steps three product-containing fractions (most polar: 253 mg, medium polarity: 112 mg, least polar: 92 mg). LCMS calcd for M+H: 619.35, found 619.45.

Each fraction of Example 77 was run separately. To a solution of carbamate (253 mg most polar isomer, 112 mg medium polarity isomer, 92 mg least polar isomer) in DCM (2 mL) was added TFA (250, 111, 91 µL, respectively, 8 equiv). The mixture was stirred for 16 h at 40° C., then concentrated in vacuo to give the product.TFA, which was purified by reverse phase HPLC to give 151 mg of the most polar isomer, 55 mg of the medium polarity isomer and 19 mg of the least polar isomer. LCMS calcd for M+H: 519.30, found 519.41.

Example 78: Preparation of two regioisomers: (6S,11bR)-6-amino-9,10-dihydroxy-2,2-dimethyl-5-oxo-N-((R)-1,2,3,4-tetrahydronaphthalen-1-yl)-2,3,5,6,7,11b-hexahydro-1H-benzo[c]pyrrolo[1,2-a]azepine-3-carboxamide and (6S,111bR)-6-amino-10,11-dihydroxy-2,2-dimethyl-5-oxo-N-((R)-1,2,3,4-tetrahydronaphthalen-1-yl)-2,3,5,6,7,11b-hexahydro-1H-benzo[c]pyrrolo[1,2-a]azepine-3-carboxamide Example 79: Preparation of two regioisomers: tert-butyl ((2S)-1-(((6S,11bR)-9,10-dihydroxy-2,2-dimethyl-5-oxo-3-(((R)-1,2,3,4-tetrahydronaphthalen-1-yl)carbamoyl)-2,3,5,6,7,11b-hexahydro-1H-benzo[c]pyrrolo[1,2-a]azepin-6-yl)amino)-1-oxopropan-2-yl)(methyl)carbamate and tert-butyl ((2S)-1-(((6S,11bR)-10,11-dihydroxy-2,2-dimethyl-5-oxo-3-(((R)-1,2,3,4-tetrahydronaphthalen-1-yl)carbamoyl)-2,3,5,6,7,11b-hexahydro-1H-benzo[c]pyrrolo[1,2-a]azepin-6-yl)amino)-1-oxopropan-2-yl)(methyl)carbamate

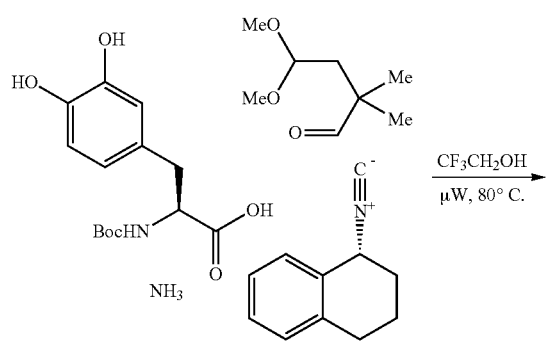

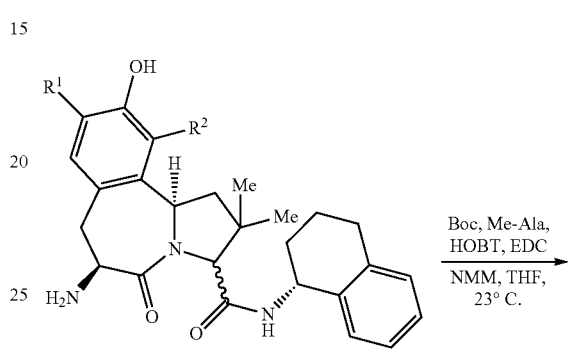

two isomers: R¹ or R² = OH
other substituent = H

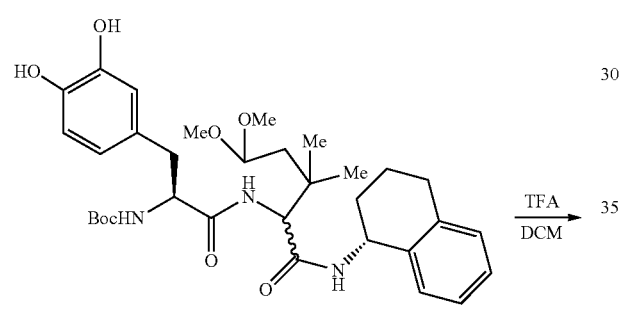

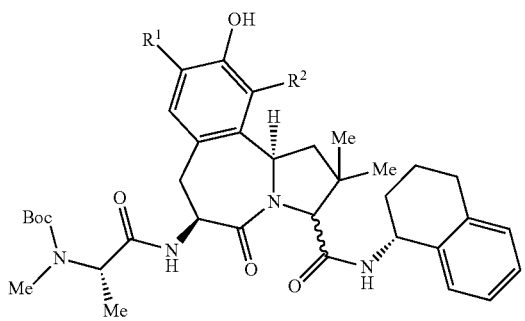

two isomers: R¹ or R² = OH
other substituent = H two isomers: R¹ or R² = OH
other substituent = H Same procedure as Example 24 with Boc-3,4-dihydroxy-L-phenylalanine (288 mg, 0.967 mmol, 1.0 equiv), aldehyde (155 mg, 0.967 mmol, 1.0 equiv), isocyanide (152 mg, 0.967 mmol, 1.0 equiv) and 7 M ammonia in MeOH (276 µL, 1.93 mmol, 2.0 equiv) in TFE (4 mL). The resultant oil was combined with TFA (369 µL, 4.82 mmol, 8 equiv) in DCM (5 mL) and stirred at 35° C. for 14 h. The mixture was concentrated in vacuo and the crude product used without further purification in the next step.

Same procedure as Example 25 using crude amine (339 mg, 0.602 mmol, 1.0 equiv), Boc-N-Me-Ala-OH (122 mg, 0.602 mmol, 1.0 equiv), HOBT.xH₂O (101 mg, 0.662 mmol, 1.1 equiv), NMM (198 µL, 1.80 mmol, 3 equiv and EDC.HCl (121 mg, 0.632 mmol, 1.05 equiv) in THF (10 mL). The resultant oil was not purified (to avoid degradation) and used crude in the next step. LCMS calcd for M+H: 635.34, found 635.16.

Example 80: Preparation of two regioisomers: (6S,11bR)-9,10-dihydroxy-2,2-dimethyl-6-((S)-2-(methylamino)propanamido)-5-oxo-N-((R)-1,2,3,4-tetrahydronaphthalen-1-yl)-2,3,5,6,7,11b-hexahydro-1H-benzo[c]pyrrolo[1,2-a]azepine-3-carboxamide and (6S,11bR)-10,11-dihydroxy-2,2-dimethyl-6-((S)-2-(methylamino)propanamido)-5-oxo-N-((R)-1,2,3,4-tetrahydronaphthalen-1-yl)-2,3,5,6,7,11b-hexahydro-1H-benzo[c]pyrrolo[1,2-a]azepine-3-carboxamide

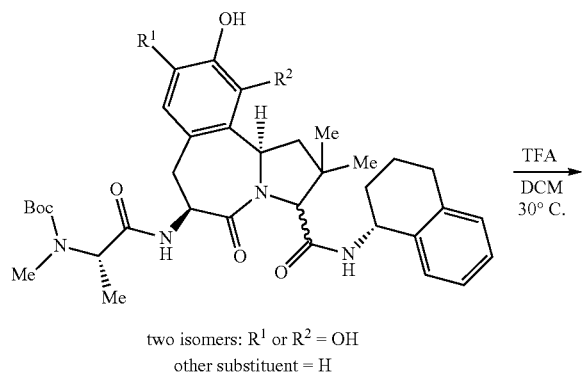

two isomers: $R^1$ or $R^2$ = OH
other substituent = H

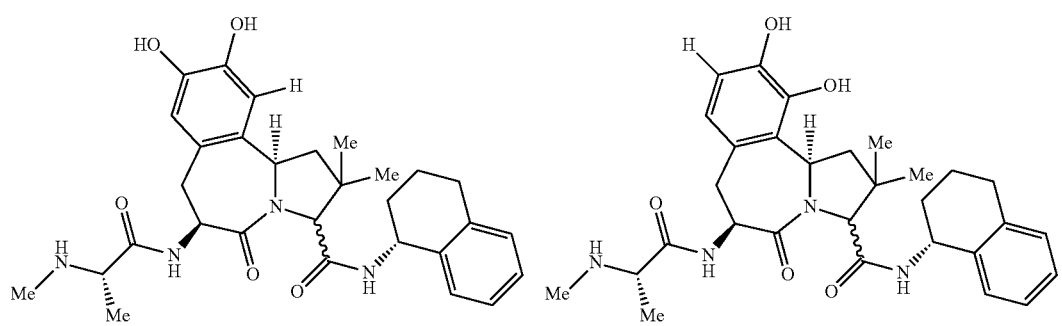

To a solution of carbamate (54 mg, 0.00851 mmol, 1 equiv) in DCM (2 mL) was added TFA (52 μL, 0.681 mmol, 8 equiv). The mixture was stirred for 16 h at 25° C., then concentrated in vacuo to give the product.TFA, which was purified by reverse phase HPLC to give 3.7 mg of a more polar isomer and 7 mg of a less polar isomer. LCMS calcd for M+H: 535.29, found 535.17.

BIOLOGY EXAMPLES

Example B-1

5000 PPC-1 cells were plated and grown overnight. Compounds were plated and 4 hrs later, TRAIL was added to half of the plate while RPMI was added to the other half of the plate as a control. Plates were return to the incubator for 24 hrs. Plates were removed from the incubator and placed on the bench for 30 min and then 25 uL of Cell Titer Glo were added per well. Plates were placed on a rocker and then read on a luminometer. 5000 MDA-MB-231 cells were plated per well. Compound was added and 4 hrs later, TRAIL was added at 5 ng/mL; RPMI was added for a minus TRAIL control. Plates were incubated an additional 24 hrs, removed to the bench for 30 min. and then 25 uL of cell titer glo was added per well. Plates were placed on a rocker and read on a luminometer. Data were fit using PRISM.

Table B-1 below shows assay data for certain compounds described herein.

TABLE B-1

| Structure | Compd No. | XIAP BIR1/2 Ki (μM) | XIAP BIR3 Ki (μM) | ML-IAP Ki (μM) |
|---|---|---|---|---|
| 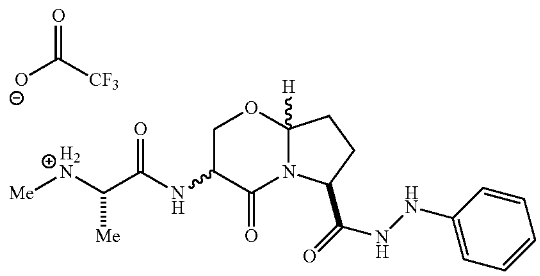 | 1 | | | |
| 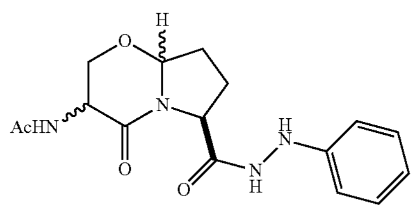 [SMILES: CC(=O)NC1COC2CC[C@@H](C(=O)NNc3ccccc3)N2C1=O] | 2 | | | |
| 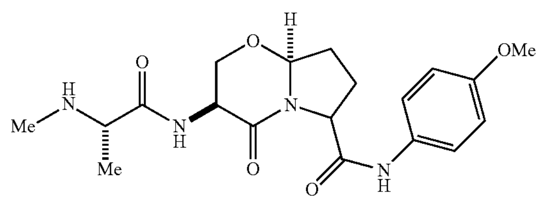 [SMILES: CN[C@@H](C)C(=O)N[C@H]1CO[C@H]2CCC(C(=O)Nc3ccc(OC)cc3)N2C1=O] | 3 | C | B | |
| 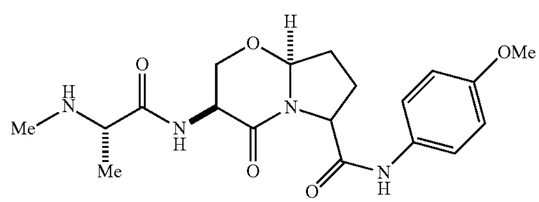 [SMILES: CN[C@@H](C)C(=O)N[C@H]1CO[C@H]2CCC(C(=O)Nc3ccc(OC)cc3)N2C1=O] | 4 | C | B | |
| 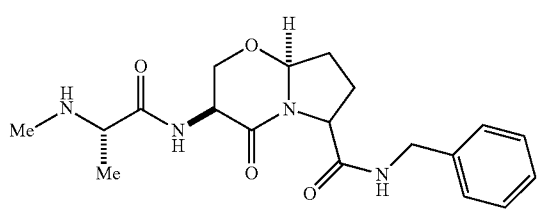 [SMILES: CN[C@@H](C)C(=O)N[C@H]1CO[C@H]2CCC(C(=O)NCc3ccccc3)N2C1=O] | 5 | C | B | |
| 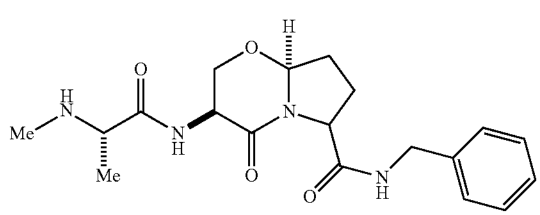 [SMILES: CN[C@@H](C)C(=O)N[C@H]1CO[C@H]2CCC(C(=O)NCc3ccccc3)N2C1=O] | 6 | C | B | |
| 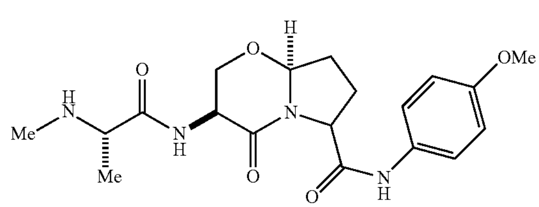 [SMILES: CN[C@@H](C)C(=O)N[C@H]1CO[C@H]2CCC(C(=O)Nc3ccc(OC)cc3)N2C1=O] | 7 | C | B | |

TABLE B-1-continued

| Structure | Compd No. | XIAP BIR1/2 Ki (μM) | XIAP BIR3 Ki (μM) | ML-IAP Ki (μM) |
|---|---|---|---|---|
| 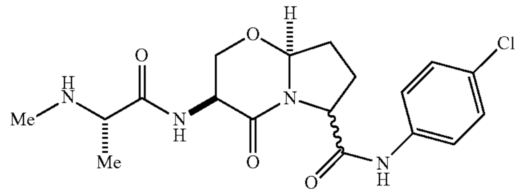 [SMILES: CN[C@@H](C)C(=O)N[C@H]1CO[C@H]2CCC(C(=O)Nc3ccc(Cl)cc3)N2C1=O] | 8 | C | B | |
| 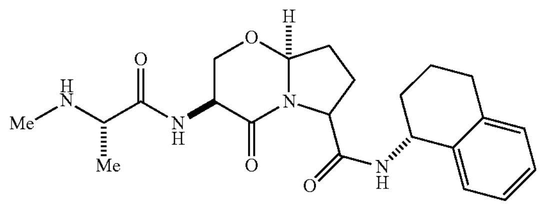 | 9 | C | A | |
| 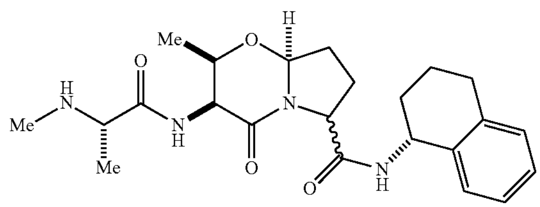 | 10 | C | A | A |
| 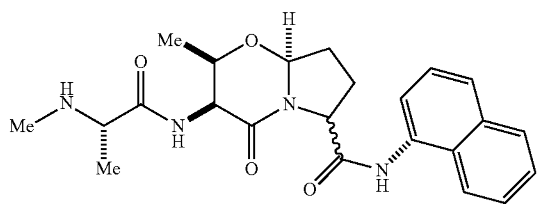 | 11 | C | B | |
| 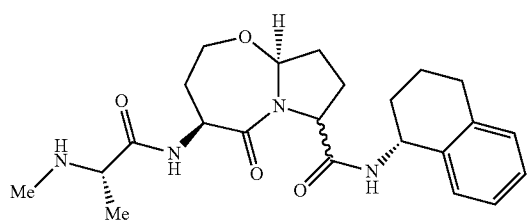 [SMILES: CN[C@@H](C)C(=O)N[C@H]1CCO[C@H]2CCC(C(=O)N[C@@H]3CCCc4ccccc43)N2C1=O] | 12 | C | A | A |
| 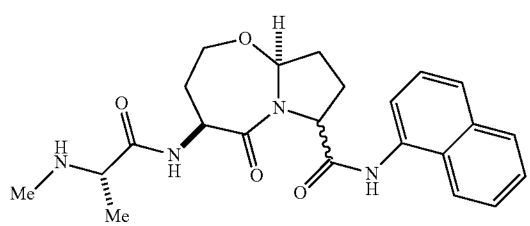 [SMILES: CN[C@@H](C)C(=O)N[C@H]1CCO[C@H]2CCC(C(=O)Nc3cccc4ccccc34)N2C1=O] | 13 | A | A | |
| 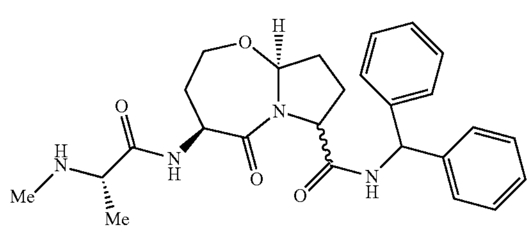 [SMILES: CN[C@@H](C)C(=O)N[C@H]1CCO[C@H]2CCC(C(=O)NC(c3ccccc3)c3ccccc3)N2C1=O] | 14 | C | A | A |

TABLE B-1-continued
| Structure | Compd No. | XIAP BIR1/2 Ki (μM) | XIAP BIR3 Ki (μM) | ML-IAP Ki (μM) |
|---|---|---|---|---|
| 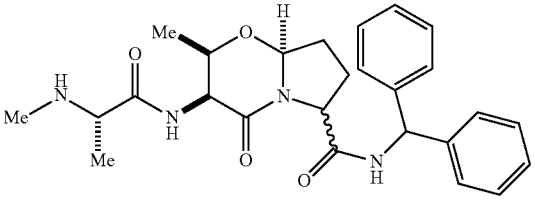 [SMILES: CN[C@@H](C)C(=O)N[C@@H]1C(=O)N2C(C(=O)NC(c3ccccc3)c3ccccc3)CC[C@@H]2O[C@@H]1C] | 15 | C | B | |
| 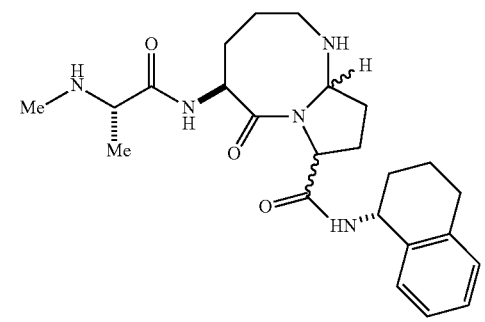 | 16 | B | A | |
| 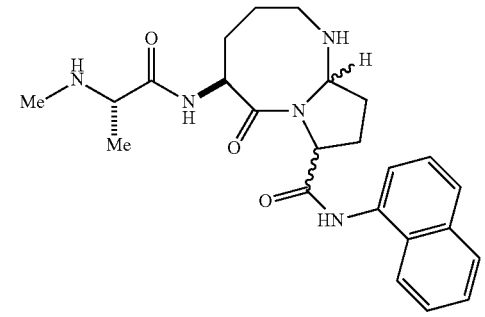 [SMILES: CN[C@@H](C)C(=O)N[C@H]1CCCNC2CCC(C(=O)Nc3cccc4ccccc34)N2C1=O] | 17 | A | A | |
| 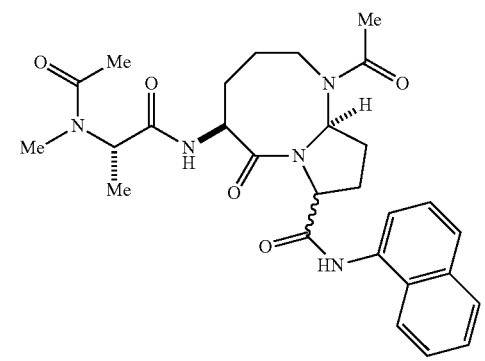 [SMILES: CC(=O)N(C)[C@@H](C)C(=O)N[C@H]1CCCN(C(C)=O)[C@H]2CCC(C(=O)Nc3cccc4ccccc34)N2C1=O] | 18 | C | B | |

TABLE B-1-continued

| Structure | Compd No. | XIAP BIR1/2 Ki (μM) | XIAP BIR3 Ki (μM) | ML-IAP Ki (μM) |
|---|---|---|---|---|
| 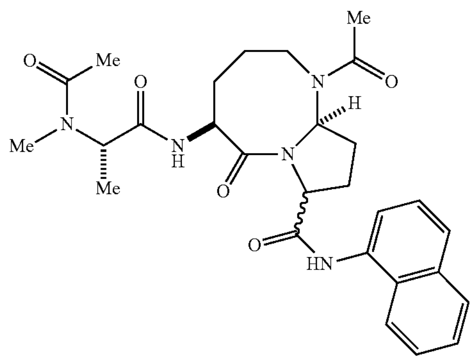 [SMILES: CC(=O)N(C)[C@@H](C)C(=O)N[C@H]1CCCN(C(C)=O)[C@H]2CCC(C(=O)Nc3cccc4ccccc34)N2C1=O] | 19 | C | B | |
| 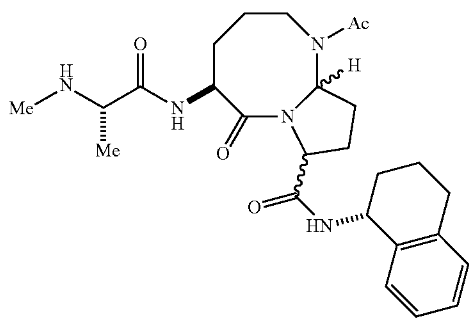 | 20 | C | A | |
| 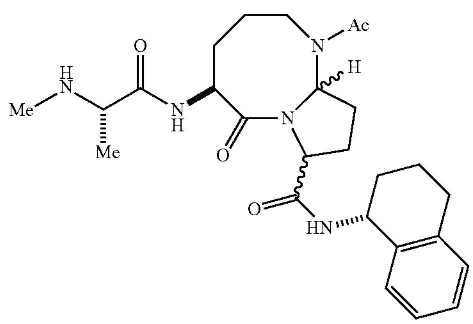 | 21 | C | A | |
| 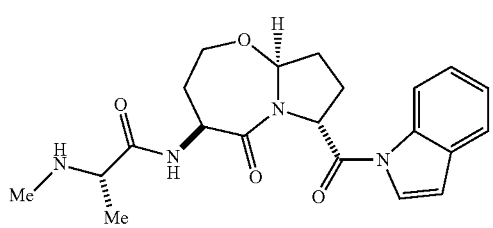 [SMILES: CN[C@@H](C)C(=O)N[C@H]1CCO[C@H]2CC[C@H](C(=O)n3ccc4ccccc43)N2C1=O] | 22 | C | B | |
| 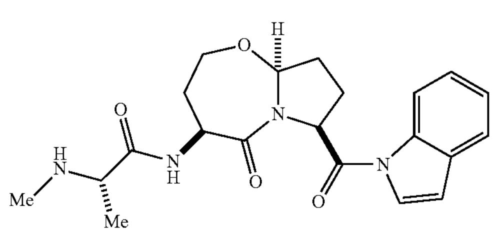 [SMILES: CN[C@@H](C)C(=O)N[C@H]1CCO[C@H]2CC[C@@H](C(=O)n3ccc4ccccc43)N2C1=O] | 23 | C | B | |

TABLE B-1-continued

| Structure | Compd No. | XIAP BIR1/2 Ki (μM) | XIAP BIR3 Ki (μM) | ML-IAP Ki (μM) |
| --- | --- | --- | --- | --- |
| 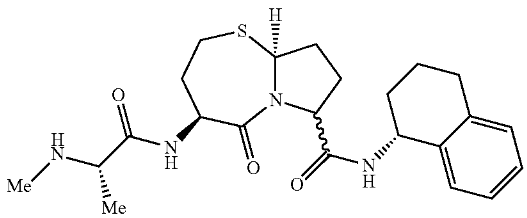 | 24 | C | A | A |
| 6:1 d.r. | 25 | A | A | |
| >10:1 d.r. | 26 | A | A | A |
| 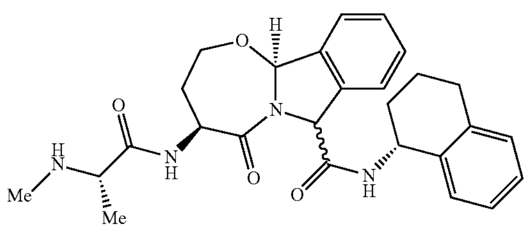 [SMILES: CN[C@@H](C)C(=O)N[C@H]1CCO[C@H]2c3ccccc3C(C(=O)N[C@@H]3CCCc4ccccc43)N2C1=O] | 27 | C | A | A |
| 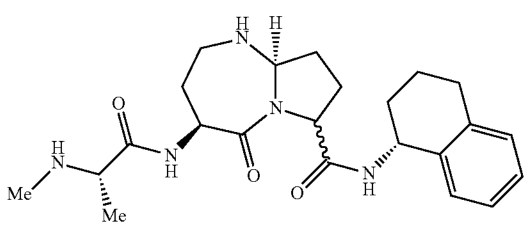 [SMILES: CN[C@@H](C)C(=O)N[C@H]1CCN[C@H]2CCC(C(=O)N[C@@H]3CCCc4ccccc43)N2C1=O] | 28 | C | B | |
| 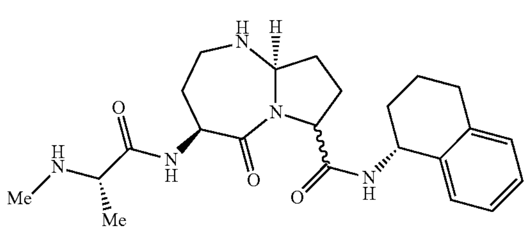 [SMILES: CN[C@@H](C)C(=O)N[C@H]1CCN[C@H]2CCC(C(=O)N[C@@H]3CCCc4ccccc43)N2C1=O] | 29 | C | C | |

TABLE B-1-continued

| Structure | Compd No. | XIAP BIR1/2 Ki (μM) | XIAP BIR3 Ki (μM) | ML-IAP Ki (μM) |
|---|---|---|---|---|
| 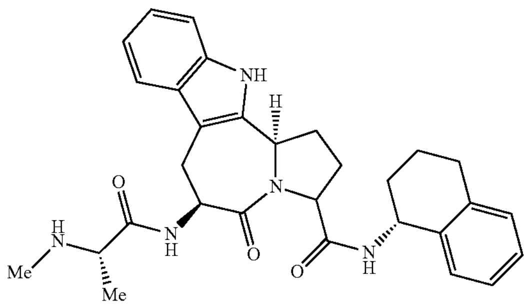 [SMILES: CN[C@@H](C)C(=O)N[C@H]1Cc2c([nH]c3ccccc23)[C@H]2CCC(C(=O)N[C@@H]3CCCc4ccccc43)N2C1=O] | 30 | C | B | |
| 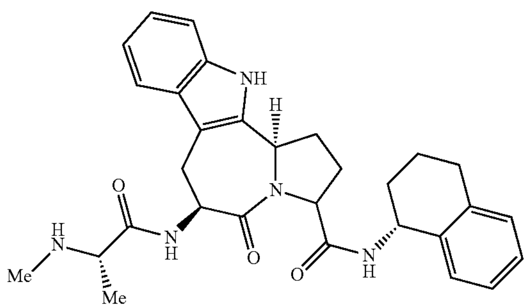 [SMILES: CN[C@@H](C)C(=O)N[C@H]1Cc2c([nH]c3ccccc23)[C@H]2CCC(C(=O)N[C@@H]3CCCc4ccccc43)N2C1=O] | 31 | A | A | |
| 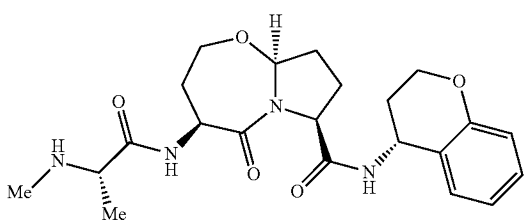 [SMILES: CN[C@@H](C)C(=O)N[C@H]1CCO[C@H]2CC[C@@H](C(=O)N[C@@H]3CCOc4ccccc43)N2C1=O] | 32 | C | A | A |
| (3:1 d.r.) | 33 | C | A | A |
| (>8:1 d.r.) | 34 | C | A | A |

TABLE B-1-continued
| Structure | Compd No. | XIAP BIR1/2 Ki (μM) | XIAP BIR3 Ki (μM) | ML-IAP Ki (μM) |
|---|---|---|---|---|
| 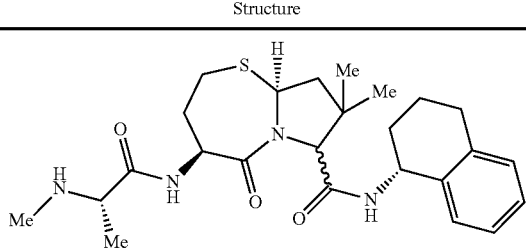 | 35 | A | A | A |
| 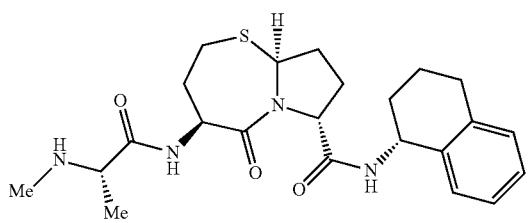 3:1 d.r. | 36 | C | A | A |
| 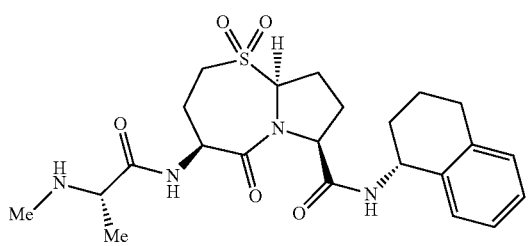 [SMILES: CN[C@@H](C)C(=O)N[C@H]1CCS(=O)(=O)[C@H]2CC[C@@H](C(=O)N[C@@H]3CCCc4ccccc43)N2C1=O] | 37 | C | A | |
| 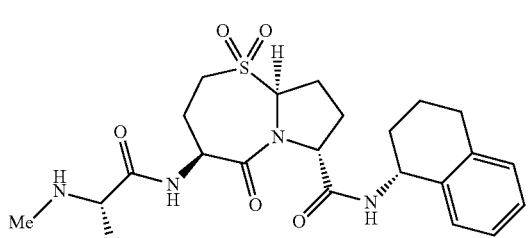 | 38 | C | B | |
| 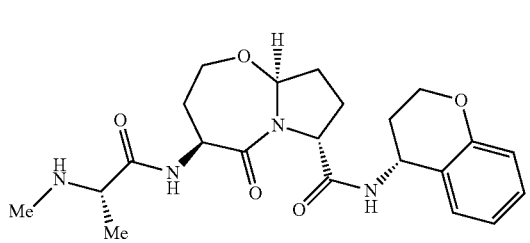 [SMILES: CN[C@@H](C)C(=O)N[C@H]1CCO[C@H]2CC[C@H](C(=O)N[C@@H]3CCOc4ccccc43)N2C1=O] | 39 | C | B | |
| 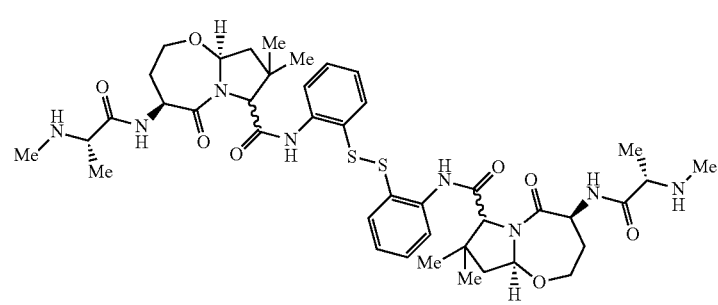 [SMILES: CN[C@@H](C)C(=O)N[C@H]1CCO[C@H]2CC(C)(C)C(C(=O)Nc3ccccc3SSc3ccccc3NC(=O)C3N4C(=O)[C@@H](NC(=O)[C@H](C)NC)CCO[C@H]4CC3(C)C)N2C1=O] | 40 | A | A | |

TABLE B-1-continued

| Structure | Compd No. | XIAP BIR1/2 Ki (μM) | XIAP BIR3 Ki (μM) | ML-IAP Ki (μM) |
| --- | --- | --- | --- | --- |
| 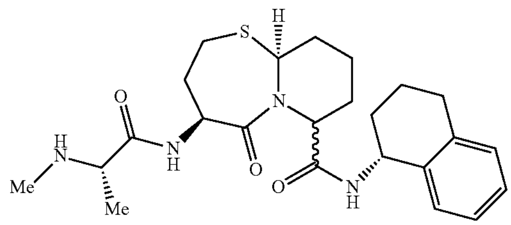 [SMILES: CN[C@@H](C)C(=O)N[C@H]1CCS[C@H]2CCCC(C(=O)N[C@@H]3CCCc4ccccc43)N2C1=O] | 41 | A | A | |
| 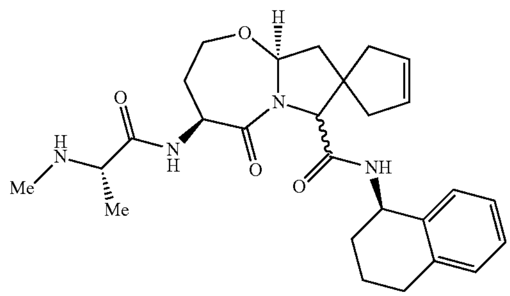 | 42 | A | A | A |
| 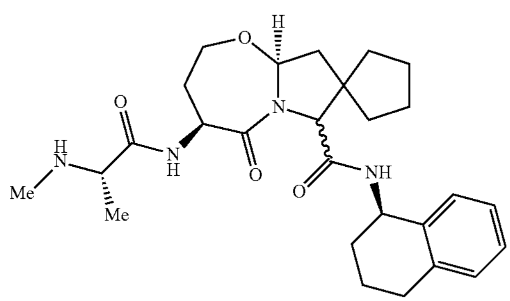 [SMILES: CN[C@@H](C)C(=O)N[C@H]1CCO[C@H]2CC3(CCCC3)C(C(=O)N[C@@H]3CCCc4ccccc43)N2C1=O] | 43 | A | A | |
| 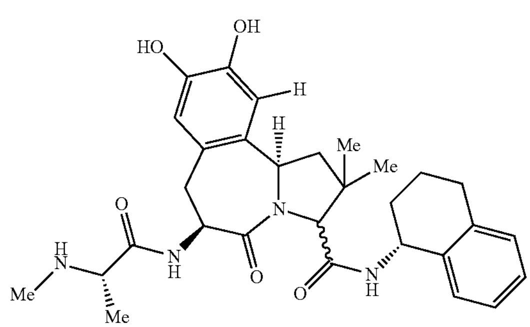 [SMILES: CN[C@@H](C)C(=O)N[C@H]1Cc2cc(O)c(O)cc2[C@H]2CC(C)(C)C(C(=O)N[C@@H]3CCCc4ccccc43)N2C1=O] | 44 | A | A | A |

TABLE B-1-continued

| Structure | Compd No. | XIAP BIR1/2 Ki (µM) | XIAP BIR3 Ki (µM) | ML-IAP Ki (µM) |
|---|---|---|---|---|
| (structure) | 45 | A | A | |
| (structure) | 46 | C | A | A |
| (structure) | 47 | A | A | A |
| (structure) | | | | |

KEY:
A = ≤25 micromolar;
B >25 and ≤50 micromolar;
C >50 micromolar

Example B-2—Effect of Knockdown of BIRC2 Gene Expression on HIV Transcription and Expression The effect of siRNA-mediated knockdown of BIRC2 gene expression on HIV transcription was assayed on HEK 293T cells and found to affect the levels of HIV transcription. HEK 293T cells were transfected with siRNAs targeting BIRC2 and infected with a VSVg-pseudotyped HIV-1 pNL4.3 luciferase reporter virus. pNL43-Luc-E-R+ (HIV-1 wild-type Δenv, encoding firefly luciferase GL3) vector was used to generate VSV-G-pseudotyped lentiviral supernatant ("HIV-VSVg"). siRNAs were transfected into HEK 293T cells following a reverse transfection protocol. 0.15 µl RNAiMAX transfection reagent (Life Technologies) was diluted in 25 µl OptiMEM media (Life Technologies) and added to each well of a 96-well assay plate. After 5 minutes, 25 µl of a 50 nM siRNA solution in OptiMEM (Life Technologies) were added to each well. After 20 min incubation time at room temperature 10,000 HEK 293T cells in 50 g DMEM supplemented with 20% fetal bovine serum (Gibco) were added to each well. After a 48 hour post transfection period, HIV-VSVg diluted in 10 µl DMEM/10% fetal bovine serum were added to each well for 24 hours.

To determine the levels of total HIV DNA, corresponding to the levels of reverse transcription, and integrated provirus DNA from cells treated as described above, DNA was prepared using the DNeasy Blood & Tissue Kit (Qiagen). DNA was quantitated using the Quant-iT™ PicoGreen R dsDNA Assay Kit (Life Technologies) and a Cytofluoro Multi-well plate reader Series 4000 (Applied Biosystems). Proviral DNA content was measured using Alu-PCR and total HIV DNA using internal PCR primers (Alu Forward GCCTCCCAAAGTGCTGGGATTACAG, HIV Gag Reverse GCTCTCGCACCCATCTCTCTCC, HIV LTR (R) Forward GCCTCAATAAAGCTTGCCTTGA, HIV LTR (U5) Reverse TCCACACTGACTAAAAGGGTCTGA, LTR Molecular Beacon FAM-GCGAGTGCCCGTCTGTTGTGTGACTCTGGTAACTA GCTCGC-Dabcyl) as previously described (Butler S. L., Hansen M. S., Bushman F. D.: A quantitative assay for HIV DNA integration in vivo. *Nat Med* 2001, 7:631-634; O'Doherty U., Swiggard W. J., Jeyakumar D., McGain D., Malim M. H.: A sensitive, quantitative assay for human immunodeficiency virus type 1 integration. *J Virol* 2002, 76:10942-10950; König R., Zhou Y., Elleder D., Diamond T. L., Bonamy G. M., Irelan J. T., Chiang C. Y., Tu B. P., De Jesus P. D., Lilley C. E., et al: Global analysis of host-pathogen interactions that regulate early-stage HIV-1 replication. *Cell* 2008, 135:49-60) using an Applied Biosystems 7500 Fast Real Time PCR system. All steps were performed using an Epmotion 5075 robot (Eppendorf). Values were normalized to non-targeting control siRNAs.

To determine the levels of HIV mRNA and BIRC2 mRNA, corresponding to the levels of HIV transcription and target gene expression, respectively, RNA was isolated and cDNA was prepared from HEK 293T cells treated as described above using the Ambion Cells-to-Ct Kit (Life Technologies). HIV-1 and BIRC2 mRNA levels were measured by quantitative PCR and normalized to the cellular gene GAPDH using the following primers pairs: HIV-1 late RT primers (TGTGTGCCCGTCTGTTGTGT and GAGTCCTGCGTCGAGAGATC), BIRC2 primers (GAATCTGGTTTCAGCTAGTCTGG and GGTGG-GAGATAATGAATGTGCAA), and GAPDH primers (CATGAGAAGTATGACAACAGCCT and AGTCCTTCCAC-GATACCAAAGT). Values were normalized to non-targeting control siRNAs.

Viability of HEK 293T cells treated as described above was determined using the CellTiter-Glo assay system (Promega). Values were normalized to non-targeting control siRNAs.

The levels of luciferase reporter expression, corresponding to expression of viral proteins, in HEK 293T cells treated as described above was determined using the Bright-Glo assay system (Promega). Values were normalized to non-targeting control siRNAs.

FIG. 1A-1C show the effect of siRNA-mediated knockdown of the BIRC2 gene on HIV reverse transcription, integration, transcription, and expression of viral proteins in HEK 293T cells. siRNA-mediated knockdown of the BIRC2 gene caused an enhancement of HIV transcription and expression of viral proteins in HEK 293T cells.

Example B-3—Effect of Knockdown of BIRC2 Gene Expression on NF-κB Dependent HIV Transcription and Expression The effect of siRNA-mediated knockdown of BIRC2 gene expression on NF-κB dependent HIV transcription was assayed on HEK 293T cells. HEK 293T cells were transfected with siRNAs targeting BIRC2 or CASP8AP2, an unrelated gene, as control. After a 48 hour transfection period, the cells were infected with HIV virus containing either a wild-type (wt) or mutant (dNFkB) NF-κB binding site in the viral LTR. LTR mutations in the NF-κB binding site were generated by mutagenesis in HIV as previously described (Bosque A., Planelles V.: Induction of HIV-1 latency and reactivation in primary memory CD4+ T cells. *Blood* 2009, 113:58-65). These viruses were produced by standard transfection of HEK 293T cells with the viral vector and a plasmid encoding VSV-G as described previously (König R., Chiang C. Y., Tu, B. P., Yan, S. F., DeJesus P. D., Romero A., Bergauer T., Orth A., Krueger U., Zhou Y., Chanda S. K.: A probability-based approach for the analysis of large-scale RNAi screens. *Nat Methods* 2007, 4:847-849). After a 24 hour infection period, cells were lysed, cDNA was synthesized, and qPCR reactions were set up according to manufacturer's instruction using the Ambion Cells-to-Ct kit (Life Technologies). HIV-1 mRNA levels were measured by qPCR and normalized to the cellular gene GAPDH using the following primers pairs: HIV-1 late RT primers (TGTGTGCCCGTCTGTTGTGT and GAGTCCTGCGTCGAGAGATC), and GAPDH primers (CATGAGAAGTATGACAACAGCCT and AGTCCTTC-CACGATACCAAAGT). Values were normalized to a non-targeting control siRNA.

Figure 2:
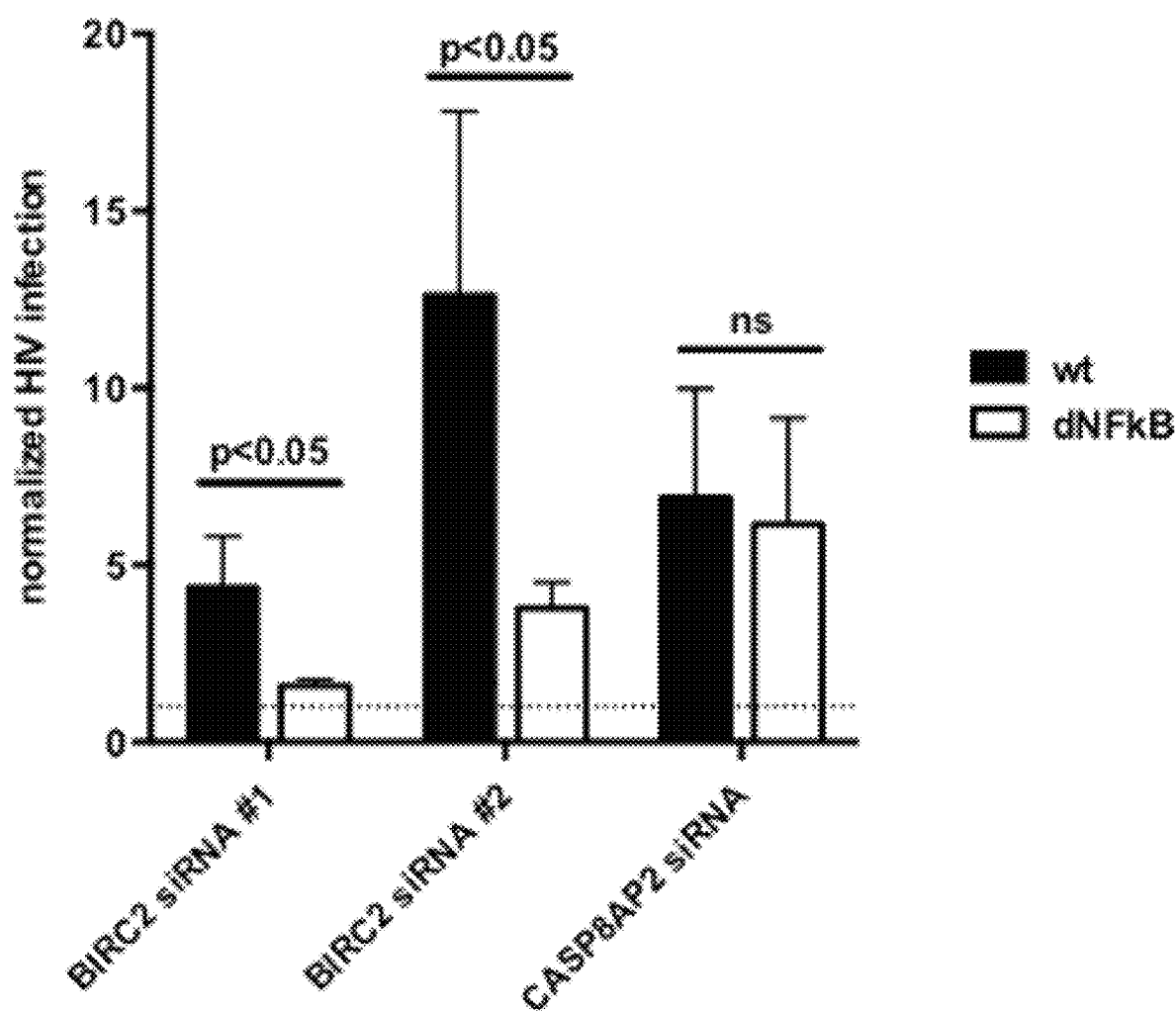
FIG. 2 shows the enhancement of HIV infection, determined by measurement of HIV mRNA levels, of HEK 293T cells that were infected with HIV containing either a wild-type (wt) or mutant (dNFkb) NF-κB binding site in the viral LTR.

FIG. 2 shows the enhancement of HIV infection, determined by measurement of HIV mRNA levels, of HEK 293T cells that were infected with HIV containing either a wild-type (wt) or mutant (dNFkb) NF-κB binding site in the viral LTR. The enhancement of viral gene expression upon BIRC2 knockdown was significantly reduced in the absence of functional NF-κB binding sites in the viral LTR, indicating that this phenotype is dependent of NF-κB signaling. siRNAs targeting CASP8AP2 served as control. Cells transfected with siRNAs targeting CASP8AP2 showed no significant difference in the enhancement of infection between the two viruses.

Example B-4—Effects of IAP Antagonist on BIRC2/cIAP1 Expression in HEK 293T Cells The effect of IAP antagonist Compound 35 on BIRC2/cIAP1 expression was assayed by treating HEK 293T cells with increasing concentrations of Compound 35 in the presence of HIV-VSVg for 24 hours. Cells were infected with HIV-VSVg and treated with Compound 35 in parallel for 24 hours before luciferase expression was determined using the Brite-Glo assay system (Promega). Upon treatment of HEK 293T cells with Compound 35, the enhancement of viral gene transcription, as measured by luciferase expression, was proportional to the loss of BIRC2/cIAP1 protein. BIRC2 and BIRC3 protein expression levels upon treatment with Compound 35 were determined by Western blotting. 250,000 HEK 293T cells in 2.5 ml DMEM supplemented with 10% fetal bovine serum were plated in a 6-well plate per well. After 24 hours, 277.8 μl media containing concentrations of Compound 35 ranging from 0.15 nM to 10 μM were added to the samples and incubated for 16 hours. Cells were washed with DPBS and lysed in RIPA buffer. The lysate was analyzed by gel electrophoresis and subsequent Western blotting using a cIAP pan-specific antibody (clone 315301, R&D Systems).

Figure 3A:
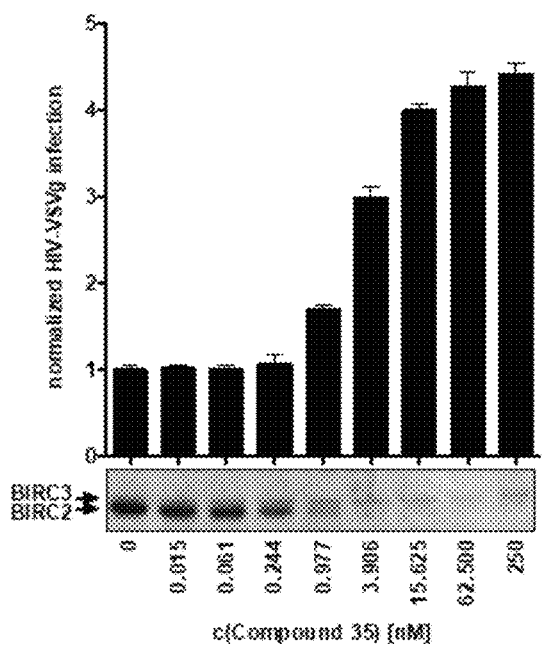
FIG. 3A shows the expression of luciferase following HIV-VSVg infection of HEK 293T cells treated with Compound 35. BIRC2 and BIRC3 expression levels are also shown.

FIG. 3A shows the expression of luciferase following HIV-VSVg infection of HEK 293T cells treated with Compound 35 and the expression of BIRC2 and BIRC3.

Example B-5—Reactivation of HIV in Latently Infected Cells with IAP Antagonists The ability of IAP antagonist Compound 35 to reactivate HIV expression in latently infected cells was assayed by using a Jurkat cell-based JLat latency model system or HEK293T cells.

JLat 10.6 cells were treated with increasing concentrations of the IAP antagonist Compound 35 for 24 hours. $1 \times 10^5$ Jurkat cells were diluted in 135 µl RPMI media supplemented with 10% fetal bovine serum. 15 µl media containing compound concentrations from 0.169 nM to 1.11 µM were added to the samples. Following an incubation of 24 hours at 37° C. the media was removed and cells were resuspended in 50 µl DPBS. Reactivation of the virus in cells was determined by measuring GFP expression by flow cytometry.

Figure 3B:
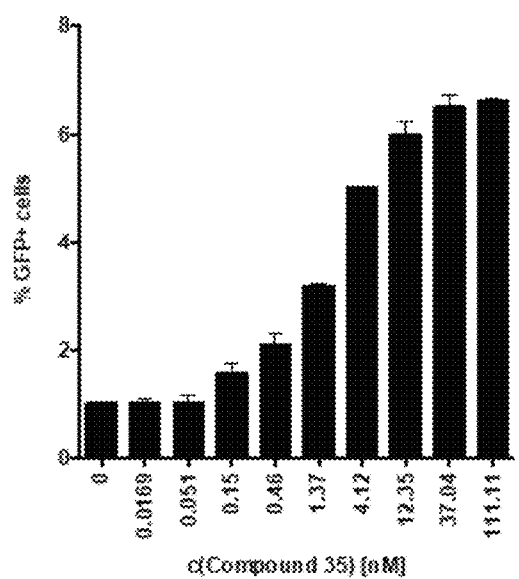
FIG. 3B shows the effect of Compound 35 on activating HIV transcription in latently infected JLat10.6 cells.

FIG. 3B shows the effect of Compound 35 on activating HIV transcription in latently infected JLat 10.6 cells. Treatment of latently infected JLat 10.6 cells with Compound 35 caused reactivation of HIV as determined by enhanced GFP reporter expression in the cells.

Figure 3C:
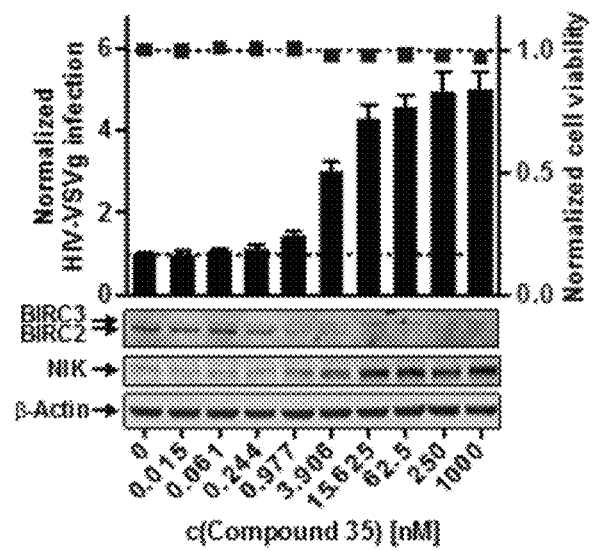
FIG. 3C shows the effect of Compound 35 on activating HIV transcription in HEK293T cells.

HEK293T cells were treated with Compound 35 and infected with HIV-1 (VSVg) for 24 hours. Levels of infection were evaluated by measuring luciferase reporter activity. Lysate of Compound 35-treated cells was evaluated for BIRC2 and NIK protein levels by Western blotting. FIG. 3C shows the effect of Compound 35 on HIV transcription in HEK293T cells.

The ability of Compound 35, panobinostat, vorinostat, HMBA (hexamethylene bisacetamide), or combinations thereof to activate HIV transcription in latently infected cells was assayed by using JLat 10.6 cells. $1 \times 10^5$ Jurkat cells were diluted in 115 µl RPMI media supplemented with 10% fetal bovine serum. 30 µl media containing 80 nM Compound 35, 5 µM Panobinostat, 5 µM Vorinostat, 50 mM HMBA, DMSO as negative control, or a combination thereof was added to the cells. Following an incubation of 24 hours at 37° C. the media was removed and cells were resuspended in 50 µl DPBS. Reactivation of virus was subsequently determined by measuring GFP expression in treated cells by flow cytometry. Cell viability was determined by measuring cellular ATP content in a separate set of samples using the ATPlite assay (PerkinElmer).

Additionally, the ability of TL32711 to activate HIV transcription in latently infected cells was assayed. JLat 10.6 cells were treated with TL32711 and GFP expression was determined. $1 \times 10^5$ Jurkat cells were diluted in 135 µl RPMI media supplemented with 10% fetal bovine serum. 15 µl media containing 50 µM TL32711 (obtained from Active Biochemicals) were added to the samples. Following an incubation of 24 hours at 37° C. the media was removed and cells were resuspended in 50 µl DPBS. Reactivation of virus was subsequently determined by measuring GFP expression in treated cells by flow cytometry. Cell viability of cells treated with TL32711 was determined by measuring cellular ATP content in a separate set of samples using the ATPlite assay (PerkinElmer).

Figure 4A:
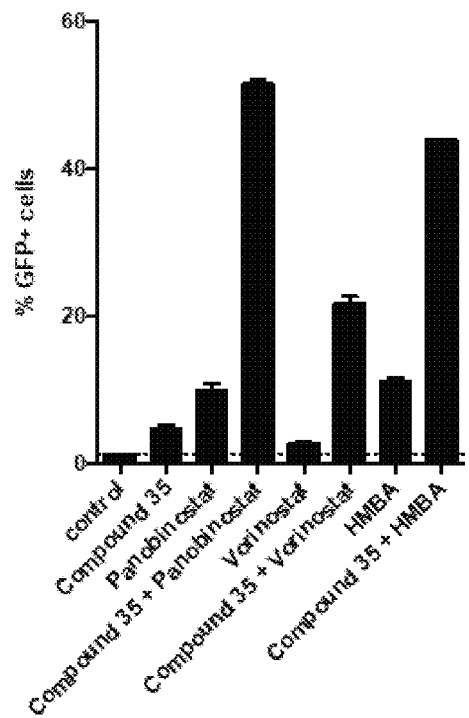
FIG. 4A shows the effects of Compound 35, panobinostat, vorinostat, HMBA or combinations thereof on activating HIV transcription in latently infected JLat10.6 cells.
Figure 4B:
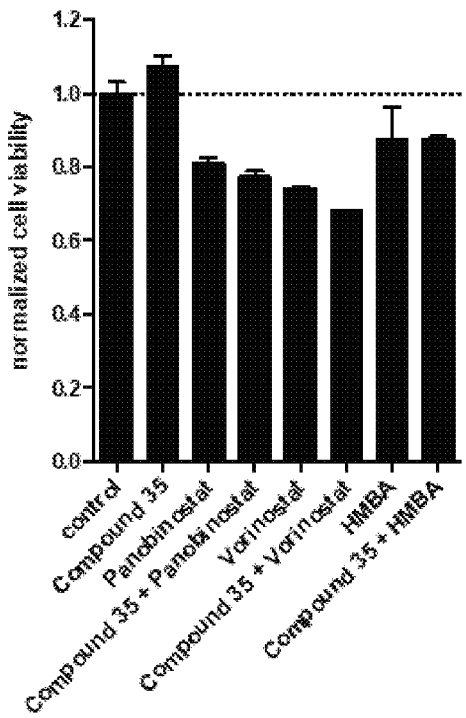
FIG. 4B shows that the cell viability was determined by measuring cellular ATP content.

FIG. 4A shows the effects of Compound 35, panobinostat, vorinostat, HMBA (hexamethylene bisacetamide) or combinations thereof on activating HIV transcription in latently infected JLat 10.6 cells. Treatment of a JLat 10.6 cells with a combination of Compound 35 and with one of the following: Panobinostat, Vorinostat, or HMBA resulted in a greater effect than treatment with any of the components alone.

Figure 4C:
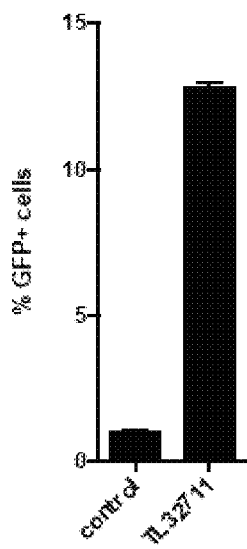
FIG. 4C shows the effects of TL32711 on activating HIV transcription in latently infected JLat10.6 cells.
Figure 4D:
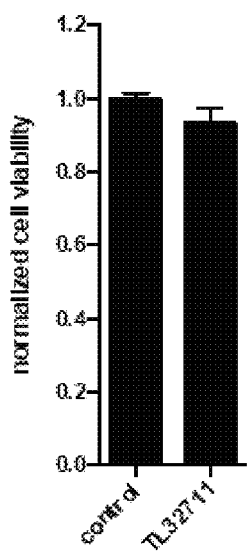
FIG. 4D shows the cell viability of TL32711 was determined by measuring cellular ATP content.

FIG. 4C shows the effects of TL32711 on activating HIV transcription in latently infected JLat 10.6 cells. Reactivation of latent HIV in JLat 10.6 cells was achieved with the IAP antagonist TL32711 (obtained from Active Biochemicals).

Furthermore, the ability of Compound 26, LCL161 and/or GDC-0152 to activate HIV transcription in latently infected cells was also assayed. Latently infected Jurkat 2D10 cells were treated with Compound 35, Compound 26, TL32711 (Tetralogic), LCL161 (Novartis), or GDC-0152 (Genetech) for 36 hours. Reversal of HIV latency was evaluated after 36 hours by analyzing GFP expression using flow cytometry. Cell viability was determined by measuring cellular ATP levels in a separate set of samples using the ATPlite assay system (PerkinElmer).

Figure 5A:
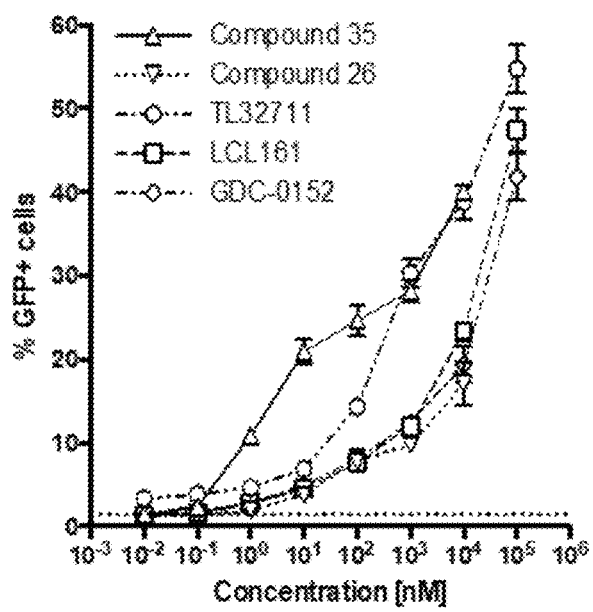
FIG. 5A shows the effects of Compound 35, Compound 26, TL32711, LCL161, and GDC-0152 on activating HIV transcription in latently infected Jurkat 2D10 cells.
Figure 5B:
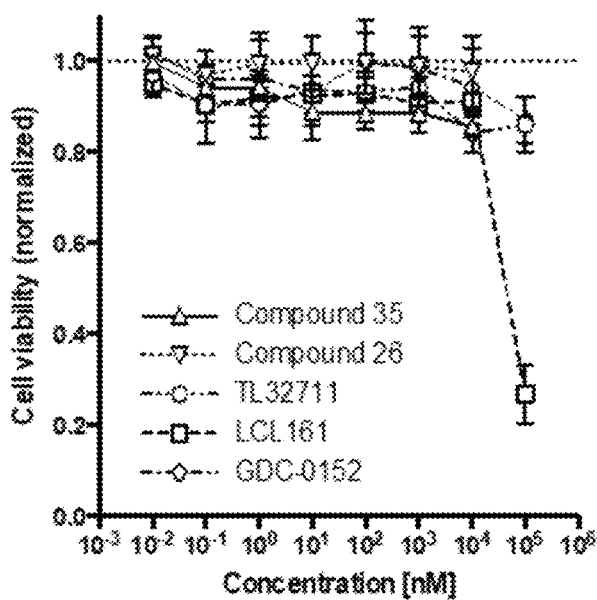
FIG. 5B shows that the cell viability was determined by measuring cellular ATP levels.

FIG. 5A shows the effect of Compound 35, Compound 26, TL32711 (Tetralogic), LCL161 (Novartis), or GDC-0152 (Genetech) on activating HIV transcription in latently infected Jurkat 2D10 cells. Data is shown as means±SD of three biological replicates. Dotted line in FIG. 5B represents values of untreated cells.

Example B-6—Combined Treatment with IAP Antagonists and HDAC Inhibitors Reverses HIV-1 Latency in Patient-Derived Resting CD4+ T Cells The ability of Compound 35, panobinostat, LCL161, or combinations thereof to activate HIV transcription in CD4+ T cells was assayed. Resting CD4+ T cells from three HIV-1 infected patients under anti retroviral treatment were treated with 100 nM panobinostat, 10 µM LCL161, 10 µM Compound 35, or a combination thereof for 48 hours. Viral production was subsequently evaluated by detection of viral mRNA in supernatant using qPCR.

Three aviremic HIV-1 infected patients on anti-retroviral treatment (ART) were recruited for phlebotomy according to an approved institutional review board protocol at the University of Utah. Inclusion criteria mandated viral suppression (less than 50 HIV-1 RNA copies/mL) for a minimum of six months, ART initiation during chronic HIV-1 infection (greater than six months since seroconversion) and compliance with a stable ART regimen for a minimum of twelve months per participant and provider report. Informed consent and phlebotomy were performed in the Center for Clinical and Translational Science Clinical Services Core at the University of Utah Medical Center.

Peripheral blood mononuclear cells were isolated from whole blood immediately after phlebotomy via density gradient centrifugation, followed by negative selection of resting CD4+ T cells using magnetic bead separation (Miltenyi Biotec and StemCell Technologies). Aliquots of $5 \times 10^6$ resting CD4+ T cells were cultured under multiple conditions: culture medium and DMSO (solvent) alone (negative control), CD3/CD28 antibody-coated magnetic beads (positive control) and medium containing 100 nM Panobinostat, 10 µM LCL161, 10 µM Compound 35, or a combination thereof. At 48 hours culture supernatants were collected for real time quantitative polymerase chain reaction (qPCR). Supernatant from each sample was collected for quantification of cell-free virions using a two-step qPCR that makes use of a primer and probe set for conserved regions of the 3' LTR of HIV-1 mRNA.

Figure 6:
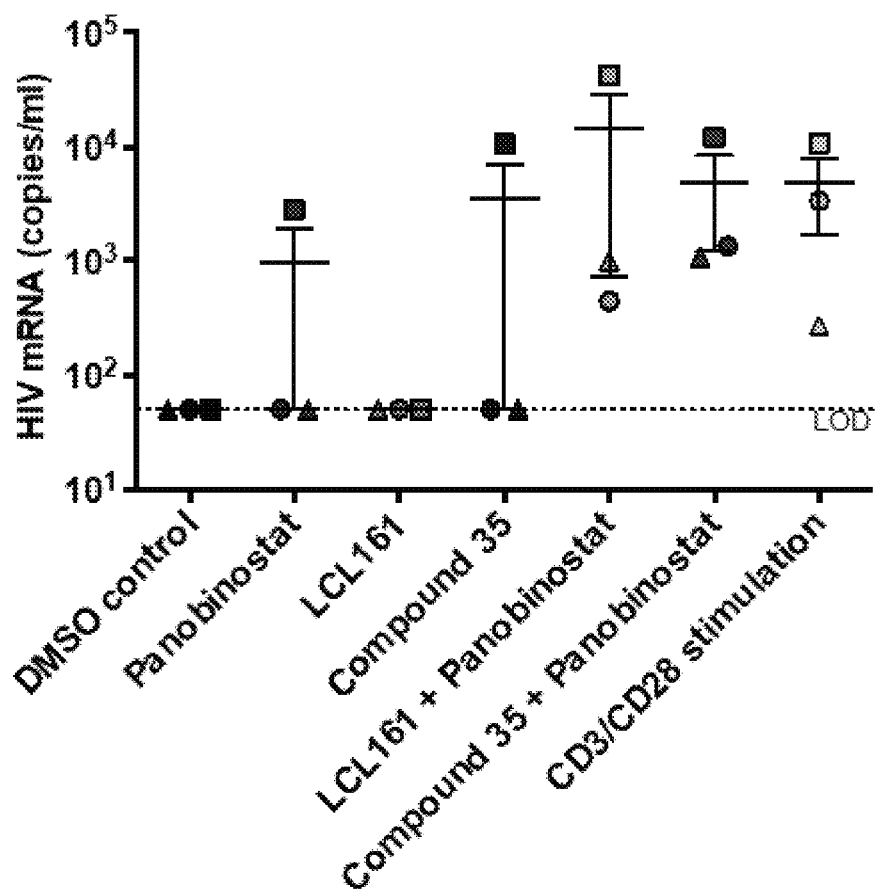
FIG. 6 shows Compound 35, panobinostat, or LCL161 alone or combinations thereof on reversing HIV latency in resting CD4+ T cells isolated from HIV infected patients undergoing antiretroviral therapy.

FIG. 6 shows Compound 35, panobinostat, or LCL161 alone or combinations thereof on reversing HIV latency in resting CD4+ T cells. Data points represented means of at least three technical replicates from each donor. Dotted line indicates limit of detection (LOD).

Example B-7—Evaluation of HDAC Inhibitors in Combinatorial Treatment with Compound 35

Latently infected Jurkat JLat 10.6 cells were treated with combinations of Compound 35 and HDAC inhibitors (indicated by CAS number, see Table B-2) for 36 hours. Reversal of HIV latency was evaluated by analyzing GFP expression using flow cytometry. Induction of GFP expression was measured and normalized against background of HDAC inhibitors alone. Binning is as follows. Combinations of compound 35 with the specific HDAC inhibitor leading to an increase of GFP+ cells: A 0-25%, B 25-50% and C 50-75%.

TABLE B-2 illustrates the HDAC inhibitors used during this experiment.

| CAS Number | IUPAC | Common Name | Group |
|---|---|---|---|
| 1027139-05-4 | 3H-1,2,4-Triazol-3-one, 5-[[2-[2-[3,5-bis(trifluoromethyl)phenyl]propyl]-3-(4-fluorophenyl)-4-morpholinyl]methyl]-1,2-dihydro- | NKL 22 | A |
| 1037543-26-2 | Retinoic acid, 4-[(1-oxobutoxy)methyl]phenyl ester | ATRA-BA Hybrid | A |
| 1045792-66-2 | Carbamic acid, N-[4-[3 -[[[7-(hydroxyamino)-7-oxolteptyl]amino]carbonyl]-5-isoxazolyl]phenyl]-, 1,1-dimethylethyl ester | BML-281 | B |
| 1069-66-5 | Pentanoic acid, 2-propyl-, sodium salt (1:1) | Valproic acid | A |
| 112522-64-2 | Benzamide, 4-(acetylamino)-N-(2-aminophenyl)- | CI-994 | A |
| 117378-93-5 | 2-Propenamide, N-hydroxy-3-[1-methyl-4-(4-methylbenzoyl)-1H-1-pyrrol-2-yl]- | MC-1293 | B |
| 149647-78-9 | Octanediamide, N1-hydroxy-N8-phenyl- | Vorinostat | A |
| 149648-08-8 | Octanediamide, N1-(4-fluorophenyl)-N8-hydroxy- | p-Fluoro-SAHA | A |
| 151720-43-3 | 2-Penten-4-ynamide, N-hydroxy-5-[3-[(phenylsulfonyl)amino]phenyl]-, (2E)- | Oxamflatin | C |
| 1716-12-7 | Benzenebutanoic acid, sodium salt (1:1) | Phenylbutyrate·Na | A |
| 183506-66-3 | Cyclo[(2S)-2-amino-8-oxodecanoyl-1 methoxy-L-tryptophyl-L-isoleucyl-(2R)-2-piperidinecarbonyl] | Apicidin | C |
| 251456-60-7 | Benzamide, 4-(dimethylamino)-N-[7-(hydroxyamino)-7-oxoheptyl]- | M344 | C |
| 287383-59-9 | 1H-Benz[de]isoquinoline-2(3H)-hexanamide, N-hydroxy-1,3-dioxo- | Scriptaid | C |
| 3565-26-2 | 8-Quinolinol, 5-nitroso- | NSC-3852 | B |
| 38937-66-5 | Octanediamide, N1,N8-dihydorxy- | Suberoyl bis-hydroxamic acid | B |
| 537034-17-6 | Octanediamide, N1-(2-aminophenyl)-N8-phenyl- | BML-210 | A |
| 58880-19-6 | 2,4-Heptadienamide, 7-[4-(dimethylamino)phehyl]-N-hydroxy-4,6-dimethyl-7-oxo-, (2E,4E,6R)- | Trichostatin A | C |
| 848354-66-5 | Propanethioic acid, 2-methyl-,S-[7-oxo-7-[(4-phenyl-2-thiazolyl)amino]heptyl] ester | NCH-51 | A |
| 926908-04-5 | Heptanamide, N-hydroxy-7-(2-naphthalenylthio)- | HNHA | B |
| 99873-43-5 | Butanamide, 4-(4-chloro-2-methylphenoxy)-N-hydroxy- | Droxinostat | B |

Figure 7A:
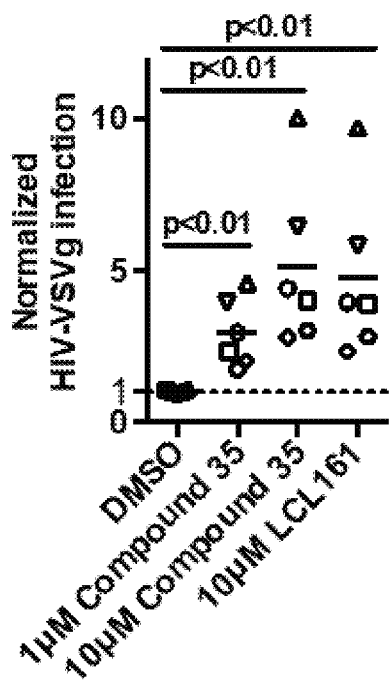
FIG. 7A shows the expression of luciferase following HIV-VSVg infection of primary activated CD4+ T cells.
Figure 7B:
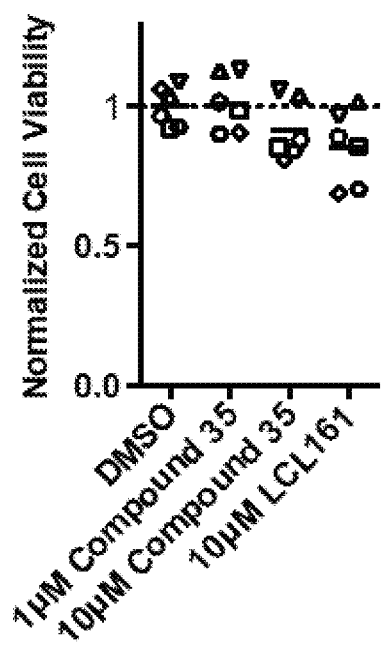
FIG. 7B shows that cell viability was evaluated by measuring cellular ATP levels. Each data point indicates mean of biological triplicates from a single donor. Lines indicate mean of 6 donors.
Figure 7C:
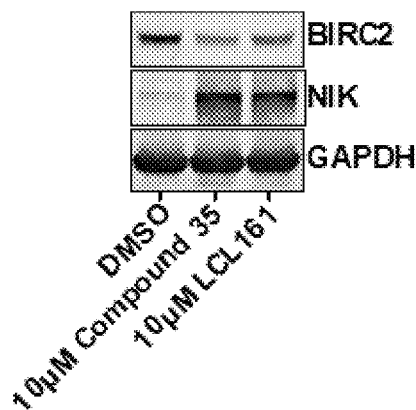
FIG. 7C shows BIRC2 depletion and NIK accumulation analyzed by Western blotting.

Example B-8—Treatment with IAP Inhibitors Enhances HIV Transcription in Primary CD4+ T Cells Primary activated CD4+ T cells isolated from 6 healthy donors were treated with IAP inhibitors Compound 35 or LCL161 (Novartis) at the indicated concentrations for 24 hours. Cells were subsequently infected with HIV-1(VSVg) for 48 hours before analysis of luciferase reporter activity (FIG. 7A). Cell viability was evaluated by measuring cellular ATP levels (FIG. 7B). Each data point indicates mean of biological triplicates from a single donor. Lines indicate mean of 6 donors. BIRC2 depletion and NIK accumulation were analyzed by Western blotting (FIG. 7C).

Peripheral blood mononuclear cells (PBMCs) were isolated by Ficoll density gradient centrifugation (Histopaque, Sigma Aldrich) from buffy coats of healthy human donors (San Diego Blood Bank). CD4+T cells were subsequently isolated by negative selection using magnetic beads (CD4+ T cell isolation kit II; Miltenyi Biotec). CD4+ T cells were cultured in RPMI1640 supplemented with 10% FBS, 100 IU penicillin, 100 µg/ml streptomycin, 0.1 M HEPES, 2 mM L-glutamine, and 20 units/ml interleukin-2 (IL-2) (NIH AIDS Reagent Program). Cells were activated with 4 µg/ml phytohaemagglutinin-P (PHA) (Sigma) for 48 hours. Activated CD4+ T cells were treated with Compound 35, LCL-161, DMSO, or mock treated for 24 hours prior to infection with HIV-1(VSVg). VSV-G-pseudotyped lentiviral supernatant (HIV-1(VSVg)) was generated using the pNL43-Luc-E-R+ (HIV-1 wild-type Δenv, encoding firefly luciferase GL3) vector as previously described (König, R., Chiang, C. Y., Tu, B. P., Yan, S. F., DeJesus, P. D., Romero, A., Bergauer, T., Orth, A., Krueger, U., Zhou, Y., et al.: A probability-based approach for the analysis of large-scale RNAi screens. Nat Methods 2007, 4:847-849). Luciferase expression levels were determined using Bright-Glo Luciferase Assay System (Perkin Elmer). Cell viability of treated cells was determined using ATPlite cell viability assay (Perkin Elmer). Values were normalized to mock-treated cells; average value of DMSO-treated cells was defined as 1.

Figure 8:
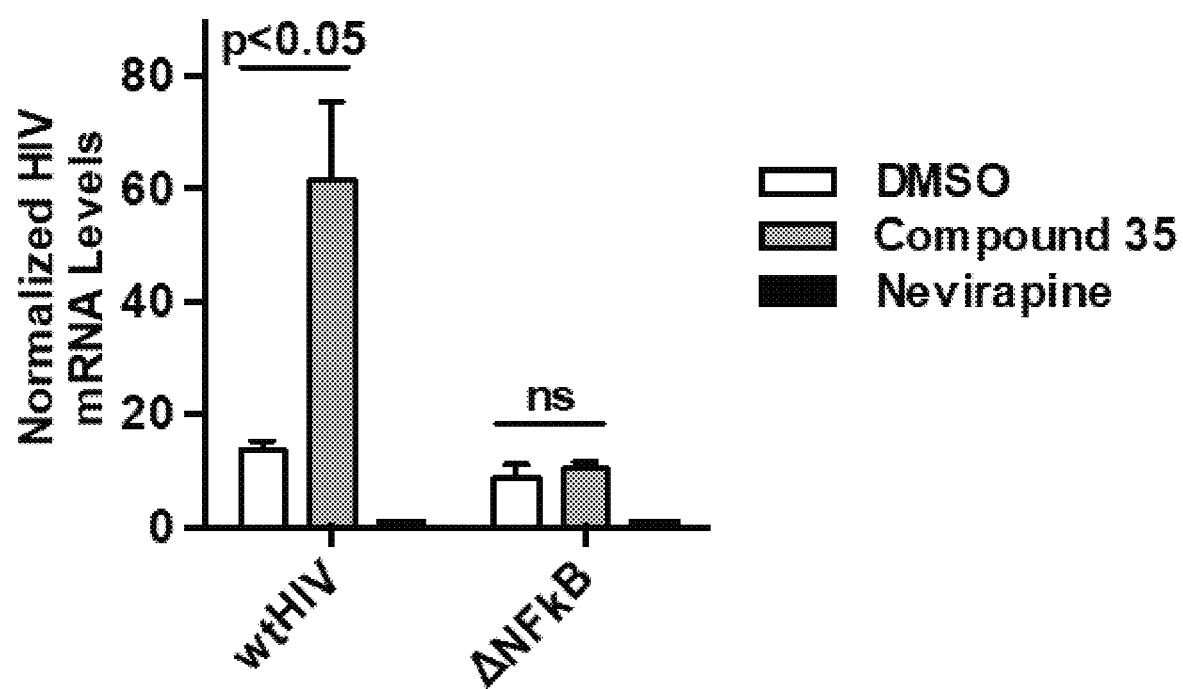
FIG. 8 shows that the effect of IAP antagonist treatment on HIV transcription is NF-κB-dependent.

Example B-9—Effect of IAP Antagonist Treatment on HIV Transcription is NF-κB-Dependent HEK293T cells were treated with 1 μM Compound 35 and infected for 24 hours with HIV-1(VSVg) containing either a functional (wtHIV) or mutated (ΔNFkB) NF-κB binding site in the viral LTR. FIG. 8 illustrates the HIV-1 mRNA levels quantified by qPCR and normalized to samples from cells treated with 5 μM nevirapine.

B-10—Parenteral Composition

To prepare a parenteral pharmaceutical composition suitable for administration by injection, 100 mg of a water-soluble salt of a compound of Formula A, Formula B, Formula C, Formula D, Formula E, Formula F, or Formula G, or pharmaceutically acceptable salt, N-oxide, racemate or stereoisomer thereof, is dissolved in 2% HPMC, 1% Tween 80 in DI water, pH 2.2 with MSA, q.s. to at least 20 mg/mL. The mixture is incorporated into a dosage unit form suitable for administration by injection.

Example B-11—Oral Composition

To prepare a pharmaceutical composition for oral delivery, 400 mg of a compound of Formula A, Formula B, Formula C, Formula D, Formula E, Formula F, or Formula G, or pharmaceutically acceptable salt, N-oxide, racemate or stereoisomer thereof, and the following ingredients are mixed intimately and pressed into single scored tablets.

| Tablet Formulation | |
|---|---|
| Ingredient | Quantity per tablet mg |
| compound | 400 |
| cornstarch | 50 |
| croscarmellose sodium | 25 |
| lactose | 120 |
| magnesium stearate | 5 |

The following ingredients are mixed intimately and loaded into a hard-shell gelatin capsule.

| Capsule Formulation | |
|---|---|
| Ingredient | Quantity per capsule mg |
| compound | 200 |
| lactose spray dried | 148 |
| magnesium stearate | 2 |

The Examples and embodiments described herein are illustrative and various modifications or changes suggested to persons skilled in the art are to be included within this disclosure. It should be understood that various alternatives to the embodiments of the invention described herein may be employed in practicing the invention.

What is claimed is:

1. A method of treating human immunodeficiency virus (HIV) in an individual in need thereof comprising administering a therapeutically effective amount of at least one inhibitor of apoptosis proteins (IAP) antagonist, wherein the IAP antagonist is a small molecule that has the following structure of Formula B-I, or pharmaceutically acceptable salt, N-oxide, racemate or stereoisomer thereof:

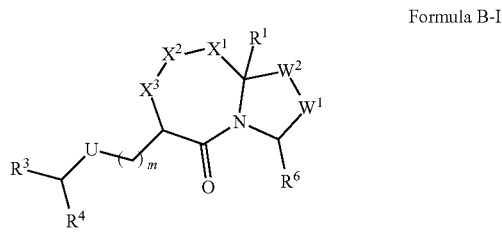

Formula B-I wherein,
$R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);
$X^1$ is O;
$X^2$ is $CR^{2c}R^{2d}$;
$X^3$ is $CR^{2a}R^{2b}$;
$W^1$ is $C(R^{8a})(R^{8b})$;
$W^2$ is $C(R^{8c})(R^{8d})$,
$R^{2a}$, $R^{2b}$, $R^{2c}$, and $R^{2d}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), and —C(=O)$R^B$;
$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;
$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), and —$C_1$-$C_6$alkyl-(substituted or unsubstituted heteroaryl);
m is 0, 1, or 2;
—U— is —NHC(=O)— or —C(=O)NH—;
$R^3$ is $C_1$-$C_3$alkyl or $C_1$-$C_3$fluoroalkyl;
$R^4$ is —$NHR^5$;
each $R^5$ is independently selected from H, $C_1$-$C_3$alkyl, $C_1$-$C_3$haloalkyl, $C_1$-$C_3$heteroalkyl, and —$C_1$-$C_3$alkyl-($C_3$-$C_5$cycloalkyl);

$R^6$ is —C(=O)NHR$^7$;

each R$^7$ is independently selected from C$_1$-C$_6$alkyl, C$_1$-C$_6$haloalkyl, C$_1$-C$_6$heteroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_6$alkyl-(substituted or unsubstituted C$_3$-C$_{10}$cycloalkyl), —C$_1$-C$_6$alkyl-(substituted or unsubstituted C$_2$-C$_{10}$heterocycloalkyl), —C$_1$-C$_6$alkyl-(substituted or unsubstituted aryl), —C$_1$-C$_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), and -(substituted or unsubstituted heteroaryl)-(substituted or unsubstituted heteroaryl);

p is 0, 1, or 2;

R$^{8a}$, R$^{8b}$, R$^{8c}$, and R$^{8d}$ are independently selected from H, C$_1$-C$_6$alkyl, C$_1$-C$_6$fluoroalkyl, C$_1$-C$_6$ alkoxy, C$_1$-C$_6$heteroalkyl, and substituted or unsubstituted aryl;

or:

R$^{8a}$ and R$^{8d}$ are as defined above, and R$^{8b}$ and R$^{8c}$ together with the atoms to which they are attached form a substituted or unsubstituted fused 5-7 membered saturated, or partially saturated carbocyclic ring or heterocyclic ring comprising 1-3 heteroatoms selected from S, O, and N, a substituted or unsubstituted fused 5-10 membered aryl ring, or a substituted or unsubstituted fused 5-10 membered heteroaryl ring comprising 1-3 heteroatoms elected from S, O, and N;

or:

R$^{8c}$ and R$^{8d}$ are as defined above, and R$^{8a}$ and R$^{8b}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, cycloalkyl, heterocycloalkyl, aryl or heteroaryl is substituted with 1-3 R$^9$; and each R$^9$ is independently selected from halogen, —OH, —SH, (C=O), CN, C$_1$-C$_4$alkyl, C$_1$-C$_4$ fluoroalkyl, C$_1$-C$_4$ alkoxy, C$_1$-C$_4$ fluoroalkoxy, —NH$_2$, —NH(C$_1$-C$_4$alkyl), —N(C$_1$-C$_4$alkyl)$_2$, —C(=O)OH, —C(=O)NH$_2$, —C(=O)C$_1$-C$_3$alkyl, —S(=O)$_2$CH$_3$, —NH(C$_1$-C$_4$alkyl)-OH, —NH(C$_1$-C$_4$alkyl)-O-(C$_1$-C$_4$alkyl), —O(C$_1$-C$_4$alkyl)-NH$_2$, —O(C$_1$-C$_4$alkyl)-NH—(C$_1$-C$_4$alkyl), and —O(C$_1$-C$_4$alkyl)-N-(C$_1$-C$_4$alkyl)$_2$; or two R$^9$ together with the atoms to which they are attached form a methylenedioxy or ethylenedioxy ring substituted or unsubstituted with halogen, —OH, or C$_1$-C$_3$alkyl.

2. The method of claim 1, wherein the compound of Formula B-I has the following structure of Formula B-III-1, or pharmaceutically acceptable salt, N-oxide, racemate or stereoisomer thereof:

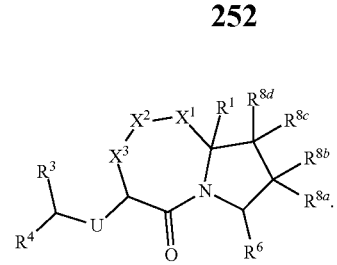

Formula B-III-1

3. The method of claim 1, wherein the compound of Formula B-I has the following structure of Formula B-VII-2, or a pharmaceutically acceptable salt, N-oxide, racemate or stereoisomer thereof:

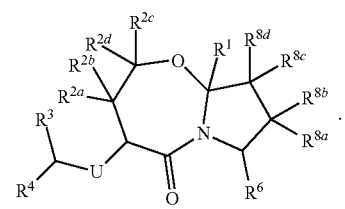

Formula B-VII-2

4. The method of claim 1, wherein the compound of Formula B-I has the following structure of Formula B-XII, or pharmaceutically acceptable salt, N-oxide, racemate or stereoisomer thereof:

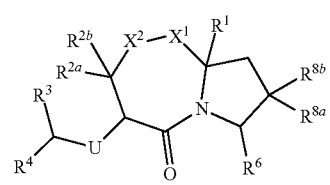

Formula B-XII wherein R$^{8a}$ and R$^{8b}$ are independently selected from H and C$_1$-C$_3$alkyl.

5. The method of claim 1, wherein the compound of Formula B-I has the following structure of Formula B-XVI-1 or Formula B-XVI-3 or pharmaceutically acceptable salt, N-oxide, racemate or stereoisomer thereof:

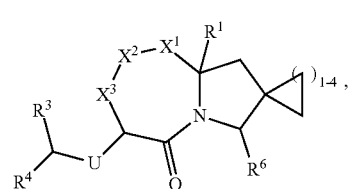

Formula B-XVI-1

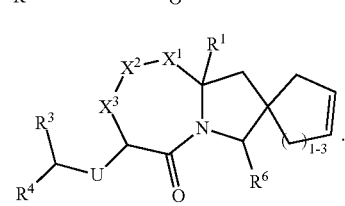

Formula B-XVI-3

6. The method of claim 1, wherein the compound of Formula B-I has the structure of Formula B-XXII, or pharmaceutically acceptable salt, N-oxide, racemate or stereoisomer thereof:

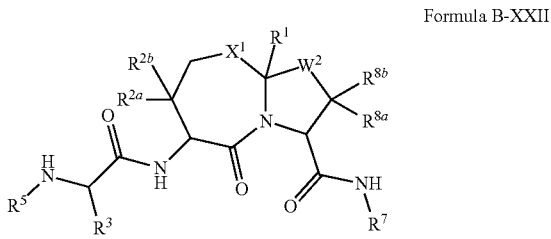

Formula B-XXII wherein,
$W^2$ is $C(R^{8c})(R^{8d})$;
$R^1$ is H or $C_1$-$C_6$alkyl;
$X^1$ is O;
$R^{2a}$ and $R^{2b}$ are independently selected from H, substituted or unsubstituted $C_1$-$C_6$alkyl, and —C(=O)$R^B$;
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;
$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), and —$C_1$-$C_6$alkyl-(substituted or unsubstituted heteroaryl);
$R^3$ is $C_1$-$C_3$alkyl or $C_1$-$C_3$fluoroalkyl;
each $R^5$ is independently selected from H, $C_1$-$C_3$alkyl, $C_1$-$C_3$haloalkyl, $C_1$-$C_3$heteroalkyl, and —$C_1$-$C_3$alkyl-($C_3$-$C_5$cycloalkyl);
each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), and -(substituted or unsubstituted heteroaryl)-(substituted or unsubstituted heteroaryl);
p is 0, 1, or 2;
$R^{8a}$ and $R^{8b}$ are independently selected from H, $C_1$-$C_6$alkyl, and $C_1$-$C_6$fluoroalkyl;
$R^{8c}$ and $R^{8d}$ are independently selected from H, $C_1$-$C_6$alkyl, and $C_1$-$C_6$fluoroalkyl;
where each substituted alkyl, heteroalkyl, cycloalkyl, heterocycloalkyl, aryl, or heteroaryl is substituted with 1-3 $R^9$; and
each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —N($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O-($C_1$-$C_4$alkyl), —O($C_1$-$C_4$alkyl)-NH$_2$, —O($C_1$-$C_4$alkyl)-NH—($C_1$-$C_4$alkyl), and —O($C_1$-$C_4$alkyl)-N-($C_1$-$C_4$alkyl)$_2$; or two $R^9$ together with the atoms to which they are attached form a methylene dioxy or ethylene dioxy ring substituted or unsubstituted with halogen, —OH, or $C_1$-$C_3$alkyl.

7. The method of claim 1, wherein the compound of Formula B-I has one of the following structures:

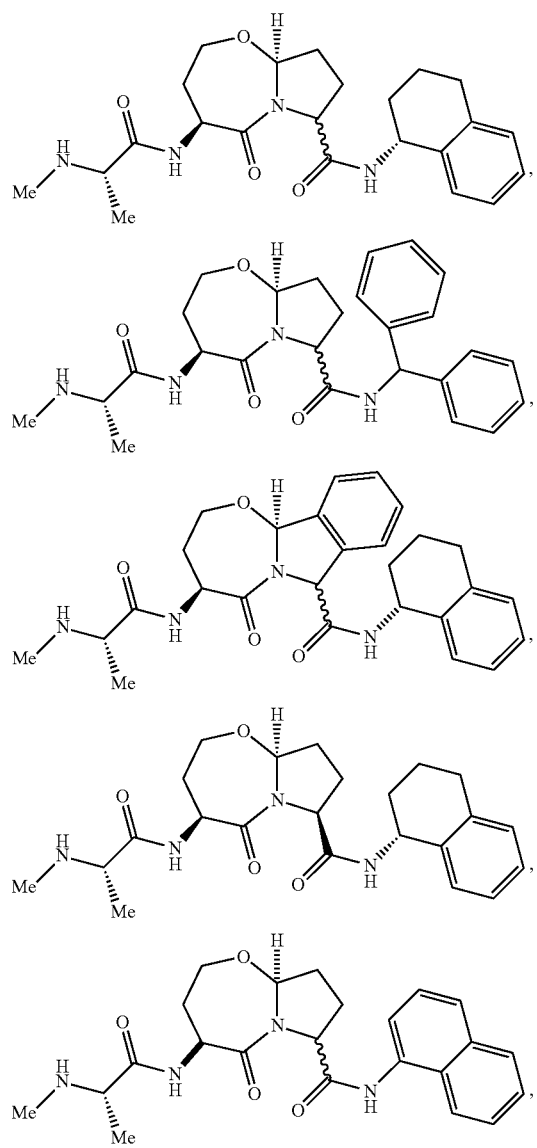

255

-continued

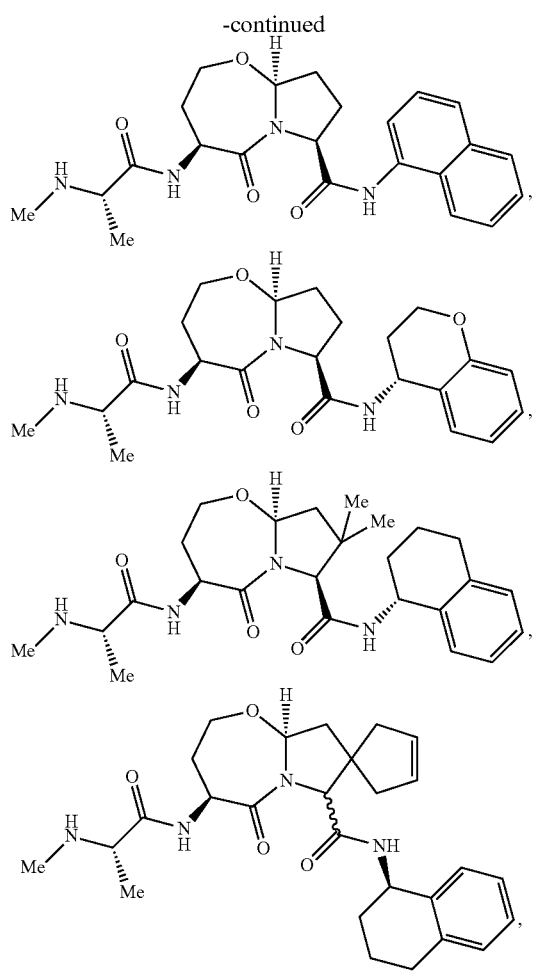

256

-continued

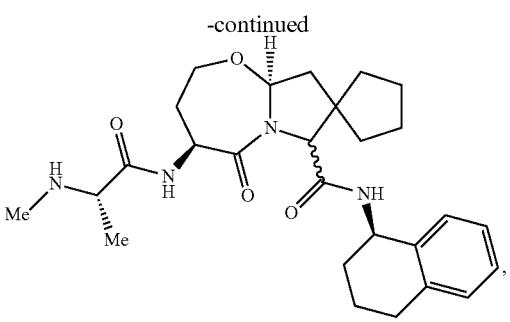

or pharmaceutically acceptable salt, N-oxide, racemate or stereoisomer thereof.

8. The method of claim 1, wherein the method comprises reducing dormant, replication competent human immunodeficiency virus (HIV) in the individual, or making dormant, replication competent human immunodeficiency virus (HIV) susceptible to immune system clearance in the individual, or making dormant, replication competent human immunodeficiency virus (HIV) susceptible to the effects of antiretroviral therapy in the individual, or eliminating replication competent human immunodeficiency virus (HIV) in the individual, or inducing long term control of human immunodeficiency virus (HIV) replication and growth in the absence of antiretroviral therapy in the individual, or activating human immunodeficiency virus (HIV) transcription in latently infected cells in the individual, or reducing human immunodeficiency virus (HIV) reservoirs of latently infected cells in the individual.

9. The method of claim 1, wherein the individual is receiving concomitant antiretroviral therapy.

* * * * *